US010687731B2

(12) United States Patent
Bennet-Guerrero

(10) Patent No.: US 10,687,731 B2
(45) Date of Patent: Jun. 23, 2020

(54) METHODS AND APPARATUS FOR GUIDING MEDICAL CARE BASED ON DETECTED GASTRIC FUNCTION

(71) Applicant: Gravitas Medical, Inc., San Francisco, CA (US)

(72) Inventor: Elliott Bennet-Guerrero, Chapel Hill, NC (US)

(73) Assignee: Gravitas Medical, Inc., San Francisco, CA (US)

( * ) Notice: Subject to any disclaimer, the term of this patent is extended or adjusted under 35 U.S.C. 154(b) by 366 days.

(21) Appl. No.: 15/360,625

(22) Filed: Nov. 23, 2016

(65) Prior Publication Data

US 2017/0071502 A1   Mar. 16, 2017

Related U.S. Application Data

(63) Continuation of application No. 13/495,990, filed on Jun. 13, 2012, now Pat. No. 9,532,739.
(Continued)

(51) Int. Cl.
*A61B 5/05* (2006.01)
*A61B 5/053* (2006.01)
(Continued)

(52) U.S. Cl.
CPC ............ *A61B 5/0538* (2013.01); *A61B 5/073* (2013.01); *A61B 5/14503* (2013.01);
(Continued)

(58) Field of Classification Search
CPC ... A61B 5/0538; A61B 5/7445; A61B 5/4238; A61B 5/14507; A61B 5/14539;
(Continued)

(56) References Cited

U.S. PATENT DOCUMENTS

| 4,381,011 A | 4/1983 | Somers, 3rd |
| 4,823,808 A * | 4/1989 | Clegg ................... A61B 5/07 |
| | | 128/903 |

(Continued)

FOREIGN PATENT DOCUMENTS

WO   WO 1992/017150   10/1992

OTHER PUBLICATIONS

Parkman, HP. et al. Effect of gastric acid suppressants on human gastric motility. But 1998; 42: 243-250.*
(Continued)

*Primary Examiner* — Amber R Stiles
(74) *Attorney, Agent, or Firm* — Levine Bagade Han LLP

(57) ABSTRACT

Embodiments relate to guiding medical care based on detected gastric function. For example, gastric acid stimulant or suppressant is administered, and then a change in the gastric juice H+ concentration is measured. This change is compared to a guidance H+ concentration differential indicative of relatively healthy gastric function. Medical care is guided based on a relatively healthy gastric function if the measured H+ concentration differential is equal to or exceeds the guidance H+ concentration differential, while medical care is guided based on a relatively unhealthy gastric function if the measured H+ concentration differential is less than the guidance H+ concentration differential. Disclosed embodiments implementing this procedure include, but are not limited to, methods, apparatus, processors, computer programs, and computer-readable mediums.

20 Claims, 13 Drawing Sheets

Related U.S. Application Data

(60) Provisional application No. 61/496,800, filed on Jun. 14, 2011.

(51) Int. Cl.
*A61B 5/07* (2006.01)
*A61B 5/145* (2006.01)
*A61B 5/00* (2006.01)
*A61K 9/00* (2006.01)
*A61K 31/194* (2006.01)
*A61K 31/341* (2006.01)
*A61K 31/4439* (2006.01)
*A61K 33/00* (2006.01)
*A61K 38/08* (2019.01)
*A61B 10/00* (2006.01)

(52) U.S. Cl.
CPC ...... *A61B 5/14507* (2013.01); *A61B 5/14539* (2013.01); *A61B 5/4238* (2013.01); *A61B 5/4839* (2013.01); *A61B 5/7445* (2013.01); *A61K 9/0053* (2013.01); *A61K 31/194* (2013.01); *A61K 31/341* (2013.01); *A61K 31/4439* (2013.01); *A61K 33/00* (2013.01); *A61K 38/08* (2013.01); *A61B 2010/0061* (2013.01)

(58) Field of Classification Search
CPC ... A61B 5/4839; A61B 5/14503; A61B 5/073; A61B 2010/0061; A61K 38/08; A61K 33/00; A61K 31/4439; A61K 31/341; A61K 31/194; A61K 9/0053; A61J 15/00; A61J 15/0003; A61J 15/0011; A61J 15/0015; A61J 15/0026; A61J 15/008; A61J 15/0084
See application file for complete search history.

(56) References Cited

U.S. PATENT DOCUMENTS

| | | | |
|---|---|---|---|
| 4,836,214 A | 6/1989 | Sramek | |
| 4,921,481 A | 5/1990 | Danis et al. | |
| 5,105,812 A | 4/1992 | Corman | |
| 5,479,935 A * | 1/1996 | Essen-Moller | A61B 5/037 600/547 |
| 5,500,430 A | 3/1996 | Makoveo et al. | |
| 5,690,960 A | 11/1997 | Bengtsson et al. | |
| 5,833,625 A | 11/1998 | Essen | |
| 6,334,064 B1 | 12/2001 | Fiddian-green | |
| 6,357,447 B1 | 3/2002 | Swanson et al. | |
| 6,365,128 B1 * | 4/2002 | Bennett-Guerrero | A61K 49/0004 424/1.11 |
| 6,482,170 B1 | 11/2002 | Andersen | |
| 6,815,414 B2 | 11/2004 | Chowers et al. | |
| 7,141,016 B2 * | 11/2006 | Lykke | A61B 5/07 600/300 |
| 7,374,547 B2 | 5/2008 | Eerdmans | |
| 7,818,155 B2 * | 10/2010 | Stuebe | A61B 5/053 703/11 |
| 8,147,486 B2 | 4/2012 | Honour et al. | |
| 8,568,336 B2 * | 10/2013 | Gewolb | A61B 5/11 600/300 |
| 8,613,702 B2 | 12/2013 | Feer et al. | |
| 8,617,070 B2 * | 12/2013 | Imran | A61B 5/0538 600/309 |
| 8,696,567 B2 * | 4/2014 | Carr | C12Q 1/34 435/18 |
| 8,986,230 B2 | 3/2015 | Nishtala | |
| 9,179,971 B2 | 11/2015 | Kirschenman | |
| 9,226,878 B2 | 1/2016 | Elia et al. | |
| 9,295,395 B2 | 3/2016 | Elia et al. | |
| 9,532,739 B2 * | 1/2017 | Bennett-Guerrero | A61B 5/073 |
| 9,610,227 B2 | 4/2017 | Elia | |
| 9,642,779 B2 | 5/2017 | Elia et al. | |
| 9,713,579 B2 | 7/2017 | Elia et al. | |
| 2003/0092040 A1 * | 5/2003 | Bader | G06F 19/18 435/6.11 |
| 2004/0253179 A1 * | 12/2004 | Chang | A61K 49/0004 424/9.1 |
| 2005/0149142 A1 | 7/2005 | Starkebaum | |
| 2006/0074335 A1 * | 4/2006 | Ben-Oren | A61B 5/083 600/532 |
| 2007/0078494 A1 * | 4/2007 | Mintchev | A61N 1/36007 607/40 |
| 2007/0207959 A1 | 9/2007 | Pisegna et al. | |
| 2007/0255335 A1 * | 11/2007 | Herbert | A61N 1/05 607/40 |
| 2007/0255336 A1 * | 11/2007 | Herbert | A61N 1/36007 607/40 |
| 2008/0077043 A1 * | 3/2008 | Malbrain | A61B 5/036 600/547 |
| 2008/0097179 A1 * | 4/2008 | Russo | A61B 5/0421 600/343 |
| 2008/0167607 A1 | 7/2008 | Pfeiffer et al. | |
| 2008/0219928 A1 | 9/2008 | Becker et al. | |
| 2008/0287833 A1 * | 11/2008 | Semler | A61B 5/037 600/593 |
| 2009/0104250 A1 | 4/2009 | Boyden et al. | |
| 2009/0105531 A1 | 4/2009 | Boyden et al. | |
| 2009/0105561 A1 | 4/2009 | Boyden et al. | |
| 2009/0105694 A1 | 4/2009 | Boyden et al. | |
| 2009/0110714 A1 | 4/2009 | Boyden et al. | |
| 2009/0112048 A1 | 4/2009 | Boyden et al. | |
| 2009/0112189 A1 | 4/2009 | Boyden et al. | |
| 2009/0112190 A1 | 4/2009 | Boyden et al. | |
| 2009/0112191 A1 | 4/2009 | Boyden et al. | |
| 2009/0137866 A1 | 5/2009 | Boyden et al. | |
| 2009/0183894 A1 | 6/2009 | Boyden et al. | |
| 2009/0192449 A1 | 7/2009 | Boyden et al. | |
| 2010/0087715 A1 * | 4/2010 | Van Bommel | A61B 5/0421 600/301 |
| 2010/0137746 A1 | 6/2010 | Holte | |
| 2011/0060215 A1 * | 3/2011 | Tupin, Jr. | A61B 5/0507 600/425 |
| 2012/0016256 A1 * | 1/2012 | Mabary | A61B 5/0538 600/547 |
| 2012/0277619 A1 | 11/2012 | Starkebaum et al. | |
| 2012/0323091 A1 * | 12/2012 | Bennett-Guerrero | A61B 5/073 600/309 |
| 2013/0225946 A1 | 8/2013 | Feer et al. | |
| 2016/0113843 A1 | 4/2016 | Elia et al. | |
| 2016/0129223 A1 | 5/2016 | Kirschenman | |
| 2017/0202750 A1 | 7/2017 | Elia | |
| 2018/0078195 A1 * | 3/2018 | Sutaria | A61B 5/00 |
| 2018/0161249 A1 | 6/2018 | Elia et al. | |

OTHER PUBLICATIONS

"Hospira Sodium Bicarbonate Injection 8.4% 50 MI Vials—Mountainside Medical Equipment", Web. Jun. 2, 2011. <http://www.mountainside-medical.com/products/Sodium-Bicarbonate.html>.

"Neutralization (chemistry)." Wikipedia, the Free Encyclopedia. Wikimedia Foundation, Inc., Apr. 13, 2011. Web. Apr. 13, 2011. <http://en.wikipedia.org/wiki/Neutralization—(chemistry)>.

"Pentagastrin as a stimulant of maximal gastric acid response in man," A Multicentre Pilot Study, The Lancet, 1967; Feb. 11, pp. 291-295.

Ackland et al., "Understanding gastrointestinal perfusion in critical care: so near, and yet so far", Critical Care Medicine, 2000, vol. 4(5), pp. 269-281.

Ali et al., "Stress-Induced ulcer Bleeding in Critically Ill Patients." Gastroenterology Clinics of North America. 2009;38:245-65.

Al-Mufarrej et al., "Understanding Intra-Abdominal Hypertension: From the Bench to Bedside." Journal of intensive Care Medicine 2011, Web. Apr. 27, 2011.

(56) References Cited

OTHER PUBLICATIONS

Artinian et al. "Effects of Early Enteral Feeding on the Outcome of Critically Ill Mechanically Ventilated Medical Patients", Chest 2006, vol. 129, pp. 960-967.

Atanassoff et al., "Effects of Single-Dose Intravenous Omeprazole and Ranitidine on Gastric PH During General Anesthesia", Anesth Analg, 1992, 75:95-98.

Atanassoff et al., "Effects of Single-dose Oral Ranitidine and Sodium Citrate on Gastric PH during and after General Anaesthesia", Canadian Journal of Anaesthesia, 1995, 42.5: 382-86.

Beak et al., "Repeated Intravenous Bolus Injections of Omeprazole: Effects on 24-Hour Intragastric PH, Serum Gastrin, and Serum Pepsinogen A and C", Scand J Gastroenterol, 1991, 26:737-46.

Balogh et al., "Secondary abdominal compartment syndrome is an elusive early complication of traumatic shock resuscitation." American Journal of Surgery 2002: 184:538-44.

Becton, Dickinson and Company. Web Jun. 12, 2012. <http://catalog.bd.com/bdCat/viewProduct.doCustomer?productNumber=301031>.

Berstad, et al; "Effect of graded doses of pentagastrin in patients with and without gastritis". GUT 1970 11:299-302, Nov. 6, 2012.

Blahitka et al., "Blood Flow in Rats During Hemorrhagic Shock: Differences Between Surviving and Dying Animals", Circulatory Shock, 1977, 4:79-93.

Braunschweig et al., "Enteral compared with parenteral nutrition: a meta-analysis", American Journal of Clinical Nutrition, 2001, vol. 74, pp. 534-542.

Bredenoord et al., "Technology Review: Esophageal Impedance Monitoring." American Journal of Gastroenterology, 2007, 102:187-94.

British Society of Gastroenterology Endoscopy Committee. Non-variceal upper gastrointestinal haemorrhage: guidelines. Gut, 2002: 5 (Suppl IV):iv1-6.

Brunner et al., "Drugs for pH control in upper gastrointestinal bleeding", Aliment Phamracol Ther, 1995, 9:47-50.

Brunner et al., "Optimizing the Intragastric pH as a Supportive Therapy in Upper GI Bleeding ", Yale Journal of Biology and Medicine, 1996, 69, pp. 225-231.

Bulkley et al., "Control of gastric vascular resistance in cardiogenic shock", Surgery, 1985, 98:2, pp. 213-223.

Calvet et al., "Effect of Ranitidine on Gastric Intramucosal pH in Critically Ill Patients", Intensive Care Medicine, 1998, vol. 24, pp. 12-17.

Calvet et al., "Effect of Sucralfate on Gastric intramucosal pH in Critically Ill Patients", Intensive Care Medicine, 1997, vol. 23, pp. 738-742.

Carmel R. "In Vitro Studies of Gastric Juice in Patients with Food-Cobalamin Malabsorption", Digestive Diseases and Sciences, 1994, vol. 39, No. 12, pp. 2516-2522.

Carter et al., "Redistribution of blood flow after thermal injury and hemorrhagic shock", J. Appl Physiol, 1988; 65(4): 1782-1788.

Chapman et al., "Glucose absorption and gastric emptying in critical illness", Critical Care Medicine, 2009, vol. 13(4), p. 190.

Cohn et al., "Splanchnic Perfusion Evaluation during Hemorrhage and Resuscitation with Gastric Near-Infrared Spectroscopy", J Trauma, 2001, 50:629-635.

Cook et al, "Risk Factors for Gastrointestinal Bleeding in Critically Ill Patients", New England Journal of Medicine, 1994;330:377-81.

Dandeles et al., "Efficacy of Agents to Prevent and Treat Enteral Feeding Tube Clogs." The Annals of Pharmacotherapy, 2011, 45:676-680.

Dewan, David M. "Sodium Citrate Pretreatment in Elective Cesarean Section Patients." Anesth Analg, 1985, 64.34: 382-86.

Drover et al., "Nutrition Therapy for the Critically Ill Surgical Patient: We Need to Do Better?", J Parenteral and Enteral Nutrition 2010, 34: 644.

Feldman, Mark. "Gastric Bicarbonate Secretion in Humans: Effect of Pentagastrin, Bethanechol, and 11, 16, 16-Trimethyl Prostaglandin E2", Journal of Clinical Investigation, 1983, 72:295-303.

Fiddian-Green, Richard G., "Stress Ulceration: a focal manifestation of mucosal ischemia", Splanchnic Ischernia and Multiple Organ Failure, 253-9, 1989.

Franklin et al., "Physician-Delivered Malnutrition: Why Do Patients Receive Nothing by Mouth or a Clear Liquid Diet in a University Hospital Setting?", J Parenter Enteral Nutr. 2011, 35:337-342.

Frey et al., "Non-occlusive small bowel necrosis during gastric tube feeding: a case report", Intensive Care Medicine 2001, 27: 1422-1425.

Gabriel et al., "Placement of Nasoenteral Feeding Tubes Using External Magnetic Guidance", Journal of Parenteral and Enteral Nutrition, 2004, 28:119-122.

Gibbs et al, "The Effectiveness of Sodium Citrate as an Antacid", American Society of Anesthesiologists, 1982, 57:44-46.

Grossan., "Proteolytic Enzymes for Ear, Nose, & Throat Problems." Dr. Grossan's Ear, Nose and Throat Consultant Pages, Jun. 12, 2012, Web. <http://www.ent-consult.com/enzymes.html>.

Hamilton et al., "The Relationship Between a Pentagastrin-Stimulated Gastric Luminal Acid Production Test (Gastrotest) and Enteral Feeding-Related Gastrointestinal Complications in Critically Ill Patients", Anesthesia & Analgesia, 2005, vol. 100, pp. 1447-1452.

Heath et al., "Intragastric pH measurement using a novel disposable sensor", Intensive Care Med, 1988, 14:232-235.

Herzig et al. "Acid-Suppressive Medication Use and the Risk for Hospital-Acquired Pneumonia." Journal of the American Medical Association, 2009;301(20):2120-8.

Heyland et al., "Canadian clinical practice guidelines for nutrition support in mechanically ventilated, critically ill adult patients." Journal Parenteral Enteral Nutrition, 2003;27:355-73.

Heyland et al., "Review or ICU Early vs. Delayed Feeding Randomized Trials." Jan. 31, 2009.

Higgins et al., "Low intramucosal pH is associated with failure to acidify the gastric lumen in response to pentagastrin," Intensive Care Med, 1994, 20, pp. 105-108.

Hirst et al., "Relationship Between Hydrogen Ion Concentration and Flow of Gastric Juice Durin Inhibition of Gastric Secretion in the Cat" J. Physiol., 1980, 306:51-63.

Ho et al., "A comparison of early gastric and post-pyloric feeding in critically ill patients: a meta-analysis", Intensive Care Medicine, 2006, vol. 32, No. 5, pp. 639-649.

Howell et al., "Iatrogenic Gastric Acid Suppression and the Risk of Nosocomial Clostridium difficile Infection.", Arch Intern Med. 2010;170(9):784-790.

Isenberg et al., "Increased Sensitivity to Stimulation of Acid Secretion by Pentagastrin in Duodenal Ulcer", Journal of Clinical Investigation, 1975 55:330-37.

Katz et al., "Intraoperative Assessment of Blood Flow to Strangulated Stomach by Pulse Oximetry", Journal of Pediatric Surgery, 1992, vol. 27, No. 4 (Apr.), pp. 509-510.

Laine et al., "Intragastric pH With Oral vs Intravenous Bolus Plus Infusion Proton-Pump Inhibitor Therapy in Patients With Bleeding Ulcers." Gastroenterology, 2008, 134:7, pp. 1836-1841.

Lanas et al., "Clinical predictors of poor outcomes among patients with nonvariceal upper gastrointestinal bleeding in Europe", Alimentary Pharmacology and Therapeutics, 2011, 33:1225-1233.

Lau et al., "Effect of Intravenous Omeprazole on Recurrent Bleeding After Endoscopic Treatment of Bleeding Peptic Ulcers", The New England Journal of Medicine, 2000, 343:6, pp. 310-318.

Makhlouf et al., "Gastroenterology." Official Publication of the American Gastroenterological Association, 1966, 51.4:455-65.

Martindale et al., "The evolving role of the critical care dietician." Critical Connections of the Society of Critical Care Medicine 2011. <http://www.sccm.org/Publications/Critical-Connections/Archives/August2011/Pages/RoleofDietitian.aspx>. Web, Jun. 12, 2012.

McClave et al., "Guidelines for the Provision and Assessment of Nutrition Support Therapy in the Adult Critically Ill Patient." Society of Critical Care Medicine (SCCM) and American Society for Parenteral and Enteral Nutrition (ASPEN). J Parent Enteral Nutrition, 2009.

Metheny et al., Tracheobronchial aspiration of gastric contents in critically ill tube-fed patients: Frequency, outcomes, and risk factors, Critical Care Medicine, 2006;34(4): 1007-15.

(56) References Cited

OTHER PUBLICATIONS

Miller et al., "Can We Feed? A Mnemonic to Merge Nutrition and Intensive Care Assessment of the Critically Ill", Parenter Enteral Nutr, 2011, 35:643-659.
Mohsenifar et al., "Gastric Intramural pH as a Predictor of Success or Failure in Weaning Patients from Mechanical Ventilation", Annals of Internal Medicine, 1993, vol. 199, pp. 794-798.
Montejo, Juan C., "Enteral nutrition-related gastrointestinal complications in critically ill patients: A multicenter study", Critical Care Medicine, 1999, vol. 27, Issue 8, pp. 1447-1453.
Moore et al., "Early Enteral Feeding, Compared With Parenteral, Reduces Postoperative Septic Complications", Annals of Surgery, 1992, vol. 216, No. 2, pp. 172-183.
Mufarrej et al., "Understanding Intra-Abdominal Hypertension: From the Bench to the Bedside." Journal of Intensive Care Medicine, 2011, pp. 1-16.
Neligan, Patrick. "Stress Ulceration in Critical Care—What Causes It?" Welcome to Critical Care Medicine Tutorials. Critical Care Medical Tutorials. Web. Jun. 2, 2011, <http://www.ccmtutorials.com/support/ulcers/page-03.htm>.
Netzer et al., "Effect of Repeated injection and Continuous Infusion of Omeprazole and Ranitidine on intragastric pH Over 72 Hours", American Journal of Gastroenterology, 1999: 94:2, pp. 351-357.
Nguyen et al., "The impact of delaying enteral feeding on gastric emptying, plasma cholecystokinin, and peptide YY concentrations in critically ill patients", Critical Care Medicine, 2008, vol. 36(5), pp. 1469-1474.
Pentagastrin BP Monograph, 2008.
Peterson et al., "Pentagastrin Dose-Response in Peptic Ulcer Disease", J. Gastroent., 1975, 10:705:714.
Pratha et al., "Inhibition of Pentagastrin-Stimulated Gastric Acid Secretion by Pantoprazole and Omeprazole in Healthy Adults", Digestive Diseases and Sciences, 2006, vol. 51, No. 1 pp. 123-131.
Preiser et al., "Management of Nutrition in European Intensive Care Units: Results of a Questionnaire", Intensive Care Medicine, 1999, vol. 25, pp. 95-101.
Raghavendran et al., "Aspiration-induced lung injury," Critical Care Medicine, 2011, 39:4, pp. 818-826.
Raschke et al, "The Weight-based Heparin Dosing Nomogram Compared with a "Standard Care" Nomogram." Annals of Internal Medicine, 1993, 119.9:874-81.
Rice et al., Randomized trial of initial trophic versus full-energy enteral nutrition in mechanically ventilated patients with acute respiratory failure, Crit Care Med, 2011, vol. 39, No. 6, pp. 1-8.
Rudholm, et al; "Bravo capsule system optimizes intragastric pH monitoring over prolonged time: Effects of ghrelin on gastric acid and hormone secretion in the rat". World Journal of Gastroenterology, ISSN 1007-9327, Oct. 28, 2008.
Spain DA., "When is the seriously ill patient ready to be fed?", Journal of Parenteral Enteral Nutrition, 2002, vol. 26, Supp.6, pp. 65-68.
Stannard et al., "Gastric exocrine "failure" in critically ill patients: incidence and associated features." British Medical Journal. 1988, vol. 296, pp. 155-156.
Takala et al., "Splanchnic perfusion in intensive care patients", Minerva Anestesiol, 2000, 66:333-6.
Takala J, "Determinants of splanchnic blood flow", British Journal of Anaesthesia, 1997, 77:50-58.
Van Rensburg et al., "Intragastric pH During Continuous Infusion With Pantoprazole in Patients With Bleeding Peptic Ulcer", The American Journal of Gastroenterology, 2003, 98:12, pp. 2635-2641.
Woo et al., "Early vs Delayed Enteral Nutrition in Critically Ill Medical Patients", Nutr Clin Pract, 2010, 25:205-211.
World Society of the Abdominal Compartment Syndrome, Web. Jun. 2, 2011, <http://www.wsacs.org/patients.php>.
Wyeth Ayerst official prescribing information for pentagastrin (Peptavlon). In; 1995:2787.

* cited by examiner

METHODS AND APPARATUS FOR GUIDING MEDICAL CARE BASED ON DETECTED GASTRIC FUNCTION

CROSS-REFERENCE TO RELATED APPLICATIONS

This application is a continuation of U.S. patent application Ser. No. 13/495,990 filed Jun. 13, 2012, which claims priority to U.S. Provisional Patent Application No. 61/496,800 filed Jun. 14, 2011, the contents of each of which are hereby incorporated by reference in their entirety.

BACKGROUND

Many patients receive care in an intensive care unit or similar setting following surgery, injury, trauma, or acute medical illness. These and other patients may suffer from dysfunction or failure of one or more organ systems. Although some patients succumb from their illness and die, most eventually recover, albeit after application of intensive care techniques and prolonged hospitalization.

During application of intensive care techniques and/or hospitalization, decisions are made as to whether and when patients are ready for normalization (or accelerated normalization) of their care. Normalizing care can involve several types of clinical problems and intensive care techniques, some of which are discussed below.

I. Initiation of Enteral Feeding

Enteral feeding. i.e., instilling food into the stomach or intestines via a feeding tube or the mouth, is beneficial to some patients but deleterious to those patients whose gastrointestinal perfusion and function is suboptimal. Failures in enteral feeding can be classified as either "underfeeding" or "overfeeding". Underfeeding results when a critically ill patient is either not started on enteral feeds or else is administered suboptimal calories. Underfeeding can result in malnutrition and its associated complications (e.g., infections, low colloid oncotic pressure), resulting in prolongation of Intensive Care Unit (ICU) treatment and hospitalization. Overfeeding, in contrast, results when a patient is enterally fed but the patient's gastrointestinal tract (or overall circulatory system) is not yet sufficiently healthy to tolerate the increased stress of enteral feeding. Overfeeding can result in vomiting and aspiration of enteral feeds into the lungs, leading to aspiration pneumonitis/pneumonia. Overfeeding can also lead to ileus, fever, and abdominal tenderness, which can mimic other serious disorders, such as abdominal abscess/infection, and dead bowel syndrome.

II. Weaning from Mechanical Ventilation

Mechanical ventilation is used to support adequate oxygenation and ventilation in patients with pulmonary dysfunction. Providing mechanical ventilation to a patient when it is not necessary can lead to recognized complications, such as muscle weakness and aspiration pneumonia, resulting in unnecessarily prolonged hospitalization. Discontinuing or weaning mechanical ventilation in a patient prematurely can lead to complications, such as pulmonary failure, intestinal dysfunction, cardiac arrhythmias, and a general setback in a patient's recovery.

III. Weaning of Vasoactive Medications

Vasoactive agents, such as epinephrine, dobutamine, dopamine, norepinephrine, and milrinone, are commonly administered to critically ill patients in order to insure adequate perfusion of vital organs. Unnecessary administration of these agents can result in prolonged hospitalization and may cause complications, such as cardiac arrhythmias. In contrast, insufficient administration of these agents can result in inadequate organ perfusion, resulting in organ dysfunction and death.

SUMMARY

I. General

In the related art, it may be difficult to determine whether to initiate, terminate, or otherwise regulate intensive care techniques, including those discussed above, and exemplary embodiments generally relate to guiding medical care based on detected gastric function. For example, an amount, such as an effective dose, of a pharmacological challenge agent, such as a gastric acid stimulant or suppressant, is administered, and then a change, such as an acute change, in the gastric juice pH is measured. Medical care can then be guided based on the detected change in gastric juice pH. For example, patients demonstrating sufficient or significant change in gastric juice pH may have their medical care normalized in an accelerated fashion, while those not sufficiently responsive cannot and may even require more support.

Tests can be and have been performed showing advantages of guiding medical care based on detected gastric function. Results of such tests should, in many cases, be consistent or substantially consistent, with the following prophetic example.

A. Related Art Procedure

An exemplary related art procedure and articulated result is provided below.

A 70 year old patient develops severe pneumonia requiring admission to an intensive care unit, intubation of the trachea, and mechanical ventilation. After three days of illness, enteral feeding is started. Two days later, enteral feeding is stopped as her abdomen has become swollen and tender, and there is a suspicion that she may have aspirated gastric contents. The following day ($6^{th}$ day of illness), her respiratory support has to be increased. On day nine of her illness, enteral feeding is restarted successfully.

By day fourteen, she is beginning to wean from the ventilator, but once again her abdomen becomes swollen and tender and so feeding is stopped. Weaning continues but is unsuccessful, and by day twenty-one she is back on full respiratory support and receiving total parenteral nutrition. On day twenty-five she develops bacteremia from an infection of her intravenous feeding line. The line is removed and broad spectrum antibiotics are started. By day thirty-two she is again fed enterally, and is slowly weaning from the ventilator. On day forty-five she is discharged from the ICU, having made a complete recovery.

B. Basic Procedure Guiding Medical Care Based on Detected Gastric Function

An exemplary basic procedure for guiding medical care based on detected gastric function and its anticipated result is provided below.

The following prophetic test involves application of a gastric stimulation test on the same patient from section I(A) (Related Art Procedure). The 70 year old patient develops severe pneumonia requiring admission to an intensive care unit, intubation of the trachea, and mechanical ventilation. After three days of illness, it is decided that she would benefit from enteral nutrition. A commercially available probe, such as a VersaFlex pH sensor from Sierra Scientific Instruments, Los Angeles, Calif., is inserted into the gastric lumen and connected to a pH recording device (e.g., Digitrapper from Sierra Scientific Instruments, Los Angeles.

Calif.). The baseline gastric juice pH is 5.4 and shows no change 20 minutes after the administration of pentagastrin (6 micrograms/kg subcutaneously). Attempts at feeding or weaning from the ventilator are postponed.

One day later (day four) the baseline gastric juice pH is 6.2 and again shows no change 20 minutes after the administration of pentagastrin (6 micrograms/kg subcutaneously). Additional intravenous fluids and a low dose of intravenous Dobutamine are given in an attempt to improve splanchnic perfusion. One day later (day five) the baseline gastric juice pH is 5.9 and decreases to 1.8, 20 minutes after the administration of pentagastrin (6 micrograms/kg subcutaneously). Based on this positive challenge test, enteral feeding is initiated and is well tolerated by the patient. The patient gains strength and by day fourteen the dobutamine has been stopped and she is beginning to wean from the ventilator. On day seventeen she is weaned from the ventilator. On day eighteen (as opposed to day forty-five—see section I(A) above) she is discharged from the ICU, having made a complete recovery.

II. Exemplary Embodiments

Various embodiments are directed to methods and apparatus (including processors, computer readable mediums, computer programs, etc.) for guiding medical care of a patient based on detected gastric function. Some of these embodiments are summarized below.

A. Methods

One exemplary method of guiding medical care of a patient based on detected gastric function includes: measuring the patient's gastric juice H+ concentration to obtain a baseline gastric juice H+ concentration; determining a guidance H+ concentration differential indicative of relatively healthy gastric function; administering a gastric acid stimulant or suppressant; measuring the patient's gastric juice H+ concentration after the administration of the gastric acid stimulant or suppressant to obtain a stressed gastric juice H+ concentration; calculating a measured H+ concentration differential between the baseline gastric juice H+ concentration and the stressed gastric juice H+ concentration; and performing one of the following based on a comparison between the guidance H+ concentration differential and the measured H+ concentration differential: 1) guiding medical care based on a relatively healthy gastric function if the measured H+ concentration differential is equal to or exceeds the guidance H+ concentration differential; and 2) guiding medical care based on a relatively unhealthy gastric function if the measured H+ concentration differential is less than the guidance H+ concentration differential.

In a second embodiment, the method may further include: performing multiple measurements of the patient's gastric juice H+ concentration after the administration of the gastric acid stimulant or suppressant to obtain multiple stressed gastric juice H+ concentration values; calculating a rate of change of the gastric juice H+ concentration based on at least one of: differentials between the baseline gastric juice H+ concentration and the multiple stressed gastric juice H+ concentration values, and differentials between different stressed gastric juice H+ concentration values; and guiding medical care based on the calculated rate of change of the gastric juice H+ concentration.

In a third embodiment, the method may further include converting the baseline gastric juice H+ concentration and stressed gastric juice H+ concentration to baseline gastric juice pH and stressed gastric juice pH, respectively; wherein: the determining step includes determining a guidance pH differential indicative of relatively healthy gastric function based on the baseline gastric juice pH; the calculating step includes calculating a measured pH differential between the baseline gastric juice pH and the stressed gastric juice pH; and the performing step includes performing one of the following based on a comparison between the guidance pH differential and the measured pH differential: 1) guiding medical care based on a relatively healthy gastric function if the measured pH differential is equal to or exceeds the guidance pH differential; and 2) guiding medical care based on a relatively unhealthy gastric function if the measured pH differential is less than the guidance pH differential.

In the third embodiment, the determining step may include determining the guidance pH differential indicative of relatively healthy gastric function to be relatively low if the baseline gastric juice pH is relatively low, and determining the guidance pH differential indicative of relatively healthy gastric function to be relatively high if the baseline gastric juice pH is relatively high.

The third embodiment alternatively may further include: setting a minimum baseline gastric juice pH; comparing the measured baseline gastric juice pH to the minimum baseline gastric juice pH; administering a pharmacological agent to raise gastric juice pH if the measured baseline gastric juice pH is less than the minimum baseline gastric juice pH; and measuring the patient's gastric juice pH after the pharmacological agent administration to obtain a modified baseline gastric juice pH; wherein the calculating step includes calculating the measured pH differential between the modified baseline gastric juice pH and the stressed gastric juice pH.

In a fourth embodiment, the guiding of medical care consistent with a relatively healthy gastric function includes providing instructions to perform at least one of: initiation, maintenance, or increase of enteral feeding; failing to initiate, reduction, or termination of mechanical ventilation; and failing to initiate, reduction, or termination of use of vasoactive agents; and the guiding of medical care consistent with a relatively unhealthy gastric function includes providing instructions to perform at least one of: failing to initiate, reduction, or termination of enteral feeding; initiation, maintenance, or increase of mechanical ventilation; and initiation, maintenance, or increase of use of vasoactive agents.

In the fourth embodiment, the guiding of medical care consistent with a relatively healthy gastric function may include providing instructions to initiate enteral feeding. This method may further include measuring the patient's gastric juice H+ concentration after initiation of enteral feeding to obtain a post-feeding gastric juice H+ concentration, and guiding medical care based on the post-feeding gastric juice H+ concentration.

In a fifth embodiment, the administering step includes administering approximately 6 micrograms/kg of pentagastrin subcutaneously.

In a sixth embodiment, the method further includes determining a pharmacologically effective dosage of gastric acid stimulant; wherein the administering step includes administering the determined pharmacologically effective dosage of the stimulant that includes pentagastrin.

In the sixth embodiment, the determining of the pharmacologically effective dosage of pentagastrin is based on patient characteristics, including at least one of: age, gender, fitness, weight, body composition, percentage of body fat, ethnicity, family history, personal medical history, aspects of current personal medical condition, and genetics.

Alternatively, in the sixth embodiment, the determining of the pharmacologically effective dosage of pentagastrin is based on patient weight in accordance with one of the following: a stepped methodology wherein 250 mcg is determined to be the pharmacologically effective dosage for patients weighing 40-70 kg, 500 mcg is determined to be the pharmacologically effective dosage for patients weighing 71-100 kg, and 750 mcg is determined to be the pharmacologically effective dosage for patients weighing more than 100 kg; and a linear methodology wherein the pharmacologically effective dosage of pentagastrin is based on 6 mcg/kg, such that 300 mcg is determined to be the pharmacologically effective dosage for a patient weighing 50 kg, 450 mcg is determined to be the pharmacologically effective dosage for patients weighing 75 kg, and 600 mcg is determined to be the pharmacologically effective dosage for patients weighing 100 kg.

In a seventh embodiment, the determining step includes determining the guidance H+ concentration differential to be approximately 0.01 millimole per liter.

In an eighth embodiment, the determining step includes determining the guidance H+ concentration differential based on patient characteristics, including at least one of: age, gender, fitness, weight, body composition, percentage of body fat, ethnicity, family history, personal medical history, aspects of current personal medical condition, and genetics.

In a ninth embodiment, the method also includes measuring the patient's gastric contents volume prior to the administering of the gastric acid stimulant or suppressant; and wherein the determining step includes determining the guidance H+ concentration differential based on the measured gastric contents volume.

Alternatively, in the ninth embodiment, the determining step includes: determining the guidance H+ concentration differential to be relatively lower if the gastric contents volume is relatively high, and determining the guidance H+ concentration differential to be relatively higher if the gastric contents volume is relatively low.

In a tenth embodiment, the method further includes: performing multiple measurements of the patient's gastric juice H+ concentration after obtaining the stressed gastric juice H+ concentration; displaying the multiple H+ concentration measurements as a curve via a graph, with the x-axis representing the time that the H+ concentration measurements were taken and the y-axis representing H+ concentration values; calculating an area defined under the curve; and guiding medical care based on the calculated area.

In an eleventh embodiment, the method further includes: performing multiple measurements of the patient's gastric juice H+ concentration after obtaining the stressed gastric juice H+ concentration; determining a rate of change of the multiple H+ concentration measurements via the derivative of at least one of the following functions: d(H(t))dt, where the function H(t) represents the measurement of H+ concentration in moles per liter (mol), and H(t), which represents the multiple measurements of H+ concentration in moles per liter (mol); and guiding medical care based on the determined rate of change, such that a relatively fast rate of change indicates a relatively healthy gastric function, and a relatively slow rate of change indicates a relatively unhealthy gastric function.

In a twelfth embodiment, the guiding of medical care includes providing instructions to perform at least one of: determining patient disposition within a medical care facility; determining adequacy of resuscitation; detecting risk of developing stress ulcers; guiding usages of suppressants to reduce risk of at least one of stress ulcers and bleeding; determining risk of aspiration and guiding care to reduce the risk of aspiration; aiding detection of at least one of gut ischemia and abdominal compartment syndrome; and monitoring of gastric motility to reduce gastric residuals and risk of aspiration.

B. Processors

One exemplary apparatus for guiding medical care of a patient based on detected gastric function is a processor that is used with at least one administering device that administers a gastric acid stimulant or suppressant, and at least one sensor that measures the patient's gastric juice H+ concentration prior to the administration of the gastric acid stimulant or suppressant to obtain a baseline gastric juice H+ concentration, and that measures the patient's gastric juice H+ concentration after the administration of the gastric acid stimulant or suppressant to obtain a stressed gastric juice H+ concentration. The processor includes: a determination unit that determines a guidance H+ concentration differential indicative of relatively healthy gastric function; a calculation unit that calculates a measured H+ concentration differential between the baseline gastric juice H+ concentration and the stressed gastric juice H+ concentration; a comparison unit that compares the guidance H+ concentration differential to the measured H+ concentration differential; a primary instruction unit that provides instructions to guide medical care based on a relatively healthy gastric function if the measured H+ concentration differential is equal to or exceeds the guidance H+ concentration differential; and an alternative instruction unit that provides instructions to guide medical care based on a relatively unhealthy gastric function if the measured H+ concentration differential is less than the guidance H+ concentration differential.

In a second embodiment, the sensor performs multiple measurements of the patient's gastric juice H+ concentration after the administration of the gastric acid stimulant or suppressant to obtain multiple stressed gastric juice H+ concentration values; the calculation unit calculates a rate of change of the gastric juice H+ concentration based on at least one of: differentials between the baseline gastric juice H+ concentration and the multiple stressed gastric juice H+ concentration values, and differentials between the different stressed gastric juice H+ concentration values; and the primary instruction unit or the alternative instruction unit provides instructions to guide medical care based on the calculated rate of change of the gastric juice H+ concentration.

A third embodiment further includes a conversion unit that converts the baseline gastric juice H+ concentration and stressed gastric juice H+ concentration to baseline gastric juice pH and stressed gastric juice pH, respectively, wherein: the determination unit determines a guidance pH differential indicative of relatively healthy gastric function based on the baseline gastric juice pH; the calculation unit calculates a measured pH differential between the baseline gastric juice pH and the stressed gastric juice pH; and the primary instruction unit or the alternative instruction unit performs one of the following based on a comparison between the guidance pH differential and the measured pH differential: 1) guiding medical care based on a relatively healthy gastric function if the measured pH differential is equal to or exceeds the guidance pH differential; and 2) guiding medical care based on a relatively unhealthy gastric function if the measured pH differential is less than the guidance pH differential.

In an alternative of the third embodiment, the determination unit determines the guidance pH differential indicative of relatively healthy gastric function to be relatively low if the baseline gastric juice pH is relatively low, and determines the guidance pH differential indicative of relatively healthy gastric function to be relatively high if the baseline gastric juice pH is relatively high.

Another alternative of the third embodiment further includes a comparison unit that sets a minimum baseline gastric juice pH, and compares the measured baseline gastric juice pH to the minimum baseline gastric juice pH; wherein the administering device administers a pharmacological agent to raise gastric juice pH if the comparison unit determines that the measured baseline gastric juice pH is less than the minimum baseline gastric juice pH; the sensor measures the patient's gastric juice pH after the pharmacological agent administration to obtain a modified baseline gastric juice pH; and calculation unit calculates the measured pH differential between the modified baseline gastric juice pH and the stressed gastric juice pH.

In a fourth embodiment, the primary instruction unit provides instructions to perform at least one of: initiation, maintenance, or increase of enteral feeding failing to initiate, reduction, or termination of mechanical ventilation; and failing to initiate, reduction, or termination of use of vasoactive agents; and the alternative instruction unit provides instructions to perform at least one of: failing to initiate, reduction, or termination of enteral feeding; initiation, maintenance, or increase of mechanical ventilation; and initiation, maintenance, or increase of use of vasoactive agents.

In an alternative of the fourth embodiment, the primary instruction unit provides instructions to initiate enteral feeding; the sensor measures the patient's gastric juice H+ concentration after initiation of enteral feeding to obtain a post-feeding gastric juice H+ concentration; and the primary instruction unit or the alternative instruction unit guides medical care based on the post-feeding gastric juice H+ concentration.

In a fifth embodiment, the administering device is configured to administer approximately 6 micrograms/kg of pentagastrin subcutaneously.

A sixth embodiment further includes a dosage determination unit that determines a pharmacologically effective dosage of gastric acid stimulant; wherein the administering device is configured to administer the determined pharmacologically effective dosage of the stimulant that includes pentagastrin.

In an alternative of the sixth embodiment, the dosage determination unit determines the pharmacologically effective dosage of pentagastrin based on patient characteristics, including at least one of: age, gender, fitness, weight, body composition, percentage of body fat, ethnicity, family history, personal medical history, aspects of current personal medical condition, and genetics.

In another alternative of the sixth embodiment, the dosage determination unit determines the pharmacologically effective dosage of gastric acid stimulant or suppressant based on patient weight in accordance with one of the following: a stepped methodology wherein 250 mcg is determined to be the pharmacologically effective dosage for patients weighing 40-70 kg, 500 mcg is determined to be the pharmacologically effective dosage for patients weighing 71-100 kg, and 750 mcg is determined to be the pharmacologically effective dosage for patients weighing more than 100 kg and a linear methodology wherein the pharmacologically effective dosage of pentagastrin is based on 6 mcg/kg, such that 300 mcg is determined to be the pharmacologically effective dosage for a patient weighing 50 kg, 450 mcg is determined to be the pharmacologically effective dosage for patients weighing 75 kg, and 600 mcg is determined to be the pharmacologically effective dosage for patients weighing 100 kg.

In a seventh embodiment, the determination unit determines the guidance H+ concentration differential to be approximately 0.01 millimole per liter.

In an eighth embodiment, the determination unit determines the guidance H+ concentration differential based on patient characteristics, including at least one of: age, gender, fitness, weight, body composition, percentage of body fat, ethnicity, family history, personal medical history, aspects of current personal medical condition, and genetics.

In a ninth embodiment, the processor is used with a volume measuring device for measuring the patient's gastric contents volume prior to the administering of the gastric acid stimulant or suppressant; and the determination unit determines the guidance H+ concentration differential based on the measured gastric contents volume.

In an alternative of the ninth embodiment, the determination unit: determines the guidance H+ concentration differential to be relatively lower if the gastric contents volume is relatively high, and determines the guidance H+ concentration differential to be relatively higher if the gastric contents volume is relatively low.

In a tenth embodiment, the sensor performs multiple measurements of the patient's gastric juice H+ concentration after obtaining the stressed gastric juice H+ concentration; the processor further comprises a display for displaying the multiple H+ concentration measurements as a curve via a graph, with the x-axis representing the time that the H+ concentration measurements were taken and the y-axis representing H+ concentration values; and an area calculation unit to calculate an area defined under the curve; and wherein the primary instruction unit or the alternative instruction unit guides medical care based on the calculated area.

In an eleventh embodiment, the sensor performs multiple measurements of the patient's gastric juice H+ concentration after obtaining the stressed gastric juice H+ concentration; the processor further comprises a rate determination unit for determining a rate of change of the multiple H+ concentration measurements via the derivative of at least one of the following functions: $d(H(t))/dt$, where the function $H(t)$ represents the measurement of H+ concentration in moles per liter (mol), and $H(t)$, which represents the multiple measurements of H+ concentration in moles per liter (mol); and wherein the primary instruction unit or the alternative instruction unit guides medical care based on the determined rate of change, such that a relatively fast rate of change indicates a relatively healthy gastric function, and a relatively slow rate of change indicates a relatively unhealthy gastric function.

In a twelfth embodiment, the guiding of medical care includes providing instructions to perform at least one of: determining patient disposition within a medical care facility; determining adequacy of resuscitation; detecting risk of developing stress ulcers; guiding usages of suppressants to reduce risk of at least one of stress ulcers and bleeding; determining risk of aspiration and guiding care to reduce the risk of aspiration; aiding detection of at least one of gut ischemia and abdominal compartment syndrome; and monitoring of gastric motility to reduce gastric residuals and risk of aspiration.

C. Apparatus

Some exemplary embodiments focus even more directly on parts of the apparatus, other than or in addition to a processor, for guiding medical care of a patient based on detected gastric function. At least one sensor is used to measure the patient's gastric juice H+ concentration to obtain a baseline gastric juice H+ concentration, and the patient's gastric juice H+ concentration after the administration of the gastric acid stimulant or suppressant to obtain a stressed gastric juice H+ concentration. Exemplary embodiments are intended to cover any apparatus and/or method for performing these measurements, including but not limited to the ComforTec Z/pH probes and ZepHR pH recording device from Sandhill Scientific, Inc. and the VersaFlex pH sensor and Digitrapper pH recording device from Sierra Scientific Instruments. Similarly, exemplary embodiments are intended to cover any apparatus and/or method for administering the gastric acid stimulant or suppressant, including but not limited to a needle(s) with syringe(s), etc.

In addition, exemplary embodiments are intended to cover any apparatus and/or method for determining a guidance H+ concentration differential indicative of relatively healthy gastric function. In some exemplary embodiments, a processor or other device/method is used to set the guidance H+ concentration differential based on one or more factors, including but not limited to patient characteristics, including at least one of age, gender, fitness, weight, body composition, percentage of body fat, ethnicity, family history, personal medical history, aspects of current personal medical condition, and genetics. In other embodiments, a processor or other device/method is used to set the guidance H+ concentration differential based on one or more factors, including but not limited to the measured baseline gastric juice H+ concentration or measured baseline gastric juice pH. In still other embodiments, a processor or other device/method is not used, and instead the guidance H+ concentration differential is always set at a same value, such as approximately 0.01 millimole per liter.

Exemplary embodiments are also intended to cover any apparatus and/or method of calculating a measured H+ concentration differential between the baseline gastric juice H+ concentration and the stressed gastric juice H+ concentration; and any apparatus and/or method of performing one of the following based on a comparison between the guidance H+ concentration differential and the measured H+ concentration differential: 1) guiding medical care based on a relatively healthy gastric function if the measured H+ concentration differential is equal to or exceeds the guidance H+ concentration differential; and 2) guiding medical care based on a relatively unhealthy gastric function if the measured H+ concentration differential is less than the guidance H+ concentration differential.

D. Computer Program/Non-Transitory Recording Medium

Still other exemplary embodiments focus on a computer program and/or non-transitory recording medium that stores a computer program for guiding medical care of a patient based on detected gastric function, and for use with an administering device that administers a gastric acid stimulant or suppressant, and at least one sensor that measures the patient's gastric juice H+ concentration prior to the administration of the gastric acid stimulant or suppressant to obtain a baseline gastric juice H+ concentration, and that measures the patient's gastric juice H+ concentration after the administration of the gastric acid stimulant or suppressant to obtain a stressed gastric juice H+ concentration.

The program causes a computer to perform the following determining a guidance H+ concentration differential indicative of relatively healthy gastric function; calculating a measured H+ concentration differential between the baseline gastric juice H+ concentration and the stressed gastric juice H+ concentration; comparing the guidance H+ concentration differential to the measured H+ concentration differential; providing instructions to guide medical care based on a relatively healthy gastric function if the measured H+ concentration differential is equal to or exceeds the guidance H+ concentration differential; and providing instructions to guide medical care based on a relatively unhealthy gastric function if the measured H+ concentration differential is less than the guidance H+ concentration differential.

III. Other Exemplary Embodiments

Some other exemplary embodiments relate to: 1) specialized apparatus for enhancing this test, such as software and electronics facilitating and implementing this test, 2) specialized methods for enhancing results of this test, such as by using certain dosages of stimulant or supplement, or tailoring feeding based on specific changes in gastric juice pH, and 3) using the test results to enhance care, such as by guiding patients' dispositions within a hospital, monitoring adequacy or resuscitation, or detecting stress ulcers. However, this listing is merely provided for exemplary purposes to generally introduce the disclosed subject matter, and many exemplary embodiments are beyond the above categorizations. For example, some exemplary embodiments do not involve gastric juice pH, and instead focus on other methodologies, such as gastric volume. In fact, exemplary embodiments are intended to cover any method of assessing gastric function.

Throughout the present disclosure, various terms are used to describe and/or identify effects of pharmacological agents on the gastrointestinal system. Some of these terms are used consistently with common usage in the art, while others are used in a more generic fashion for convenience, breadth, accuracy, etc. For example, it is typical in the art to use the terms "robust." "moderate," and "modest" to reflect magnitudes, such as with regard to pH values, volumes, etc., and some of these terms are used herein consistent with this usage. Other terms, such as "acute," are sometimes used in the art merely to reflect rates of change or timing of change. However, the present disclosure deviates from this narrow usage and "acute" is used more broadly to also reflect magnitudes, such as with regard to pH values, volumes, etc.

The present disclosure also makes many references to effects on the gastrointestinal system by administrations of pharmacological agents, including but not limited to gastric acid stimulants and suppressants. It is common in the art to refer to administrations of gastric acid stimulants in terms of causing a challenge or stress to the gastrointestinal system, while administrations of gastric acid suppressants as blocking such reactions. However, the present disclosure describes such effects in a more generic fashion. For example, in the present disclosure, for reasons of convenience, breadth, accuracy, etc., all effects of gastric acid stimulants, suppressants, etc., are referred to in terms of "stress," such as "stress tests" involving the administrations of gastric acid stimulants, suppressants, etc. In other words, the present disclosure uses the term "stress" in a generic and broad fashion in many instances so as to be synonymous with challenge, reaction, effect, etc.

As a further example, many of the disclosed exemplary embodiments can be categorized in a completely different manner than discussed above. For example, many exemplary embodiments can be categorized as relating to: 1) enhancing the accuracy of pH differential based test results, 2) enhancing the efficiency of pH differential based tests, and 3) methodology bases other than pH differential based tests. Exemplary embodiments relating to these categories cover any applicable form and context, including but not limited to methods, apparatus, processors, computer readable mediums, software and computer programs, etc. A summary of certain embodiments is provided below in the context of the above categorizations for exemplary purposes only, and is not intended to constitute a complete listing or disclosure of inventive concepts captured by the present application.

A. Enhancing Accuracy of pH Differential Based Test Results

As disclosed above, some exemplary embodiments can be categorized as different methods, apparatus, processors, computer programs, etc., for enhancing the accuracy of pH differential based test results. The below listing of embodiments that enhance the test result accuracy is not intended as limiting, and instead is merely provided for exemplary purposes.

Enhancing test result accuracy can enable the state of health of the gastric system to be more precisely defined, such as by predicting the gastric system as being very healthy, healthy, moderately healthy, relatively unhealthy, unhealthy, very unhealthy, etc. This more precise definition of health can be beneficial in numerous respects, such as by enabling medical treatments to be more exactly tailored to a patient's actual condition, thereby improving the patient's response to medical treatment. More precisely estimating gastric system health can also enhance or improve diagnoses of various medical conditions, and in some cases may even enable the diagnoses of certain medical conditions that could not otherwise be diagnosed absent precise gastric system health data.

Enhancing the test result accuracy can also enable the state of health of the gastric system to be more reliably defined, such as by more certainly predicting whether a patient's gastric system is healthy or unhealthy. This more reliable indication of gastric system health can be beneficial by helping to ensure both accuracy of diagnoses and that patients are subjected to appropriate medical treatments, i.e., that gastric systems are reliably deemed as sufficiently healthy or insufficiently healthy to receive certain medical treatments.

1. Administer Stimulant if Baseline pH is High, or Suppressant if Baseline pH is Low Exemplary embodiments, which are intended to cover all applicable mediums of expression including but not limited to methods, apparatus, processors, computer programs, etc., enhance the guiding of care based on gastric function that is detected/determined by challenging the gastric system. Some exemplary embodiments measure a patient's gastric juice pH to obtain a baseline gastric juice pH, and then challenge the gastric system by administering either a gastric acid stimulant or suppressant depending on the measured baseline gastric juice pH. This procedure provides enhanced results at least because a gastric acid stimulant based challenge is relatively more effective with a relatively high baseline gastric juice pH, while a gastric acid suppressant based challenge is relatively more effective with a relatively low baseline gastric juice pH.

The determination of whether to administer a gastric acid stimulant or suppressant depending on the measured baseline gastric juice pH can be performed in any applicable manner. For example, a certain baseline gastric juice pH can be selected to delineate administration of gastric acid stimulant versus suppressant, such that gastric acid stimulant is administered if the baseline gastric juice pH equals or exceeds the selected certain baseline gastric juice pH, while gastric acid suppressant is administered if the baseline gastric juice pH fails to equal or exceed the selected certain baseline gastric juice pH. In such exemplary embodiments, the certain baseline gastric juice pH can be selected based on any applicable criteria. In some exemplary embodiments, the certain baseline gastric juice pH is approximately at least 2.5 pH units, and in other exemplary embodiments, the certain baseline gastric juice pH is approximately at least 3.0 pH units. However, these values are only provided for exemplary purposes, and exemplary embodiments are intended to cover any selected baseline gastric juice pH applicable for such delineations.

Examples of such exemplary embodiments are provided below in the contexts of methods, apparatus, processors, and computer programs. However, these contexts are merely provided for exemplary purposes, and exemplary embodiments are intended to cover all possible mediums.

a. Method

An exemplary method in accordance with this embodiment includes measuring the patient's gastric juice pH to obtain a baseline gastric juice pH, and administering a gastric acid stimulant or a gastric acid suppressant depending on the baseline gastric juice pH. The gastric acid stimulant is administered if the baseline gastric juice pH is equal to or exceeds a certain value, while the gastric acid suppressant is administered if the baseline gastric juice pH is less than the certain value. The patient's gastric juice pH is measured after the administration of the gastric acid stimulant or suppressant to obtain a stressed gastric juice pH. A pH differential, between the baseline gastric juice pH and the stressed gastric juice pH, is calculated to determine gastric function, and medical care is guided based on the determined gastric function.

b. Apparatus

An exemplary method in accordance with this embodiment includes a pH sensor for measuring the patient's gastric juice pH to obtain a baseline gastric juice pH, a processor that determines whether the baseline pH equals or exceeds a certain value; and an administering device that administers a gastric acid stimulant if the baseline gastric juice pH is equal to or exceeds the certain value, or a gastric acid suppressant if the baseline gastric juice pH is less than the certain value. The sensor measures the patient's gastric juice pH after the administration of the gastric acid stimulant or suppressant to obtain a stressed gastric juice pH. The processor calculates a pH differential between the baseline gastric juice pH and the stressed gastric juice pH to determine gastric function so that medical care can be guided based on the determined gastric function.

c. Processor

An exemplary processor in accordance with this embodiment is used with an administering device that administers a gastric acid stimulant or suppressant, and a pH sensor that measures the patient's gastric juice pH prior to the administration of the gastric acid stimulant or suppressant to obtain a baseline gastric juice pH, and that measures the patient's gastric juice pH after the administration of the gastric acid stimulant or suppressant to obtain a stressed gastric juice pH.

The processor includes a determination unit that determines whether the baseline pH equals or exceeds a certain value, and an instruction unit that provides instructions for the administering device to administer a gastric acid stimulant if the baseline gastric juice pH is equal to or exceeds the certain value, or to administer a gastric acid suppressant if the baseline gastric juice pH is less than the certain value. The processor also includes a calculation unit that calculates a pH differential between the baseline gastric juice pH and the stressed gastric juice pH to determine gastric function so that medical care can be guided based on the determined gastric function.

d. Computer Program

An exemplary computer program in accordance with this embodiment is used with a processor for guiding medical care of a patient based on detected gastric function, the processor being used with an administering device that administers a gastric acid stimulant or suppressant, and a pH sensor that measures the patient's gastric juice pH prior to the administration of the gastric acid stimulant or suppressant to obtain a baseline gastric juice pH, and that measures the patient's gastric juice pH after the administration of the gastric acid stimulant or suppressant to obtain a stressed gastric juice pH.

The computer program includes a determination program for determining whether the baseline pH equals or exceeds a certain value, and an instruction program for providing instructions for the administering device to administer a gastric acid stimulant if the baseline gastric juice pH is equal to or exceeds the certain value, or to administer a gastric acid suppressant if the baseline gastric juice pH is less than the certain value. A calculation program calculates a pH differential between the baseline gastric juice pH and the stressed gastric juice pH to determine gastric function so that medical care can be guided based on the determined gastric function.

2. Perform Alternative Test with Other of Stimulant or Suppressant if pH Differential Fails to Demonstrate at Least an Acute Change in pH Exemplary embodiments, which are intended to cover all applicable mediums of expression including but not limited to methods, apparatus, processors, computer programs, etc., enhance the guiding of care based on gastric function that is detected/determined by challenging the gastric system. Some exemplary embodiments calculate a pH differential between gastric juice pH prior to and after administration of a gastric system stress agent (such as gastric juice stimulant or suppressant, for example), and guide medical care consistent with a relatively healthy gastric function if the pH differential constitutes an acute change. An alternative gastric system stress test is conducted with a different gastric system stress agent if an acute change is not demonstrated. For example, the alternative test stresses the gastric system with a gastric juice suppressant if a stimulant was used in the originally challenge, or vice versa.

This procedure provides enhanced results at least because it enables identification of patients with a relatively healthy gastric function who, for whatever reason, fail to demonstrate an acute pH differential in the initial challenge. In other words, some patients may not demonstrate an acute pH differential after a challenge with one of stimulant or suppressant, even though their gastric system is relatively healthy. Conducting a challenge test with the other of stimulant or suppressant allows all or some of those patients to be identified and medical care to be guided accordingly.

Examples of such exemplary embodiments are provided below in the contexts of methods, apparatus, processors, and computer programs. However, these contexts are merely provided for exemplary purposes, and exemplary embodiments are intended to cover all possible mediums.

a. Method

An exemplary method in accordance with this embodiment includes measuring the patient's gastric juice pH to obtain a baseline gastric juice pH, administering one of gastric acid stimulant and gastric acid suppressant, measuring the patient's gastric juice pH after the administration of the one of gastric acid stimulant and gastric acid suppressant to obtain a stressed gastric juice pH, and calculating a primary pH differential between the baseline gastric juice pH and the stressed gastric juice pH.

Medical care is guided consistent with a relatively healthy gastric function if the calculated primary pH differential demonstrates an acute change in pH. An alternative pH test is conducted if the calculated primary pH differential fails to demonstrate an acute change in pH. The alternative pH test includes: administering the other of gastric acid stimulant and gastric acid suppressant, measuring the patient's gastric juice pH after the administration of the other of gastric acid stimulant and gastric acid suppressant to obtain an alternative stressed gastric juice pH, calculating an alternative pH differential between the baseline gastric juice pH and the alternative stressed gastric juice pH, guiding medical care consistent with a relatively healthy gastric function if the calculated alternative pH differential demonstrates an acute change in pH, and guiding medical care consistent with a relatively unhealthy gastric function if the calculated alternative pH differential fails to demonstrate an acute change in pH.

b. Apparatus

An exemplary apparatus in accordance with this embodiment includes an administering device that administers one of gastric acid stimulant and gastric acid suppressant, a pH sensor that measures the patient's gastric juice pH prior to the administration of the one of gastric acid stimulant and gastric acid suppressant to obtain a baseline gastric juice pH, and that measures the patient's gastric juice pH after the administration of the one of gastric acid stimulant and gastric acid suppressant to obtain a stressed gastric juice pH, and a processor that calculates a primary pH differential between the baseline gastric juice pH and the stressed gastric juice pH.

The processor guides medical care consistent with a relatively healthy gastric function if the calculated primary pH differential demonstrates an acute change in pH. An alternative pH test is performed if the calculated primary pH differential fails to demonstrate an acute change in pH. In the alternative pH test: the administering device administers the other of gastric acid stimulant and gastric acid suppressant, the sensor measures the patient's gastric juice pH after the administration of the other of gastric acid stimulant and gastric acid suppressant to obtain an alternative stressed gastric juice pH, the processor calculates an alternative pH differential between the baseline gastric juice pH and the alternative stressed gastric juice pH, the processor guides medical care consistent with a relatively healthy gastric function if the calculated alternative pH differential demonstrates an acute change in pH, and the processor guides medical care consistent with a relatively unhealthy gastric function if the calculated alternative pH differential fails to demonstrate an acute change in pH.

c. Processor

An exemplary processor in accordance with this embodiment is used with an administering device that administers one of gastric acid stimulant and gastric acid suppressant, and a pH sensor that measures the patient's gastric juice pH prior to the administration of the one of gastric acid stimulant and gastric acid suppressant to obtain a baseline gastric juice pH, and that measures the patient's gastric juice pH after the administration of the one of gastric acid stimulant and gastric acid suppressant to obtain a stressed gastric juice pH.

The processor includes a calculation unit that calculates a primary pH differential between the baseline gastric juice pH and the stressed gastric juice pH, and a primary guidance unit that provides advice for guiding medical care consistent with a relatively healthy gastric function if the calculated primary pH differential demonstrates an acute change in pH. The processor also includes an alternative guidance unit that provides instructions for conducting an alternative pH test if the calculated primary pH differential fails to demonstrate an acute change in pH. In the alternative pH test, the processor: a) instructs the pH sensor to measure the patient's gastric juice pH after the administration of the other of gastric acid stimulant and gastric acid suppressant to obtain an alternative stressed gastric juice pH, b) calculates an alternative pH differential between the baseline gastric juice pH and the alternative stressed gastric juice pH, c) provides advice for guiding medical care consistent with a relatively healthy gastric function if the calculated alternative pH differential demonstrates an acute change in pH, and d) provides advice for guiding medical care consistent with a relatively unhealthy gastric function if the calculated alternative pH differential fails to demonstrate an acute change in pH.

d. Computer Program

An exemplary computer program in accordance with this embodiment is used with a processor for guiding medical care of a patient based on detected gastric function, the processor being used with an administering device that administers one of gastric acid stimulant and gastric acid suppressant, and a pH sensor that measures the patient's gastric juice pH prior to the administration of the one of gastric acid stimulant and gastric acid suppressant to obtain a baseline gastric juice pH, and that measures the patient's gastric juice pH after the administration of the one of gastric acid stimulant and gastric acid suppressant to obtain a stressed gastric juice pH.

The computer program includes a calculation program for calculating a primary pH differential between the baseline gastric juice pH and the stressed gastric juice pH, a primary guidance program for providing advice for guiding medical care consistent with a relatively healthy gastric function if the calculated primary pH differential demonstrates an acute change in pH, and an alternative guidance program for providing instructions for conducting an alternative pH test if the calculated primary pH differential fails to demonstrate an acute change in pH. The alternative pH test includes: instructing the administering device to administer the other of gastric acid stimulant and gastric acid suppressant, instructing the pH sensor to measure the patient's gastric juice pH after the administration of the other of gastric acid stimulant and gastric acid suppressant to obtain an alternative stressed gastric juice pH, calculating an alternative pH differential between the baseline gastric juice pH and the alternative stressed gastric juice pH, providing advice for guiding medical care consistent with a relatively healthy gastric function if the calculated alternative pH differential demonstrates an acute change in pH, and providing advice for guiding medical care consistent with a relatively unhealthy gastric function if the calculated alternative pH differential fails to demonstrate an acute change in pH.

3. If Baseline pH is Low, Use an Agent to Raise pH to Enable Use of Stimulant

Exemplary embodiments, which are intended to cover all applicable mediums of expression including but not limited to methods, apparatus, processors, computer programs, etc., enhance the guiding of care based on gastric function that is detected/determined by challenging the gastric system. Some exemplary embodiments measure a patient's gastric juice pH to determine a baseline gastric juice pH, and challenge the patient's gastric system with a stimulant if the determined baseline gastric juice pH is relatively high. A pharmacological agent. e.g., rapid acting acid suppressant and/or acid neutralizing buffer, is administered to raise the gastric juice pH if the determined baseline gastric juice pH is relatively low, and the patient's gastric system is challenged with stimulant after such rise in gastric juice pH.

It is often beneficial to conduct gastric system challenges with stimulant instead of suppressant, but gastric acid stimulant based challenges are often only effective with a relatively high baseline gastric juice pH. Thus, this procedure provides enhanced results at least because it enables stimulant based stress tests, even if the initially determined baseline gastric juice pH is too low. In other words, the benefits of a gastric acid stimulant based challenge are ensured by administering a pharmacological agent to raise the gastric juice pH to a sufficient pH level, if necessary.

The determination of whether the baseline gastric juice pH is sufficiently high to tolerate a stimulant based challenge can be performed in any applicable manner. For example, a certain baseline gastric juice pH can be selected to determine whether a pharmacological agent needs to be administered to raise the gastric juice pH before conducting the stimulant based challenge. For example, the stimulant based challenge can be conducted if the baseline gastric juice pH equals or exceeds the certain baseline gastric juice pH, while a pharmacological agent is administered to raise the gastric juice pH before conducting the stimulant based challenge if the baseline gastric juice pH fails to equal or exceed the certain baseline gastric juice pH. In such exemplary embodiments, the certain baseline gastric juice pH can be selected based on any applicable criteria. In some exemplary embodiments, the certain baseline gastric juice pH is approximately at least 2.5 pH units, and in other exemplary embodiments the certain baseline gastric juice pH is approximately at least 3.0 pH units. However, these values are only provided for exemplary purposes, and exemplary embodiments are intended to cover any selected baseline gastric juice pH applicable for such delineations.

Examples of such exemplary embodiments are provided below in the contexts of methods, apparatus, processors, and computer programs. However, these contexts are merely provided for exemplary purposes, and exemplary embodiments are intended to cover all possible mediums.

a. Method

An exemplary method in accordance with this embodiment includes measuring the patient's gastric juice pH to obtain a primary baseline gastric juice pH, and administering a gastric acid stimulant if the primary baseline gastric juice pH equals or exceeds the certain value. If the primary baseline gastric juice pH is less than the certain value, then a pharmacological agent is administered to raise gastric juice pH, the patient's gastric juice pH is measured after the pharmacological agent administration to obtain a secondary baseline gastric juice pH, and a gastric acid stimulant is administered after the gastric juice pH has been raised.

The method also includes measuring the patient's gastric juice pH after the gastric acid stimulant administration to obtain a stressed gastric juice pH, calculating a pH differential between: 1) one of the primary and the secondary baseline gastric juice pH, and 2) the stressed gastric juice pH, to determine gastric function, and guiding medical care based on the determined gastric function.

b. Apparatus

An exemplary apparatus in accordance with this embodiment includes stimulant and pharmacological agent administering devices, a pH sensor that measures the patient's gastric juice pH to obtain a primary baseline gastric juice pH, and a processor that determines whether the primary baseline gastric juice pH equals or exceeds a certain value. The stimulant administering device administers a gastric acid stimulant if the primary baseline gastric juice pH is determined to equal or exceed the certain value.

An alternative operation is performed if the primary baseline gastric juice pH is determined to be less than the certain value. In the alternative operation, the pharmacological agent administers device administers a pharmacological agent to raise gastric juice pH, the pH sensor measures the patient's gastric juice pH after the pharmacological agent administration to obtain a secondary baseline gastric juice pH, and the stimulant administering device administers a gastric acid stimulant after the gastric juice pH has been raised. The pH sensor measures the patient's gastric juice pH after the gastric acid stimulant administration to obtain a stressed gastric juice pH. The processor calculates a pH differential between: 1) one of the primary and the secondary baseline gastric juice pH, and 2) the stressed gastric juice pH, to determine gastric function, so that medical care can be guided based on the determined gastric function.

c. Processor

An exemplary processor in accordance with this embodiment is used with stimulant and pharmacological agent administering devices, and a pH sensor that measures the patient's gastric juice pH to obtain a primary baseline gastric juice pH. The processor includes a determination unit that determines whether the primary baseline gastric juice pH equals or exceeds a certain value, and a primary instruction unit that instructs the stimulant administering device to administer a gastric acid stimulant if the primary baseline gastric juice pH is determined to equal or exceed the certain value.

The processor also includes an alternative instruction unit that instructs that an alternative operation be performed if the primary baseline gastric juice pH is determined to be less than the certain value. In the alternative operation, the processor: a) instructs the pharmacological agent administering device to administer a pharmacological agent to raise gastric juice pH, b) instructs the pH sensor to measure the patient's gastric juice pH after the pharmacological agent administration to obtain a secondary baseline gastric juice pH, and c) instructs the stimulant administering device to administers a gastric acid stimulant after the gastric juice pH has been raised. The processor also includes a measurement instruction unit that instructs the pH sensor to measure the patient's gastric juice pH after the gastric acid stimulant administration to obtain a stressed gastric juice pH, and a calculation unit that calculates a pH differential between: a) one of the primary and the secondary baseline gastric juice pH, and b) the stressed gastric juice pH, to determine gastric function, so that medical care can be guided based on the determined gastric function.

d. Computer Program

An exemplary computer program in accordance with this embodiment is used with a processor for guiding medical care of a patient based on detected gastric function, the processor being used with stimulant and pharmacological agent administering devices, and a pH sensor that measures the patient's gastric juice pH to obtain a primary baseline gastric juice pH. The computer program includes a determination program for determining whether the primary baseline gastric juice pH equals or exceeds a certain value, a primary instruction program for instructing the stimulant administering device to administer a gastric acid stimulant if the primary baseline gastric juice pH is determined to equal or exceed the certain value, and an alternative instruction program for instructing that an alternative operation be performed if the primary baseline gastric juice pH is determined to be less than the certain value.

The alternative operation includes: instructing the pharmacological agent administering device to administer a pharmacological agent to raise gastric juice pH, instructing the pH sensor to measure the patient's gastric juice pH after the pharmacological agent administration to obtain a secondary baseline gastric juice pH, and instructing the stimulant administering device to administers a gastric acid stimulant after the gastric juice pH has been raised. A measurement instruction program instructs the pH sensor to measure the patient's gastric juice pH after the gastric acid stimulant administration to obtain a stressed gastric juice pH. A calculation program calculates a pH differential between: 1) one of the primary and the secondary baseline gastric juice pH, and 2) the stressed gastric juice pH, to determine gastric function, so that medical care can be guided based on the determined gastric function.

4. Setting pH Differential for Healthy Gastric Function Low if Baseline pH is Low, and Setting pH Differential for Healthy Gastric Function High if Baseline pH is High Exemplary embodiments, which are intended to cover all applicable mediums of expression including but not limited to methods, apparatus, processors, computer programs, etc., enhance the guiding of care based on gastric function that is detected/determined by challenging the gastric system. Some exemplary embodiments determine gastric function based on a pH differential between gastric juice pH measured before and after administration of a gastric system stress agent, such as gastric acid stimulant or suppressant. The pH differential used to delineate healthy versus unhealthy gastric function can be determined based on the initially measured gastric juice pH prior to gastric system stress agent administration. i.e., baseline gastric juice pH. In other words, the pH differential values deemed sufficient to indicate healthy gastric function can vary depending on the baseline gastric juice pH.

Because pH differential values that indicate a healthy gastric function may vary depending on different patients or patient conditions, setting a static pH differential value to indicate healthy gastric function for all patients in all circumstances may result in less precise determinations of gastric function health. Thus, the above procedure provides enhanced results at least because tailoring pH differential values to indicate healthy gastric function enhances the accuracy of such determinations.

The varying of pH differential values that indicate a healthy gastric function can be performed in any applicable manner. For example, a guidance pH differential suitable to guide care can be determined based on the baseline gastric juice pH, and gastric function health can be determined by comparing the guidance pH differential to the actual gastric juice pH differential measured before and after administration of the gastric acid stimulant or suppressant. Medical care can be guided based on a relatively healthy gastric function if the actual gastric juice pH differential equals or exceeds the guidance pH differential, while medical care can be guided based on a relatively unhealthy gastric function if the actual gastric juice pH differential fails to equal or exceed the guidance pH differential.

In some exemplary embodiments, the guidance pH differential is set to be relatively low if the baseline gastric juice pH is relatively low, but set to be relatively high if the baseline gastric juice pH is relatively high. This setting of the guidance pH differential based on baseline gastric juice pH can be performed in any applicable manner. For example, some exemplary embodiments set the guidance pH based on baseline gastric juice pH using a logarithmic scale. More particularly, a logarithmic scale can be used that separates pH unit whole numbers by factors of ten, such that 7 pH units is separated from 6 pH units by a factor of 10, 6 pH units is separated from 5 pH units by a factor of 10, and 5 pH units is separated from 4 pH units by a factor of 10, etc. However, exemplary embodiments are intended to cover setting the guidance pH using procedures other than logarithms.

Examples of such exemplary embodiments are provided below in the contexts of methods, apparatus, processors, and computer programs. However, these contexts are merely provided for exemplary purposes, and exemplary embodiments are intended to cover all possible mediums.

a. Method

An exemplary method in accordance with this embodiment includes measuring the patient's gastric juice pH to obtain a baseline gastric juice pH, determining a guidance pH differential suitable to guide care based on the baseline gastric juice pH, administering a gastric acid stimulant or suppressant, measuring the patient's gastric juice pH after the administration of the gastric acid stimulant or suppressant to obtain a stressed gastric juice pH, and calculating a measured pH differential between the baseline gastric juice pH and the stressed gastric juice pH. Medical care is guided based on a relatively healthy gastric function if the measured pH differential is equal to or exceeds the guidance pH differential. Alternatively, medical care is guided based on a relatively unhealthy gastric function if the measured pH differential is less than the guidance pH differential.

b. Apparatus

An exemplary apparatus in accordance with this embodiment includes an administering device that administers a gastric acid stimulant or suppressant, a pH sensor that measures the patient's gastric juice pH prior to the administration of the gastric acid stimulant or suppressant to obtain a baseline gastric juice pH, and that measures the patient's gastric juice pH after the administration of the gastric acid stimulant or suppressant to obtain a stressed gastric juice pH, and a processor that determines a guidance pH differential suitable to guide care based on the baseline gastric juice pH, and that calculates a measured pH differential between the baseline gastric juice pH and the stressed gastric juice pH. The processor provides advice based on a comparison between the guidance pH differential and the measured pH differential. For example, the processor guides medical care based on a relatively healthy gastric function if the measured pH differential is equal to or exceeds the guidance pH differential, or alternatively guides medical care based on a relatively unhealthy gastric function if the measured pH differential is less than the guidance pH differential.

c. Processor

An exemplary processor in accordance with this embodiment is used with an administering device that administers a gastric acid stimulant or suppressant, and a pH sensor that measures the patient's gastric juice pH prior to the administration of the gastric acid stimulant or suppressant to obtain a baseline gastric juice pH, and that measures the patient's gastric juice pH after the administration of the gastric acid stimulant or suppressant to obtain a stressed gastric juice pH.

The processor includes a determination unit that determines a guidance pH differential suitable to guide care based on the baseline gastric juice pH, a calculation unit that calculates a measured pH differential between the baseline gastric juice pH and the stressed gastric juice pH, and a comparison unit that compares the guidance pH differential to the measured pH differential. The processor also includes a primary instruction unit that provides instructions to guide medical care based on a relatively healthy gastric function if the measured pH differential is equal to or exceeds the guidance pH differential, and an alternative instruction unit that provides instructions to guide medical care based on a relatively unhealthy gastric function if the measured pH differential is less than the guidance pH differential.

d. Computer Program

An exemplary computer program in accordance with this embodiment is used with a processor for guiding medical care of a patient based on detected gastric function, the processor being used with an administering device that administers a gastric acid stimulant or suppressant, and a pH sensor that measures the patient's gastric juice pH prior to the administration of the gastric acid stimulant or suppressant to obtain a baseline gastric juice pH, and that measures the patient's gastric juice pH after the administration of the gastric acid stimulant or suppressant to obtain a stressed gastric juice pH.

The computer program includes a determination program for determining a guidance pH differential suitable to guide care based on the baseline gastric juice pH, a calculation program for calculating a measured pH differential between the baseline gastric juice pH and the stressed gastric juice pH, and a comparison program for comparing the guidance pH differential to the measured pH differential. A primary instruction program provides instructions to guide medical care based on a relatively healthy gastric function if the measured pH differential is equal to or exceeds the guidance pH differential. An alternative instruction unit provides instructions to guide medical care based on a relatively unhealthy gastric function if the measured pH differential is less than the guidance pH differential.

5. Guiding Levels of Care Based on Whether the pH Differential Demonstrates: 1) Acute pH Change, 2) Moderate pH Change, or 3) Less than a Moderate pH Change Exemplary embodiments, which are intended to cover all applicable mediums of expression including but not limited to methods, apparatus, processors, computer programs, etc., enhance the guiding of care based on gastric function that is detected/determined by challenging the gastric system. Some exemplary embodiments determine gastric function based on a pH differential between gastric juice pH measured before and after administration of a gastric system stress agent, such as gastric acid stimulant or suppressant. The measured pH differential can be used to delineate various and multiple levels of gastric function health. For example, medical care is guided consistent with a very healthy gastric function if the calculated pH differential demonstrates an acute change in pH, while medical care can be guided consistent with a moderately healthy gastric function if the calculated pH differential only demonstrates a moderate change in pH. Further, medical care can guided consistent with an unhealthy gastric function if the calculated pH differential fails to demonstrate at least a moderate change in pH.

This procedure provides enhanced results by at least more particularly quantifying the health of the gastric system, so that medical care can be better tailored to actual gastric system health, thereby improving the patient's response to medical treatment. Also, as disclosed above, more precisely estimating gastric system health can be beneficial with regard to diagnoses of various medical conditions.

The pH differentials used to indicate acute and moderate pH changes can be determined in any applicable manner. In some exemplary embodiments, the pH changes deemed acute and moderate are pre-set. For example, in some of these exemplary embodiments, a change in pH that is greater than approximately 1 unit can be deemed acute, while a change in pH that is between approximately 0.5 unit and approximately 1 unit can be deemed moderate.

Examples of such exemplary embodiments are provided below in the contexts of methods, apparatus, processors, and computer programs. However, these contexts are merely provided for exemplary purposes, and exemplary embodiments are intended to cover all possible mediums.

a. Method

An exemplary method in accordance with this embodiment includes measuring the patient's gastric juice pH to obtain a baseline gastric juice pH, administering one of gastric acid stimulant and gastric acid suppressant, measuring the patient's gastric juice pH after the administration of the one of gastric acid stimulant and gastric acid suppressant to obtain a stressed gastric juice pH, and calculating a pH differential between the baseline gastric juice pH and the stressed gastric juice pH. Medical care is guided consistent with a very healthy gastric function if the calculated pH differential demonstrates an acute change in pH. Medical care is guided consistent with a moderately healthy gastric function if the calculated pH differential demonstrates a moderate change in pH. Medical care is guided consistent with an unhealthy gastric function if the calculated pH differential fails to demonstrate at least a moderate change in pH.

b. Apparatus

An exemplary apparatus in accordance with this embodiment includes an administering device that administers one of gastric acid stimulant and gastric acid suppressant, and a pH sensor that measures the patient's gastric juice pH prior to the administration of the one of gastric acid stimulant and gastric acid suppressant to obtain a baseline gastric juice pH, and that measures the patient's gastric juice pH after the administration of the one of gastric acid stimulant and gastric acid suppressant to obtain a stressed gastric juice pH. A processor calculates a pH differential between the baseline gastric juice pH and the stressed gastric juice pH, and provides advice based on the calculated pH differential. For example, medical care is guided consistent with a very healthy gastric function if the calculated pH differential demonstrates an acute change in pH, medical care is guided consistent with a moderately healthy gastric function if the calculated pH differential demonstrates a moderate change in pH, and medical care is guided consistent with an unhealthy gastric function if the calculated pH differential fails to demonstrate at least a moderate change in pH.

c. Processor

An exemplary processor in accordance with this embodiment is used an administering device that administers one of gastric acid stimulant and gastric acid suppressant, and a pH sensor that measures the patient's gastric juice pH prior to the administration of the one of gastric acid stimulant and gastric acid suppressant to obtain a baseline gastric juice pH, and that measures the patient's gastric juice pH after the administration of the one of gastric acid stimulant and gastric acid suppressant to obtain a stressed gastric juice pH.

The processor includes a calculation unit that calculates a pH differential between the baseline gastric juice pH and the stressed gastric juice pH, and a primary instruction unit that provides advice to guide medical care consistent with a very healthy gastric function if the calculated pH differential demonstrates an acute change in pH. The processor also includes a secondary instruction unit that provides advice to guide medical care consistent with a moderately healthy gastric function if the calculated pH differential demonstrates a moderate change in pH, and a tertiary instruction unit that provides advice to guide medical care consistent with an unhealthy gastric function if the calculated pH differential fails to demonstrate at least a moderate change in pH.

d. Computer Program

An exemplary computer program in accordance with this embodiment is used with a processor for guiding medical care of a patient based on detected gastric function, the processor being used with an administering device that administers one of gastric acid stimulant and gastric acid suppressant, and a pH sensor that measures the patient's gastric juice pH prior to the administration of the one of gastric acid stimulant and gastric acid suppressant to obtain a baseline gastric juice pH, and that measures the patient's gastric juice pH after the administration of the one of gastric acid stimulant and gastric acid suppressant to obtain a stressed gastric juice pH.

The computer program includes a calculation program for calculating a pH differential between the baseline gastric juice pH and the stressed gastric juice pH, a primary instruction program for providing advice to guide medical care consistent with a very healthy gastric function if the calculated pH differential demonstrates an acute change in pH, a secondary instruction program for providing advice to guide medical care consistent with a moderately healthy gastric function if the calculated pH differential demonstrates a moderate change in pH, and a tertiary instruction program for providing advice to guide medical care consistent with an unhealthy gastric function if the calculated pH differential fails to demonstrate at least a moderate change in pH.

B. Enhancing Efficiency of pH Differential Based Tests

Other exemplary embodiments can be categorized as different methods, apparatus, processors, computer programs, etc., for enhancing the efficiency of pH differential based tests. The listing of embodiments that enhance the test efficiency is not intended as limiting, and instead is merely provided for exemplary purposes.

Enhancing the test efficiency can be beneficial in numerous respects. For example, enhancing efficiency can enable tests to be conducted at a lower cost, both in terms of labor and material, thereby helping to reduce otherwise rising medical costs while also enabling medical care providers to spend time saved on other activities. In addition, trauma caused to patients by undergoing the tests can be reduced, such as by reducing the patient's exposure to pharmacological agents (with regard to amount and/or concentration of the agents), and by reducing the amount of time that the patients undergo the tests. Increasing test efficiency can also facilitate early indication of gastric system health, which can be beneficial by expediting diagnoses of medical conditions and treatments, thereby improving the patient's medical condition.

1. Administer Minimum Dosage of Stimulant or Suppressant, and if pH Differential is Low, Administer Standard Dose of Stimulant or Suppressant Exemplary embodiments, which are intended to cover all applicable mediums of expression including but not limited to methods, apparatus, processors, computer programs, etc., enhance the guiding of care based on gastric function that is detected/determined by challenging the gastric system. Some exemplary embodiments conduct an initial gastric system stress test with a minimum dosage of gastric system stress agent, such as gastric acid stimulant or suppressant. A pH differential is calculated between gastric juice pH prior to and after administration of the minimum dosage, and medical care is guided consistent with a relatively healthy gastric function if the pH differential constitutes an acute change. An alternative gastric system stress test is conducted with a standard dosage of gastric system stress agent if an acute change is not demonstrated, and medical care is guided based on the results of the alternative test. i.e., medical care is guided consistent with a relatively healthy/unhealthy gastric function depending on whether the pH differential constitutes an acute change after administration of the standard dosage.

This procedure provides enhanced results at least by providing the opportunity of reducing the dosage of stress agent (pharmacological challenge agent) administered to the patient. This procedure may be beneficial by reducing, minimizing, or preventing any side-effects caused by the stress agent. Other, potentially secondary, benefits may also be achieved, such as reducing medical costs by virtue of the decreased stress agent dosage, etc.

In some exemplary embodiments, the gastric system stress agent is a gastric acid stimulant. In particular, some exemplary embodiments use pentagastrin as the gastric acid stimulant, wherein the minimum dosage of gastric acid stimulant is approximately 0.6 mcg/kg of pentagastrin, and the standard dosage of stimulant is approximately 6 mcg/kg of pentagastrin. Also, in some exemplary embodiments, a pH differential of approximately 1 pH unit is deemed sufficient to constitute an acute change to thereby indicate a relatively healthy gastric function. However, exemplary embodiments are intended to cover any dosages and pH differentials that are applicable to determine gastric function so that medical care can be guided accordingly.

Examples of such exemplary embodiments are provided below in the contexts of methods, apparatus, processors, and computer programs. However, these contexts are merely provided for exemplary purposes, and exemplary embodiments are intended to cover all possible mediums.

a. Method

An exemplary method in accordance with this embodiment includes measuring the patient's gastric juice pH to obtain a baseline gastric juice pH, administering a minimum dosage of a gastric acid stimulant or suppressant, measuring the patient's gastric juice pH after the administration of the gastric acid stimulant or suppressant to obtain a primary stressed gastric juice pH, and calculating a primary pH differential between the baseline gastric juice pH and the primary stressed gastric juice pH to determine gastric function. Medical care is guided consistent with a relatively healthy gastric function if the calculated primary pH differential demonstrates an acute change in pH.

An alternative test is conducted if the calculated primary pH differential fails to demonstrate an acute change in pH. The alternative test includes: a) administering a standard dosage of gastric acid stimulant or suppressant that exceeds the minimum dosage, b) measuring the patient's gastric juice pH after the administration of the standard dosage of the gastric acid stimulant or suppressant to obtain an alternative stressed gastric juice pH, c) calculating an alternative pH differential between: i) one of the baseline gastric juice pH and the primary stressed gastric juice pH, and ii) the alternative stressed gastric juice pH, d) guiding medical care consistent with a relatively healthy gastric function if the calculated alternative pH differential demonstrates an acute change in pH, and e) guiding medical care consistent with a relatively unhealthy gastric function if the calculated alternative pH differential fails to demonstrate an acute change in pH. In some exemplary embodiments, the alternative pH differential is calculated between the baseline gastric juice pH and the alternative stressed gastric juice pH, while in other exemplary embodiments, the alternative pH differential is calculated between the primary stressed gastric juice pH and the alternative stressed gastric juice pH.

b. Apparatus

An exemplary apparatus in accordance with this embodiment includes an administering device that administers a minimum dosage of a gastric acid stimulant or suppressant, and a pH sensor that measures the patient's gastric juice pH prior to the administration of the minimum dosage of gastric acid stimulant or suppressant to obtain a baseline gastric juice pH, and that measures the patient's gastric juice pH after the administration of the minimum dosage of gastric acid stimulant or suppressant to obtain a primary stressed gastric juice pH. A processor calculates a primary pH differential between the baseline gastric juice pH and the primary stressed gastric juice pH to determine gastric function. The processor guides medical care consistent with a relatively healthy gastric function if the calculated primary pH differential demonstrates an acute change in pH.

An alternative test is conducted if the calculated primary pH differential fails to demonstrate an acute change in pH. In the alternative test, a) the administering device administers a standard dosage of gastric acid stimulant or suppressant that exceeds the minimum dosage, b) the pH sensor measures the patient's gastric juice pH after the administration of the standard dosage of the gastric acid stimulant or suppressant to obtain an alternative stressed gastric juice pH, and c) the processor calculates an alternative pH differential between: i) one of the baseline gastric juice pH and the primary stressed gastric juice pH, and ii) the alternative stressed gastric juice pH, such that the processor guides medical care consistent with a relatively healthy gastric function if the calculated alternative pH differential demonstrates an acute change in pH, and guides medical care consistent with a relatively unhealthy gastric function if the calculated alternative pH differential fails to demonstrate an acute change in pH. In some exemplary embodiments, the alternative pH differential is calculated between the baseline gastric juice pH and the alternative stressed gastric juice pH, while in other exemplary embodiments, the alternative pH differential is calculated between the primary stressed gastric juice pH and the alternative stressed gastric juice pH.

c. Processor

An exemplary processor in accordance with this embodiment is used with an administering device that administers a minimum dosage of a gastric acid stimulant or suppressant, and a pH sensor that measures the patient's gastric juice pH prior to the administration of the minimum dosage of gastric acid stimulant or suppressant to obtain a baseline gastric juice pH, and that measures the patient's gastric juice pH after the administration of the minimum dosage of gastric acid stimulant or suppressant to obtain a primary stressed gastric juice pH.

The processor includes a calculation unit that calculates a primary pH differential between the baseline gastric juice pH and the primary stressed gastric juice pH to determine gastric function, and a primary instruction unit that instructs medical care to be guided consistent with a relatively healthy gastric function if the calculated primary pH differential demonstrates an acute change in pH. The processor also includes an alternative instruction unit that instructs that an alternative test be conducted if the calculated primary pH differential fails to demonstrate an acute change in pH. In the alternative operation, the processor: a) instructs the administering device to administer a standard dosage of gastric acid stimulant or suppressant that exceeds the minimum dosage, b) instructs the pH sensor to measure the patient's gastric juice pH after the administration of the standard dosage of the gastric acid stimulant or suppressant to obtain an alternative stressed gastric juice pH, and c) calculates an alternative pH differential between: i) one of the baseline gastric juice pH and the primary stressed gastric juice pH, and ii) the alternative stressed gastric juice pH, such that instructions are provided to guide medical care consistent with a relatively healthy gastric function if the calculated alternative pH differential demonstrates an acute change in pH, and instructions are provided to guide medical care consistent with a relatively unhealthy gastric function if the calculated alternative pH differential fails to demonstrate an acute change in pH. In some exemplary embodiments, the alternative pH differential is calculated between the baseline gastric juice pH and the alternative stressed gastric juice pH, while in other exemplary embodiments, the alternative pH differential is calculated between the primary stressed gastric juice pH and the alternative stressed gastric juice pH.

d. Computer Program

An exemplary computer program in accordance with this embodiment is used with a processor for guiding medical care of a patient based on detected gastric function, the processor being used with an administering device that administers a minimum dosage of a gastric acid stimulant or suppressant, and a pH sensor that measures the patient's gastric juice pH prior to the administration of the minimum dosage of gastric acid stimulant or suppressant to obtain a baseline gastric juice pH, and that measures the patient's gastric juice pH after the administration of the minimum dosage of gastric acid stimulant or suppressant to obtain a primary stressed gastric juice pH.

The computer program includes a calculation program for calculating a primary pH differential between the baseline gastric juice pH and the primary stressed gastric juice pH to determine gastric function, and a primary instruction program for instructing medical care to be guided consistent with a relatively healthy gastric function if the calculated primary pH differential demonstrates an acute change in pH. An alternative instruction program instructs that an alternative test be conducted if the calculated primary pH differential fails to demonstrate an acute change in pH. The alternative test includes: a) instructing the administering device to administer a standard dosage of gastric acid stimulant or suppressant that exceeds the minimum dosage, b) instructing the pH sensor to measure the patient's gastric juice pH after the administration of the standard dosage of the gastric acid stimulant or suppressant to obtain an alternative stressed gastric juice pH, and c) calculating an alternative pH differential between: i) one of the baseline gastric juice pH and the primary stressed gastric juice pH, and ii) the alternative stressed gastric juice pH, such that instructions are provided to guide medical care consistent with a relatively healthy gastric function if the calculated alternative pH differential demonstrates an acute change in pH, and instructions are provided to guide medical care consistent with a relatively unhealthy gastric function if the calculated alternative pH differential fails to demonstrate an acute change in pH. In some exemplary embodiments, the alternative pH differential is calculated between the baseline gastric juice pH and the alternative stressed gastric juice pH, while in other exemplary embodiments, the alternative pH differential is calculated between the primary stressed gastric juice pH and the alternative stressed gastric juice pH.

2. Take Initial Stressed pH Measurement Early (Such as at Earliest Significant Gastric Response of Most People to Stimulant or Suppressant), and Take a Subsequent Stressed pH Measurement if a Negative Response is Determined Exemplary embodiments, which are intended to cover all applicable mediums of expression including but not limited to methods, apparatus, processors, computer programs, etc., enhance the guiding of care based on gastric function that is detected/determined by challenging the gastric system. Some exemplary embodiments conduct an initial gastric system stress test, such as by calculating a pH differential between a baseline pH and a stressed pH that is taken early, and in some cases, at or soon after a minimum period defined by the earliest significant gastric response of many patients to a stress agent (including gastric acid stimulant or suppressant). Medical care can be guided consistent with a relatively healthy gastric function if the pH differential constitutes an acute change. An alternative gastric system stress test is conducted after a subsequent period if an acute change is not demonstrated, and medical care is guided based on the results of the alternative test, i.e., medical care is guided consistent with a relatively healthy/unhealthy gastric function depending on whether the pH differential constitutes an acute change after administration of the standard dosage. The subsequent period exceeds the minimum period, but is no greater than a duration of a healthy or relatively healthy volunteer's gastric response to the stress agent, i.e., the known or estimated duration of action of the stress or challenge agent. For example, the subsequent period may not exceed an estimated duration of gastric response to the stress agent.

This procedure provides enhanced results at least by providing the opportunity of expediting the test results. Patients demonstrating an acute change in gastric juice pH in the initial gastric system stress test can have medical care guided early, i.e., after the minimum period defined by the earliest significant gastric response of many patients to a stress agent, instead of having to wait until after a longer standard period. Even patients failing to demonstrate an acute change in gastric juice pH in the initial gastric system stress test may benefit by the closer monitoring of pH changes in the subsequent test, which provides additional information regarding gastric system health.

Exemplary embodiments are intended to cover taking stressed pH measurements after any and all applicable minimum and standard periods. For example, in some exemplary embodiments, the minimum period is approximately 15 minutes, such that the patient's gastric juice pH is measured at approximately 15 minutes after administration of the gastric system stress agent to obtain the initial stressed gastric juice pH. Also in some of these embodiments, the subsequent period is approximately 45 minutes, such that the patient's gastric juice pH is measured at approximately 45 minutes after the pentagastrin administration to obtain the subsequent stressed gastric juice pH.

Examples of such exemplary embodiments are provided below in the contexts of methods, apparatus, processors, and computer programs. However, these contexts are merely provided for exemplary purposes, and exemplary embodiments are intended to cover all possible mediums.

a. Method

An exemplary method in accordance with this embodiment includes measuring the patient's gastric juice pH to obtain a baseline gastric juice pH, administering one of gastric acid stimulant and gastric acid suppressant, and estimating a minimum period for a gastric response to administration of the stimulant or suppressant. The patient's gastric juice pH is measured approximately at the minimum period to obtain an initial stressed gastric juice pH, and an initial pH differential, between the baseline gastric juice pH and the initial stressed gastric juice pH, is calculated to determine gastric function. Medical care is guided consistent with a relatively healthy gastric function if the calculated initial pH differential demonstrates an acute change in pH.

A subsequent test is conducted if the calculated initial pH differential fails to demonstrate an acute change in pH. The subsequent test includes: estimating a subsequent period for gastric response to administration of the stimulant or suppressant, the subsequent period exceeding the minimum period and being no greater than an estimated duration of gastric response to the stimulant or suppressant, measuring the patient's gastric juice pH approximately at the subsequent period to obtain a subsequent stressed gastric juice pH, calculating a subsequent pH differential between the baseline gastric juice pH and the subsequent stressed gastric juice pH to determine gastric function, guiding medical care consistent with a relatively healthy gastric function if the calculated subsequent pH differential demonstrates an acute change in pH, and guiding medical care consistent with a relatively unhealthy gastric function if the calculated subsequent pH differential fails to demonstrate an acute change in pH.

b. Apparatus

An exemplary apparatus in accordance with this embodiment includes a pH sensor that measures the patient's gastric juice pH to obtain a baseline gastric juice pH, an administering device that administers one of gastric acid stimulant and gastric acid suppressant, and a processor that estimates a minimum period for a gastric response to the administration of the stimulant or suppressant. The pH sensor measures the patient's gastric juice pH approximately at the minimum period to obtain an initial stressed gastric juice pH. The processor calculates an initial pH differential between the baseline gastric juice pH and the initial stressed gastric juice pH to determine gastric function. The processor guides medical care consistent with a relatively healthy gastric function if the calculated initial pH differential demonstrates an acute change in pH.

A subsequent test is conducted if the calculated initial pH differential fails to demonstrate an acute change in pH. In the subsequent test, the processor estimates a subsequent period for gastric response to administration of the stimulant or suppressant, the subsequent period exceeding the minimum period and being no greater than an estimated duration of gastric response to the stimulant or suppressant, the pH sensor measures the patient's gastric juice pH approximately at the subsequent period to obtain a subsequent stressed gastric juice pH, and the processor calculates a subsequent pH differential between the baseline gastric juice pH and the subsequent stressed gastric juice pH to determine gastric function, such that the processor guides medical care consistent with a relatively healthy gastric function if the calculated subsequent pH differential demonstrates an acute change in pH, and the processor guides medical care consistent with a relatively unhealthy gastric function if the calculated subsequent pH differential fails to demonstrate an acute change in pH.

c. Processor

An exemplary processor in accordance with this embodiment is used with a pH sensor that measures the patient's gastric juice pH to obtain a baseline gastric juice pH, and an administering device that administers one of gastric acid stimulant and gastric acid suppressant. The processor includes an estimating unit that estimates a minimum period for a gastric response to the administration of the stimulant or suppressant, a pH measurement instruction unit that instructs the pH sensor to measure the patient's gastric juice pH approximately at the minimum period to obtain an initial stressed gastric juice pH, and a calculation unit that calculates an initial pH differential between the baseline gastric juice pH and the initial stressed gastric juice pH to determine gastric function.

The processor also includes a primary instruction unit that instructs that medical care be guided consistent with a relatively healthy gastric function if the calculated initial pH differential demonstrates an acute change in pH, and an alternative instruction unit that instructs that a subsequent test be conducted if the calculated initial pH differential fails to demonstrate an acute change in pH. In the subsequent test, the processor: a) estimates a subsequent period for gastric response to administration of the stimulant or suppressant, the subsequent period exceeding the minimum period and being no greater than an estimated duration of gastric response to the stimulant or suppressant, b) instructs the pH sensor to measure the patient's gastric juice pH approximately at the subsequent period to obtain a subsequent stressed gastric juice pH, and c) calculates a subsequent pH differential between the baseline gastric juice pH and the subsequent stressed gastric juice pH to determine gastric function, such that instructions are provided to guide medical care consistent with a relatively healthy gastric function if the calculated subsequent pH differential demonstrates an acute change in pH, and instructions are provided to guide medical care consistent with a relatively unhealthy gastric function if the calculated subsequent pH differential fails to demonstrate an acute change in pH.

d. Computer Program

An exemplary computer program in accordance with this embodiment is used with a processor for guiding medical care of a patient based on detected gastric function, the processor being used with a pH sensor that measures the patient's gastric juice pH to obtain a baseline gastric juice pH, and an administering device that administers one of gastric acid stimulant and gastric acid suppressant. The computer program includes an estimating program for estimating a minimum period for a gastric response to the administration of the stimulant or suppressant, a pH measurement instruction program for instructing the pH sensor to measure the patient's gastric juice pH approximately at the minimum period to obtain an initial stressed gastric juice pH, and a calculation program for calculating an initial pH differential between the baseline gastric juice pH and the initial stressed gastric juice pH to determine gastric function.

A primary instruction program instructs that medical care be guided consistent with a relatively healthy gastric function if the calculated initial pH differential demonstrates an acute change in pH, and an alternative instruction program for instructing that a subsequent test be conducted if the calculated initial pH differential fails to demonstrate an acute change in pH. The subsequent test includes: estimating a subsequent period for gastric response to administration of the stimulant or suppressant, the subsequent period exceeding the minimum period and being no greater than an estimated duration of gastric response to the stimulant or suppressant, instructing the pH sensor to measure the patient's gastric juice pH approximately at the subsequent period to obtain a subsequent stressed gastric juice pH, and calculating a subsequent pH differential between the baseline gastric juice pH and the subsequent stressed gastric juice pH to determine gastric function, such that instructions are provided to guide medical care consistent with a relatively healthy gastric function if the calculated subsequent pH differential demonstrates an acute change in pH, and instructions are provided to guide medical care consistent with a relatively unhealthy gastric function if the calculated subsequent pH differential fails to demonstrate an acute change in pH.

C. Methodology Bases Other than pH Differential Based Tests

Still other exemplary embodiments can be categorized as different methods, apparatus, processors, computer programs, etc., for determining or helping to determine gastric system health using methodologies different or even unrelated to the measurements of pH differentials. The below listing of embodiments that use other methodologies to determine gastric system health is not intended as limiting, and instead is merely provided for exemplary purposes.

The use of methodologies that do not purely rely on pH differentials to determine gastric system health can be beneficial in numerous respects. For example, certain methodologies may provide advantages over relying on pH differentials (under all or only certain circumstances) in various respects, such as in terms of costs, reliability, accuracy, speed, efficiency, etc. In some cases, these other methodologies can be used with and/or in addition to pH differential measurements to enhance accuracy, reliability and/or efficiency of gastric system health determinations. Use of the other methodologies can thereby help to provide at least all of the benefits discussed above with regard to enhancing test accuracy and efficiency.

1. Obtaining Multiple Stressed Gastric Juice Measurements, and Calculating a Rate of Change of pH Based on the Multiple Measurements Exemplary embodiments, which are intended to cover all applicable mediums of expression including but not limited to methods, apparatus, processors, computer programs, etc., enhance the guiding of care based on gastric function that is detected/determined by challenging the gastric system. Some exemplary embodiments measure a patient's baseline gastric juice pH, administer a gastric system stress agent (such as gastric acid stimulant or suppressant, for example), and then obtain multiple stressed gastric juice pH values. A rate of change of gastric juice pH is calculated based on the baseline pH and the multiple stressed pH values, and gastric function is determined based on the calculated rate of change.

This procedure provides enhanced results at least because it can provide more data, and thus a deeper understanding of gastric function, than tests that rely purely on pH differential between baseline pH and a single stressed pH. This procedure may, in some cases, also enable gastric system health to be determined on an expedited basis. For example, in some cases, gastric system health can be determined early based on an initial high rate of pH change calculated from stressed pH values measured shortly after stress agent administration (and well prior to measurement of the stressed pH measurement forming the basis of tests that rely purely on pH differential).

Exemplary embodiments are intended cover any applicable manner of determining rate of change of gastric juice pH. For example, the patient's gastric juice pH can be measured on at least one of a continuous basis, substantially continuous bases, semi-continuous basis, and periodic basis. In some exemplary embodiments, the patient's gastric juice pH is measured on a continuous basis via streaming data.

Exemplary embodiments are also intended to cover any applicable use derived from the determined rate of change of gastric juice pH. In some exemplary embodiments, medical care is guided consistent with a relatively healthy gastric function if the calculated rate of change of gastric juice pH demonstrates an acute rate of change, while medical care is guided consistent with a relatively unhealthy gastric function if the calculated rate of change of gastric juice pH fails to demonstrate an acute rate of change.

Exemplary embodiments are further intended to cover integrations of other types of data, different from rate of change of gastric juice pH, in order to determine gastric system health. For example, the volume of the patient's gastric juice secreted after the stimulant or suppressant administration can be measured, and a guidance rate of change of gastric juice pH sufficient to indicate healthy gastric function can be set based on the measured gastric volume. In some of these exemplary embodiments, the guidance rate of change of gastric juice pH sufficient to indicate healthy gastric function can be set to be relatively lower if the measured gastric volume is relatively high, while the guidance rate of change of gastric juice pH sufficient to indicate healthy gastric function can be set to be relatively higher if the measured gastric volume is relatively low. A relatively healthy gastric function can be determined if the calculated rate of change of gastric juice pH equals or exceeds the guidance rate of change of gastric juice pH, while a relatively unhealthy gastric function can be determined if the calculated rate of change of gastric juice pH is less than the guidance rate of change of gastric juice pH.

Examples of such exemplary embodiments are provided below in the contexts of methods, apparatus, processors, and computer programs. However, these contexts are merely provided for exemplary purposes, and exemplary embodiments are intended to cover all possible mediums.

a. Method

An exemplary method in accordance with this embodiment includes measuring the patient's gastric juice pH to obtain a baseline gastric juice pH, administering a gastric acid stimulant or suppressant, and performing multiple measurements of the patient's gastric juice pH after the administration of the gastric acid stimulant or suppressant to obtain multiple stressed gastric juice pH values. A rate of change of gastric juice pH is calculated based on the baseline gastric juice pH and the stressed gastric juice pH values to determine gastric function, and medical care is guided based on the determined gastric function.

b. Apparatus

An exemplary apparatus in accordance with this embodiment includes an administering device that administers a gastric acid stimulant or suppressant, and a pH sensor that measures the patient's gastric juice pH prior to the administration of the gastric acid stimulant or suppressant to obtain a baseline gastric juice pH, and that performs multiple measurements of the patient's gastric juice pH after the administration of the gastric acid stimulant or suppressant to obtain multiple stressed gastric juice pH values. A processor calculates a rate of change of gastric juice pH based on the baseline gastric juice pH and the stressed gastric juice pH values to determine gastric function, such that medical care can be guided based on the determined gastric function.

c. Processor

An exemplary processor in accordance with this embodiment is used with an administering device that administers a gastric acid stimulant or suppressant, and a pH sensor that measures the patient's gastric juice pH prior to the administration of the gastric acid stimulant or suppressant to obtain a baseline gastric juice pH, and that performs multiple measurements of the patient's gastric juice pH after the administration of the gastric acid stimulant or suppressant to obtain multiple stressed gastric juice pH values.

The processor includes a calculation unit that calculates a rate of change of gastric juice pH based on the baseline gastric juice pH and the stressed gastric juice pH values, and a primary instruction unit that provides instructions to guide medical care consistent with a relatively healthy gastric function if the calculated rate of change of gastric juice pH demonstrates an acute rate of change. The processor also includes a secondary instruction unit that provides instructions to guide medical care consistent with a relatively unhealthy gastric function if the calculated rate of change of gastric juice pH fails to demonstrate an acute rate of change.

d. Computer Program

An exemplary computer program in accordance with this embodiment is used with a processor for guiding medical care of a patient based on detected gastric function, the processor being used with an administering device that administers a gastric acid stimulant or suppressant, and a pH sensor that measures the patient's gastric juice pH prior to the administration of the gastric acid stimulant or suppressant to obtain a baseline gastric juice pH, and that performs multiple measurements of the patient's gastric juice pH after the administration of the gastric acid stimulant or suppressant to obtain multiple stressed gastric juice pH values.

The computer program includes a calculation program for calculating a rate of change of gastric juice pH based on the baseline gastric juice pH and the stressed gastric juice pH values, and a primary instruction program for providing instructions to guide medical care consistent with a relatively healthy gastric function if the calculated rate of change of gastric juice pH demonstrates an acute rate of change. A secondary instruction program provides instructions to guide medical care consistent with a relatively unhealthy gastric function if the calculated rate of change of gastric juice pH fails to demonstrate an acute rate of change.

2. Determining Gastric Function Based on Gastric Juice Volume Secreted after Administration of a Pharmacological Challenge Agent Exemplary embodiments, which are intended to cover all applicable mediums of expression including but not limited to methods, apparatus, processors, computer programs, etc., enhance the guiding of care based on gastric function that is detected/determined by challenging the gastric system. Some exemplary embodiments determine gastric juice volume secreted after administration of a pharmacological challenge agent (such as a gastric system stress agent, including but not limited to gastric acid stimulants and suppressants), and guide medical care based on the measured gastric juice volume secreted. This procedure is inherently beneficial by providing an alternative to gastric system stress tests based solely on pH differential(s), and in some cases may provide specific benefits over such tests at least in terms of cost, reliability, accuracy, speed, efficiency, etc. In some cases, the gastric volume measurements can be used with and/or in addition to pH differential measurements to enhance accuracy, reliability and/or efficiency of gastric system health determinations, thereby providing benefits discussed above with regard to enhancing test accuracy and efficiency.

Exemplary embodiments are intended to cover any and all applicable implementations of the above volume based stress test. In some exemplary embodiments, the patient's gastric juice volume is measured prior to and after administration of the pharmacological challenge agent to obtain a baseline gastric juice volume and a stressed gastric juice volume. A volume differential, between the baseline and stressed gastric juice volumes, is calculated to determine the gastric juice volume secreted after the pharmacological challenge agent administration. In other exemplary embodiments, the patient's gastric juice contents are aspirated prior to the pharmacological challenge agent administration, and the gastric juice volume is measured after the administration of the pharmacological challenge agent to determine the gastric juice volume secreted.

Exemplary embodiments are also intended to cover any and all applicable usages and applications of the above volume based stress test. For example, in some exemplary embodiments, medical care is guided consistent with a relatively healthy gastric function if the measured gastric juice volume secreted demonstrates an acute change in volume, while medical care is guided consistent with a relatively unhealthy gastric function if the measured gastric juice volume secreted fails to demonstrate an acute change in volume.

Examples of such exemplary embodiments are provided below in the contexts of methods, apparatus, processors, and computer programs. However, these contexts are merely provided for exemplary purposes, and exemplary embodiments are intended to cover all possible mediums.

a. Method

An exemplary method in accordance with this embodiment includes administering a pharmacological challenge agent, determining gastric juice volume secreted a period after administration of the pharmacological challenge agent, and guiding medical care based on the measured gastric juice volume secreted.

b. Apparatus

An exemplary apparatus in accordance with this embodiment includes an administering device that administers a pharmacological challenge agent, a volume sensor that measures gastric juice volume, and a processor that determines gastric juice volume secreted a period after the administration of the pharmacological challenge agent, and provides advice for guiding medical care based on the determined gastric juice volume secreted.

c. Processor

An exemplary processor in accordance with this embodiment is used with an administering device that administers a pharmacological challenge agent, and a volume sensor that measures gastric juice volume. The processor includes a determination unit that communicates with the volume sensor to determine gastric juice volume secreted a period after the administration of the pharmacological challenge agent, and a primary instruction unit that provides instructions to guide medical care consistent with a relatively healthy gastric function if the determined gastric juice volume secreted demonstrates an acute change in volume. The processor also includes a secondary instruction unit that provides advice to guide medical care consistent with a relatively unhealthy gastric function if the determined gastric juice volume secreted fails to demonstrate an acute change in volume.

d. Computer Program

An exemplary computer program in accordance with this embodiment is used with a processor for guiding medical care of a patient based on detected gastric function, the processor being used with an administering device that administers a pharmacological challenge agent, and a volume sensor that measures gastric juice volume. The computer program includes a determination program for communicating with the volume sensor to determine gastric juice volume secreted a period after the administration of the pharmacological challenge agent, and a primary instruction program for providing instructions to guide medical care consistent with a relatively healthy gastric function if the determined gastric juice volume secreted demonstrates an acute change in volume. A secondary instruction program provides advice to guide medical care consistent with a relatively unhealthy gastric function if the determined gastric juice volume secreted fails to demonstrate an acute change in volume.

3. Determining Gastric Function Based on Gastrointestinal Motility Change after Pharmacological Challenge Agent Administration Exemplary embodiments, which are intended to cover all applicable mediums of expression including but not limited to methods, apparatus, processors, computer programs, etc., enhance the guiding of care based on gastric function that is detected/determined by challenging the gastric system. Some exemplary embodiments measure a patient's gastrointestinal motility prior to and after administration of a pharmacological challenge agent (such as a gastric system stress agent, including but not limited to gastric acid stimulants and suppressants) to determine baseline and stressed motilities, and calculate a motility differential between the baseline and stressed motilities.

This procedure is inherently beneficial by providing an alternative to gastric system stress tests based solely on pH differential(s) and/or volume differential(s), and in some cases may provide specific benefits over such tests at least in terms of cost, reliability, accuracy, speed, efficiency, etc. In some cases, the gastrointestinal motility measurements can be used with and/or in addition to pH and/or volume differential measurements to enhance accuracy, reliability and/or efficiency of gastric system health determinations, thereby providing benefits discussed above with regard to enhancing test accuracy and efficiency.

Exemplary embodiments are also intended to cover any and all applicable usages and applications of the above motility based stress test. For example, in some exemplary embodiments, medical care is guided consistent with a relatively healthy gastric function if the motility differential demonstrates an acute change in gastrointestinal motility, while medical care is guided consistent with a relatively unhealthy gastric function if the motility differential fails to demonstrate an acute change in gastrointestinal motility.

Examples of such exemplary embodiments are provided below in the contexts of methods, apparatus, processors, and computer programs. However, these contexts are merely provided for exemplary purposes, and exemplary embodiments are intended to cover all possible mediums.

a. Method

An exemplary method in accordance with this embodiment includes measuring the patient's gastrointestinal motility to determine a baseline motility, administering a pharmacological challenge agent, and measuring the patient's gastrointestinal motility after the pharmacological challenge agent administration to determine a stressed motility. A motility differential, between the baseline motility and stressed motility, is calculated to determine gastric function, and medical care is guided based on the determined gastric function.

b. Apparatus

An exemplary apparatus in accordance with this embodiment includes an administering device that administers a pharmacological challenge agent, and a motility sensor that measures the patient's gastrointestinal motility prior to the administration of the pharmacological challenge agent to determine a baseline motility, and that measures the patient's gastrointestinal motility after the pharmacological challenge agent administration to determine a stressed motility. A processor calculates a motility differential between the baseline motility and stressed motility to determine gastric function so that medical care can be guided based on the determined gastric function.

c. Processor

An exemplary processor in accordance with this embodiment is used with an administering device that administers a pharmacological challenge agent, and a motility sensor that measures the patient's gastrointestinal motility prior to the administration of the pharmacological challenge agent to determine a baseline motility, and that measures the patient's gastrointestinal motility after the pharmacological challenge agent administration to determine a stressed motility. The processor includes a calculation unit that communicates with the motility sensor to calculate a motility differential between the baseline motility and stressed motility, and a primary instruction unit that guides medical care consistent with a relatively healthy gastric function if the motility differential demonstrates an acute change in gastrointestinal motility. The processor also includes a secondary instruction unit that guides medical care consistent with a relatively unhealthy gastric function if the motility differential fails to demonstrate an acute change in gastrointestinal motility.

d. Computer Program

An exemplary computer program in accordance with this embodiment is used with a processor for guiding medical care of a patient based on detected gastric function, the processor being used with an administering device that administers a pharmacological challenge agent, and a motility sensor that measures the patient's gastrointestinal motility prior to the administration of the pharmacological challenge agent to determine a baseline motility, and that measures the patient's gastrointestinal motility after the pharmacological challenge agent administration to determine a stressed motility. The computer program includes a calculation program for communicating with the motility sensor to calculate a motility differential between the baseline motility and stressed motility, and a primary instruction program for guiding medical care consistent with a relatively healthy gastric function if the motility differential demonstrates an acute change in gastrointestinal motility. A secondary instruction program guides medical care consistent with a relatively unhealthy gastric function if the motility differential fails to demonstrate an acute change in gastrointestinal motility.

D. Other Inventive Features

Exemplary embodiments include a myriad of other inventive features, some of which are combinable with any and all of the above exemplary embodiments, while others can be practiced in a separate and distinct manner from the above embodiments. As with the exemplary embodiments disclosed above, these other inventive features can be provided in any relevant form, i.e., methods, apparatus, processors, computer programs, etc.

A summary of features included in other exemplary embodiments is provided below. Each of the below features can either be practiced with and included in each of the above exemplary embodiments, or alternatively practiced separately from these embodiments. The below listing is merely provided for exemplary purposes and is not intended as a complete disclosure of inventive features.

1. Guiding of Medical Care

Exemplary embodiments are intended to cover any applicable use or application of the pH differential based stress tests. In some exemplary embodiments, medical care is guided consistent with a relatively healthy gastric function if the calculated pH differential demonstrates an acute change in pH, such as at least one pH unit, while medical care is guided consistent with a relatively unhealthy gastric function if the calculated pH differential fails to demonstrate such an acute change. However, the change of one pH unit is merely provided for exemplary purposes, and exemplary embodiments are intended to cover any applicable parameters defining an acute change in pH.

In some exemplary embodiments, the guiding of medical care consistent with a relatively healthy gastric function includes providing medical advice relating to the performance of at least one of: initiation, maintenance, or increase of enteral feeding; failing to initiate, reduction, or termination of mechanical ventilation; and failing to initiate, reduction, or termination of use of vasoactive agents. In these and other exemplary embodiments, the guiding of medical care consistent with a relatively unhealthy gastric function includes providing medical advice relating to performance of at least one of: failing to initiate, reduction, or termination of enteral feeding; initiation, maintenance, or increase of mechanical ventilation; and initiation, maintenance, or increase of use of vasoactive agents.

However, the above disclosures are not intended to constitute a complete list of types of medical care that can be guided based on results of the disclosed stress test. For example, in other exemplary embodiments, the type of medical care to be guided includes at least one of: 1) applicability of enteral feeding, ventilation, or use of vasoactive agents; 2) patient disposition within a medical care facility; 3) detection of risk of stress ulcers; and 4) adequacy of resuscitation. In still other exemplary embodiments, the guiding of medical care includes providing medical advice relating to at least one of: determining patient disposition within a medical care facility; determining adequacy of resuscitation; detecting risk of developing stress ulcers; guiding usages of suppressants to reduce risk of stress ulcers and/or bleeding; determining risk of aspiration and guiding care to reduce such risk; aiding detection of intra-abdominal hypertension and/or abdominal compartment syndrome; and monitoring of gastric motility to reduce gastric residuals and risk of aspiration. Some of these embodiments include other applicable tests and measurements to enhance the guidance of care. One such embodiment continuously measures the patient's esophageal pH to determine reflux events and risk of aspiration, and then provides advice relating to at least one of patient positioning, acid suppressant medication, and enteral feeding route, based on the determined likelihood of aspiration.

2. Pharmacological Challenge Agents

Exemplary embodiments are intended to cover administration of any applicable pharmaceutical challenge agent, such as any gastric system stress agent, including but not limited to gastric acid stimulants and suppressants. Some exemplary embodiments administer pentagastrin as a stimulant, and/or omeprazole as a suppressant.

a. Determining Type of Pharmacological Challenge Agent

Exemplary embodiments are intended to cover any applicable method of determining the type of gastric acid stimulant or suppressant to be administered. Some exemplary embodiments determine the type of gastric acid stimulant or suppressant based on baseline gastric juice pH. Other exemplary embodiments determine the type of gastric acid stimulant or suppressant to be administered based on patient characteristics, including at least one of: age, gender, fitness, weight, body composition, percentage of body fat, ethnicity, family history, personal medical history, and genetics.

b. Determining Dosage

Exemplary embodiments are intended to cover any applicable method of determining dosage, such as a pharmaceutically effective dosage, of the pharmaceutical challenge agent, such as gastric juice stimulant or suppressant. For example, some exemplary embodiments determine the pharmacologically effective dosage of gastric acid stimulant or suppressant based on the type of medical care to be guided. Other exemplary embodiments administer a set dosage of stimulant or suppressant. In one such embodiment, 6 mcg/kg of pentagastrin is administered.

In other exemplary embodiments, the determination of the pharmacologically effective dosage of gastric acid stimulant or suppressant is based on patient characteristics, including at least one of age, gender, fitness, weight, body composition, percentage of body fat, ethnicity, family history, personal medical history, and genetics. In some of these embodiments, the pharmacologically effective dosage of gastric acid stimulant (such as pentagastrin) or suppressant (such as omeprazole) is determined based on patient weight. As an example of this weight based dosing, one embodiment determines dosages such that: 250 mcg is determined to be the pharmacologically effective dosage for patients weighing 40-70 kg, 500 mcg is determined to be the pharmacologically effective dosage for patients weighing 71-100 kg, and 750 mcg is determined to be the pharmacologically effective dosage for patients weighing more than 100 kg. In another embodiment, the pharmacologically effective dosage of pentagastrin is based on 6 mcg/kg, such that 300 mcg is determined to be the pharmacologically effective dosage for a patient weighing 50 kg, 450 mcg is determined to be the pharmacologically effective dosage for patients weighing 75 kg, and 600 mcg is determined to be the pharmacologically effective dosage for patients weighing 100 kg.

Exemplary embodiments are also intended to cover issues involving dosing other than determining a pharmaceutically effective dose. For example, some exemplary embodiments determine a maximum dosage of gastric acid stimulant or suppressant, such that a dosage of gastric acid stimulant or suppressant is administered that does not exceed the maximum dosage. Exemplary embodiments are intended to cover any manner of determining the maximum dosage. In some embodiments, the maximum dosage is determined based on potentially disadvantageous side effect reduction.

Exemplary embodiments are intended to cover any applicable manner of introduction of the pharmacological challenge agent, such as gastric acid stimulant or suppressant. Exemplary embodiments also cover tailoring the manner of administration of the gastric acid stimulant or suppressant. In one embodiment, the manner of introduction of gastric acid stimulant or suppressant is determined based on whether a gastric acid stimulant or a gastric acid suppressant is administered. In other words, the fact that a stimulant or suppressant is used determines the manner of administration. In one such embodiment, gastric acid stimulants are administered subcutaneously, while gastric acid suppressants are administered intravenously.

c. Manner of Administration

In other exemplary embodiments, the manner of introduction of gastric acid stimulant or suppressant is determined based on patient characteristics, including at least one of: age, gender, fitness, weight, body composition, percentage of body fat, ethnicity, family history, personal medical history, and genetics. In one such embodiment, the manner of introduction is tailored such that gastric acid stimulant is administered intravenously for patients with relatively poor peripheral circulation.

3. Period Separating Agent Administration and Stress Measurement

Exemplary embodiments are intended to cover any applicable period separating pharmacological challenge agent (such as gastric acid stimulant or suppressant) administration and the measuring of the patient's gastric juice pH, gastric juice volume, gastrointestinal motility, etc., to determine stressed pH, volume, motility, etc. Some exemplary embodiments set a standard period between the administering of the gastric acid stimulant or suppressant and the measuring of the patient's gastric juice pH, volume, motility, etc., to obtain the stressed gastric juice pH, volume, motility, etc. In one such embodiment, the standard period is approximately 45 minutes, such that approximately 45 minutes always separates the gastric acid stimulant or suppressant administration and the measuring of gastric juice pH, volume, motility, etc. to obtain the stressed gastric juice pH, volume, motility, etc.

4. Aspiration

Exemplary embodiments are intended to cover any applicable manner of facilitating and/or enhancing accuracy of gastric juice pH measurements. For example, some exemplary embodiments aspirate gastric contents prior to the measuring of the patient's gastric juice pH to obtain a stressed gastric juice pH to provide enhanced results, such as to enhance freshness of gastric juice for measurement. In other words, some exemplary embodiments aspirate the gastric contents in an effort to remove gastric contents secreted prior to gastric response to the pharmacological challenge agent so that the gastric contents measured reflect those contents secreted as a result of the challenge agent. In one such embodiment, the aspiration of the gastric contents is performed after the administration of the gastric acid stimulant or suppressant, but of course prior to the measuring of the stressed gastric juice pH. In this exemplary embodiment, the aspiration can be performed approximately 15 minutes prior to the measuring of the stressed gastric juice pH.

5. pH Differential

Exemplary embodiments are intended to cover any beneficial usage of pH differentials to indicate gastric system health. Some exemplary embodiments set a standard pH differential as indicating a healthy gastric system for all patients, while other embodiments use various criteria to vary the pH differential sufficient to indicate healthy gastric function. One such embodiment measures the volume of the patient's gastric juice secreted after the stimulant or suppressant administration, and sets a guidance pH differential sufficient to indicate healthy gastric function based on the measured gastric volume. In other words, the guidance pH differential sufficient to indicate healthy gastric function varies depending on the volume of the patient's gastric juice secreted after the stimulant or suppressant administration. The guidance pH differential sufficient to indicate healthy gastric function can be set to be relatively lower if the measured gastric volume is relatively high, or set to be relatively higher if the measured gastric volume is relatively low. A relatively healthy gastric function can be determined if the calculated pH differential equals or exceeds the guidance pH differential, or a relatively unhealthy gastric function can be determined if the calculated pH differential is less than the guidance pH differential.

6. Additional Tests and Measurements

Exemplary embodiments are intended to cover additional tests conducted subsequent to any and all of the disclosed tests based on pH differential, gastric juice volume, gastrointestinal motility, etc., that enhance the guidance of medical care. In some embodiments that guide care to include enteral feeding, the patient's gastric juice pH is measured after initiation of enteral feeding to obtain a post-feeding gastric juice pH, and medical care is guided based on the post-feeding gastric juice pH. In one such embodiment, care is guided to include providing advice to maintain or increase the rate of nutrition if the post-feeding gastric juice pH is less than or equal to the stressed gastric juice pH, or providing advice to decrease the rate of nutrition if the post-feeding gastric juice pH is greater than the stressed gastric juice pH.

Other exemplary embodiments that involve tests conducted subsequent to the disclosed tests based on pH differential, gastric juice volume, gastrointestinal motility, etc., performing multiple measurements of the patient's gastric juice pH after obtaining the stressed gastric juice pH, and displaying the multiple measurements. The multiple pH measurements can be displayed as a curve via a graph, with the x-axis representing the time that the pH measurements were taken and the y-axis representing pH values.

Exemplary embodiments are intended to cover any applicable and beneficial usages and applications of the displayed pH measurements disclosed above. For example, some exemplary embodiments calculate the area defined under the curve, and provide medical advice based on the calculated area. One such embodiment determines the rate of change of the multiple pH measurements via the derivative of the curve, and provides medical advice based on the determined rate of change, such that a relatively fast rate of change indicates a relatively healthy gastric function, while a relatively slow rate of change indicates a relatively unhealthy gastric function. Another embodiment determines the period for reaching the pH low point via the second derivative of the curve, and provides medical advice based on the determined period, such that a relatively short period indicates a relatively healthy gastric function, while a relatively long period indicates a relatively unhealthy gastric function.

Yet another embodiment stores the curve data representing the multiple pH measurements as a function of time and patient profile data including at least one of age, gender, fitness, weight, body composition, percentage of body fat, ethnicity, family history, personal medical history, and genetics, compares the stored curve to curves of multiple patients with similar profiles, and provides medical advice based on the comparison. The comparing can include calculating differences between data points and the curve using the total non-linear least squares data modeling technique. Medical advice can be provided based on responses to medical care of patients with similar profiles and/or gastric contents volume measurements. Alternatively, medical advice can be provided based on algorithms that receive data relating to at least one of pH measurements, gastric contents volume measurements, and patient profile, and recommend certain medical treatments based on the data. The algorithms can be based on non-linear regression analysis, can have artificial intelligence capabilities, or can take any other applicable or beneficial form.

Other exemplary embodiments involve tests conducted prior to, during, or subsequent to, the disclosed tests based on pH differential, gastric juice volume, gastrointestinal motility, etc. One such embodiment determines an angle of incline of the patient laying on a bed or table, the angle being defined by a line, extending from the patient's sternal notch to umbilicus, and a surface on which the bed or table rests. Medical care can then be guided based on the determined angle of incline.

These and other features and advantages are described in, and will be apparent from, the following detailed description of various exemplary embodiments.

BRIEF DESCRIPTION OF THE DRAWINGS

Various exemplary embodiments are described in detail with reference to the following figures, wherein.

DETAILED DESCRIPTION

Figure 1:
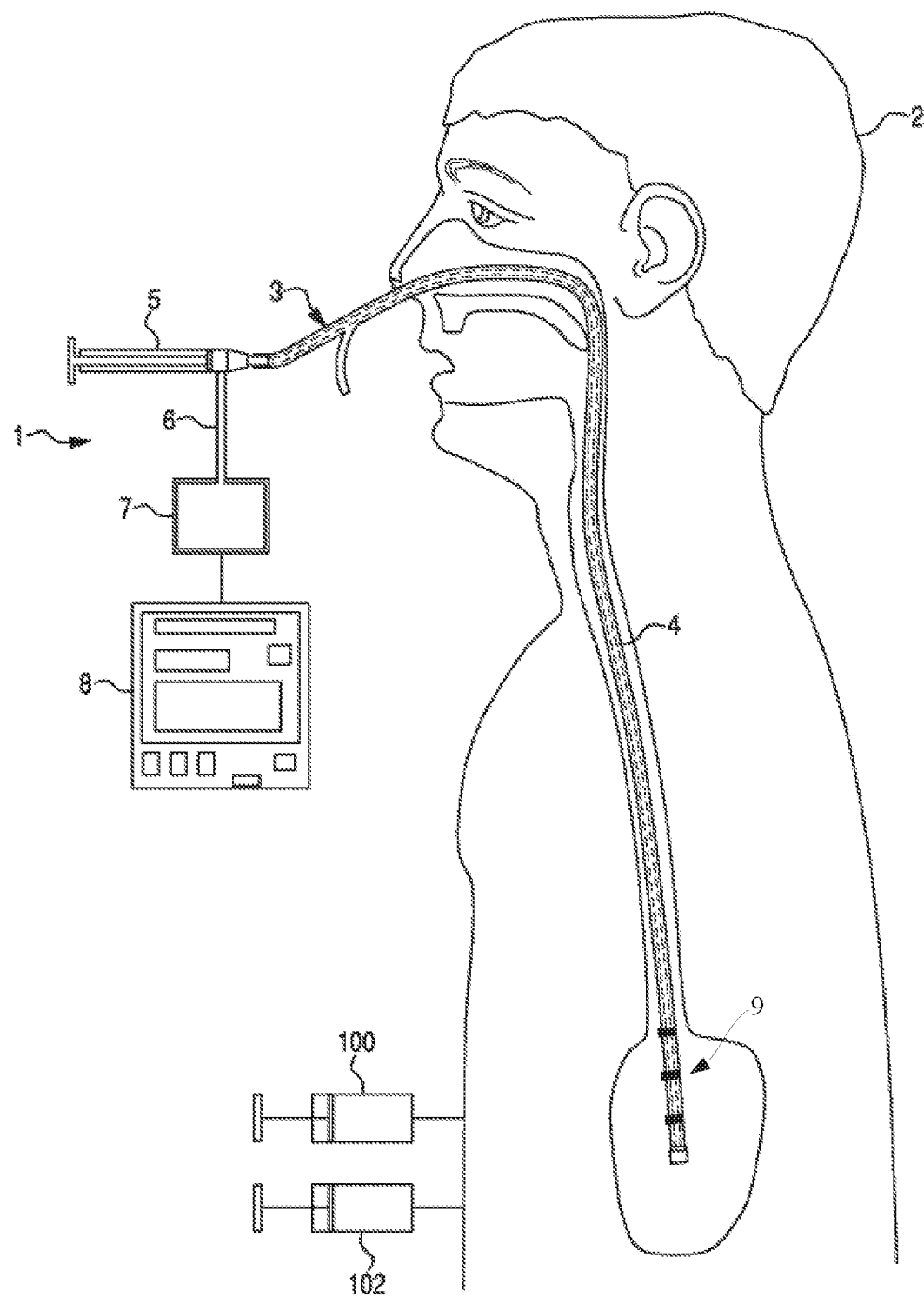
FIG. 1 is a schematic of an apparatus in accordance with an exemplary embodiment.

For convenience of explanation, exemplary embodiments are described below with reference to the figures in the context of guiding medical care of human patients based on detected gastric function. However, the specifically disclosed embodiments are not intended to be limiting and are merely provided for exemplary purposes. For example, all embodiments are intended to be used in any applicable field of endeavor, such as care of non-human patients including but not limited to animals, less complex organisms, chemical or pharmaceutical production, etc.

A table of contents of exemplary embodiments specifically disclosed in the Detailed Description is provided below.

I. Overview
  A. General Procedure
  B. Exemplary Uses of the Procedure
  C. Exemplary Recipients of the Procedure II. Types of Pharmaceutical Challenge Agents (Stimulants/Suppressants)
  A. Use of Stimulant Versus Suppressant
    1. Automatic Use of Stimulant or Suppressant
    2. Based on Baseline Gastric Juice pH
    3. Ambiguous Results
  B. Stimulant Administration in Patients with Relatively Low Gastric Juice pH
    1. Sodium Citrate
    2. Sodium Bicarbonate
    3. Gastric Acid Suppressant
    4. Administrating Neutralizing Agent Prior to Measuring Baseline Gastric Juice pH
  C. Exemplary Stimulants
    1. Pentagastrin
    2. Stimulant Selection Methodologies
    3. Other Exemplary Stimulants
  D. Exemplary Suppressants
    1. Omeprazole and Ranitidine
    2. Suppressant Selection Methodologies III. Dosages and Administrations of Pharmacological Challenge Agents (Stimulants/Suppressants/Acid Neutralizers)
  A. Dosages
  B. Administrations
  C. Vial Size IV. Gastric Juice H+/pH Measurement, Determining GI Tract's Response to Challenge, and Guiding Care Based on Measured H+/pH
  A. Timing of Gastric Juice H+/pH Measurement
  B. Exemplary Methods and Apparatus for Determining Gastric Juice H+/pH
    1. Gastric Juice Obtaining/Sampling Device
    2. H+/pH Measuring Device
    3. Enhanced pH Measurements
    4. Calibration
    5. Other Exemplary Embodiments
  C. Methods and Apparatus for Determining GI Tract's Response to Challenge and Guiding Care Based on Determined H+/pH
    1. Gastric Juice H+/pH Data Interpretation
      a. Gastric Juice pH Differential
      b. Gastric Juice H+ Concentration Differential
      c. Gastric Juice pH, H+ Concentration, and Volume
      d. Gastric Juice pH, H+ Concentration, and Volume Trending
      e. Gastric Juice pH, H+ Concentration, and Volume Algorithms
    2. Spectrum of Intensities of Care
    3. Gastric Juice pH Indicator/Controller
      a. Dedicated Inputs/Outputs
      b. Touchscreen Display
      c. Incline Controller
      d. Other Exemplary Structures and Operations
  D. Exemplary Packaging of Equipment
    1. Kit
    2. Processor
    3. Computer Program V. Other Exemplary Types of Enhanced Care
  A. Disposition of Patients Within a Hospital
  B. Adequacy of Resuscitation
  C. Detection of Risk for Stress Ulcers
  D. Detection of Effect of Acid Suppressant Medication
  E. Detection of Risk of Aspiration of Gastric Contents
  F. Gastric Residual Volume Monitoring
  G. Detection of Gut Ischemia in Intra-abdominal Hypertension H. Drug Absorption
I. Enteral Tolerance
J. Combination of Methodologies in Guiding Care
K. Exemplary Processes and Devices in Guiding Care
VI. Other Diagnostic Methodologies
  A. Gastric Perfusion
    1. Pulse Oximetry
    2. Near Infrared Spectroscopy
  B. Gastric Volume
  C. Motility
  D. Combination of Methodologies
VII. Other Therapeutic Exemplary Embodiments
  A. Feeding Intolerance I. Overview A. General Procedure Exemplary embodiments generally relate to guiding medical care based on detected gastric function. For example, an amount, such as an effective dose, of a pharmacological challenge agent, such a gastric acid stimulant or suppressant, is administered, and then a change, such as an acute change, in the gastric juice pH is measured.

In some exemplary embodiments, patients demonstrating significant or sufficient change in gastric juice pH may have their medical care normalized in an accelerated fashion, while those not responsive may not, and may even require more support. However, in some situations, such as with patients failing to demonstrate an acute change in gastric juice pH over a prolonged period, other exemplary embodiments include cautiously initiating enteral feeding. For example, in these exemplary embodiments, enteral feeding is initiated at a slow rate and closely monitored to quickly recognize any negative side effects that would warrant cessation of the enteral feeding. However, the above disclosure is merely provided for exemplary purposes, and other embodiments may be significantly different. For example, some exemplary embodiments do not even monitor gastric juice pH, and instead employ other methodologies, such as monitoring gastric volume. In fact, exemplary embodiments are intended to cover any method of assessing gastric function.

B. Exemplary Uses of the Procedure

The ability of the gastric cells to respond to a pharmacological challenge, such as the one disclosed above, is a good indicator of the perfusion and function of the gastrointestinal tract. In contrast to related art pharmacological tests for use in the diagnoses of specific chronic illnesses and rare endocrine disorders, the exemplary embodiments relate to the use of this challenge test to guide the care of patients suffering from a wide variety of illnesses. These illnesses include, and are not limited to, acute critical illnesses, and also include illnesses related to or unrelated to the gastrointestinal tract. Exemplary embodiments can also be used for patients who are subjected to a wide variety of treatments, including those directly related to the gastrointestinal tract as well as those unrelated to the gastrointestinal tract. For example, exemplary embodiments can allow for the monitoring of organs unrelated to gastric acid secretion or suppression per se.

Thus, exemplary uses of this test may include assessing gastrointestinal perfusion and/or gastric function in order to (among other things): 1.) guide the decision to extubate and/or wean a patient from mechanical ventilation (i.e. decrease ventilating support), or to increase ventilating support; 2.) guide the decision to initiate, increase, terminate, or wean enteral feeding; 3.) guide the decision to initiate, increase, terminate, or wean vasoactive agents; 4.) guide decisions relating to care (including critical care) options based on the adequacy of resuscitation; 5.) guide usages of acid suppressants to more effectively manage the risk of stress ulcers and/or bleeding; 6) determining risk of aspiration and guiding care to reduce such risk; 7.) aiding detection of intra-abdominal hypertension and/or abdominal compartment syndrome; and/or 8.) monitoring of gastric motility to reduce gastric residuals and risk of aspiration. However, as disclosed above, exemplary embodiments are not limited to these uses and can cover other uses not specifically described herein, such as those directly related to gastric function as well as those not directly related to or even completely unrelated to the gastric function.

C. Exemplary Recipients of the Procedure

Any patient with an acute or other illness may be subjected to and/or benefit from the above exemplary procedure. As an example, patients receiving care in an ICU or similar setting following surgery, injury, trauma, or acute medical illness, are likely candidates. In particular, patients with acute organ failure are at risk for inadequate gastrointestinal perfusion and dysfunction and are candidates for use of this method. Patients for whom decisions need to be made regarding either initiating, terminating, weaning, or otherwise modifying enteral feeding vasoactive agents, mechanical ventilation, acid suppressants, and/or motility agents, may benefit from the use of the disclosed method. These patients face acute medical situations, in which their condition may be changing and appropriate changes in medical treatment may be required.

However, exemplary embodiments are not limited to the above exemplary patients. For example, exemplary embodiments may be applicable to people who are not subjected to critical care. Exemplary embodiments may be applicable to non-ICU patients at a hospital, patients at a nursing home (such as at an assisted living facility, for example). However, the disclosed procedures can also be used for patients who are not even hospitalized. Exemplary embodiments are intended to cover apparatus and methods performed outside of a professional care facility, and may even be performed by the patient himself/herself. In fact, exemplary embodiments are not even limited to human patients and can be performed on animals, such as pets, zoo animals, etc., or even less complex organisms.

II. Types of Pharmacological Challenge Agents (Stimulants/Suppressants)

Exemplary embodiments are intended to cover and include any currently known or later developed methods, apparatus, compositions, etc., that challenge a patient's gastrointestinal (GI) tract or otherwise enable assessment of gastric function. For example, exemplary embodiments can include, but are not limited to, pharmacological challenge agents, such as any one or more currently known or later developed gastric acid stimulants or suppressants. Any one of multiple conditions of the patient, such as gastric juice pH, gastric volume, etc., can be monitored before and after administration of the pharmacological challenge agent (such as gastric acid stimulant or suppressant) to assess gastric function. Patient care, such as initiating, terminating, or otherwise modifying ventilation, enteral feeding, use of vasoactive agents, use of acid suppressants, and/or use of motility agents, for example, can then be performed based on this gastric function assessment.

Exemplary uses of gastric acid stimulants and suppressants are discussed below for exemplary purposes only. As discussed above, other exemplary embodiments are intended to cover any method of assessing gastric function and can include methods that do not include use of gastric acid stimulants and suppressants.

A. Use of Stimulant Versus Suppressant

Exemplary embodiments that assess gastric function by using gastric acid stimulants and/or suppressants are intended to cover and include use of either gastric acid stimulants or suppressants, as well as use of both stimulants and suppressants. In other words, some embodiments include use of only stimulants, while others include use of only suppressants, and still others include use of both stimulants and suppressants.

1. Automatic Use of Stimulant or Suppressant

The use of a stimulant versus a suppressant can be automatically determined, such as via automatic protocols. For example, a stimulant may always be used in some exemplary embodiments, while other exemplary embodiments may always use a suppressant. Exemplary embodiments that always use a stimulant or always use a suppressant can be beneficial because of simplicity. In other words, methods in accordance with these exemplary embodiments are easy to perform because there is no analysis as to whether a stimulant or suppressant is to be used, which may be beneficial by reducing performance errors, increasing speed of performance, etc.

As one exemplary alternative to always using a stimulant or always using a suppressant, the use of a stimulant or suppressant can be dictated based on one or more patient characteristics. These patient characteristics can include one or a combination of factors, including but not limited to: age, gender, fitness, weight, body composition such as percentage of body fat, ethnicity, family history, personal medical history, genetics, or any other factor currently known or later determined to be relevant or applicable.

2. Based on Baseline Gastric Juice pH

However, still other exemplary embodiments can include an analysis as to whether a benefit may be achieved via use of a stimulant verses a suppressant (or acid neutralizer), and vice versa, to ultimately assess gastric function. Exemplary embodiments are intended to cover and include any methods and apparatus for making this determination. For example, this determination can be made based on the detected baseline gastric juice pH. It may be beneficial to use a gastric acid stimulant if the baseline gastric juice pH is greater than a certain amount, such as 2.5 pH units or in some cases 3 pH units. Alternatively, it may be beneficial to use a gastric acid suppressant if the baseline gastric juice pH is less than a certain amount, such as 2.5 pH units and in some cases 3 pH units. In other words, a relatively high baseline gastric juice pH may, under certain circumstances, make it beneficial to use a gastric acid stimulant, while a relatively low baseline gastric juice pH may warrant a gastric acid suppressant or use of an acid neutralizer before the stimulant is used.

If the baseline gastric juice pH is very low, e.g., 1 or 2 pH units, then even in the presence of good gastric function, it will be difficult (or unlikely) to detect a significant decrease in pH in response to the stimulant. This difficulty relates to the fact that pH is a LOG function, and thus the amount of acid needed for the pH to decrease from 2 to 1 is much greater than the amount of acid needed for the pH to decrease from 6 to 5. In cases with very low baseline gastric juice pH, it may be desirable to use a gastric acid suppressant in the test and assess for an increase in gastric juice pH. Alternatively, and as discussed in more detail below in section II(B), the baseline gastric juice pH can be increased by administering an acid suppressant (e.g., H2 blocker) or acid neutralizer (e.g., sodium citrate), and then administering an acid stimulant for the test using the new (and higher) baseline gastric juice pH, e.g., pH of 2.5, 3, 4 pH units, or higher.

The above embodiment is only provided as one example and is not intended to be limiting. For example, other factors can be used to dictate usage of a gastric acid stimulant versus a suppressant, including but not limited to patient characteristics, such as one or any combination of factors, including but not limited to: age, gender, fitness, weight, body composition such as percentage of body fat, ethnicity, family history, personal medical history, genetics, or any other factor currently known or later determined to be relevant or applicable.

3. Ambiguous Results

A positive signal indicating a healthy gastric function may be manifested by a change in several pH units from the baseline value, although a change of 1.0 pH unit in response to the challenge agent is usually indicative of a positive signal. A change of 1 pH unit typically unambiguously indicates a relatively healthy gastric function because, as discussed above, gastric acid production measured in pH units is a LOG function. Therefore, a decrease in "only" 1 pH unit corresponds to a 10 fold change, e.g., 1000 percent increase, in the hydrogen ion concentration.

However, failure to demonstrate a change of 1 pH unit or more does not necessarily indicate an unhealthy gastric function for use to guide medical care as disclosed above. Thus, exemplary embodiments are directed to situations in which the differential between the baseline and stressed pH tests is less than one.

In accordance with one such exemplary embodiment, after an ambiguous test (resulting in a pH differential of less than 1 pH unit), the test is repeated with the opposite pharmacological agent. For example, if stimulant (such as pentagastrin) is initially used and yields a negative response (failing to demonstrate an acute change in gastric juice pH, such as a change of 1 pH unit), a challenge test is subsequently conducted with a suppressant (such as with omeprazole). In this case, it may be beneficial to allow for at least 1-3 hours in between tests. This exemplary embodiment may be particularly applicable in situations where the baseline pH itself is moderately low, such as 2.0-3.0 pH units.

For patients continuing to fail to demonstrate an acute change in gastric juice pH for an extended period, it may be beneficial to conduct a pharmacological challenge once every 1-3 days, although more frequent measurements can be made if deemed useful. If the patient is receiving enteral nutrition, it may be preferable to discontinue feeding for several hours (e.g., 2 hrs.) prior to a pharmacological challenge. Alternatively, one can discontinue feeding immediately prior to the test but begin the test by first removing/aspirating all of the gastric contents (including enteral feeds) through the indwelling tube (e.g. nasogastric Salem Sump tube). At this point after a brief period of equilibration (e.g., 15 minutes), the baseline gastric pH can be determined and the pharmacological challenge initiated. This reduces, minimizes or prevents any confounding effect from the presence of significant quantities of residual enteral feeds or other gastric contents, e.g. gastric secretions.

B. Stimulant Administration in Patients with Relatively Low Gastric Juice pH

As indicated above in section II(A)(2) (Use of Stimulant Versus Suppressant/Based on Baseline Gastric Juice pH), it may be beneficial to use a gastric acid stimulant if the baseline gastric juice pH is greater than a certain amount, such as 2.5 or 3 pH units. Most critically ill patients typically have a gastric juice pH sufficiently high enough to allow for a reduction following administration of the gastric acid stimulant, e.g., pentagastrin. Thus, a gastric acid stimulant can typically be used as the pharmacological challenge agent.

However, some patients have a relatively low baseline gastric juice pH, such as less than 2.5 pH units. The exemplary embodiments discussed in section II(A)(2) above administer a gastric acid suppressant to perform the pharmacological challenge under these circumstances. However, alternatively, a pharmacological agent could be administered to raise the gastric juice pH to a sufficiently high level to enable measurement of gastric function challenge with a gastric acid stimulant.

Thus, exemplary embodiments are intended to cover additional steps to enable usage of stimulants for patients evidencing a lower baseline gastric juice pH. For example, for patients evidencing a relatively low baseline pH, such as less than 2.5 pH units, an additional step of neutralizing the pH in the stomach can be performed by administering a small dose/volume of concentrated buffer/base into the stomach, such as through an indwelling tube with access to the stomach. e.g., commonly a nasogastric or orogastric tube.

FIG. 1 shows an exemplary administering device 102 that administers to a patient the pharmacological agent to raise the gastric juice pH to a sufficiently high level to enable measurement of gastric function challenge with the gastric acid stimulant. However, the administering device 102 shown in FIG. 1 is not intended as limiting, and as discussed above, exemplary embodiments are intended to cover any currently known and later developed methods and apparatus for introducing the pharmacological agent. For example, the exemplary administering device 102 shown in FIG. 1 is not intended as limiting with regard to structure of the device, manner of administration, location on the patient of administration, etc.

1. Sodium Citrate

For example, if the baseline gastric juice pH is low (e.g., less than or equal to 2.5 pH units), 5-30 ml (½ to 1 ounce) of a 0.3 mole/L commercially available non-particulate antacid (e.g., sodium citrate) can be administered via the NGT or OGT, and the gastric juice pH can be measured at a later time, such as in 5 minutes. This administration should increase the gastric juice pH in most patients and may allow for a more reliable determination of pentagastrin (or other stimulant) induced gastric acid stimulation. If the above antacid administration is not sufficient, then an additional dose of this antacid can be administered to attain a higher gastric juice pH, such as pH of at least 4 pH units prior to challenging the patient with gastric acid stimulant.

Many over-the-counter antacids are particulate. The administration of a particulate antacid is not as desirable since if it gets into the lungs, e.g., after aspiration of gastric contents, it can cause toxicity. For this reason, in situations of low baseline gastric pH it is preferable to raise the pH with a non-particulate antacid such as sodium citrate or sodium bicarbonate (describe above) since this will minimize the risk of aspiration in hospitalized patients who are already at increased risk of aspiration of gastric contents.

Table 2 (below), as disclosed in Gibbs, Charles P., Lynn Spohr, and Donald Schmidt. *The Effectiveness of Sodium Citrate as an Antacid*. Rep. no. 57:44-46, 1982. Ed. Ronald D. Miller. American Society of Anesthesiologists. Print., hereafter "Gibbs," which is hereby incorporated in its entirety herein by reference, shows that 30 ml of 0.3 M sodium citrate can neutralize up to 255 ml of acid (pH 1.0). This disclosure is particularly relevant to the above analysis because gastric volume of a patient is typically less than 200 ml in the fasted state.

TABLE 2

Volume (ml) of HCI (pH 0.8, 1.0, and 1.5) Neutralized by 30 ml 0.3M Sodium Citrate Kolantyl Gel ®, and Mylanta ®

| | Hydrochloric Acid pH | | |
|---|---|---|---|
| | 0.8 | 1 | 1.5 |
| Sodium Citrate (8.5) | 140 | 255 | 750 |
| Kolantyl Gel ® (8.1) | 100 | 160 | 360 |
| Mylanta ® (8.0) | 75 | 100 | 300 |

Figure 3:
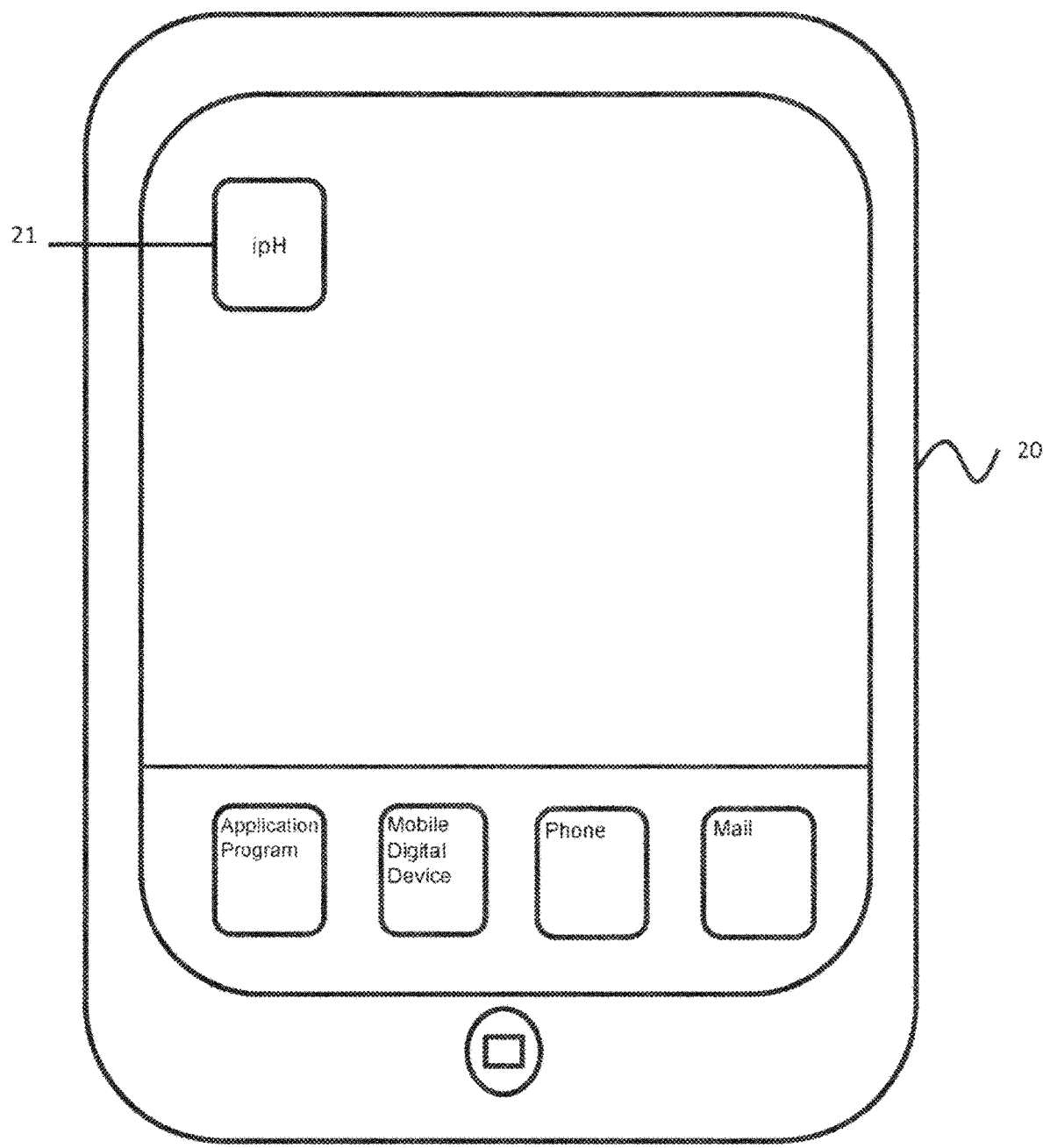
FIG. 3 is a schematic of an indicator/controller in accordance with another exemplary embodiment.

In another example, Atanassoff, Peter G., Roman Rohling, Eli Alon, and Sorin J. Brull. "Effects of Single-dose Oral Ranitidine and Sodium Citrate on Gastric PH during and after General Anesthesia." *Canadian Journal of Anesthesia* 42.5 (1995): 382-86. Print., hereafter "Atanassoff (1995)," which is hereby incorporated in its entirety herein by reference, studied the effects of sodium citrate on gastric juice pH. The gastric juice pH in elective surgical patients was (mean±SEM) 1.2±0.1, at baseline prior to the administration of sodium citrate. Sodium citrate (50 ml of 0.3 M) administered into the stomach via a nasogastric tube significantly increased the gastric juice pH to a mean of 4.8 (range 6.7-7.0) within two minutes of administration. FIG. 3 of this publication demonstrates that gastric juice pH was well maintained above 6 for at least 2 hours after administration.

In another example, Dewan, David M. "Sodium Citrate Pretreatment in Elective Cesarean Section Patients." *ANESTH ANALG* 64.34 (1985): 382-86. Print., hereafter "Dewan," which is hereby incorporated in its entirety herein by reference, reported that administration of 30 ml of 0.3 M sodium citrate resulted in a significant increase in gastric juice pH when used as pretreatment in elective cesarean section patients. These and other publications report effectiveness of sodium citrate to increase gastric juice pH, and in particular prior to surgery requiring general anesthesia. For this reason, sodium citrate is administered to many patients prior to general anesthesia to reduce the risk of possible aspiration with acidic gastric contents.

2. Sodium Bicarbonate

As an alternative to sodium citrate, sodium bicarbonate, which is an FDA approved and commercially available drug typically available in ICUs, can be used to raise the gastric juice pH to a sufficiently high level to enable measurement of gastric function with a gastric acid stimulant. For example, 8.4% sodium bicarbonate (50 ml vial) (such as is disclosed in "Hospira Sodium Bicarbonate Injection 8.4% 50 Ml Vials—Mountainside Medical Equipment." *Medical Supplies|Medical Equipment|Hospital Medical Supplies|Hospital Equipment*. Web. 2 Jun. 2011. <http://www-.mountainside-medical.comiproducts/Sodium-Bicarbonate.html>., hereafter "Hospira," which is hereby incorporated in its entirety herein by reference), can be used. In particular, 5 mls of this 8.4% solution can be administered into a patient's stomach at least 15 minutes prior to baseline measurement of gastric juice pH and administration of stimulant, such as pentagastrin. Approximately 5 ml of this drug is adequate to neutralize 50 ml of gastric juice that has a pH of 1.0 unit.

As an alternative to this procedure, 1 ml of this sodium bicarbonate buffer solution can be administered every 10 minutes, checking the pH after each administration and continuing until the pH rises to at least 3 units. As a further alternative, 15 ml of a 0.3 ml of a 0.3 M solution of sodium citrate can be administered every 10 minutes, checking the pH after each administration and continuing until the pH rises to at least 3 units. These exemplary embodiments involve simple titration of acid with a base, such as known base, such as is disclosed in "Neutralization (chemistry)." *Wikipedia, the Free Encyclopedia.* Wikimedia Foundation, Inc., 13 Apr. 2011. Web. 13 Apr. 2011. <http://en.wikipedia.org/wiki/Neutralization_(chemistry)>., hereafter "Neutralization (chemistry)" which is hereby incorporated in its entirety herein by reference. This disclosure explains that, in chemistry, neutralization is a chemical reaction whereby an acid and a base react to form a salt, and discloses an application in which excess gastric acid in the stomach (acid indigestion) is typically neutralized by the ingestion of sodium bicarbonate (NaHCO3) or another neutralizing agent, such as an antacid.

3. Gastric Acid Suppressant

As an alternative to using the above compositions that neutralize the gastric juice pH in the stomach in situations involving low baseline gastric juice pH, such as a pH of less than 2.5 or 3.0 units, a gastric acid suppressant (e.g., ranitidine 50 mg IV) can be administered. Based on the pharmacokinetics and pharmacodynamics effects of ranitidine, this administration should increase the gastric pH over the next several hours after administration. For example, at four hours after administration of IV ranitidine, the gastric juice pH should be sufficiently high (e.g., at least 2.5, 3.0, or 4.0 pH units) to enable measurement of gastric function challenge with a gastric acid stimulant, such as pentagastrin.

For example, Atanassoff. Peter G., Eli Alon, and Thomas Pasch. "Effects of Single-Dose Intravenous Omeprazole and Ranitidine on Gastric PH During General Anesthesia." *ANESTH ANALG* 75.95 (1992): 95-98. Print., hereafter "Atanassoff (1992)," which is hereby incorporated in its entirety herein by reference, discloses effects of ranitidine or omeprazole on gastric juice pH in patients. As shown in Atannasof's FIG. 2, intravenous administration of ranitidine (50 or 100 mg) increased the gastric juice pH from approximately 1.5 to at least 3.5 after a median of 43 and 48 min, respectively. Similar results were observed after intravenous administration of omeprazole in this study (such as FIG. 1).

In another example, Baak, L. C., J. B. Jansen, and C. B. Lamers. "Repeated Intravenous Bolus Injections of Omeprazole: Effects on 24-Hour Intragastric PH, Senim Gastrin, and Serum Pepsinogen A and C." *Scand J Gastroenterol* 26 (1991): 737-46. Print., hereafter "Baak," which is hereby incorporated in its entirety herein by reference, discloses that the baseline median gastric juice pH in study subjects was 1.4 (range, 1.0-1.7). After administration of intravenous omeprazole, gastric juice pH increased from less than 2 at Baseline to greater than 5 within 1.5 hours. These data indicate that omeprazole could be administered to patients with low baseline gastric juice pH in order to temporarily increase gastric juice pH to a more optimal level for testing with pentagastrin or another potent gastric acid stimulant. These data also indicate that the acid inhibitory effect of the omeprazole wanes over time, thereby allowing testing with a potent acid stimulant (e.g., pentagastrin 6 mcg/kg) with a low likelihood of a false negative result.

The above exemplary embodiment thereby uses a gastric acid suppressant to raise gastric juice pH to a level sufficiently high to enable challenge with a gastric acid stimulant, such as pentagastrin. This exemplary procedure is thereby different from the procedure in section II(A) (Use of Stimulant versus Suppressant), wherein gastric function is determined based on sufficiency of response to administration of a gastric acid suppressant.

4. Administering Neutralizing Agent Prior to Measuring Baseline Gastric Juice pH Another exemplary embodiment takes more of an active or preventative approach to the issue of stimulant administration in patents with a relatively low gastric juice pH. For example, a pharmacological agent, such as any of the agents disclosed above, can be initially administered prior to measuring the patient's gastric juice pH. This alternative exemplary embodiment may be advantageous by ensuring, or at least increasing the likelihood, that the patient's baseline gastric juice pH will be sufficiently high to enable use of gastric acid stimulant (such as pentagastrin) to assess gastric function.

C. Exemplary Stimulants

1. Pentagastrin

Any currently known or later developed gastric acid stimulant can be used in accordance with the disclosed exemplary embodiments. It may be beneficial in certain exemplary embodiments to use pentagastrin under certain circumstances. Pentagastrin is a synthetic pentapeptide that contains the carboxyl terminal tetrapeptide responsible for the actions of natural gastrins, and its most prominent action is in the stimulation of gastric acid secretion. In many patients, pentagastrin stimulates gastric acid secretion approximately 10 minutes after subcutaneous, intramuscular, or intravenous injection, with peak response occurring in most cases 20-30 minutes after administration. The duration of activity of pentagastrin in most patients is usually between 60-80 minutes. In addition, pentagastrin has a short half-life of approximately 10 minutes.

A potentially beneficial route of administration of gastric acid stimulant, such as pentagastrin, is subcutaneous, although any alternative route, e.g., intravenous, intramuscular, oral, etc., may be acceptable. It may be beneficial to use any dosage of gastric acid stimulant that has minor, relatively minor, or no significant side effects, and that is effective at stimulating gastric acid secretion. However, it is possible to use a dosage and route of administration of the gastric acid stimulant causing significant side effects, depending on circumstances.

A typically beneficial dose of pentagastrin in most patients is equal to or approximately 6 micrograms/kg for subcutaneous administration. For example, Isenberg, Jon I., Morton I. Grossman, Vernon Maxwell, and John H. Walsh. "Increased Sensitivity to Stimulation of Acid Secretion by Pentagastrin in Duodenal Ulcer." Journal of Clinical Investigation 55 (1975): 330-37. Print, hereafter "Isenberg." which is hereby incorporated in its entirety herein by reference, discloses that gastric acid output (mEq/30 minutes), in response to different doses of pentagastrin, plateaus in the 2 to 6 mcg/kg range. Isenberg's disclosed relationship between pentagastrin dosage and acid production in 30 minutes is provided below.

| Pentagastrin Dosage | Acid Production in 30 Minutes |
|---|---|
| 0 mcg/kg | mean 1.9 mEq |
| 0.2 mcg/kg | mean 7.8 mEq |
| 2 mcg/kg | mean 13.6 mEq |
| 6 mcg/kg | mean 14.2 mEq |

However, as disclosed above, any stimulant that is beneficial can be used. In fact, even nutrition can be used in place of stimulant. For example, a patient may have a gastric juice pH of 4.0 with no, or a small amount of, nutrition. Nutrition can then be administered, such as 50 ml of liquid food that is typically used for enteral nutrition. e.g., osmolite 1 cal. This nutrition can be administered into the stomach via the mouth or a tube (such as a plastic tube and/or standard nasogastric tube). A transient increase in gastric juice pH may occur. However, a decrease in gastric juice pH (such as an acute decrease. e.g., 2.5 pH units) at a later time (such as approximately 45 minutes later) may indicate a positive response indicative of gastric perfusion sufficient for administration of enteral nutrition. This exemplary embodiment is particularly effective to determine gastric function because the administration of food, and in particular protein, into the stomach stimulates gastric acid secretion in a relatively healthy gut.

2. Stimulant Selection Methodologies

The use of a certain type of stimulant can be automatically determined, such as via automatic protocols. For example, a certain stimulant (such as pentagastrin) may always be used in some exemplary embodiments, while other exemplary embodiments may always use another specific stimulant. Pentagastrin is especially beneficial since its effects on gastric acid production have been well characterized, and it has a very good safety profile. In addition, its short half-life and duration of effect (less than 90 minutes) are desirable because of its speedy effect in the stimulation test, but then its short half-life enables its effects to quickly wear off without (or with minimal or minor) residual effects.

However, still other exemplary embodiments can include an analysis as to whether a benefit may be achieved via use of a certain type of stimulant. Exemplary embodiments are intended to cover and include any methods and apparatus for making this determination. For example, this determination can be made based on detected baseline gastric juice pH. It may be beneficial to use a certain stimulant after detection of a relatively high baseline gastric juice pH, while it may be beneficial to use a completely different stimulant after detection of a relatively low baseline gastric juice pH. However, other factors can be used to dictate usage of a specific stimulant, including but not limited to patient characteristics, such as one or any combination of factors, including but not limited to: age, gender, fitness, weight, body composition such as percentage of body fat, ethnicity, family history, personal medical history, genetics, or any other factor currently known or later determined to be relevant or applicable.

3. Other Exemplary Stimulants

As discussed above, the various methods and apparatus of the disclosed exemplary embodiments are intended to include any useful or beneficial type of stimulant. For example, some exemplary embodiments use pure gastrin, while other embodiments use the four-peptide version of gastrin, i.e., tetragastrin, and still other embodiments use histamine or betazole hydrocholoride.

In situations where acid secretory responses to the above stimulants are not significantly different, it may be beneficial to choose the appropriate stimulant to test gastric function based on safety, possibility of side-effects, availability, and/or cost. For example, large doses of histamine have been reported to produce severe hypotension, while orally administered betazole hydrocholoride has been reported to have few side effects.

D. Exemplary Suppressants

1. Omeprazole and Ranitidine

Any currently known or later developed acute acting gastric acid suppressant can be used. Exemplary gastric acid suppressants include proton pump inhibitors (e.g., omeprazole) and histamine H2 receptor antagonists (e.g., ranitidine). Proton pump inhibitors may be beneficial to determine gastric function given their direct mechanism of action.

As discussed above regarding stimulants, beneficial dosages and routes of administration for the gastric acid suppressant are relatively free of side effects and result in a significant pharmacological effect within several hours (such as less than 2 or 3 hours) of administration. Exemplary doses that are typically free or relatively free from potentially negative side effects include omeprazole (80 mg intravenous) or ranitidine (50 mg intravenous). However, it is possible to use a dosage and route causing significant side effects depending on circumstances 2. Suppressant Selection Methodologies The use of a certain type of suppressant can be automatically determined, such as via automatic protocols. For example, a certain suppressant (such as omeprazole) may always be used in some exemplary embodiments, while other exemplary embodiments may always use another specific suppressant.

However, still other exemplary embodiments can include an analysis as to whether a benefit may be achieved via use of a certain type of suppressant. Exemplary embodiments are intended to cover and include any methods and apparatus for making this determination. For example, this determination can be made based on detected baseline gastric juice pH. It may be beneficial to use a certain suppressant after detection of a relatively high baseline gastric juice pH, while it may be beneficial to use a completely different suppressant after detection of a relatively low baseline gastric juice pH. However, other factors can be used to dictate usage of a specific suppressant, including but not limited to patient characteristics, such as one or any combination of factors, including but not limited to: age, gender, fitness, weight, body composition such as percentage of body fat, ethnicity, family history, personal medical history, genetics, or any other factor currently known or later determined to be relevant or applicable.

III. Dosages and Administrations of Pharmacological

Challenge Agents (Stimulants/Suppressants/Acid Neutralizers)

A. Dosages

It may be advantageous to tailor the amount and/or concentration (dosage) of pharmacological challenge agent, such as a gastric acid stimulant or suppressant, administered to patients. For example, benefits may be achieved by limiting administration to only a dosage of stimulant or suppressant that is necessary to sufficiently challenge a patient's GI tract. Limiting the amount of administered stimulant or suppressant to only that amount needed to sufficiently challenge the GI tract may be beneficial by reducing, minimizing or preventing any potentially disadvantageous side effects of the stimulant or suppressant.

In one exemplary embodiment, a dose of 1 mcg/kg of pentagastrin is administered, either subcutaneously or intramuscularly, which is typically large enough to stimulate gastric acid secretion in a healthy adult. A dose of 1 mcg/kg is also sufficiently small to reduce or minimize the likelihood of potential adverse effects because adverse effects are typically dose related, with larger doses being more likely to cause adverse effects or poorer tolerability.

However, the amount of GI tract challenge deemed sufficient can vary based on a number of factors, such as the reason for the test, i.e., whether the test is being used to determine: 1) applicability of enteral feeding, ventilation and/or use of vasoactive agents, 2) guiding the disposition of a patient within a hospital, such as whether the patient should remain in an intensive care unit (ICU), emergency room, etc., 3) detection of risk for stress ulcers, and/or 4) adequacy of other treatment or resuscitation. In other words, the maximum dosage of stimulant or suppressant can vary based on the reason for conducting the test. For example, a relatively large dosage of stimulant or suppressant may be necessary to determine whether to initiate enteral feeding, while a lower amount may be sufficient to monitor adequacy of resuscitation, and an even lower dosage of stimulant or suppressant can be sufficient to determine whether a patient should remain in an ICU.

Other factors can be used to determine dosage of stimulant or suppressant as an alternative to the above analysis, or as part of the above analyses relating to dosage determination. For example, dosage of stimulant or suppressant can be determined based on patient characteristics, such as one or more combination of factors, including but not limited to: age, gender, fitness, weight, body composition such as percentage of body fat, ethnicity, family history, personal medical history, genetics, and/or other factors currently known or later determined to be relevant or applicable.

For example, if body weight is used to affect or dictate the dosage, some exemplary embodiments administer a relatively higher dosage to relatively heavy patients, and contrarily a relatively lower dosage to relatively lighter patients. A chart is provided below showing exemplary dosages for various weights.

|  | Patient Weight | | |
| --- | --- | --- | --- |
|  | 40-70 kg | 71-100 kg | 101 kg or more |
| Pentagastrin Dosage | 250 mcg | 500 mcg | 750 mcg |

The above chart shows dosages based on stepped changes in weight, i.e., 40-70 kg, 71-100 kg, 101 kg or more. This stepped weight dosing is justified with the flat dose response curve for pentagastrin at 2 to 6 mcg/kg observed in many studies, e.g., Isenberg et al (1975) described above. However, the above stepped weight changes may not be the most accurate way to determine dosages, especially if weight is the sole factor in determining dosage. For example, in this scheme, a 70 kg patient receives a much lower dosage of stimulant or suppressant than a 71 kg patient, even though only 1 kg separates the two patients.

Thus, other schemes may be more accurate. For example, dosages can be determined more linearly based on a patient's weight, such as by other weight based dosing techniques. For example, a certain dosage of stimulant or suppressant (such as 6 mcg) can be used based on any weight increment (such as 1 kg increments). A chart is provided below in accordance with one example of this scheme, i.e., 6 mcg/kilogram.

|  | Patient Weight | | | |
| --- | --- | --- | --- | --- |
|  | 50 kg | 75 kg | 100 kg | 125 kg |
| Pentagastrin Dosage | 300 mcg | 450 mcg | 600 mcg | 750 mcg |

Weight based dosing may be effective and/or beneficial in many medical applications. For example, drugs can be administered, especially drugs for injection (i.e., liquid state), using weight based dosing. This is in contrast to pills (or capsules, tablets, etc.) that are only available to medical care providers in a limited number of dosage amounts. However, liquids for injection can be administered in many different amounts (volumes), thereby allowing for many different dosage amounts, if required, based on different body weights.

For example, Raschke, Robert A., Brendan M. Reilly, James R. Guidry, Joseph R. Fontana, and Sandhya Srinivas. "The Weight-based Heparin Dosing Nomogram Compared with a "Standard Care" Nomogram." *Annals of internal Medicine* 119.9 (1993): 874-81. Print., hereafter "Raschke," which is hereby incorporated in its entirety herein by reference, discloses employing weight based dosing for the administration of heparin, which is an injectable drug commonly administered to hospitalized patients. Pentagastrin can similarly be administered using weight based dosing because it is generally available in an injectable form, i.e., as a liquid. As disclosed above, a dose of 6 mcg/kg can elicit a robust gastric acid secretory response and is thus a beneficial method of dosing.

It may also be advantageous to set a maximum dosage (amount and/or concentration) of pharmacological challenge agent, such as stimulant or suppressant, regardless of other factors, such as patient's weight. Setting a maximum dosage may be beneficial for a variety of reasons, such as would be the case if a certain dosage causes certain potentially disadvantageous side effects in a threshold number or percentage of patients. For example, a certain relatively high dosage of stimulant or suppressant should not be used if it causes a certain potentially disadvantageous side effect in a relatively high number or percentage of patients, and even for patients weighing over 101 kg. A chart is provided below illustrating an example of this analysis for patients weighing more than 101 kg.

| Dosages | Percentage of Patients Demonstrating a certain Potentially Disadvantageous Side Effect |
| --- | --- |
| 250 mcg | .001% |
| 500 mcg | .01% |
| 600 mcg | .02% |
| 750 mcg | 10% |

In the above example, the percentage of occurrence of the side effect is nominal for 250 mcg-600 mcg, but becomes much more significant (10%) at 750 mcg. Thus, in this case, it may be beneficial (in some or all cases) to avoid administration of a 750 mcg dosage, and thus a maximum dosage may be set at 600 mcg. For example, a 150 kg patient would still receive a maximum dosage of 600 mcg.

This approach to dosing medications can be effective and/or beneficial in many aspects of clinical practice. For example, administration of acetaminophen (Tylenol) can be weight based (10-15 mg/kg) in small individuals, e.g., in children. However, in the related art, the maximum dose typically administered is 1000 mg every 6 hours, even in patients with significant obesity. For example, a 120 kg individual may receive this maximum dose of 1000 mg, but should not be dosed with 1200-1800 mg (corresponding with 10-15 mg/kg).

Other exemplary embodiments address reducing, minimizing, or preventing side effects of the pharmacological agent in other ways. For example, some exemplary embodiments initiate administration of the pharmacological challenge agent at a low or very low dosage regardless of patient weight. In one exemplary embodiment, a low dosage of 0.6 mcg/kg of pharmacological agent, such as gastric acid stimulant (for example, pentagastrin), is initially administered. A sufficient change in gastric juice pH, such as a drop of at least 1 pH unit, may indicate a healthy or reasonably healthy GI tract response. However, if there is no change in gastric juice pH, or an insufficient change in pH, then the pharmacological challenge agent can be re-administered after a sufficient period, such as at least one hour, at a higher dosage, such as 6 mcg/kg. A sufficient change in gastric juice pH may then indicate a somewhat healthy GI tract and care can be provided accordingly.

In some exemplary embodiments, the low dosage can be referred to as a minimum dosage, and the higher dosage can be referred to as a standard dosage. In the above exemplary embodiment, the minimum dosage (e.g., 0.6 mcg/kg) would be 10% of the standard dosage (e.g., 6 mcg/kg). However, exemplary embodiments are not limited to these dosages, and are instead intended to cover any dosage relationship that may be beneficial. For example, the minimum dosage can be any amount less than the standard dosage.

In fact, the minimum and standard dosages can be determined based on the same or similar methodology as discussed above with regard to maximum dosages. Thus, in some exemplary embodiments, the minimum dosage can be set to an amount that is very low and thus very unlikely to cause potentially disadvantageous side effects, while sufficiently high to cause an acute change in gastric juice pH in patients with a healthy gastric function.

B. Administrations

Exemplary embodiments are intended to cover and include any known or later developed methods and apparatus for challenging a patient's GI tract. These methods and apparatus include any known or later developed pharmacological agent, including but not limited to the gastric acid stimulants and suppressants discussed in Section II (Types of Pharmacological Challenge Agents).

Exemplary embodiments can also include any currently known and later developed methods and apparatus for introducing a pharmacological agent, such as a gastric acid stimulant or suppressant, to a patient. For example, the pharmacological challenge agent can be introduced subcutaneously, intramuscularly, intravenously, orally, in gaseous form, etc. In fact, some embodiments administer the pharmacological challenge agent, such as pentagastrin, as snuff and inhaling. This embodiment would thereby also include use of the pharmacological challenge agent as a suspended liquid.

As one example, FIG. 1 shows an exemplary administering device 100 that administers to a patient a pharmacological challenge agent, such as a gastric acid stimulant or suppressant. However, the administering device 100 shown in FIG. 1 is not intended as limiting, and as discussed above, exemplary embodiments are intended to cover any currently known and later developed methods and apparatus for introducing the pharmacological challenge agent. For example, the exemplary administering device 100 shown in FIG. 1 is not intended as limiting with regard to structure of the device, manner of administration, location on the patient of administration, etc.

In fact, the manner of introduction of the pharmacological challenge agent can be tailored to achieve some benefit. It may be beneficial to tailor the manner of introduction based on whether a stimulant is used versus a suppressant. For example, it may be beneficial to administer a stimulant (such as pentagastrin) subcutaneously because it has a very rapid onset. Administration of pentagastrin subcutaneously has been shown to elicit a robust acid secretory response in less than 1 hour. In contrast, onset of action can be longer with gastric acid suppressants, such as famotidine or omeprazole, and it is therefore desirable to administer these suppressants intravenously to speed up the pharmacological response. The manner of introduction can also, or alternatively, be determined based on the specific type of stimulant or suppressant.

Alternatively, or in addition to the above analysis, the manner of introduction can be determined based on patient characteristics, such as one of any combination of factors, including but not limited to: age, gender, fitness, weight, body composition such as percentage of body fat, ethnicity, family history, personal medical history, genetics, or any other factor currently known or later determined to be relevant or applicable.

As one example, patients with poor peripheral circulation (perfusion), such as can occur with severe diabetes or severe peripheral vascular disease, for example, may respond better to an intravenous dose of stimulant. This beneficial response may be due to the fact that poor peripheral perfusion may impair absorption and transport of stimulant from the subcutaneous space to the central circulation and target site (parietal cells of the stomach).

However, the above disclosure is only provided as one example of tailoring introduction of the pharmacological challenge agent to achieve a benefit. Exemplary embodiments are intended to cover any beneficial tailoring of the administration of the pharmacological challenge agent consistent with the disclosed guiding of medical care based on detected gastric function.

In fact, as yet another example, the manner of introduction can be determined based on speed of the GI tract's response. In other words, a certain manner of introduction, such as subcutaneous or intravenous administration, may cause a faster GI tract response, which may be beneficial under certain circumstances. For example, in many circumstances, the onset of a decrease in gastric juice pH is likely to be faster following intravenous rather than subcutaneous administration.

In general, tailoring administration of the pharmacological challenge agent to achieve a faster GI tract response can be beneficial because it can speed up gastric function detection. Determining that gastric function is sufficient to tolerate nutrition would allow ramping up to goal calories more quickly. As disclosed above, health benefits are achieved by providing patients with nutrition as soon as the nutrition can be tolerated. Other benefits could also be achieved by achieving a faster GI tract response.

Further, in some exemplary embodiments, the manner of introduction is based on reducing, minimizing or preventing potentially negative side effects caused by the pharmacological challenge agents. In other words, a certain manner of introduction may reduce, minimize or prevent such potentially negative side effects. For example, intravenous administration of pentagastrin can cause transient mild side effects, e.g., anxiety, palpitations, etc. However, subcutaneous administration may reduce, minimize, or even prevent these effects, such as by enabling a more gradual increase in serum concentration. However, as previously disclosed, the above exemplary embodiments are not intended to be limiting, and other exemplary embodiments can cover other tailorings of pharmacological challenge agent administrations to provide the above or other benefits.

C. Vial Size

Exemplary embodiments are intended to cover any useful or beneficial method and/or apparatus for facilitating storage, delivery and/or administration of the pharmacological challenge agent to patients. In many embodiments, the pharmacological challenge agent is stored in a vial and administered to the patient from the vial using known, related art, and/or later developed techniques. A few embodiments that include different vial sizes, dosages, and types of administration are disclosed below in the context of the pharmacological challenge agent being pentagastrin, however, as disclosed above, embodiments are not limited to pentagastrin and instead are intended to cover any useful or beneficial pharmacological challenge agent.

One exemplary embodiment includes a vial size appropriate for a pentagastrin dose of 1 mcg/kg. In some of these embodiments, it may be beneficial to provide this dose at a concentration of 250 mcg/ml in a vial containing a volume of 0.5 to 1.0 ml (125 to 250 mcg of drug). This concentration may enable a relatively small volume of the pentagastrin to be administered, which may be beneficial in certain situations, e.g., subcutaneous or intramuscular dosing, where it may be generally preferable to inject a small volume so as to reduce, minimize or prevent potential patient discomfort associated with the injection.

In another exemplary embodiment of pentagastrin dosing of 1 mcg/kg, a vial is used that contains a less concentrated formulation (e.g., 100 mcg/ml), which may be beneficial or otherwise desirable, such as for use with a vial containing 2 ml (200 mcg in 2 ml). For example, a patient weighing 80 kg may receive a dose of 80 mcg (0.8 ml volume).

This lower concentration (100 mcg/ml) may reduce, minimize or prevent any stinging, pain, or other adverse effects associated with subcutaneous or intramuscular administration. This lower concentration may also be beneficial or otherwise desirable if the drug is administered intravenously, because this concentration may reduce, minimize or prevent possible irritation of the vein that could cause pain and/or phlebitis. Another potential benefit to a less concentrated formulation is potentially greater or enhanced ease in measuring the correct dose and/or greater or enhanced accuracy of the dose. For example, with a higher concentration (250 mcg/ml), a 1 mcg/kg dose in a 50 kg patient would be one-fifth of 1 ml (equal to 0.2 ml), which can be challenging to obtain accurately. Contrarily, the lower concentration (e.g., 100 mcg/ml) would require a volume of 0.5 ml in this same patient, which may be easier to accurately draw-up in the syringe. The above dosages, volumes, etc., are merely provided for exemplary purposes, and are not intended as limiting or an exhaustive list of possible dosages, volumes, etc.

Another exemplary embodiment uses a higher dose of pentagastrin, such as 6 mcg/kg, and the vial contains 3 ml of pentagastrin (250 mcg/ml equal to 750 mcg in 3 ml). This vial size may be beneficial by enabling dosing of even large patients, e.g., 100 kg patient, who would require 600 mcg that may be contained in this 750 mcg vial.

Yet another exemplary embodiment enables incrementally higher dosing based on a patient's initial response to the pharmacological challenge agent. This incrementally higher dosing can be performed with a vial containing 3 ml of pentagastrin (250 mcg/ml or 750 mcg in 30 ml). For example, in order to reduce or minimize potential side effects, a lower but generally effective dose of pentagastrin is initially administered (e.g., 1 mcg/kg subcutaneously). A sufficiently positive gastric secretory response obviates additional doses of pentagastrin from this vial. However, an inadequate or equivocal response to the lower dose (1 mcg/kg) indicates that the patient can be challenged with a higher dose (e.g., 6 mcg/kg). The exemplary vial size enables dosing of even large patients. e.g., 100 kg patient who would require a low dose of 100 mcg followed, in some cases, by a higher dose of 600 mcg, totaling 700 mcg that may be contained in the 750 mcg vial.

As indicated above, in all of the above exemplary embodiments, the dosages, volumes, etc., are merely provided for exemplary purposes, and are not intended as limiting or an exhaustive list of possible dosages, volumes, etc.

IV. Gastric Juice H+/pH Measurement, Determining GI Tract's Response to Challenge, and Guiding Care Based on Measured H+/DH Exemplary embodiments are intended to cover any and all currently known and later developed apparatus that measure gastric function and enable medical care to be guided based on the detected gastric function, in accordance with the above disclosures. More specifically, exemplary embodiments can include apparatus that enable a patient's GI tract to be challenged, such as by use of one or any number of pharmacological challenge agents, to then measure the GI tract's reaction to the challenge, and to then guide care based on the GI tract's measured reaction.

Components of the exemplary apparatus can include one or any combination of: 1) apparatus for administering a pharmacological agent (discussed in section (B) above), 2) apparatus for obtaining and/or measuring gastric juice H+ concentration or pH (such as for performing the baseline H+ concentration or pH test and/or stressed H+ concentration or pH test(s)), 3) apparatus for determining the GI tract's response to the pharmacological challenge, such as by determining any differential between the baseline and stressed H+ concentration or pH tests, and 4) apparatus for guiding care based on the GI tract's response. Each of these components is discussed below.

A. Timing of Gastric Juice H+/pH Measurement

In general, exemplary embodiments relate to guiding medical care based on detected gastric function. The gastric function can be detected by initially measuring gastric juice H+ concentration or pH prior to administration of the pharmacological challenge agent. This initial measurement can be termed a baseline H+ concentration or pH test. A pharmacological challenge agent, such as a gastric acid stimulant or suppressant, is administered to a patient. After a period, the patient's gastric juice H+ concentration or pH is again measured, which can be termed a stressed H+ concentration or pH test. Any H+ concentration or pH differential between the baseline and stressed H+ concentration or pH tests is then determined. The following examples are provided in terms of pH, but are also applicable in terms of H+ concentrations.

Exemplary embodiments are intended to cover any period, i.e., time between baseline pH test and/or pharmacological challenge agent administration and stressed pH test. In many exemplary embodiments, the period is measured between administration of pharmacological challenge agent and stressed pH test. It is advantageous for the period to be the time that it takes for the patient's GI tract to react to the pharmacological challenge agent to provide information sufficient to guide the patient's care. An exemplary reaction could be a pH change of 1 unit to indicate that the patient's GI tract is sufficiently healthy to initiate enteral feeding.

This period can be set to a certain standard time for all patients under all circumstances, such as, for example, 45 minutes. In other words, in this example, a 45 minute gap would always separate the pharmacological challenge agent administration and stressed pH test. Exemplary embodiments using the standard time are particularly applicable if the GI tracts of a large number (such as a substantial majority) of different types of patients react to the pharmacological challenge agents at a uniform or fairly uniform rate. A standard time is particularly beneficial because of simplicity, ease of administration, error avoidance, etc. For example, one exemplary, typical reported duration of action of pentagastrin is 60 to 90 minutes. Therefore, 45 minutes falls into a time period where sufficient time has elapsed since administration to ensure that the drug has arrived at the target cell (i.e., parietal cells), thereby enabling the patient's gastric system to react, and yet is within the known duration of action of this drug such that effects of the pharmacological challenge agent have not deteriorated or worn off.

However, some exemplary embodiments do not necessarily use a standard time for all patients and/or under all circumstances. For example, certain circumstances could warrant using different periods. In an exemplary embodiment, a relatively shorter period could be used in urgent situations, such as situations where it would be beneficial to urgently apply a certain treatment that is dictated by the test results. For example, it may be very beneficial to expedite initiation of enteral feeding or other treatment in certain critically ill patients. Alternatively, determining whether a certain patient should remain in an ICU may not be so urgent and thus a relatively larger period could be used.

Alternatively, or in addition to this analysis, various patient characteristics can be used to determine the period, such as one or any combination of aspects including but not limited to: age, gender, fitness, weight, body composition such as percentage of body fat, ethnicity, family history, personal medical history, genetics, or any other factor currently known or later determined to be relevant or applicable.

In accordance with some exemplary embodiments as discussed above, gastric acid stimulant or suppressant, such as pentagastrin, is administered, and then gastric juice pH is measured 45 minutes later (which approximates time of peak acid production). However, peak acid production can occur earlier or perhaps later, and even as late as 75 minutes after pentagastrin administration. Therefore, another exemplary embodiment measures the gastric juice pH earlier than the exemplary embodiments discussed above, such as at 15 minutes post pentagastrin administration. If a positive response (such as at least 1 unit decrease) is detected, then no further measurements need to be taken and care can be provided assuming a healthy gastric response. This procedure provides the benefit of expediting the guiding of care based on a healthy gastric function.

However, if the response is negative at 15 minutes, then the gastric juice pH can be measured at a later time, i.e., such as at 30 minutes post pentagastrin administration. If a positive response is detected, then further measurements do not need to be taken and care can be provided based on a fairly healthy gastric response. If a negative response is detected, then the gastric juice pH can be measured at a still later time, i.e., gastric juice pH can be measured such as at 45 minutes or even 75 minutes from pentagastrin administration.

The initial and subsequent stressed pH measurements can be performed at any times post stimulant or suppressant administration that may be beneficial. For example, the initial stressed pH measurement can be set to the earliest significant gastric response of most patients to the stimulant or suppressant, which may be approximately 15 minutes post pentagastrin administration, for example. The last subsequent stressed pH measurement can be set to the end of duration of gastric response of most patients to the stimulant or suppressant, which may be approximately 90 minutes post pentagastrin administration. Also, exemplary embodiments are intended to cover any number of subsequent stressed pH measurements that may be beneficial.

In addition or as an alternative to the above analysis, other exemplary embodiments can take into account the peak gastric response of most patients to the gastric acid stimulant or suppressant. For example, the peak acid production response for most patients to pentagastrin is approximately 45 minutes after administration, and the latest peak acid production for many patients to pentagastrin is approximately 75 minutes after administration. Thus, in some exemplary embodiments, the initial stressed pH measurement is performed at approximately 45 minutes after pentagastrin administration. If a negative response is detected, then a subsequent stressed pH measurement is taken in approximately another 30 minutes, i.e., approximately 75 minutes after the pentagastrin administration. As with other exemplary embodiments, another negative response results in care being guided based on a relatively unhealthy gastric function, while a positive response results in care being guided based on a relatively healthy gastric function.

The above exemplary embodiments, which include initial and subsequent stressed pH measurements (after an initial negative response), are beneficial because they ensure that gastric function is more accurately tested. The fact that earlier measurements of pH (e.g., at 15 minutes post pentagastrin administration) are negative is generally not useful if a positive response is eventually noted within the expected duration of action of the drug, e.g., 90 minutes from pentagastrin administration. In other words, if two measurements of gastric pH are performed 15 and 45 minutes after pentagastrin administration, and one pH measurement (at 15 minutes) is negative (less than 1 unit pH change) and one pH measurement (at 45 minutes) is positive (greater than 1 unit pH change), the negative pH value in this context has only a limited or even no diagnostic value.

The above exemplary embodiments aspirate gastric juice at the time of pH measurement. In other words, the stimulant or suppressant is administered, and after a suitable period has expired, the gastric juice is aspirated and the pH measured. However, it is possible that gastric secretion of mucous and other non-acid containing secretions may remain and increase in volume in the stomach, such that aspirated and collected gastric juice (at the time of pH measurement) includes freshly secreted acid diluted with other gastric secretions. Therefore, it may be beneficial at a certain time before pH measurement to aspirate all of the gastric contents, wait a period, and then aspirate the gastric contents for pH measurement. This results in measurement of a smaller and fresher aliquot of gastric juice, enhancing reliability of the measurement.

Figure 6:
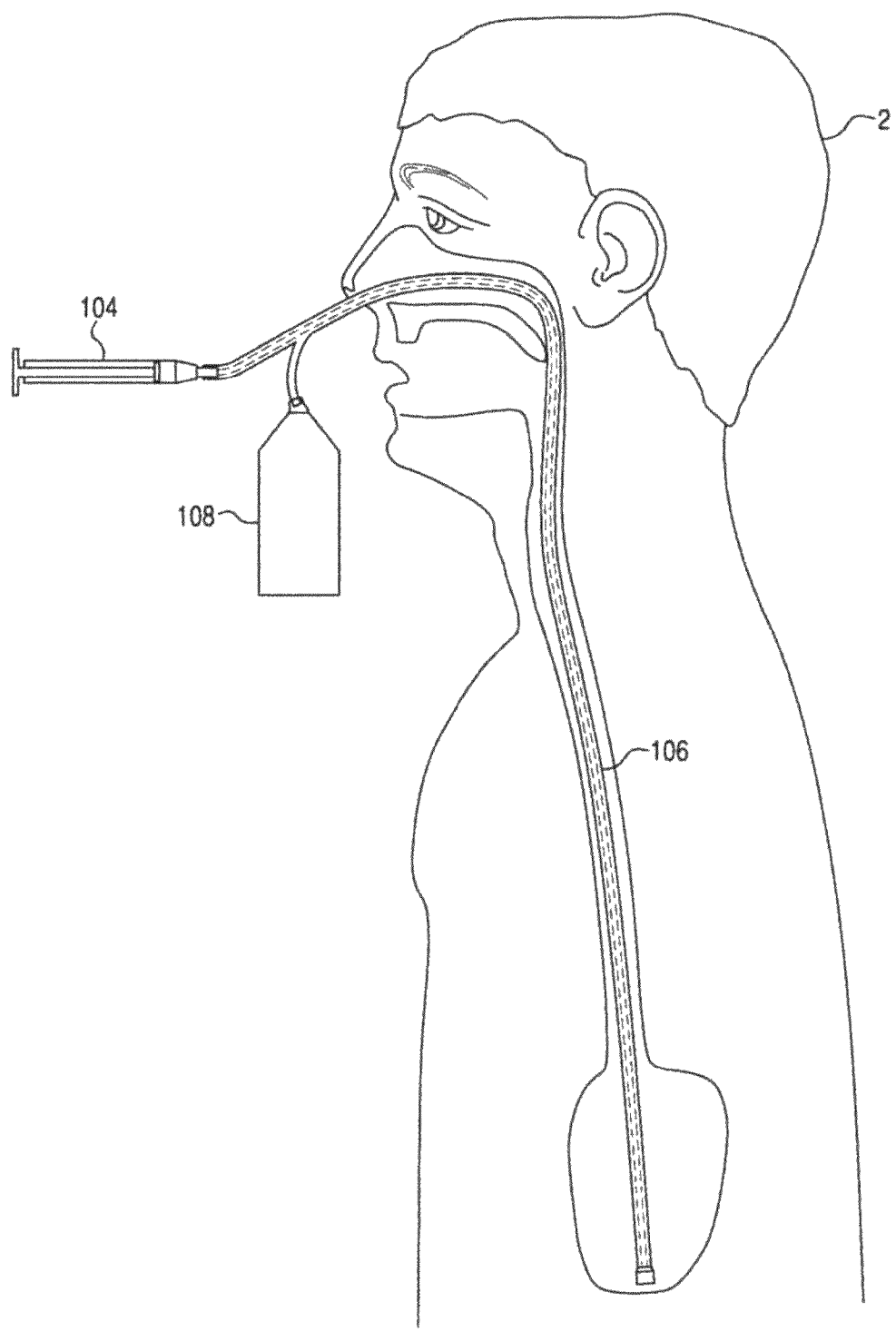
FIG. 6 is a schematic of an apparatus in accordance with another exemplary embodiment, and particularly shows an aspirator that aspirates gastric contents.

FIG. 6 is a schematic of an apparatus in accordance with an exemplary embodiment that includes an aspirator 104 that aspirates gastric contents. The aspirator 104 provides a suction or other force so that gastric contents are sucked or otherwise moved from the stomach of the patient 2, through orogastric or nasogastric tube 106, and into a collector 108 or other structure.

In accordance with an exemplary embodiment discussed above, the patient's gastric juice pH is measured approximately 45 minutes after pentagastrin administration. This exemplary embodiment (as well as other embodiments) can be modified to include the above additional procedure by aspirating all of the gastric contents at some period before pH measurement, such as at approximately 30 minutes after pentagastrin administration. The gastric juice for pH measurement would then be generated between approximately 30 to approximately 45 minutes after pentagastrin administration to reduce, minimize, eliminate, or prevent dilution of freshly secreted acid with other gastric secretions. This procedure enables detection of small quantities of acid secretion, which still reflect a well perfused gut.

The above example of aspirating all of the gastric contents approximately 30 minutes after pentagastrin administration is only provided as an example. This aspiration can be provided at any time that is beneficial, and can occur prior to stimulant or suppressant administration or even prior to measurement of baseline pH.

The above procedure can be combined with use of a pH probe/sensor, in which aspiration of gastric contents can be performed with a NGT or OGT, while pH measurements may be performed with an indwelling pH probe/sensor (e.g., VersaFlex pH sensor from Sierra Scientific Instruments, Los Angeles, Calif.). In yet other alternative embodiments, the above measurements of pH, such as at 15, 30, 45, 60 minutes, etc., can each be performed after aspirating gastric contents so as to reduce, minimize or avoid measurement of freshly secreted gastric juice that has been diluted with other gastric secretions. In other words, in exemplary embodiments including multiple pH measurements, all or some of these measurements can be performed after aspiration of gastric contents.

B. Exemplary Methods and Apparatus for Determining Gastric Juice H+/pH

Exemplary embodiments are intended to cover any and all currently known and later developed methods and apparatus for determining gastric juice H+ concentration or pH. The following examples are provided in terms of pH, but are also applicable in terms of H+ concentrations.

FIG. 1 is a schematic of an apparatus in accordance with an exemplary embodiment, including an apparatus 1 for measuring gastric juice pH in a patient 2. Exemplary embodiments of the measuring apparatus 1 are intended to cover and include any method and device 3 for obtaining and/or sampling the patient's gastric juice so that the gastric juice pH can be measured, and any method and device 7, 8 to measure the gastric juice pH. FIG. 1 also shows an exemplary orogastric or nasogastric tube 4, exemplary syringe 5 for aspiration, and exemplary connector 6 that connects to the pH measuring device 7, 8. FIG. 1 further shows an administering device 100 that administers a pharmacological challenge agent, and an administering device 102 that administers a pharmacological agent to raise gastric pH so that the stress test can be conducted with a gastric acid stimulant. Exemplary methods and apparatus are discussed below.

1. Gastric Juice Obtaining/Sampling Device

Exemplary embodiments include any currently known or later developed method and device 3 for obtaining/sampling gastric juice so that the gastric juice pH can be measured. Specific methods and apparatus can be selected based on a variety of factors, including but not limited to one or a combination of any of: ease of use; cost, such as cost of the device, cost of servicing the device, etc.; invasiveness/noninvasiveness of the device; reducing minimizing or preventing side effects; etc., for example.

Some exemplary embodiments are discussed below wherein the obtaining/sampling device 3 includes at least one of a catheter, a probe and a sensor. However, the below disclosures of these devices are only provided for exemplary purposes and not intended as limiting. Each of these exemplary devices is discussed below.

Some exemplary embodiments are intended to include any currently known or later developed catheter capable of performing the above operation. For example, a related art catheter is a plastic (usually disposable) device that is inserted into the patients body and has at least one lumen useful for aspirating things from the body, e.g., aspiration of gastric juice from the stomach, or aspiration of residual enteral feeds from the stomach. This same lumen (or a separate lumen) can, when not being used for aspirating, be used to administer drugs or enteral feed into the patient. A currently known or later developed Salem Sump tube (often 16 F or 18 F in size) can be inserted through the nose (nasogastric) or mouth (orogastric) into the stomach. This catheter/tube can be used to aspirate gastric contents, and when not being used to aspirate can be used to administer drugs or enteral feed into the stomach.

Some exemplary embodiments include a probe. Any currently known or later developed probe can be used that is applicable. One related art probe is a generally plastic (usually disposable) device that is inserted into the patient's body, and in some exemplary embodiments includes at least one sensor, e.g., pH sensor, or manometry sensor, associated with it.

The terms catheter, tube, and probe are often used interchangeably in the art because there can be considerable overlap in their structures and functions. For example, a catheter with a lumen is often understood to have one or more sensors (e.g., pH sensor) associated with it. This structure allows the user to monitor pH, also aspirate fluid, e.g., gastric juice, and insert drugs or enteral feed. However, regardless of the common usage in the art regarding this terminology, exemplary embodiments are intended to cover any apparatus or method for obtaining/sampling gastric juice.

It is often beneficial that the devices used for hospitalized patients, e.g., ICU, patients, have properties/structures allowing them to be inserted into a patient with depressed mental status or who may be sedated and/or unconscious for other reasons. e.g., recent stroke or head injury. Therefore, it may be beneficial for the catheter, tube, or probe to be sufficiently smooth and stiff to allow for easy or relatively easy insertion into the esophagus, stomach, or small bowel. Increased stiffness may also be beneficial because these patients often cannot assist with insertion, e.g., by attempting to swallow the tube, which is helpful during insertion of more flimsy tubes. Therefore, sufficient stiffness allows an operator, such as a medical care provider, to push the tube forward into the patient without the tube kinking or bending backward or coiling. Exemplary embodiments are intended to cover any structure or method of achieving the desired stiffness, including but not limited to usage of: 1) a stiffer plastic, 2) a large diameter tube. e.g., a standard 16 F or 18 F Salem Stump tube generally has sufficient stiffness to be used in hospitalized patients, and/or 3) a guide wire to allow for transient increased stiffness during insertion, after which the guide wire can be removed.

In some exemplary embodiments, the obtaining/sampling device 3 is used in conjunction with a separate apparatus to measure pH of the gastric juice and another separate apparatus to indicate the measured pH. In other exemplary embodiments, the obtaining/sampling device 3 includes the apparatus to measure the gastric juice pH. For example, the obtaining/sampling device 3 can be a plastic tube (NG or OG Salem Sump tube, or tube for post-pyloric feeding) that has a pH sensor/probe built into it. In still other exemplary embodiments, the obtaining/sampling device alternatively or additionally includes the apparatus to indicate the measured pH. In fact, in one such exemplary embodiment, the apparatus to measure the gastric juice pH is integral and/or unitary with the apparatus to indicate the measured pH. For example, the obtaining/sampling device 3 can be a plastic tube (NG or OG) that has both a pH probe and pH indicator built into it. The above embodiments can be used with any currently known, related art or later developed technologies for measuring pH, including pH sensors that require bed-side calibration as well as those not requiring such bed-side calibration, e.g., pre-calibrated sensors or sensors manufactured to sufficiently high specifications so as to obviate bed-side or further calibration.

In one exemplary embodiment, the obtaining/sampling device 3 can include a special orogastric or nasogastric tube 4 that can be inserted into a patient's stomach. This tube 4 can enable stomach contents to be suctioned and thus sampled, which is consistent with current intensive care. Alternatively, this tube 4 can additionally be used to facilitate or enable feeding. Providing the additional feeding function can be advantageous for a variety of reasons, such as enabling feeding to occur on an expedited basis should feeding be warranted, reduced invasiveness, etc.

This tube 4 can include or be used with a syringe 5 for aspiration of gastric juice from a patient's stomach. In other words, the syringe 5 can create suction within the tube 4 to obtain a sample of gastric juice. The syringe 5 can include a connector 6, such as at a tip end, that connects to a pH measuring device 7 that measures pH of the gastric juice sample. The connector 6 can include any structure to accomplish the above operation, such as a luer connector, for example. The pH measuring device 7 can also include any currently known or later developed apparatus for measuring pH. A pH measuring device can be selected based on one or a combination of any number of factors, including but not limited to accuracy, reliability, cost, ease of use and operation, ability to provide relatively fast measurement results, etc. Also, as disclosed above, the pH measuring device 7 can include the apparatus to indicate the measured pH, or alternatively send a signal to that apparatus for separate indication.

Another exemplary embodiment includes a pH measuring sensor/device that is encapsulated into the distal end of a standard 18 French tube that is inserted into the gastric lumen either through the mouth or nose. This tube would allow for the drainage of stomach contents, if necessary for other medical reasons, and administration of enteral feeds into the stomach, if feeding is deemed warranted. Alternative manufacturers of pH containing probes and pH monitors can be used. For example, a pH probe (such as a currently available Versa Flex Disposable pH Catheter manufactured by Sierra Scientific Instruments, Los Angeles, Calif.) can be connected with another commercially available pH recorder/monitor, e.g., Digitrapper (Sierra Scientific Instruments, Los Angeles, Calif.), which allows continuous or semi-continuous measurement of pH to at least 0.1 pH unit accuracy. Potential advantages provided by continuous, substantially continuous, or semi-continuous measurement of pH are disclosed below with regard to two separate exemplary embodiments.

In another exemplary embodiment, the gastric juice obtaining/sampling device and pH measuring device include a disposable pH probe that can either have no lumen, be a single lumen, or alternatively have two or more lumens. The multi-lumen probe may be advantageous by allowing for simultaneous aspiration of gastric juice with measurement of the pH of the gastric juice using pH strips or a pH monitor. This structure may also be advantageous by enabling an infusion of food into the stomach via the pH probe's lumen.

Exemplary embodiments are intended to cover a probe of any size that can perform the above operation adequately. For example, the probe can be relatively small (e.g., 4F), somewhat larger (e.g. 6 F), or even as large as a typical nasogastric tube (e.g., 16 F or 18 F). The larger tube size may be beneficial in exemplary embodiments using a multilumen probe through which one can feed the patient or administer medications.

The pH probe may have a pH sensor, such as on its tip. However, commercially available pH probes can also be used that include multiple sensors to allow for measurement of pH at 2 or even 3 separate locations. For example, the pH sensors can be spaced 20 cm apart. This structure may provide more accurate measurements and reduce, minimize or avoid errors. For example, detecting a pH of 2.0 units from the distal (tip) sensor and a pH of 7.0 units from the more proximal sensor helps to confirm that the probe is in the correct position, where the tip is in the stomach and the proximal sensor is in the esophagus, therefore resulting in less acidic gastric juice pH there. In contrast, pH measurements of 7.0 units at both sensors suggests that the probe is not in the stomach and that the pH of 7.0 units does not represent gastric juice pH. In another example, a pH of 7 units in the distal sensor and pH of 2 units in the proximal sensor would indicate that the distal tip has migrated into the duodenum.

Another exemplary embodiment includes an NG tube with a structure similar to that disclosed above, and in particular with one distal sensor and one proximal sensor. This structure may be beneficial by only requiring intubation of one tube for both feeding and sensing, saving time and resources while enhancing patient comfort. Also, providing an NG tube with sensors may obviate an x-ray to ensure the NG tube is in the correct location. In this example, detecting a pH of 2.0 units from the distal (tip) sensor and a pH of 7.0 units from the more proximal sensor helps to confirm that the NG tube is in the correct position, where the tip is in the stomach and the proximal sensor is in the esophagus, therefore resulting in less acidic gastric juice pH at that location. Providing an NG tube with a sensor also makes it easier to determine whether a prescribed PPI or H2 Blocker has sufficiently increased the pH of the stomach, and to monitor dosages and pH over time to reduce the incidence of stress ulcer prophylaxis.

In another exemplary embodiment, the NG tube may include only one sensor. This structure may still provide many of the same or similar benefits as with the NG tube having two sensors. For example, x-rays to confirm NG tube placement may still be obviated by slowly inserting the tube and observing when the pH drops suddenly, indicating that the sensor has entered the acidic environment of the stomach and thus is in the correct position.

Another exemplary embodiment includes two sensors fitted onto a small bowel feeding tube. Measuring pH at both sensors confirms that the small bowel tube has been inserted correctly. For example, a pH of 7 units in the distal sensor and a pH of 2 units in the proximal sensor indicates that the distal tip has migrated into the duodenum and thus is in the correct position. In this exemplary embodiment, it may still be advantageous to perform a pharmacological stimulation test to determine whether the gastrointestinal tract is sufficiently perfused, even though feeding will take place in the small bowel. In this example, a lower pH measurement from the proximal sensor may measure the gastric response from the pharmacological challenge, and its measured pH unit drop help indicate the level of perfusion.

Some exemplary embodiments add various features and/or operations to the catheters, tubes and/or probes disclosed above. For example, sensors can be attached to Percutaneous Endoscopic Gastrostomy (PEG) tubes often used for long term patient feeding. In one exemplary embodiment, a pH sensor is attached to a PEG tube to provide continuous, semi-continuous or intermittent pH measurements. The pH measurements provided by this pH sensor can provide data indicating the gastric system's response to the feed, whether the feed is being processed properly, necessity of further feeding or different types of feeding, etc.

In another embodiment, one or multiple pH and/or impedance sensors are attached at various locations of a jejunal feeding tube. It may be particularly advantageous to provide pH sensors at different locations within the gastrointestinal tract along the jejunal tube. For example, in the case of a nasojejunal tube separate pH sensors can be located in the stomach, upper small bowel, and lower small bowel. Measurements from these sensors can be used to provide various benefits, such as to ensure proper tube placement, to indicate motility or other aspects of food processing, etc. As an alternative, or in addition to the above pH sensors, impedance sensors can be placed along the jejunal tube, such as at the same or similar locations as those disclosed above, to provide various benefits, such as to indicate motility, etc. Exemplary embodiments are also intended to cover adding the same or other sensors and sensor configurations to other types of tubes, such as nasogastric tubes. For example, see sensors 9 in FIG. 1.

In other alternative embodiments, probes can be used that provide continuous or substantially continuous pH measurement. Using a continuous, substantially continuous, or semi-continuous method of pH measurement may be beneficial by providing additional useful information, such as the time taken for a pH decrease to occur. For example, if pH starts to drop (e.g., 1 unit) at 10 minutes after pentagastrin administration, then this likely represents a very robust splanchnic perfusion (circulation) and one can start enteral feeding very aggressively, e.g., 25% of goal with increase of 25% every 4 hours. On the other hand, if pH decreases by at least 1 unit but does not cross the 1 unit threshold for 45 minutes, this might indicate a less robust perfusion (circulation) necessitating a slower increase in enteral feeding infusion rates.

Exemplary embodiments cover still other types of apparatus that measure gastric juice pH. One such exemplary embodiment does not include a tube for obtaining the gastric juice, and instead uses a capsule that can be inserted into the patient. Once positioned, the capsule can transmit information regarding gastric juice pH to an indicator outside of the patient. One such currently commercially available catheter-free capsule is marketed as the Bravo™ pH monitoring system by Given Imaging, Ltd.

The capsule may be especially beneficial by providing data indicating gastric juice pH over short periodic increments or even continuously providing streaming data. More closely monitoring the gastric juice pH (and thus gastric function) in this way enables exemplary embodiments to further enhance care, such as is disclosed above with regard to using a continuous, semi-continuous, substantially continuous, periodic, or other method of pH measurement.

Taking multiple pH measurements enables the rate of pH change after administration of the pharmacological challenge agent to be used to better determine gastric function so that care can be provided accordingly. For example, a rapid rate of gastric juice pH change can evidence a very healthy gastric function, warranting immediate indication of a high rate of nutrition increase. Gastric juice pH changes after feeding may even indicate a fairly healthy gastric function, evidencing acceptability of increasing the amount or rate of increase of nutrition. A slow rate of gastric juice pH change may evidence a rather less healthy gastric function, warranting no increase, or a slow rate of increase, of nutrition. As discussed with other exemplary embodiments, no gastric juice pH change evidences a rather unhealthy gastric function.

In other words, in the previously disclosed exemplary embodiments, a change in pH after administration of a gastric acid stimulant or suppressant is used to determine gastric function. However, more closely monitoring gastric juice pH, such as by taking multiple pH measurements over time, enables rate of pH change to be determined. Once determined, this rate of pH change can be used as an indicator of gastric function similarly to the simple pH change of the previously disclosed embodiments. However, use of the rate of pH change may be especially beneficial for various reasons. For example, the rate of pH change may speed up the determination of gastric function In other words, in some of the previously disclosed embodiments relying on pH change, the stressed pH test(s) are not conducted until certain periods have elapsed, such at 15 minutes, 30 minutes, 45 minutes, etc., after administration of stimulant or suppressant. However, using rate of pH change, such as by taking multiple measurements over time, enables an earlier monitoring of gastric reaction. For example, a high rate of pH change may be detected well prior to the initial stressed pH measurement of the previously disclosed embodiments, such as at 5 minutes post stimulant or suppressant administration. As previously disclosed, speeding-up the determination of gastric function is beneficial by enabling care to be guided on an expedited basis.

Exemplary embodiments are not limited to the methods disclosed above. The above exemplary embodiments cover determining the rate of pH change by monitoring gastric juice pH via streaming data or otherwise monitoring pH on a continuous semi-continuous, substantially continuous periodic, or other basis. However, exemplary embodiments are intended to cover any method or apparatus that directly, indirectly, or otherwise enables assessment, estimation or determination of rate of pH change.

2. H+/pH Measuring Device

As shown in FIG. 1, in some of the above exemplary embodiments, the measuring apparatus 1 includes discrete components, i.e., the obtaining/sampling device 3 (tube 4, syringe 5, connector 6, etc.) and pH measuring device 7. However, exemplary embodiments are not limited to this structure. For example, exemplary embodiments can include one or more integral or unitary devices that combine all or some of the above components.

In an exemplary embodiment, an indicator 8 is functionally and/or structurally connected to the pH measuring device 7 to indicate the pH of the gastric juice sample to a user. In other words, the pH measuring device 7 measures the pH of gastric contents provided by the obtaining/sampling device 3, and provides or otherwise transmits the measured pH to the indicator 8 that indicates to an operator the measured and received pH. This functional and/or structural connection can be in any currently known or later developed form, such as wiring, wireless transmission equipment, etc.

Figure 10:
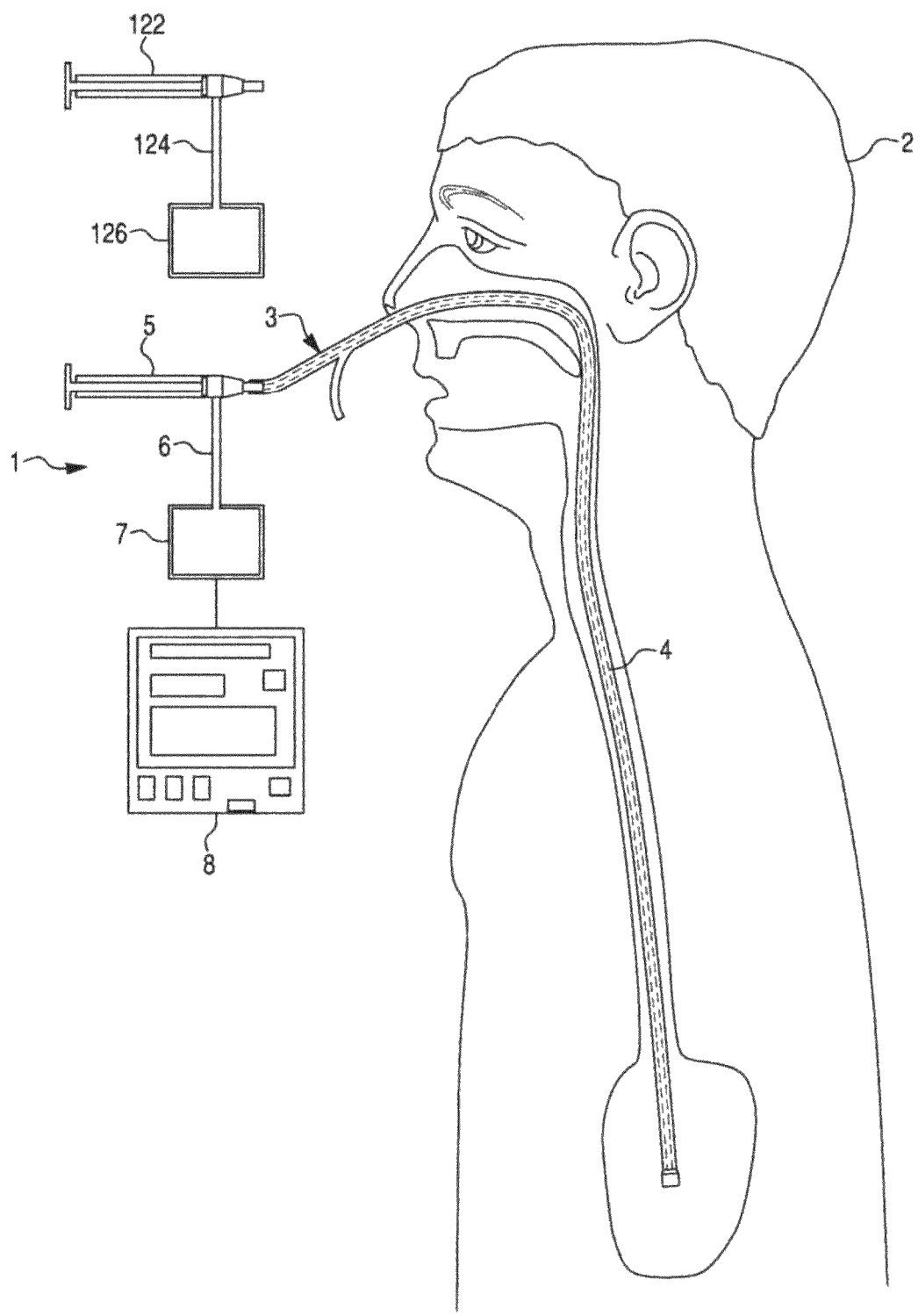
FIG. 10 is a schematic of an apparatus in accordance with another exemplary embodiment, and particularly shows a sensor that measures baseline pH and a separate sensor that measures stressed pH.

Exemplary embodiments include other structures. For example, FIG. 10 is a schematic of an apparatus in accordance with an exemplary embodiment, wherein one sensor measures baseline pH and a separate sensor measures stressed pH. Specifically, one syringe/aspirator 5, connector 6, and pH measuring device 7 is used to measure gastric contents pH to obtain a baseline pH for indication by the indicator 8. Any or all of these devices, i.e., the syringe/aspirator 5, connector 6, and pH measuring device 7, are then discarded and/or replaced with another syringe/aspirator 122, connector 124, and/or pH measuring device 126 used to measure gastric contents pH to obtain a stressed pH. The pH measuring device 126 can be connected (structurally and/or functionally) to the indicator 8 for indication of the stressed pH. In another exemplary embodiment, the pH sensor could be an in-dwelling type sensor that has been calibrated before insertion in the stomach. This in-dwelling pH sensor would measure both the baseline pH and the stressed pH, then communicate the measurements back to a common pH recorder.

Exemplary embodiments are intended to cover and include any indicator 8 that provides any sort of indication of the measured pH or of the hydrogen ion concentration, which is the basis of reflection of pH measurements. The indicator 8 can provide local indication, such as on the indicator itself and/or provide indication remote from the indicator 8. For example, the indicator can provide the indication in a part of an ICU remote from the patient, at a separate section of a hospital, or in a facility remote from a hospital, for example. In an exemplary embodiment, the measured pH is transmitted to a database accessible to a patient's medical care provider, such as the patient's doctor.

Exemplary embodiments are intended to cover and include an indicator 8 that provides any sort of pH indication. For example, the indication can be provided through sound, such as the indicator 8 generating and outputting an artificial voice signal so that the operator can hear the measured pH. Alternatively, or in addition to the above, the indicator 8 can provide visual indication of the measured pH, such as on the indicator 8 itself and/or remotely from the indicator 8. The visual indication can be provided via any currently known or later developed display, such as liquid crystal display (LCD), organic light emitting diode (OLED), etc.

As indicated above with regard to the measuring apparatus 1 components, the indicator 8 can be a separate device or be provided as integral or unitary with any or all of the measuring apparatus 1 components. In one exemplary embodiment, the indicator 8 is unitary with the pH measuring device 7. This exemplary embodiment may be advantageous by providing a simple structure that is user friendly, compact, etc.

In some exemplary embodiments, the indicator 8 indicates results of the baseline pH test and the stressed pH test. In other exemplary embodiments, the indicator additionally indicates any differential between the baseline and stressed pH tests. In still other exemplary embodiments, the indicator 8 indicates the differential and does not indicate the baseline pH and/or stressed pH.

In some exemplary embodiments, the indicator 8 also includes a controller capable of performing various operations. These operations can relate to anything relevant to the procedure, such as facilitating detection of gastric function, facilitating the guiding of care, etc.

For example, the controller can help to implement the timing of gastric juice pH measurement, as discussed above in Section IV(A) (Timing of Gastric Juice pH Measurement). As discussed in Section IV(A), a period or gap in time separates the baseline pH test/pharmacological challenge agent administration and the stressed pH test. Some exemplary embodiments use a fixed period while others use different periods based on various data. However, regardless of whether the period is fixed or changeable, the controller can help implement the period, i.e., ensure that the appropriate time elapses between the baseline pH test/pharmacological challenge agent administration and the stressed pH test.

For example, the controller may prevent the stressed pH test from occurring until after the proper period has elapsed. In addition, or as an alternative, the controller may generate and send a signal to the indicator 7 or some other apparatus to provide some indication, such as via an alarm, that a stressed pH test has been attempted prior to the proper period elapsing. In addition, or as a further alternative, the controller can generate and send a signal to the indicator 7 or some other apparatus to provide some sort of indication that the period has elapsed and the stressed pH test should be performed. This indication can help prevent the stressed pH test from being taken too late.

3. Enhanced H+/pH Measurements

Exemplary embodiments are intended to cover any and all currently known and later developed methods and apparatus for enhancing, improving and/or optimizing pH measurements, including but not limited to gastric pH and esophageal pH. For example, related art apparatus used for pH sensing over an extended period are subject to at least two types of challenges or limitations. These challenges or limitations of related art pH sensing technology are evident with antimony sensors used for ambulatory pH monitoring studies that have a duration of approximately 18-24 hours, and can be more pronounced when used for monitoring ICU patients for even longer periods, such as 48-72 hours.

The first type of challenge or limitation is caused by structural aspects of the related art sensors, and in particular the related art sensors not having a structure: 1) amenable to being deposited in the correct or desired location of the patient's body; 2) that reduces, minimizes, or avoids patient discomfort upon being deposited and remaining in the patient's body; and/or 3) that remains functional and accurate over an extended period, i.e., a long useful measurement life. The third type of challenge or limitation can be caused, at least in part, by coating of the related art pH sensors over an extended period with fluids and/or particles, including but not limited to gastric juice secretions, tube feeds, administered medications (e.g., Carafate), etc., which reduces sensor functionality and/or accuracy over time.

Exemplary embodiments provide enhanced pH sensing apparatus and methods that address the first and second challenges or limitations of the related art sensors discussed above, by providing a sensor having a structure: 1) amenable to being deposited and remaining in the correct or desired location of the patient's body over the extended period; and/or 2) that reduces, minimizes, or avoids patient discomfort upon being deposited and remaining in the patient's body over the extended period. For example, exemplary embodiments include an 18F Salem Sump type tube modified to include at least one pH sensor, 18F Salem Sump type tube modified to include 2 pH sensors (one gastric and one esophageal) and impedance sensors in the esophageal location, and a 12 F fine bore feeding tube with a removable stylet/guide wire modified to include pH and/or impedance sensors. The 18F tube is of sufficient rigidity that it can be inserted into the stomach through the nose or mouth in a patient who is not sufficiently conscious or cooperative to aid in this insertion, e.g. aided in conscious or cooperative patients by swallowing the typically thin and flimsy tube (e.g. 6 F). The 12 F fine bore tube has sufficient rigidity when the removable guide wire is inserted to facilitate insertion in an unconscious or uncooperative patient, however, after insertion the guide wire can be removed, resulting in a less rigid and more comfortable tube.

Exemplary embodiments also provide enhanced pH sensing apparatus and methods that address the third challenges or limitations of the related art sensors discussed above. For example, some exemplary embodiments can reduce, minimize, remove or otherwise prevent coating, debris or other build-up on or around the pH sensor to enhance its useful measurement life and precision over time. In one such embodiment, a fluid, such as a liquid or even gas, is used to remove or clean debris or other deposits (e.g., protein buildup) from the pH sensor.

This operation can be implemented using any currently known or later developed technology. For example, the sensor can be attached to a catheter having a lumen (i.e., a hollow tube), which is either housed within, or is external to, a larger catheter body. It may be beneficial to provide the lumen within the catheter body for various reasons, such as to make the apparatus more compact, to obviate structures on the catheter body exterior that may potentially contact or catch-on the patient, etc. However, some exemplary embodiments provide the lumen at or on the catheter body exterior. In some exemplary embodiments, the catheter body and lumen are unitary, i.e., formed from a single structure, while the catheter body and lumen of other embodiments are integral or otherwise formed of two separate structures that are connected together. The catheter body and lumen can be formed of any material, such as synthetic resin, that enables the above functionality.

The lumen can extend from a proximal end (external to the patient) to or adjacent to the gastric pH sensor at a distal end. The proximal end of the lumen can include any structure that enables introduction of a fluid, such as a liquid or gas, into the interior of the lumen. In some embodiments, a syringe is used to introduce the fluid into lumen. In these embodiments, the proximal end of the lumen includes a Leur-lock or similar adapter that allows an operator to connect the syringe, such as a standard medical grade syringe (e.g., B-D 3, 5, 10, or 20 ml). In one exemplary embodiment, the syringe is a 20 ml syringe, such as the syringe disclosed in http://catalog.bd.com/bdCat/viewProduct.doCustomer?moductNumber=301031, which is hereby incorporated by reference in its entirety.

After being introduced at the proximal end, the fluid travels distally within the lumen and is ejected from the lumen at the distal end. The fluid contacts the sensor after being ejected so as to reduce or otherwise remove debris on or at the sensor. Exemplary embodiments are intended to include any structure at the lumen distal end enabling or facilitating this ejection. In some embodiments, the lumen distal end defines a small hole, slit, or other suitable aperture disposed so as to direct the fluid to or at the sensor. In one such embodiment, the hole, slit, or other suitable aperture is disposed adjacent to, and points toward, the pH sensor. The hole, slit, or other suitable aperture can also be structured to increase the ejected fluid velocity to enhance the debris removal, such as by using a nozzle or nozzle-like effect.

In some of the embodiments discussed above, the fluid is a liquid (e.g., water, saline and/or 0.9% NaCl), that is introduced and travels through the lumen, and is ultimately squirted or otherwise ejected from the lumen in a sufficient volume, such as approximately 3 to 20 ml, in order to reduce or otherwise remove a coating, debris or other build-up on or around the pH sensor. This procedure can be performed once or several times as desired to accomplish or ensure certain results. This operation can be performed after detection of actual or suspected degradation of sensor functionality or accuracy, or alternatively can be performed prophylactically, e.g., every 12 hours (for several days), to reduce, minimize, or prevent any coating, debris or other build-up from developing on or around the sensor.

As disclosed above, some of the embodiments use water, saline and/or 0.9% NaCl as the fluid. However, embodiments are intended to cover any applicable fluid, such as a specialized liquid cleaning formula. In fact, such a formula can be advantageous if it is: 1) not toxic to patients; and 2) more likely to reduce, remove, break-down or otherwise prevent deposits (e.g., protein) on or around pH sensors. Exemplary liquid cleaning fluids include: 1) non-toxic proteolytic enzymes, such as pancreatic enzyme (which is disclosed in Dandeles, Lauren M., Amy E. Lodolce. "Efficacy of Agents to Prevent and Treat Enteral Feeding Tube Clogs." The Annals of Pharmacotherapy 45 (2011): 676-680. Print, hereafter "Dandeles et al 2011," which is hereby incorporated in its entirety herein by reference.), and/or 2) papain (which is disclosed in "Proteolytic Enzymes for Ear, Nose, & Throat Problems." Dr. Grossan's Ear. Nose and Throat Consultant Pages, 12 Jun. 2012. Web. <http://www.eut-consult.com/enzymes.html>, and hereby incorporated herein by reference in its entirety). The fluids used in other exemplary embodiments include a mixture of different liquid cleaning formulas and/or other fluids (such as water, saline and/or 0.9% NaCl).

Some of the embodiments disclosed above are directed solely to reducing, removing or otherwise preventing the coating, debris and/or other build-up on or around pH sensors used to measure gastric pH, i.e., gastric juice disposed in a patient's stomach. These embodiments may be particularly beneficial because of the increased likelihood of coating, debris, and/or other build-up on or around a gastric pH sensor (as opposed to other sensors, such as esophageal sensors) due to the fact that the gastric secretions and possibly external tube feeds are in this location and thus more likely to adversely affect the sensor's function.

However, some of the above exemplary embodiments are directed solely to reducing, removing or otherwise preventing the coating, debris or other build-up on or around pH sensors used to measure esophageal pH, i.e., fluid disposed in and/or around a patient's esophagus. Still other exemplary embodiments are directed to reducing, removing or otherwise preventing the coating, debris or other build-up on or around multiple pH sensors, such as sensors used to measure gastric pH. i.e., gastric juice disposed in a patient's stomach, and esophageal pH, i.e., fluid disposed in and/or around a patient's esophagus.

Exemplary embodiments are intended to cover any currently known or later developed apparatus and methods to perform this operation involving multiple pH sensors. One such embodiment includes the structure disclosed above for reducing or removing coating, debris or other build-up on or around the pH sensors used to measure gastric pH. i.e., gastric juice disposed in a patient's stomach, and in addition includes a separate lumen having a structure enabling fluid to exit at or otherwise proximate the esophageal pH sensor. Another embodiment includes a single lumen with separate fluid exit structures, such as small holes, slits, or other suitable apertures, disposed so as to separately direct the fluid to or at the gastric sensor and the esophageal sensor. In these embodiments, fluid is introduced at the single lumen proximal end, and travels distally to a location at or adjacent to the esophageal sensor. Some of the fluid is ejected at the esophageal sensor, while the remaining fluid travels distally past the esophageal sensor to be ejected at or adjacent to the gastric sensor.

In some embodiments, the fluid exit structures at the esophageal sensor and the gastric sensor are the same. However, other embodiments use different fluid exit structures to provide a variety of benefits. For example, it may be beneficial for the fluid exit structure adjacent the esophageal sensor to be structured to prevent or otherwise avoid an excessive amount of fluid from exiting to ensure that a sufficient volume of fluid is available for the gastric sensor, especially because coating, debris or other build-up is more likely to occur, or be heavier, at the gastric sensor. As an example, a small slit may be used as the fluid exit structure at the esophageal sensor, while a larger aperture may be more appropriate at the gastric sensor.

Exemplary embodiments are intended to cover any currently known or later developed methods and apparatus for reducing, removing or otherwise preventing coating, debris and/or other build-up on or around pH sensors, and are not limited to the exemplary embodiments disclosed above that utilize fluids. In fact, other embodiments instead involve mechanical cleaning of such sensors, which can be accomplished using any currently known or later developed technology. One such embodiment uses a lumen that extends from the proximal end of the catheter to adjacent or otherwise proximal the pH sensor. A wire or other suitable structure can be introduced along the lumen to actuate a flap back and forth over the sensor to reduce or remove the coating, debris and/or other build-up. The embodiments that utilize mechanical cleaning techniques can be applied to any of the sensors disclosed above, including gastric sensors and/or esophageal sensors.

Embodiments disclosed above involve reducing, removing or otherwise preventing coating, debris or other build-up on or around pH sensors while the sensors remain in the patient's body, thereby obviating removal of the catheters, sensors, etc., from the patients. This operation can be beneficial for a variety of reasons, such as by reducing patient trauma, discomfort, etc., reducing effort required by hospital staff, reducing or preventing interruption of pH measurements, etc.

However, other embodiments involve reducing, removing or preventing coating, debris or other build-up after removal of pH sensors from patients. In accordance with these embodiments, the catheter, sensor, etc., is removed from the patient and cleaned outside of the patient. Embodiments are intended to cover any currently known or later developed methods and apparatus for such cleaning, such as reducing, removing or preventing any coating, debris or other build-up using water, saline and/or a non-toxic abrasive method, e.g., rubbing the sensor or other related structure with any applicable material, such as clean medical grade gauze. The sensor and related structure can then be reinserted into the patient after such cleaning. The embodiments that reduce or remove the coating, debris or other build-up after removal of pH sensors from patients may be beneficial by ensuring that the sensors are sufficiently clean.

Exemplary embodiments are intended to cover still other techniques of reducing, removing or otherwise preventing coating, debris or other build-up on or around pH sensors. For example, the sensors or other adjacent structures may be formed of a material, or coated with a material, that makes it more difficult for, reduces, or prevents debris or other unwanted materials from adhering to the sensors or other adjacent structures.

4. Calibration

Exemplary embodiments include any type of currently known, related art, or later developed pH measuring device usable with any of the disclosed methods and apparatus, including pH measuring devices that require calibration. Some embodiments include pH sensors that require calibration immediately prior to use, such as 2 or 3 point calibration with USP buffers of 4.0 and 7.0 pH units. This type of calibration can be referred to as "on-site" calibration, or "bed-side" calibration.

However, it may be beneficial to use pH sensing apparatus that do not require this calibration at the bedside for various reasons, such as to reduce or minimize interruptions in patient care including direct care. A few embodiments for providing pH sensors that do not require "on-site" calibration are provided below for exemplary purposes, and are not intended as an exhaustive list of pH sensors usable with the disclosed methods and apparatus.

Some embodiments avoid "on-site" calibration by adopting certain manufacturing tolerances, such as strict manufacturing tolerances. In other words, pH sensing catheters can be manufactured with sufficient accuracy and precision that no "on-site" calibration is required. In one such example, accuracy is ±0.2 pH units and precision is ±0.1 pH units, which is sufficiently accurate and precise for many medical contexts. One such applicable medical context includes differentiation between gastric or esophageal pH of 2.0 vs. 5.0, which does not require a high degree of accuracy or precision because the differences in pH being measured are fairly large.

In addition, the pH sensor manufacturer can randomly or systematically sample manufactured sensors and test them with USP buffer solutions of known pH. This process can be performed in any sequence or any frequency, such as intermittently, in order to verify that the desired accuracy and precision is being obtained, or at least to increase the chances of obtaining the desired accuracy and precision.

In accordance with some other embodiments that avoid "on-site" calibration by performing factory testing, the pH sensor tests all manufactured sensors with USP buffer solutions of known pH in order to verify that they have the desired accuracy and precision, e.g., accuracy of 0.2 pH units and precision of ±0.1 pH units. In these embodiments, only sensors passing this testing i.e., meeting the sensor specifications, are released for commercial use. Sensors not meeting the specifications can be recycled, re-tooled, or discarded.

Still other embodiments avoid "on-site" calibration by performing factory "pre-calibration." In accordance with one such embodiment, the manufacturer calibrates all manufactured sensors in the factory with USP buffer solutions of known pH. The calibration factor for each sensor is obtained, and recorded or "burned" into an electronic memory device or other electronic recording medium. The calibration factor recorded on the recording medium can be communicated to a pH recorder or other device to receive the pH data. However, other embodiments communicate the calibration factor differently to the pH recorder or other device. In one such embodiment, the calibration factor is printed on the pH sensor packaging and can then be entered manually into the pH recorder or scanned (e.g., bar code) into the pH recorder.

5. Other Exemplary Embodiments

Exemplary embodiments are intended to include still other methods and apparatus for determining gastric juice pH. For example, in one exemplary embodiment, a feeding tube apparatus designed for safer and/or quicker insertion includes pH sensor(s) and/or impedance sensor(s), enabling pH and/or impendence monitoring for patients intubated with such an apparatus.

In one such embodiment, the pH and/or impedance sensors are integrated into a tube that contains a magnet in its tip. An external magnet is used to facilitate, enhance or optimize placement of the tip of the tube, often post-pyloric for a naso duodenal or naso jejunal tube.

In another exemplary embodiment, a feeding tube and electromagnetic insertion guidance system includes pH and/or impedance sensors. This tube can either be a nasogastric tube or a longer tube designed for post pyloric insertion. Benefits of using this modified feeding tube include ease of insertion with the capability for pH and/or impedance monitoring, e.g., in the stomach and/or esophagus. In one embodiment, pH and/or impedance sensors are integrated in a nasogastric feeding tube incorporating a mechanism for enhanced guidance and positioning (e.g., an electromagnetic device).

In other embodiments, a sensor (e.g., pH sensor) is located in the tip of a naso jejunal tube, enabling continuous, semi-continuous or intermittent pH measurements in the small bowel. Small bowel pH measurements can be useful or beneficial in several ways. For example, these pH measurements may assist with confirmation of tube placement. In this case, as the distal tip of the tube leaves the stomach (low pH) and enters the small bowel, the pH rises, thereby providing confirmation of placement. Secretion of bicarbonate into the small bowel typically results in a much less acidic environment there (e.g., pH 7) compared with the stomach (e.g., pH 2-5).

Related art systems for introducing feeding tubes may allow for relatively easy insertion of the tube, but do not provide monitoring of correct placement of the tube. This deficiency may be significant or otherwise important because it is common for feeding and other such tubes to migrate (i.e., move) within the patient due to several potential factors, such as traction/pulling of the tube by the patient. Therefore, another embodiment includes continuous or semi-continuous measurement of small bowel pH to enable the clinician to verify that the tip of the feeding tube continues to be in the correct location (small bowel) and has not migrated (i.e., moved) into the stomach. This unintended migration or otherwise improper tube placement may be particularly dangerous for a patient where it is imperative that feeds are administered only into the small bowel, and not into the stomach. One such example includes certain critically ill patients with no effective lower esophageal sphincter, which is the part of the body, which normally minimizes the retrograde movement of gastric contents into the esophagus.

C. Methods and Apparatus for Determining GI Tract's Response to Challenge and Guiding Care Based on Determined H+/pH 1. Gastric Juice H+/pH Data Interpretation Exemplary embodiments guide medical care based on detected gastric function. Some exemplary embodiments detect gastric function by determining a change in H+ concentration or pH caused by administration of a pharmacological challenge agent, such as gastric acid stimulant or suppressant. The change in gastric juice H+ concentration or pH (gastric juice H+ concentration or pH differential) can be determined by calculating the difference in gastric juice H+ concentration or pH immediately before administration of the stimulant or suppressant and the gastric juice H+ concentration or pH after a sufficient period has elapsed subsequent to administration. The following examples are provided in terms of pH, but are also applicable in terms of H+ concentrations.

In general, a relatively large change in gastric juice pH indicates a relatively healthy GI tract with robust splanchnic perfusion and care can be provided accordingly, such as by initiating enteral feeding, for example. Alternatively, no change in gastric juice pH, or a relatively small change, indicates a relatively unhealthy GI tract response and care can be provided accordingly, such as by not introducing enteral feeding, for example.

a. Gastric Juice pH Differential

Exemplary embodiments are directed to many inventive aspects further specifying and/or providing additional benefits beyond the above indications of relatively healthy/unhealthy gastric function based on relatively large/small changes in gastric juice pH. For example, certain pH differentials may be deemed sufficient in some contexts, while other entirely or slightly different pH differentials may be deemed sufficient in other contexts. Examples of some of these inventive aspects are provided below for exemplary purposes only, and are not intended to form a complete listing.

For example, the pH differential deemed sufficient may depend on the type of care at issue, i.e., enteral feeding, ventilation, vasoactive agents, patient disposition within the hospital, etc. In other words, in some exemplary embodiments, the pH differential used to indicate sufficient gastric function for a certain type of care, such as enteral feeding, may be fixed, such as at 1 pH unit. In other words, a pH differential of 1 pH unit may be deemed sufficient to initiate enteral feeding. Contrarily, in other exemplary embodiments, the pH differential deemed sufficient to determine patient disposition within the hospital, such as determining whether a patient remains in an ICU, may be different. In other words, a lower pH differential (than would be required to start enteral feeding), such as 0.5 pH units, may be sufficient to move a patient out of an ICU (assuming other data warrants such a move). In still other exemplary embodiments, the pH differential deemed sufficient to guide care may depend on patient characteristics, such as one or any combination of factors, including but not limited to: age, gender, fitness, weight, body composition, such as percentage of body fat, ethnicity, family history, current medical condition, personal medical history, genetics, or any other factor currently known or later determined to be relevant or applicable. In other words, as an example, the pH differential deemed sufficient to guide care of a young patient may be higher than that required for an older patient.

The pH differential deemed sufficient to guide care can also be affected by other factors, such as instrument accuracies. For example, some exemplary embodiments can take into account accuracy of pH monitors. A pH monitor that is accurate to 0.001 pH units easily enables detection of a difference between 1.0 pH unit and 0.8 pH unit, and thus exemplary embodiments incorporating such a monitor can make determinations as to the sufficiency of detected pH differential accordingly.

The pH differential deemed sufficient for certain types of care can be based on still other factors, such as the baseline gastric juice pH. In other words, a certain pH differential may be sufficient to guide care after detection of a relatively low baseline gastric juice pH, while a different pH differential may be sufficient to guide the same type of care after a relatively high baseline gastric juice pH. One exemplary basis for this distinction is that pH values follow a logarithmic scale in relation to hydrogen ion concentration, as indicated in the table below.

| pH | Molarity (moles/L) |
|---|---|
| 7 | 0.0000001 |
| 6 | 0.000001 |
| 5 | 0.00001 |
| 4 | 0.0001 |
| 3 | 0.001 |
| 2 | 0.01 |
| 1 | 0.1 |

As indicated above, a pH of 7 has a hydrogen ion concentration of 0.0000001 moles per liter of the gastric contents. Each unit drop in pH therefore requires 10 times the concentration of hydrogen ions. For example, a pH drop from 7 to 6 requires 10 times the hydrogen ions to be present in the sample, while a pH drop of 6 to 5 requires a further 10 times the hydrogen ions. A pH drop from 7 to 5 would therefore require 100 times the hydrogen ions, and 7 to 4, 1000 times the hydrogen ions. This increase in hydrogen ions may appear large, but these measurements are relative to a typical gastric acid response and the pH of the initial sample. For example, studies have shown that the parietal cells in the stomach produce gastric acid at a hydrogen ion concentration of 0.160 moles per liter, such as: 1) Feldman. Mark. "Gastric Bicarbonate Secretion in Humans: Effect of Pentagastrin, Bethanechol, and 11,16,16-Trimethyl Prostaglandin E2." *Journal of Clinical Investigation* 72 (1983): 295-303. Print., hereafter "Feldman," which is hereby incorporated in its entirety herein by reference, 2) Hollander, Franklin. "Variations in the Chlorine Content of Gastric Juice and Their Significance." *Studies in Gastric Secretion* 4 (1932): 585-604. Print., hereafter "Hollander," which is hereby incorporated in its entirety herein by reference, 3) Makhlouf, G. M., J. P. McManus, and W. I. Card. "Gastroenterology." *Official Publication of the American Gastroenterological Association* 51.4 (1966): 455-65. Print., hereafter "Makhlouf," which is hereby incorporated in its entirety herein by reference, and 4) Hirst. B. H., L. A. Labib, J. D. Reed, and J. G. Stephen. "Relationship Between Hydrogen Ion Concentration and Flow of Gastric Juice During Inhibition of Gastric Secretion in the Cat." *J. Physiol.* 306 (1980): 51-63. Print., hereafter "Hirst," which is hereby incorporated in its entirety herein by reference. The Feldman et al (1983) study showed the typical basal, or non-stimulated, gastric acid production in healthy adults was 31 ml/h, while pentagastrin stimulated gastric acid production over 120 ml/h.

Given such a high production of gastric acid at a high hydrogen ion concentration, it is therefore easier for gastric juice pH to decrease by at least one unit when starting at a higher pH because the inherent hydrogen ion concentration is so low at these higher pH levels. In contrast, when the initial pH is low, e.g. 2.0, it is more difficult to drop even one pH unit. Therefore, the same volume of stimulated gastric acid production can result in different units of pH drop depending on the initial pH.

The following exemplary table demonstrates the relationship of how the same volume of stimulated gastric acid production can result in different units of pH drop depending on the initial pH. The exemplary table is generated using an exemplary method of calculating the resulting pH (which is merely provided for exemplary purposes and not intended as limiting) uses the following formula:

$$pH = -\log(((H^+_{GJ1} * V_{GJ2}) + (H^+_{GJ2} * V_{GJ2}))/(V_{GJ1} + V_{GJ2}))$$

Wherein:

$H^+_{GJ1}$=Hydrogen ion concentration of the initial gastric volume in moles per liter, $V_{GJ1}$=Volume of the initial gastric contents, $H^+_{GJ2}$=Hydrogen ion concentration of the stimulated gastric juice in moles per liter, and $V_{GJ2}$=Volume of the stimulated gastric juice.

In this exemplary calculation, the volume of the initial gastric contents, $V_{GJ1}$=0.200 liters, the hydrogen ion concentration of the stimulated gastric juice, $H^+_{GJ2}$=0.147 moles/liter, and the volume of the stimulated gastric juice, $V_{GJ2}$=0.008 liters. The exemplary table thus shows that for the same volume of stimulated gastric juice, the resulting pH measurements, pH2, vary depending on the initial pH measurement, pH1. This exemplary table and calculation show that higher initial pH measurements result in a higher pH differential compared to lower initial pH measurements which result in a lower pH differential.

| pH 1 | $H^+_{GJ1}$ (M/L) | $H^+_{GJ2}$ (M/L) | pH 2 |
|---|---|---|---|
| 7 | 0.0000001 | 0.005662 | 2.24706 |
| 6 | 0.0000010 | 0.005663 | 2.24699 |
| 5 | 0.0000100 | 0.005671 | 2.24633 |
| 4 | 0.0001000 | 0.005758 | 2.23975 |
| 3 | 0.0010000 | 0.006623 | 2.17894 |
| 2 | 0.0100000 | 0.015277 | 1.81596 |
| 1 | 0.1000000 | 0.101815 | 0.99219 |

An exemplary embodiment therefore uses a non-linear scale, such that a relatively large change or decrease in pH (such as a change or drop of one or more units) is considered a sufficient pH differential if the initial pH is high, but a relatively small change or decrease in pH (such as a change or drop of less than one unit) is considered a sufficient pH differential if the initial pH is low. Another exemplary embodiment can therefore use a non-linear scale that also follows a logarithmic function, where the level of gastric acid concentration in the stimulation response is in proportion to the pH unit drop of a valid test result (sufficient pH differential). In other words, a much larger pH differential deemed sufficient to indicate healthy gastric function would be required for a high baseline pH as compared to a low baseline pH, and that this difference can be represented in magnitudes of ten. An exemplary embodiment can also display the non-linear scale of valid test results (i.e., pH differentials deemed sufficient) in a table format that can be viewed, such as by medical staff. Another exemplary embodiment may use this non-linear scale programmed as software into a pH meter, or other testing device that may calculate and then communicate the determination as to whether a valid test result is achieved.

b. Hydrogen Ion (H+) Concentration Differential

Exemplary embodiments for further specifying and/or providing indications of relatively healthy/unhealthy gastric function can be based directly on the hydrogen ion (hereafter H+) concentration of the gastric contents, as specified in moles per liter (mol) or millimoles per liter (mmol). For example, measurements can be taken of gastric juice molarity before the gastric stimulation test, documenting in moles per liter, and then measurements can be taken again after the gastric stimulation test. The differential of the two measures of H+ concentration in moles per liter can then be used to assess the relative health of the gastric function and to help guide care. Certain H+ concentration differentials may be deemed sufficient in some contexts, while other entirely or slightly different H+ concentration differentials may be deemed sufficient in other contexts. Examples of some of these inventive aspects are provided below for exemplary purposes only, and are not intended to form a complete listing.

Figure 13:
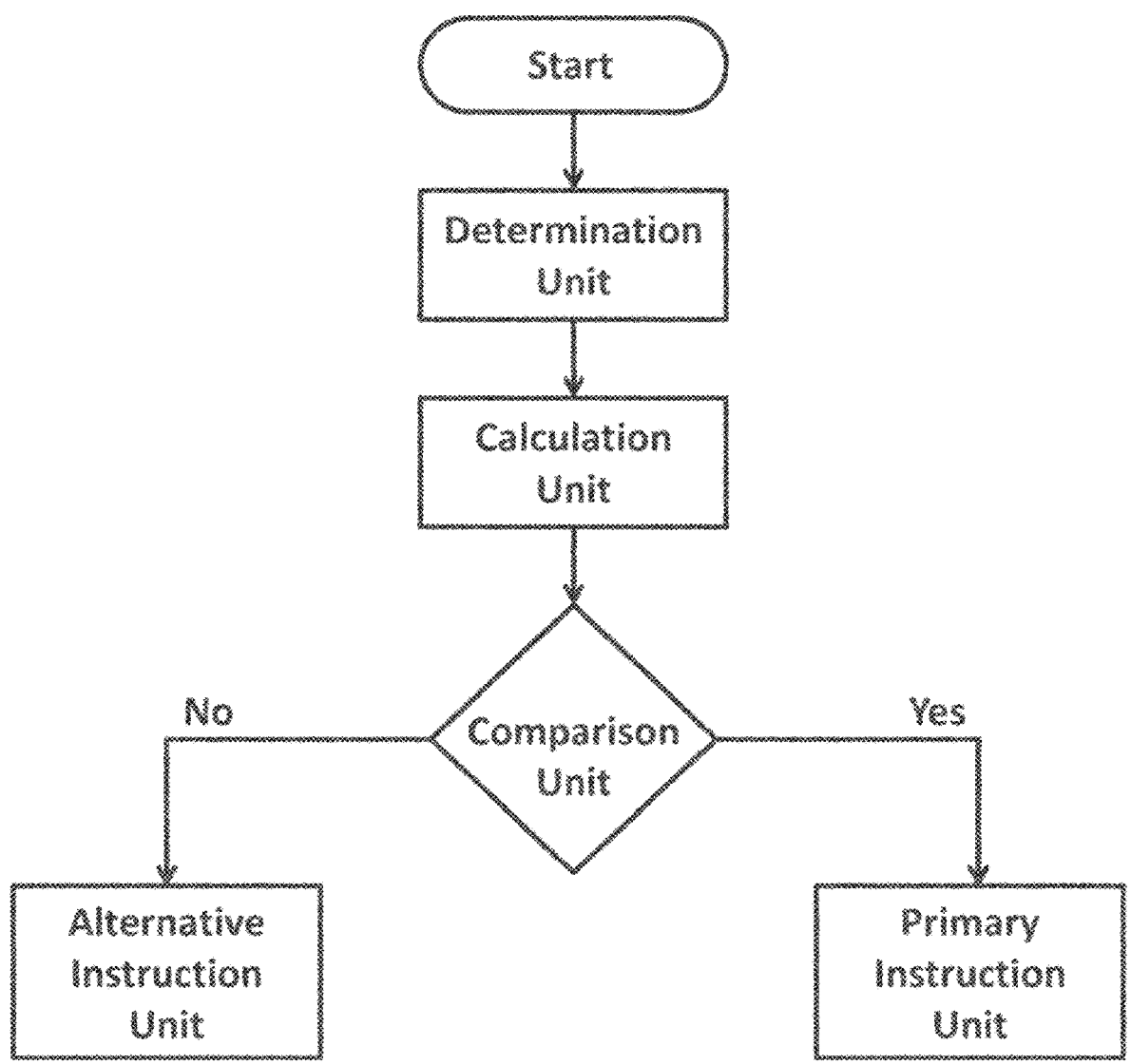
FIG. 13 is a flowchart of an exemplary method and apparatus for guiding care based on H+ concentration differential(s).

FIG. 13 is a flowchart of an exemplary method and apparatus for guiding care based on H+ concentration differential(s). In one embodiment covered by the flowchart of FIG. 13, a processor is used to guide medical care of a patient based on detected gastric function. The processor is used with at least one administering device that administers a gastric acid stimulant or suppressant, and at least one sensor that measures the patient's gastric juice H+ concentration prior to the administration of the gastric acid stimulant or suppressant to obtain a baseline gastric juice H+ concentration, and that measures the patient's gastric juice H+ concentration after the administration of the gastric acid stimulant or suppressant to obtain a stressed gastric juice H+ concentration.

As shown in FIG. 13, the processor includes a determination unit that determines a guidance H+ concentration differential indicative of relatively healthy gastric function. This determination can be performed in a variety of ways. For example, the guidance H+ concentration differential can be preset prior to initiation of the procedure, such as even before the patient is examined. In one such embodiment, as disclosed below, a certain guidance H+ concentration differential can be used for all patients, such as 0.01 mmol. Alternatively, the guidance H+ concentration differential can be determined and calculated based on data, such as patient characteristics, including at least one of age, gender, fitness, weight body composition, percentage of body fat, ethnicity, family history, personal medical history, aspects of current personal medical condition, and genetics. Depending on the patient characteristics on which the guidance H+ concentration differential is based, the determination may be performed prior to or after certain steps of the procedure are performed, such as after measurement of the baseline H+ concentration. According to these embodiments, any currently known or later developed algorithm, program, etc. can be used to make the appropriate determination of guidance H+ concentration differential, including but not limited to mathematical formulae, computational procedures, software programming, application specific integrated circuits, and any other means deemed beneficial.

The processor also includes a calculation unit that calculates a measured H+ concentration differential between the baseline gastric juice H+ concentration and the stressed gastric juice H+ concentration. Any currently known or later developed algorithm, program, etc. can be used to make the appropriate calculation of the measured H+ concentration differential, including but not limited to mathematical formulae, computational procedures, software programming, application specific integrated circuits, and any other means deemed beneficial.

The processor also includes a comparison unit that compares the guidance H+ concentration differential to the measured H+ concentration differential to determine their relative values. Any currently known or later developed algorithm, program, etc. can be used to make the appropriate calculation of the measured H+ concentration differential, including but not limited to mathematical formulae, computational procedures, software programming, application specific integrated circuits, and any other means deemed beneficial.

The processor also includes a primary instruction unit that provides instructions to guide medical care based on a relatively healthy gastric function if the measured H+ concentration differential is equal to or exceeds the guidance H+ concentration differential. In other words, if the comparison unit determines that the measured H+ concentration differential is equal to or exceeds the guidance H+ concentration differential, i.e., "Yes," then the primary instruction unit provides instructions to guide medical care based on a relatively healthy gastric function. Any currently known or later developed algorithm, program, etc. can be used to provide the appropriate instructions regarding guidance of care that correspond to the comparison between measured H+ concentration differential and guidance H+ concentration differential, including but not limited to mathematical formulae, computational procedures, software programming, application specific integrated circuits, and any other means deemed beneficial.

Similarly, the processor includes an alternative instruction unit that provides instructions to guide medical care based on a relatively unhealthy gastric function if the measured H+ concentration differential is less than the guidance H+ concentration differential. In other words, if the comparison unit determines that the measured H+ concentration differential is less than the guidance H+ concentration differential, i.e., "No," then the alternative instruction unit provides instructions to guide medical care based on a relatively unhealthy gastric function. Any currently known or later developed algorithm, program, etc. can be used to provide the appropriate instructions regarding guidance of care that correspond to the comparison between measured H+ concentration differential and guidance H+ concentration differential, including but not limited to mathematical formulae, computational procedures, software programming, application specific integrated circuits, and any other means deemed beneficial.

In some embodiments, the sensor performs multiple measurements of the patient's gastric juice H+ concentration after the administration of the gastric acid stimulant or suppressant to obtain multiple stressed gastric juice H+ concentration values; the calculation unit calculates a rate of change of the gastric juice H+ concentration based on at least one of: differentials between the baseline gastric juice H+ concentration and the multiple stressed gastric juice H+ concentration values, and differentials between the different stressed gastric juice H+ concentration values; and the primary instruction unit or the alternative instruction unit provides instructions to guide medical care based on the calculated rate of change of the gastric juice H+ concentration. Any currently known or later developed algorithm, program, etc. can be used to provide these operations, including but not limited to mathematical formulae, computational procedures, software programming, application specific integrated circuits, and any other means deemed beneficial.

In some embodiments, the processor further includes a conversion unit that converts the baseline gastric juice H+ concentration and stressed gastric juice H+ concentration to baseline gastric juice pH and stressed gastric juice pH, respectively, wherein: the determination unit determines a guidance pH differential indicative of relatively healthy gastric function based on the baseline gastric juice pH; the calculation unit calculates a measured pH differential between the baseline gastric juice pH and the stressed gastric juice pH; and the primary instruction unit or the alternative instruction unit performs one of the following based on a comparison between the guidance pH differential and the measured pH differential: 1) guiding medical care based on a relatively healthy gastric function if the measured pH differential is equal to or exceeds the guidance pH differential; and 2) guiding medical care based on a relatively unhealthy gastric function if the measured pH differential is less than the guidance pH differential. Any currently known or later developed algorithm, program, etc. can be used to provide these operations, including but not limited to mathematical formulae, computational procedures, software programming, application specific integrated circuits, and any other means deemed beneficial.

In some of these embodiments, the determination unit determines the guidance pH differential indicative of relatively healthy gastric function to be relatively low if the baseline gastric juice pH is relatively low, and determines the guidance pH differential indicative of relatively healthy gastric function to be relatively high if the baseline gastric juice pH is relatively high. Any currently known or later developed algorithm, program, etc. can be used to provide these operations, including but not limited to mathematical formulae, computational procedures, software programming, application specific integrated circuits, and any other means deemed beneficial.

In some of these embodiments, the processor further includes a comparison unit that sets a minimum baseline gastric juice pH, and compares the measured baseline gastric juice pH to the minimum baseline gastric juice pH; wherein the administering device administers a pharmacological agent to raise gastric juice pH if the comparison unit determines that the measured baseline gastric juice pH is less than the minimum baseline gastric juice pH; the sensor measures the patient's gastric juice pH after the pharmacological agent administration to obtain a modified baseline gastric juice pH; and calculation unit calculates the measured pH differential between the modified baseline gastric juice pH and the stressed gastric juice pH. Any currently known or later developed algorithm, program, etc. can be used to provide these operations, including but not limited to mathematical formulae, computational procedures, software programming, application specific integrated circuits, and any other means deemed beneficial.

In some embodiments, the processor further includes a dosage determination unit that determines a pharmacologically effective dosage of gastric acid stimulant; wherein the administering device is configured to administer the determined pharmacologically effective dosage of the stimulant that includes pentagastrin. The dosage determination unit can determine the pharmacologically effective dosage of pentagastrin based on patient characteristics, including at least one of: age, gender, fitness, weight, body composition, percentage of body fat, ethnicity, family history, personal medical history, aspects of current personal medical condition, and genetics. As one example, the dosage determination unit determines the pharmacologically effective dosage of gastric acid stimulant or suppressant based on patient weight in accordance with one of the following: a stepped methodology wherein 250 mcg is determined to be the pharmacologically effective dosage for patients weighing 40-70 kg, 500 mcg is determined to be the pharmacologically effective dosage for patients weighing 71-100 kg, and 750 mcg is determined to be the pharmacologically effective dosage for patients weighing more than 100 kg; and a linear methodology wherein the pharmacologically effective dosage of pentagastrin is based on 6 mcg/kg, such that 300 mcg is determined to be the pharmacologically effective dosage for a patient weighing 50 kg, 450 mcg is determined to be the pharmacologically effective dosage for patients weighing 75 kg, and 600 mcg is determined to be the pharmacologically effective dosage for patients weighing 100 kg. Any currently known or later developed algorithm, program, etc. can be used to provide these operations, including but not limited to mathematical formulae, computational procedures, software programming, application specific integrated circuits, and any other means deemed beneficial.

In some embodiments, the processor is used with a volume measuring device for measuring the patient's gastric contents volume prior to the administering of the gastric acid stimulant or suppressant; and the determination unit determines the guidance H+ concentration differential based on the measured gastric contents volume. The determination unit can determine the guidance H+ concentration differential to be relatively lower if the gastric contents volume is relatively high, and determine the guidance H+ concentration differential to be relatively higher if the gastric contents volume is relatively low. Any currently known or later developed algorithm, program, etc. can be used to provide these operations, including but not limited to mathematical formulae, computational procedures, software programming, application specific integrated circuits, and any other means deemed beneficial.

In some embodiments, the sensor performs multiple measurements of the patient's gastric juice H+ concentration after obtaining the stressed gastric juice H+ concentration; the processor further comprises a display for displaying the multiple H+ concentration measurements as a curve via a graph, with the x-axis representing the time that the H+ concentration measurements were taken and the y-axis representing H+ concentration values; and an area calculation unit to calculate an area defined under the curve; and wherein the primary instruction unit or the alternative instruction unit guides medical care based on the calculated area. In other embodiments, the sensor performs multiple measurements of the patient's gastric juice H+ concentration after obtaining the stressed gastric juice H+ concentration; the processor further comprises a rate determination unit for determining a rate of change of the multiple H+ concentration measurements via the derivative of at least one of the following functions: $d(H(t))/dt$, where the function $H(t)$ represents the measurement of H+ concentration in moles per liter (mol), and $H(t)$, which represents the multiple measurements of H+ concentration in moles per liter (mol); and wherein the primary instruction unit or the alternative instruction unit guides medical care based on the determined rate of change, such that a relatively fast rate of change indicates a relatively healthy gastric function, and a relatively slow rate of change indicates a relatively unhealthy gastric function. Any currently known or later developed algorithm, program, etc. can be used to provide these operations, including but not limited to mathematical formulae, computational procedures, software programming, application specific integrated circuits, and any other means deemed beneficial.

Various currently known or later developed algorithm(s), program(s), etc. are disclosed above as being usable to provide the above operations. However, it is understood and intended that the same, similar or other algorithm(s), program(s), etc. are usable to perform other and/or similar operations provided in other portions of the present disclosure and with regard to other contexts/embodiments.

In another exemplary embodiment, an absolute value of H+ concentration differential may be deemed sufficient to indicate a threshold where the gastric function of the patient is deemed sufficiently healthy to enable specific types of care. For example, in an exemplary embodiment an H+ concentration differential of 0.01 mmol may be sufficient to determine the patient is competent to receive enteral nutrition. This threshold of 0.01 mmol may be sufficient since it equates to a comparable drop on the pH scale to a little over pH 4 when the initial measurement is in the neutral pH range, e.g. 7. A target H+ concentration differential may be advantageous compared to pH measurement since it is an absolute measure on a linear scale and therefore is less subjective to interpretation compared to the logarithmic scale of the pH measurement. An exemplary H+ concentration differential may vary depending on the assessment being sought. For example, exemplary embodiments for H+ concentration differential may be different when assessing overall gastric perfusion, risk of stress ulcers, risk of non-occlusive bowel necrosis, etc.

le;.4qExemplary embodiments for H+ concentration differential may also vary based on other factors, such as the patient's condition and current care being received. For example, in an exemplary embodiment a patient already being enterally fed and showing signs of intolerance to enteral nutrition, e.g. vomiting, may require a higher H+ concentration differential to indicate if the patient should be fed at the same of higher level. In another example, a patient receiving acid suppressant therapy may require a higher H+ concentration differential to account for the effect of the acid suppressant medication. In exemplary embodiments, the acid suppressant dosing could be done after the gastric stimulation test to minimize any potential effect on the gastric stimulation test. In still other exemplary embodiments, the H+ concentration differential deemed sufficient to guide care may depend on patient characteristics, such as one or any combination of factors, including but not limited to: age, gender, fitness, weight, body composition, such as percentage of body fat, ethnicity, family history, current medical condition, personal medical history, genetics, or any other factor currently known or later determined to be relevant or applicable. In other words, as an example, the H+ concentration differential deemed sufficient to guide care of a young patient may be higher than that required for an older patient.

It is important to note that H+ concentration measurements and the subsequent H+ concentration differential measure are affected by many factors. For example, the volume of gastric contents will affect the H+ concentration measurement since the concentration is based on volume. In exemplary embodiments it may be advantageous to suction out the gastric contents before conducting the gastric stimulation test and H+ concentration measurements. In another example, the output of non-acidic gastric secretions via non-parietal cells will affect the H+ concentration measurement since these secretions may neutralize the gastric acid and thus lower the H+ concentration. Similarly, acid suppressant therapy may neutralize gastric acid or inhibit the production of gastric acid by the parietal cells depending on the therapy being received. In exemplary embodiments, algorithms built into software could capture and process many of these variables to help provide information to the clinician and help guide care.

c. Gastric Juice H, H+ Concentration, and Volume

In accordance with the above exemplary embodiments, the pH formulas discussed above translate directly as the log of the molarity of the gastric contents, where molarity is defined as moles of hydrogen ion (H+) per liter. The following formula for pH is used to generate the above pH/molarity table:

$$pH = -\log (\text{molarity})$$

The above, exemplary embodiments are intended to cover methodologies that base sufficiency of gastric function on a fixed gastric acid output (regardless of baseline gastric juice pH), substantially fixed gastric acid output, and non-fixed gastric acid output. However, since molarity is dependent on volume, the pH and H+ concentration measurements will vary depending on the volume of the gastric contents. For example, if there is a large volume of gastric contents before the gastric acid stimulation, the resultant gastric acid produced will be diluted by the existing gastric contents, reducing the resulting pH drop and H+ concentration differential. Conversely, if there is a small volume of gastric contents before the gastric acid stimulation, the resultant gastric acid produced will be less diluted by the existing gastric contents, increasing the resulting pH drop and H+ concentration differential. Therefore, the same volume of stimulated gastric acid production could result in different units of pH drop and H+ concentration differential depending on the initial volume of the gastric contents. One exemplary method of calculating the resulting pH (which is merely provided for exemplary purposes and not intended as limiting) uses the following formula:

$$pH = -\log(((H^+_{GJ1} * V_{GJ1}) + (H^+_{GJ2} * V_{GJ2}))/(V_{GJ1} + V_{GJ2}))$$

Wherein:

$H^+_{GJ1}$=Hydrogen ion concentration of the initial gastric volume in moles per liter. $V_{GJ1}$=Volume of the initial gastric contents, $H^+_{GJ2}$=Hydrogen ion concentration of the stimulated gastric juice in moles per liter, and $V_{GJ2}$=Volume of the stimulated gastric juice.

Utilizing the above exemplary method of calculating pH one can generate the following table that shows how the post stimulation pH measurement may vary depending on the initial gastric volume. In this exemplary table, the initial pH measurement is noted in furthermost left column. In this exemplary calculation, the patient is assumed to produce 20 ml of gastric acid in response to the stimulation. The exemplary calculation thus shows a general trend where the post-stimulation pH measurement is lower when there is less volume, such as with an initial gastric juice volume of 5 ml versus compared to when there is more volume, such as an initial gastric juice volume of 500 ml. This calculation is exemplary, as there are other factors in the gastric environment that may affect the post-stimulation pH measurements, such as the stimulation of basal secretions that will have the effect of neutralizing a portion of the acid secretions.

| | pH 2 Based on Different Levels of Vgj1 | | | | | | | | |
|---|---|---|---|---|---|---|---|---|---|
| pH 1 | 0.005 | 0.010 | 0.025 | 0.050 | 0.100 | 0.200 | 0.300 | 0.400 | 0.500 |
| 7 | 0.8951 | 0.9502 | 1.0828 | 1.2408 | 1.4475 | 1.6924 | 1.8481 | 1.9624 | 2.0528 |
| 6 | 0.8951 | 0.9502 | 1.0828 | 1.2408 | 1.4475 | 1.6924 | 1.8481 | 1.9624 | 2.0528 |
| 5 | 0.8951 | 0.9502 | 1.0828 | 1.2407 | 1.4474 | 1.6922 | 1.8478 | 1.9621 | 2.0524 |
| 4 | 0.8951 | 0.9501 | 1.0826 | 1.2403 | 1.4466 | 1.6906 | 1.8453 | 1.9588 | 2.0483 |
| 3 | 0.8947 | 0.9493 | 1.0805 | 1.2362 | 1.4384 | 1.6744 | 1.8213 | 1.9270 | 2.0090 |
| 2 | 0.8906 | 0.9411 | 1.0604 | 1.1969 | 1.3639 | 1.5387 | 1.6341 | 1.6954 | 1.7387 |
| 1 | 0.8513 | 0.8513 | 0.8666 | 0.8979 | 0.9266 | 0.9529 | 0.9726 | 0.9807 | 0.9851 |

Thus, some exemplary embodiments measure, and take into account, gastric contents volume in analyzing pH and/or H+ concentration to determine whether the pH and/or H+ concentration differential is sufficient to indicate healthy gastric function. In other words, a relatively small pH and/or H+ concentration differential would be sufficient to indicate healthy gastric function if the gastric contents volume was relatively high while a relatively high pH and/or H+ concentration differential would be sufficient to indicate healthy gastric function if the gastric contents volume was relatively low. The gastric contents volume may be obtained by aspirating all of the gastric contents (including enteral feeds) through an indwelling tube (e.g., nasogastric Salem Sump tube).

Figure 7:
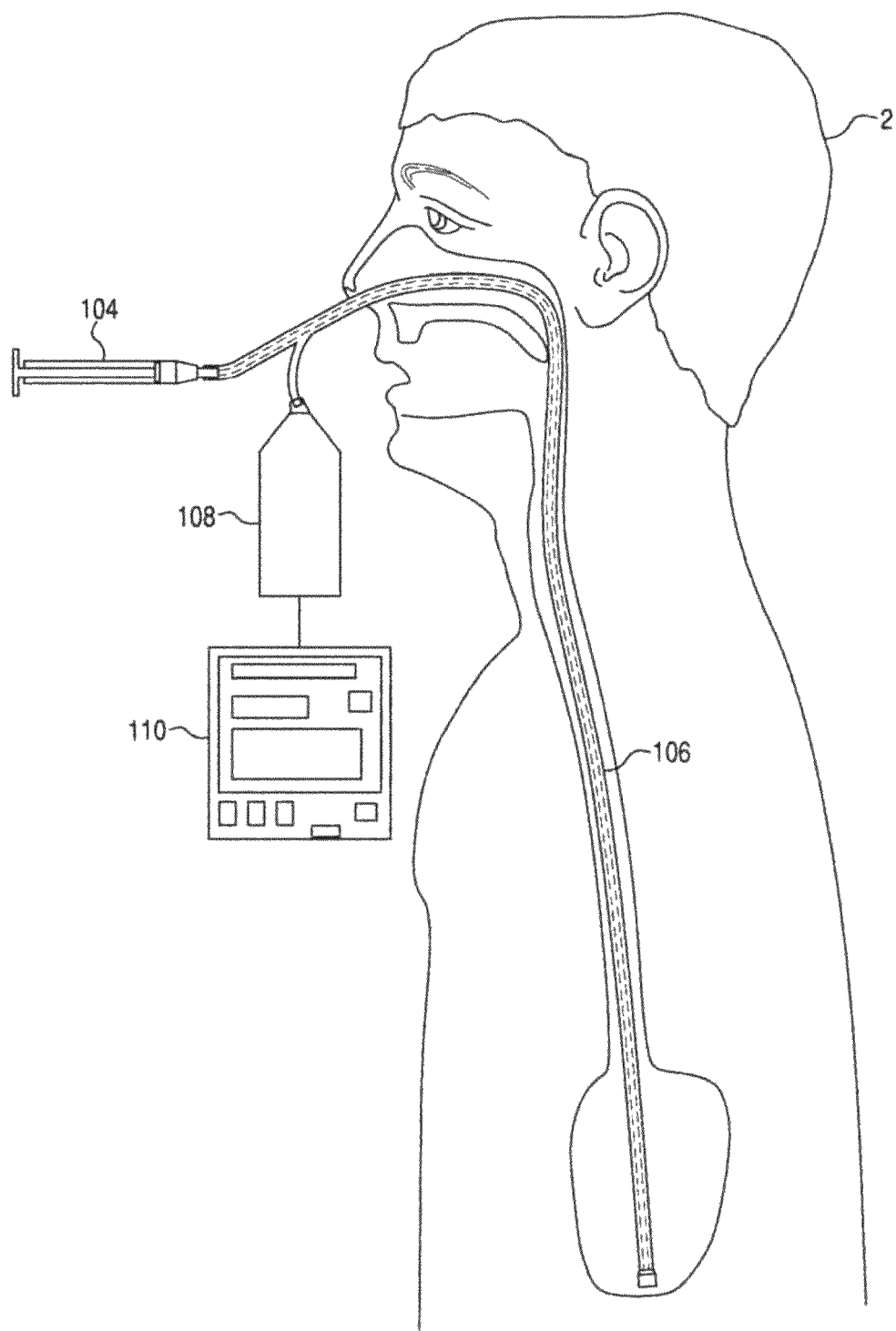
FIG. 7 is a schematic of an apparatus in accordance with another exemplary embodiment, and particularly shows a volume sensor that measures gastric volume.
Figure 8:
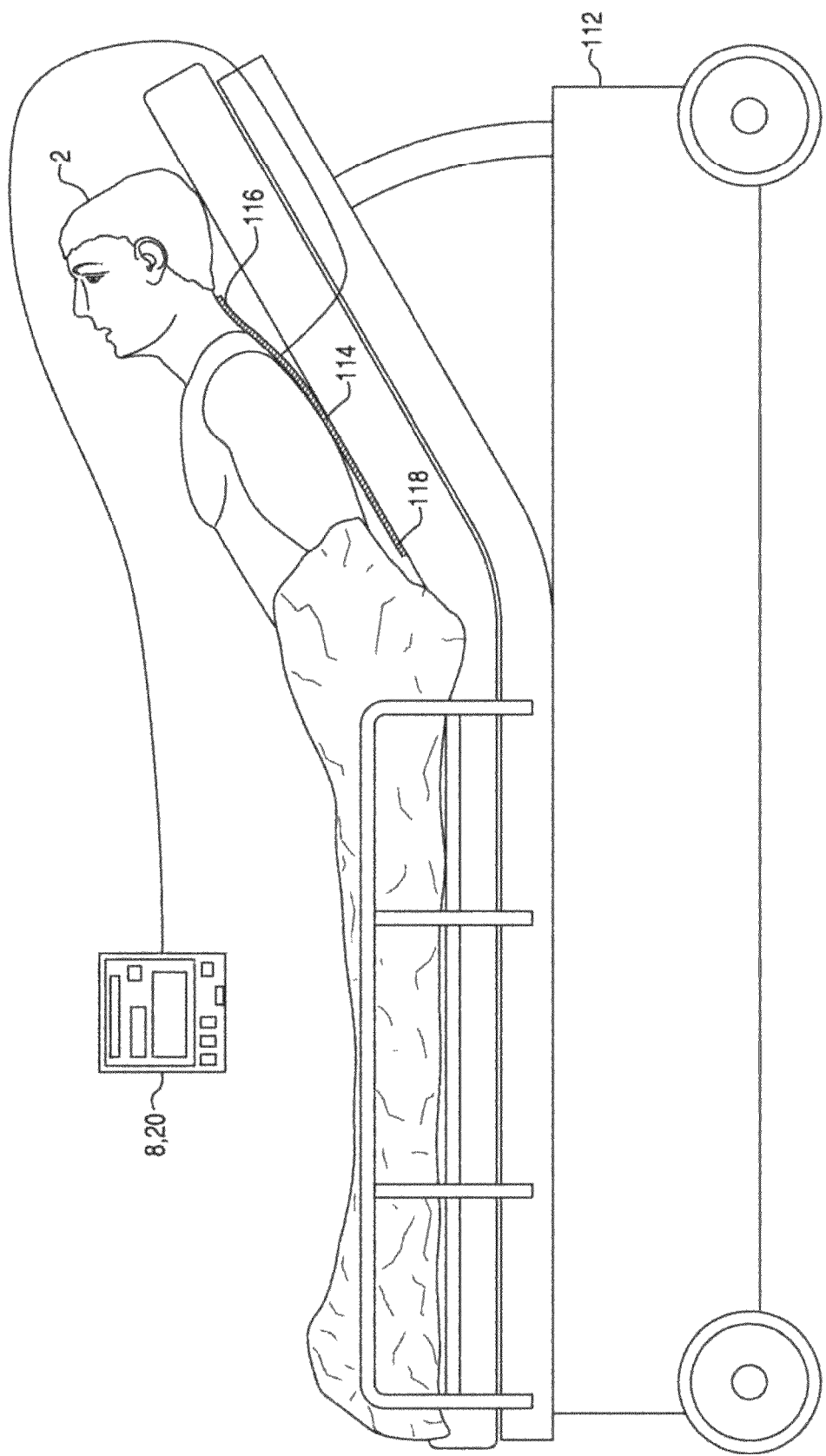
FIG. 8 is a schematic of an apparatus in accordance with another exemplary embodiment, and particularly shows an incline sensor that determines an angle of incline of a patient.

FIG. 7 is a schematic of an apparatus in accordance with an exemplary embodiment that includes a volume sensor 110 that measures gastric volume. As shown in FIG. 7, an aspirator 104 aspirates gastric contents by providing a suction or other force so that gastric contents are sucked or otherwise moved from the stomach of the patient 2, through the orogastric or nasogastric tube 106, and into the collector 108 or other structure. The volume sensor 110 measures the volume of gastric contents collected in the collector 108.

The above structures are merely provided for exemplary purposes, and not intended to be limiting. In fact, exemplary embodiments are intended to cover any currently known or later developed apparatus or method for achieving the above operation. For example, another exemplary embodiment for obtaining gastric contents volume uses impedance sensors (e.g., VersaFlex Disposable pH+impedance Catheter, size 6 F, from Sierra Scientific Instruments, Los Angeles, Calif.). While these sensors can be used to measure the passage of bolus through the esophagus, one exemplary embodiment modifies related art impedance sensors to effectively measure the passage of gastric contents from the stomach into the small bowel. In an exemplary embodiment, a series of impedance sensors would be positioned along the catheter and measure the presence and passage of bolus as it transits the length of stomach and into the small bowel. For example, see sensors 9 in FIG. 1. This approach is beneficial at least by obviating aspiration of gastric contents to determine gastric volume, enabling determination of gastric volume more quickly and easily. This approach may also be used to provide gastric volume measurements on a continuous basis, enabling new algorithms to assess patient condition and assist in the guidance of care.

In another exemplary embodiment a new type of sensor and algorithms can correlate the electrical properties of gastric contents to determine the volume of gastric contents. In other words, the electrical properties change as gastric contents are processed and volume is reduced. This approach may be advantageous in that it could be more accurate in measuring the volume of the gastric contents. This approach is beneficial at least by obviating aspiration of gastric contents to determine gastric volume, enabling determination of gastric volume more quickly and easily. This approach may also be used to provide gastric volume measurements on a continuous basis, enabling new algorithms to assess patient condition and assist in the guidance of care.

An exemplary embodiment may also display the pH, H+ concentration and gastric volume measurements and the corresponding indication of valid test results (i.e., pH and/or H+ concentration differential sufficient to indicate healthy gastric function) in a viewable table format such as by medical staff.

In another exemplary embodiment, this gastric volume. H+ concentration information, and pH information is programmed as software into a pH meter, or other testing device, that calculates and then indicates whether a valid test result is achieved (indicate whether the pH and/or H+ concentration differential is sufficient to show healthy gastric function). In this exemplary embodiment, medical staff may enter the initial pH, H+ concentration, and gastric volume measurements into the device interface, and then post stimulation enter a second pH, H+ concentration, and gastric volume measurement into the device interface. Programming via an application resident within the device, or via a remote application, may then receive the measurements, calculate a test result using algorithms, and then indicate on the interface of the device if a valid or invalid test result has occurred. In another exemplary embodiment, the device may use additional algorithms to receive the pH. H+ concentration, and volume measurements, and suggest guidance of care in areas such as level of nutrition, use of pharmacological agents, and other care decisions that can be indicated by knowing the current health and responsiveness of the gastrointestinal tract.

The above exemplary embodiments assume that the gastric contents (or a portion thereof) are returned to the patient. However, another exemplary embodiment aspirates the gastric contents and does not replace the aspirated contents prior to administering the gastric acid stimulant or suppressant. The resulting gastric contents generated after the stimulant or suppressant administration would thus mainly be secreted by virtue of the stimulant or suppressant. With less dilution from previous gastric contents, the measured pH and/or H+ concentration could be interpreted differently, with a more significant drop in pH and larger H+ concentration differential the likely overall effect.

An exemplary embodiment displays the pH. H+ concentration, and gastric volume measurements, and the corresponding indication of valid test results (pH and/or H+ concentration differential sufficient to indicate healthy gastric function) in a viewable table format such as by medical staff. Another exemplary embodiment programs this gastric volume, H+ concentration and pH information as software into a pH meter, or other testing device, that calculates and then communicates whether a valid test result (pH differential sufficient to indicate healthy gastric function) is achieved. In this exemplary embodiment, the medical staff may enter the initial pH, H+ concentration, and gastric volume measurements into the device interface, indicate the gastric contents were permanently aspirated, and then post stimulation enter a second pH and gastric volume measurement into the device interface. Programming via an application resident within the device, or via a remote application, may then receive the measurements, calculate a test result using algorithms, and then present on the interface of the device whether a valid or invalid test result has occurred. In another exemplary embodiment, the device uses additional algorithms to receive the pH, H+ concentration, and volume measurements and suggest guidance of care in areas such as level of nutrition, use of pharmacological agents, and other care decisions that can be guided by determining the current health and responsiveness of the gastrointestinal tract.

The above exemplary embodiments (including both embodiments where the gastric contents are returned to the patient and alternatively where they are retained) can be modified or expanded to include other analyses that may be beneficial. For example, the measured gastric volume, in addition to the pH and/or H+ concentration differential, can be used as a factor to help determine gastric function. In other words, the gastric contents can be aspirated and not returned prior to stimulant or suppressant administration. The gastric contents can then be measured after stimulant or suppressant administration to determine any volume differential, i.e., to determine the volume of gastric juice secreted after stimulant or suppressant administration.

The secretion of a relatively large volume of gastric juice generally indicates a relatively healthy gastric function, while the secretion of a relatively low volume generally indicates a relatively unhealthy gastric function. Thus, the gastric juice volume, measured after stimulant or suppressant administration, can be compared to volume(s) anticipated for a relatively healthy patient. This comparison can be used to provide data (in addition to the pH and H+ concentration differentials discussed above) to determine gastric function. For example, the gastric volume can be used to set the pH and/or H+ concentration differential deemed sufficient to indicate healthy gastric function.

In other words, a relatively large volume of secreted gastric juice (indicating healthy gastric function) can be used to reduce the pH and H+ concentration differential deemed sufficient to indicate healthy gastric function. Contrarily, a relatively low volume of secreted gastric juice (indicating unhealthy gastric function) can be used to increase the pH and H+ concentration differential deemed sufficient to indicate healthy gastric function. However, the above analysis is only provided for exemplary purposes and not limiting, and exemplary embodiments are intended to cover any beneficial usage of gastric volume data with other exemplary embodiments that determine gastric function based on pH and/or H+ concentration differential.

The above exemplary embodiments use volume of secreted gastric juice in the context of pH differential. However, these embodiments are merely provided for exemplary purposes and the measured volume of secreted gastric juice can be used in other contexts, such as rate of change of gastric juice pH and/or H+ concentration. In this context, a relatively large volume of secreted gastric juice (indicating healthy gastric function) can be used to reduce the rate of change of gastric juice pH and/or H+ concentration deemed sufficient to indicate healthy gastric function. Contrarily, a relatively low volume of secreted gastric juice (indicating unhealthy gastric function) can be used to increase the rate of change of gastric juice pH and/or H+ concentration deemed sufficient to indicate healthy gastric function.

An exemplary embodiment of this procedure establishes a baseline for gastric acid production and concentration in a healthy patient administered a stimulant or suppressant, and compares the baseline to the results received for the patient at issue. In this exemplary embodiment, the comparison may be expressed as a percentage relating the level of gastric acid production of the patient at issue versus a healthy subject, thus providing additional information on the amount of acid produced and the hydrogen ion concentration of that acid.

To refine this percentage measurement and enhance its accuracy and relevancy to specific patients, an exemplary embodiment obtains baseline stimulation response data for volume, H+ concentration and pH from subjects that correspond to many different profiles, including but not limited to: current medical condition, age, gender, fitness, weight, body composition such as percentage of body fat, ethnicity, family history, personal medical history, genetics, or any other factor currently known or later determined to be relevant or applicable. Using baseline data that is more closely comparable to specific patients enhances assessment accuracy, leading to more relevant guidance of care. In an exemplary embodiment, this gastric response percentage measurement may be presented in a table to help determine whether the pH differential is sufficient to indicate healthy gastric function. Another exemplary embodiment programs this gastric response percentage and pH information as software into a pH meter, or other testing device, to calculate and then communicate whether the pH differential is sufficient to indicate healthy gastric function.

d. Gastric Juice pH, H+ Concentration, and Volume Trending

Some of the exemplary embodiments disclosed above determine gastric function based on a pH and/or H+ concentration differential between a baseline pH and/or H+ concentration measurement and one stressed pH and/or H+ concentration measurement taken after administration of gastric acid stimulant or suppressant. Other exemplary embodiments discussed above take multiple stressed pH and/or H+ concentration measurements that are usable in various ways, such as to calculate multiple pH and/or H+ concentration differentials (pH and/or H+ concentration difference between the baseline pH and/or H+ concentration and each of the stressed pH and/or H+ concentration measurements), to calculate a rate of pH and/or H+ concentration change, etc. Still further exemplary embodiments modify any of the above procedures by also taking into account gastric volumes.

The exemplary embodiments that include multiple pH. H+ concentration, and volume measurements may be particularly beneficial because of their ability to utilize pH, H+ concentration, and volume trending. Various aspects of the pH. H+ concentration, and volume trending are disclosed below.

In the above embodiments that use or otherwise include multiple measurements, exemplary embodiments are intended to cover any manner of taking those measurements. In other words, these measurements can be taken by any currently known or later developed device, such as a disposable pH probe (e.g., VersaFlex, size 6 F, from Sierra Scientific Instruments, Los Angeles, Calif.). Exemplary embodiments are intended to cover any beneficial usage of this or similar probes to determine gastric function. As one example, this probe can enable a regular, periodic, or even irregular update of non-stimulated or pharmacologically stimulated pH and/or H+ concentration for a certain relevant period, such as for the first 24-48 hours (that the patient is in an ICU, for example), providing valuable information on the gastrointestinal system response to care and recovery process.

Figure 11:
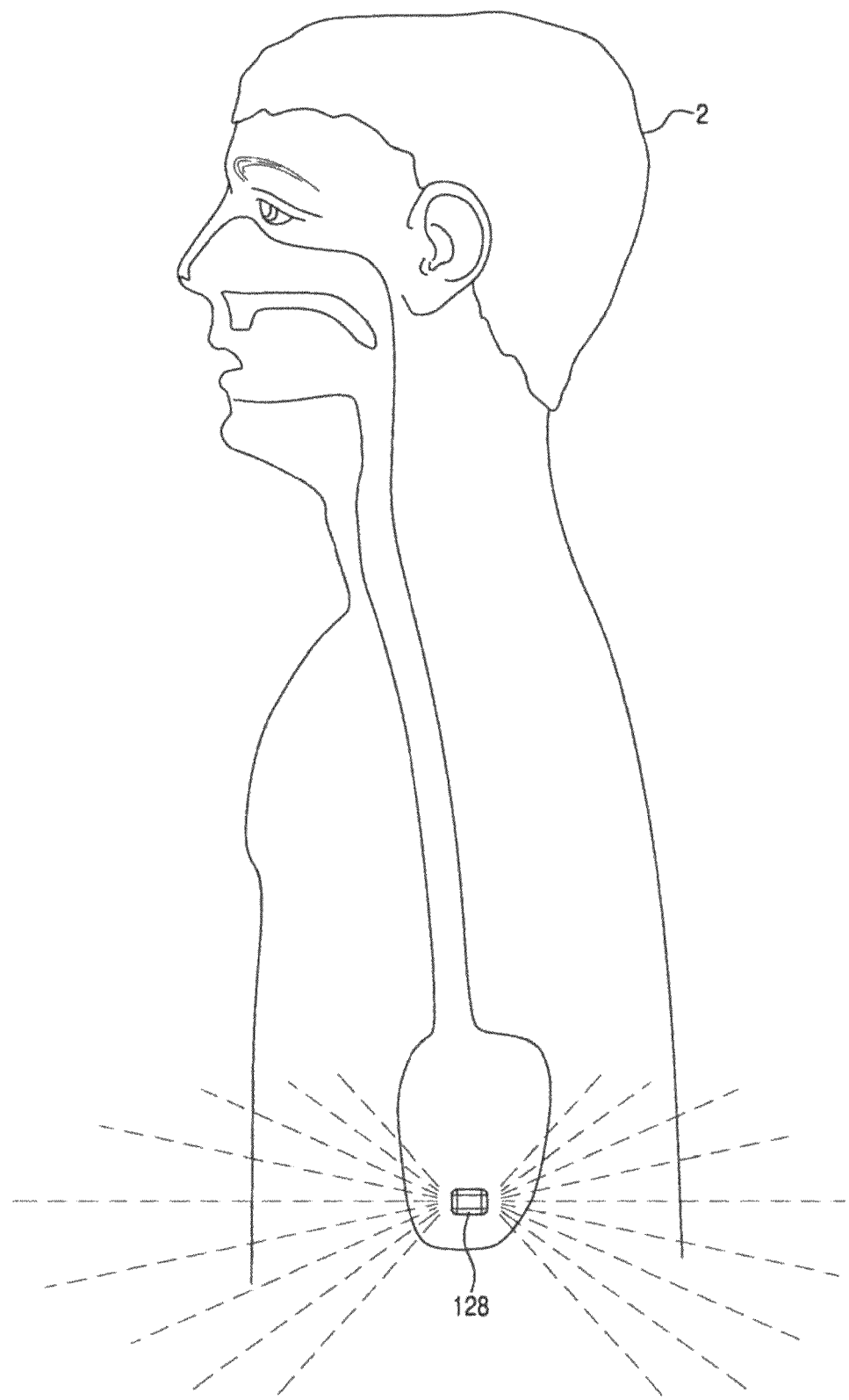
FIG. 11 is a schematic of an apparatus in accordance with another exemplary embodiment, and particularly shows a pH sensor that performs multiple measurements of gastric juice pH to obtain multiple baseline and/or stressed gastric juice pH values.

FIG. 11 is a schematic of an apparatus in accordance with an exemplary embodiment that includes a pH and/or H+ concentration sensor for performing multiple measurements of gastric juice pH and/or H+ concentration to obtain multiple baseline and/or stressed gastric juice pH and/or H+ concentration values. The exemplary embodiment of FIG. 11 includes a wireless sensor 128 that is disposed in the patient's stomach to detect pH of the gastric contents, and wirelessly transmit the detected pH and/or H+ concentration values to any of the disclosed indicators/controllers 8, 20. However, the wireless sensor 128 shown in FIG. 11 is not intended to be limiting, and exemplary embodiments are intended to cover any method and apparatus for obtaining the multiple baseline and/or stressed gastric juice pH values.

The embodiments that utilize multiple stressed pH and/or H+ concentration measurements provide additional treatment options, and in some exemplary embodiments, these multiple pH measurements enable multiple comparisons to enhance accuracy and timeliness of the patient assessment.

For example, these measurements can be used to stage various types of care, such as enteral feeding. In some exemplary embodiments, an initial or other stressed pH and/or H+ concentration measurement that indicates an initial and sufficient pH and/or H+ concentration differential (as compared to the baseline pH and/or H+ concentration) can be used to recommend initiation of enteral feeding at a certain rate. For example, after an initial positive test result, feeding can be initiated, and the patient's gastric juice pH and/or H+ concentration can be monitored during and after the feeding.

The continuing pH and/or H+ concentration measurements taken during or after the feeding can also be used in various beneficial ways. For example, if the gastric juice pH and/or H+ concentration decreases or otherwise stays below a certain level such as 3.0 pH units, during and/or soon after the feeding, then the feeding rate can be increased and possibly other types of intensive care can be affected, such as by reducing or ceasing ventilation or use of vasoactive agents. Contrarily, if the gastric juice pH and/or H+ concentration is relatively unchanged, then the current care (such as enteral feeding, ventilation, and vasoactive agent use) can be maintained. Still further, if the gastric juice pH and/or H+ concentration increases or otherwise rises above a certain level (such as 3.0 pH units), then feeding can be ceased or otherwise the rate reduced and other types of care can be affected accordingly (such as by initiating or increasing ventilation or use of vasoactive agents).

The above disclosures of using multiple pH and/or H+ concentration measurements for staging various types of treatment, such as enteral feeding, are merely provided for exemplary purposes, and multiple measurements can be used in other beneficial ways. For example in one exemplary embodiment, the pH and/or H+ concentration data over time could be plotted on a graph showing the pH and/or H+ concentration levels fluctuating, such as with the y axis representing pH or H+ concentration values and the x axis representing time. This visual representation may help medical staff understand the trends in the gastric juice pH and/or H+ concentration level and otherwise adjust the guidance of any sort of relevant care, including but not limited to the types of care discussed above, for example optimization of dosing of acid suppressant medication. In another example, a patient that exhibits high pH and/or H+ concentration levels both after a pharmacological stimulation and at other times (i.e., wherein the above graph is manifested in a straight line or otherwise shows little variance) may not be sufficiently healthy for nutrition. In addition, continuous monitoring of gastric juice pH and/or H+ concentration can be combined with continuous measurement of esophageal pH and/or H+ concentration using a catheter with a distal sensor located in the stomach and a proximal sensor located in the esophagus. Clinical staff may use this data to monitor gastric juice pH and/or H+ concentration to determine the adequacy of acid suppressant medication, e.g., maintaining a pH above 4 units. At the same time, esophageal pH and/or H+ concentration can be monitored to determine if there are reflux events, which could place the patient at higher risk of aspiration of gastric contents. As disclosed in section V(E), this information can be used to enhance, improve or even optimize patient positioning, acid suppressant medication, enteral feeding route, or other factors to reduce the risk of (or even avoid) aspiration of gastric contents.

Other exemplary embodiments use the above curve in ways other than as merely providing visual indications. For example, the area under the above or other similar curves that represent pH and/or H+ concentration data over time can be calculated and used for other beneficial reasons. For example, this area measurement may be indicative of the overall health of the patient. A relatively large area measurement may generally indicate that the patient has had higher pH values over time, and thus is not ready for nutrition and may even require other additional medical care. Similarly, for H+ concentration values a relatively small area measurement may generally indicate the patient has had lower H+ concentration values over time, and thus is not ready for nutrition and may even require other additional medical care. In contrast, a relatively small area measurement may indicate that the patient has had lower pH values over time, and thus could be ready for additional nutrition or a change in other types of care. Similarly, for H+ concentration values a relatively large area measurement may generally indicate the patient has had higher H+ concentration values over time, and thus could be ready for additional nutrition or a change in other types of care. One exemplary way of calculating the area measurement is via the following definite integral formula:

$$\int_a^b \text{pH}(t)dt$$

The function pH(t) can be represented by the previously defined exemplary formula for pH:

$$\text{pH}=-\log(((H^+_{GJ1}*V_{GJ1})+(H^+_{GJ2}*V_{GJ2}))/(V_{GJ1}+V_{GJ2}))$$

Another exemplary way of calculating the area measurement is via the following definite integral formula:

$$\int_a^b H(t)dt$$

The variable H represents hydrogen ion concentration. The function H(t) represents the measurement of hydrogen ion concentration in moles per liter (mol).

Variance, or fluctuations, in pH and/or H+ concentration level over time can be caused by a single or multiple different factors. As disclosed above, for patients with a generally healthy gastric function, gastric juice pH generally may initially increase due to the buffering capacity of the food and will then generally decrease due to the food's stimulation of gastric acid secretion. In contrast, for patients with a generally healthy gastric function, gastric juice H+ concentration generally may initially decrease due to the buffering capacity of the food and will then generally increase due to the food's stimulation of gastric acid secretion. Also as disclosed above, care can be guided based on these pH and/or H+ concentration measurements, such as by adjusting the level or rate of feeding based on the pH and/or H+ concentration response. For example, if the pH levels fail to decrease materially after feeding, the patient may not be tolerating the food and the feeding could be stopped or the level reduced. Similarly, if the H+ concentration level does not increase materially after feeding, the patient may not be tolerating the food and the feeding could be stopped or the level reduced.

In another example, for patients with a generally healthy gastric function, gastric juice pH generally increases upon the introduction of a proton pump inhibitor (PPI) or H2 Blocker. Similarly, H+ concentration decreases upon the introduction of a proton pump inhibitor (PPI) or H2 Blocker. Also as disclosed above, care can be guided based on these pH and/or H+ concentration measurements, such as by adjusting the level or rate of care. If the pH has not increased materially, other medications or procedures may be used to increase the pH. Similarly, if the H+ concentration has not decreased materially, other medications or procedures may be used to decrease the H+ concentration. In an exemplary embodiment, specific medical care actions, such as feeding and introducing suppressants, may be noted by time and be appropriately presented to the medical care provides to help interpret the pH and/or H+ concentration data. In an exemplary embodiment, this current medical care data could be stored in a database to facilitate easy entry and access, such as by medical care providers.

In addition, or as an alternative, to area, there are other ways to analyze and interpret the pH and/or H+ concentration data. In another exemplary embodiment, the derivative of the above pH(t) or H(t) functions can be calculated to provide an indication of the rate of change in the pH or H+ concentration measurements. After administering the stimulant or suppressant, a faster rate of pH or H+ concentration change may indicate that the patient has experienced a stronger gastric acid response, and thus the patient is healthier and ready for additional nutrition, for example. In contrast, a lower rate of change may indicate that the patient is not ready for nutrition and may require certain additional medical care. One exemplary way of calculating the derivative of the function pH(t) is via the following formula using Leibniz's notation:

$$d(\text{pH}(t))/dt = \text{rate of change}$$

One exemplary way of calculating the derivative of the function H(t) is via the following formula using Leibniz's notation:

$$d(\text{H}(t))/dt = \text{rate of change}$$

In another exemplary embodiment, the second derivative of the above pH(t) function can be calculated to provide an indication of when the pH has reached its lowest point. A shorter period to reach the lowest pH measure may indicate that the patient has experienced a stronger gastric acid response. Similarly, the second derivative of the above H(t) function can be calculated to provide an indication of when the H+ concentration has reached its highest point. A shorter period to reach the highest H+ concentration measure may indicate that the patient has experienced a stronger gastric acid response. This faster rate may indicate that the patient is healthier and ready for additional nutrition. In contrast, a longer period to reach the lowest pH, or highest H+ concentration, measure may indicate that the patient is not ready for nutrition and may require certain additional medical care. One exemplary way of calculating the second derivative of the function pH(t) is via the following formula using Leibniz's notation:

$$d^2(\text{pH}(t))/dt^2 = 0$$

An exemplary way of calculating the second derivative of the function H(t) is via the following formula using Leibniz's notation:

$$d^2(\text{H}(t))dt^2 = 0$$

In an exemplary embodiment, the multiple pH and/or H+ concentration measurements are stored in a database along with profile data, including but not limited to: current medical condition, current medical care, age, gender, fitness, weight, body composition including percentage of body fat, ethnicity, family history, personal medical history, genetics, or any other factor currently known or later determined to be relevant or applicable. This stored pH and/or H+ concentration measurement data enables accessing of pH and/or H+ concentration measurement data for a patient across multiple visits over time, which can be helpful to identify patient specific trends that may influence medical care recommendations. For example, the pH and/or H+ concentration measurements may show a trend in a certain patient warranting certain medical care recommendations that would otherwise not be appropriate. The profile data may similarly be used to influence medical care recommendations. For example, the pH and/or H+ concentration measurements for a certain patient profile may warrant certain medical recommendations that would not be warranted for a different patient profile.

In other words, the above data can be compared to data of other patients. Thus, previous pH and/or H+ concentration measurements for patients with similar profile data can be compared to the current patient data to help determine the current patient's health status and medical care recommendations. For example, a medical care provider can compare pH and/or H+ concentration measurements of a patient to pH and/or H+ concentration measurements of many other patients with a similar profile, such as, weight, age, and other profile data, and then recommend medical care based on the comparison. In essence, the medical care provider is comparing current measurements of the patient at issue to a curve representing the aggregate measurements of patients with similar profiles.

One exemplary way of calculating the difference between data points and a curve is to use the total non-linear least squares data modeling technique. This type of analysis can provide a numerical indication of how close the current patient's pH and/or H+ concentration values are to others, and thus can indicate the applicability and/or level of care for a patient based on past experiences with similar patients.

In an exemplary embodiment, data indicating patient response to care, such as enteral feeding, can also be stored in the database disclosed above. This additional data can be analyzed to provide insights, such as into nutrition processing, by patients with certain profiles, pH measurements, etc. For example, medical care providers can compare how patients in the past with specific conditions, profiles, pH data, etc., responded to certain care, such as certain levels of nutrition, and thus enhance, maximize, or optimize recommended nutrition rates based on this comparison. Another exemplary embodiment correlates the above database of pH data, conditions, and profile data with specific outcomes to achieve a relationship of how treatment of the gastrointestinal system and patient overall contributed to positive or negative outcomes.

As an alternative or in addition to some or all of the above data, data relating to volume of gastric contents can be entered and included in the above database. In an exemplary embodiment, the multiple pH, H+ concentration, and volume measurements are stored in a database along with profile data, including but not limited to: current medical condition, age, gender, fitness, weight, body composition, percentage of body fat, ethnicity, family history, personal medical history, genetics, or any other factor currently known or later determined to be relevant or applicable. This database can be stored on any of the disclosed devices or hosted as a network based application.

In one exemplary embodiment, gastric volume data augments the pH and/or H+ concentration data in providing an indication of the relative health of the current gastrointestinal system. In an exemplary embodiment, the guidance of care is based on the combination of multiple pH and/or H+ concentration measurements, multiple gastric volume measurements, profile data, or any combination of the data disclosed above.

In another exemplary embodiment, multiple gastric volume measurements do not augment the gastric juice pH and/or H+ concentration data, and instead replace the pH and/or H+ concentration data as the primary basis for guiding care. In this embodiment, any and all of the trending methods disclosed in the context of pH and/or H+ concentration data can instead be applied to the gastric volume data.

e. Gastric Juice pH, H+ Concentration, and Volume Algorithms

Other exemplary embodiments leverage any or all of the data disclosed above, including but not limited to pH, H+ concentration, volume, and profile data collected over time. In an exemplary embodiment, this data is used to develop algorithms that contribute to a system for providing medical care recommendations. These algorithms receive inputs, such as pH. H+ concentration, gastric volume and profile data, and then recommend specific levels and/or types of medical care. These algorithmic recommendations can be based on guidelines that can be augmented by historical data and relationships from patients. For example, after receiving the pH and/or H+ concentration measurement data, the system can recommend the nutrition goal and feeding levels to reach that goal based on the pH and/or H+ concentration data, profile and past patient data. This system can be provided in any appropriate form, and in one exemplary embodiment is a hand-held pH test device connected to a network that sends patient data and receives the results of data analysis and care recommendations.

In an exemplary embodiment, the above algorithms are based on non-linear regression analysis, which model the observational data, such as pH, H+ concentration, and gastric volume data based on profile data and independent variables, such as pharmacological stimulation, nutrition level, and other care variables. The regression analysis can create an algorithm to predict pH and/or H+ concentration levels and gastric volume levels based on the targeted feeding levels that reach a goal for a specific patient. This analysis can also be used to set an enhanced, maximized, or optimal nutrition goal and the recommended feeding levels to reach that goal.

In an exemplary embodiment, the algorithms have artificial intelligence capabilities, where the algorithms enhance and update themselves based on the continually updated patient data and feedback. This capability allows the accuracy and precision of the recommendations to improve over time.

2. Spectrum of Intensities of Care

The exemplary embodiments are not limited to either performing or not performing certain types of care or procedures based on the gastric juice pH differential. For example, some exemplary embodiments can be directed to and include providing a spectrum of intensities of certain types of care based on various data, including but not limited to gastric juice pH differential, gastric volume, patient profile data, etc. In other words, the intensity of care can be administered as a function of this data.

In one exemplary embodiment, the pace of enteral feeding is determined based on the pH differential. For example, a goal feeding rate can be determined based on any known or related art method (such as by taking into account patient characteristics). If there is an acute or otherwise significant change in gastric juice pH, such as a pH differential of 1 pH unit (between baseline pH and stressed pH), then enteral feeding may be immediately initiated at a low rate, and the feeding rate increased rapidly, e.g., start feeding at 25% of goal rate and increase feeding rate by 25% of the goal rate every 6 hours, such that the goal is achieved in 18 hours. If the pH differential is less than that disclosed above, such as a pH differential of 0.5-0.9 pH units, then feeding may still be initiated, but the rate of increase may be slower, such as an increase of 25% of the goal rate every 9 hours, achieving the goal in 27 hours. Contrarily, if the pH differential is less than 0.4 pH units, then enteral feeding may not be initiated, its initiation may be delayed, or feeding may be initiated and progress at low or very low rates. Under this circumstance, feeding may be initiated at a very low rate, such as 10%-20% of goal rate, and the rate increased very slowly, such as by 20% of the goal rate every 12 hours, achieving the goal in 36 hours (assuming nutrition began at 20% of goal).

As yet another alternative in this situation, parenteral nutrition may be initiated with the goal of starting enteral feeding later. Parenteral nutrition (nutrition administered into a vein) provides calories to the patient, but is generally not considered to be as beneficial or optimal as enteral nutrition therapy because parenteral nutrition: 1) has been associated with increases in some complications, 2) requires central venous access and usually a dedicated port/lumen, 3) is more costly, and 4) is less physiologic than enteral nutrition (food into the gut). In this regard it has been shown that enteral nutrition helps preserve the structure and function of the gut. Therefore, more rapid identification of patients who have a hypo-perfused gut and will not tolerate enteral nutrition can allow for more appropriate identification of patients who should receive parenteral nutrition.

In accordance with another exemplary embodiment, a patient can be started on bolus feeds. e.g., 320 ml every 4 hours upon demonstrating an acute or significant pH differential, such as a pH decrease of at least one pH unit subsequent to stimulant administration. Contrarily, a less robust response to the stimulant, such as 0.5-0.9 pH unit, may indicate that the patient could be started on bolus feeds but with a lower volume, e.g., 100 ml every 4 hours. As another alternative, this less robust response could be used to support a decision to feed the patient by continuous infusion (not by bolus), e.g., 30 ml per hour.

However, the above feeding levels and rates of increase are merely provided for exemplary purposes. Exemplary embodiments are intended to cover and include all beneficial uses and applications of graduating (or providing a spectrum of) any care as a function of data used to determine gastric function, such as pH differential. For example, gastric volume data may similarly be used to determine whether to initiate enteral feeding, the rate at which enteral feeding is initiated, and the rate of increase of enteral feeding. Also, the above procedure of graduating care is disclosed in the context of enteral feeding, but applies to any other type of relevant care, including but not limited to ventilation, vasoactive agent use, etc.

Monitoring of gastric pH can also be used to enhance digestive function. For example, a pH of 2-4 is optimal for conversion of pepsinogen to pepsin, an enzyme secreted by Chief cells of the stomach. Pepsin degrades food proteins into smaller proteins/peptides, enabling enhanced or optimal digestion and absorption of these nutrients. For example, if gastric pH is monitored and observed to be "too high," e.g., greater than 4 pH units, then one or more interventions can be used to lower the pH to a more enhanced or optimal range, e.g., 2-4. In one example, acidified tube feeds (e.g., tube feeds modified to have a pH of 3.5) can be administered in some cases to achieve a more enhanced or optimal pH. In another example, if an acid suppressant is being administered and is no longer needed or necessary, then it can be stopped to allow the pH to decrease. The lower pH is also beneficial by killing bacteria and thereby reducing or preventing infectious.

3. Gastric Juice pH and H+ Concentration Indicator/Controller a. Dedicated Inputs/Outputs

Figure 2:
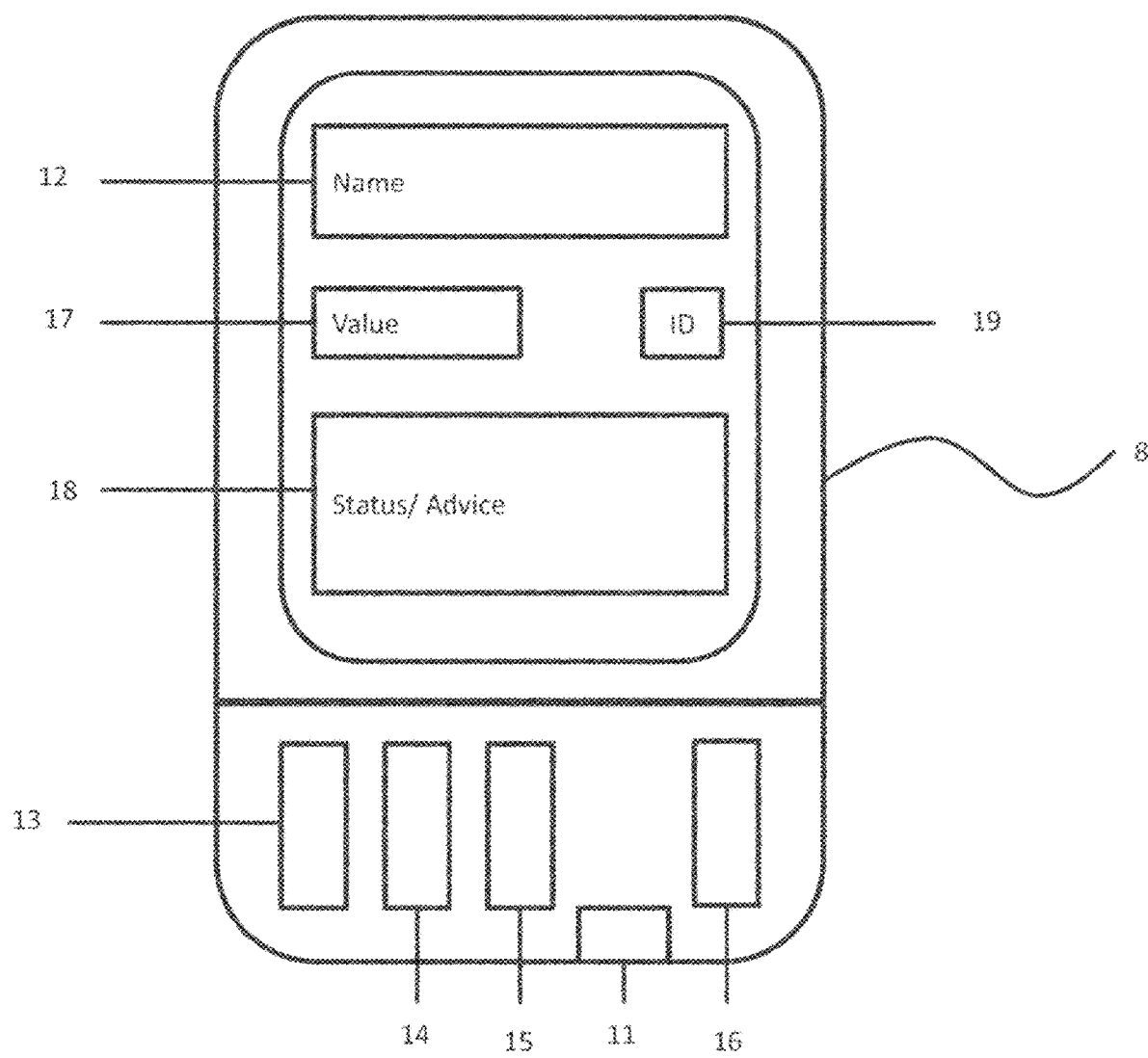
FIG. 2 is a schematic of an indicator/controller in accordance with an exemplary embodiment.

FIG. 2 is a schematic of an indicator/controller 8 in accordance with an exemplary embodiment. Exemplary indicators/controllers 8 can include any variety of features, such as input mechanisms and indicators, to facilitate any number of operations including but not limited to those discussed above. Some exemplary features are discussed below in the context of the exemplary indicator/controller 8 shown in FIG. 2 that includes dedicated inputs and outputs. However, exemplary embodiments are not limited to the features discussed below, and these features are merely provided as examples.

All figures and examples apply to both pH and H+ concentration measurement. The sensors can measure both pH and H+ concentration and the subsequent recorder, monitor (Add more disclosure)

As shown in FIG. 2, the indicator/controller 8 can include a baseline pH test input 13, which can be provided in any form, such as a manually operated button. This input 13 can be activated at, or approximately at, the time that the baseline pH test is conducted. For example, the input 13 can be activated shortly before and/or shortly after the baseline pH is tested. Operating the input 13 in this manner enables the indicator/controller 8 to read and/or store the pH data as the baseline pH. The indicator/controller 8 can also include a display 17 that displays the baseline pH value.

In an exemplary embodiment, the input 13 can similarly be activated at, or approximately at, the time that further pH measurements are taken, such as stressed pH tests. Activating the input 13 in this manner enables the indicator/controller 8 to read and/or store the relevant pH data as the appropriate stressed pH test. In this or another exemplary embodiment, the input 13 can be activated again to instruct the indicator/controller 8 to calculate the differential between the baseline and stressed pH tests, and to display the differential, such as at display 17.

In an alternative embodiment, the controller can simultaneously store the calibration data for several pH sensors. This would enable the controller/recorder to measure a first patient's pH. The controller/recorder may then be moved to measure a different patient's pH. A unique identifying number, e.g., the patient's hospital medical record number (MRN), may be entered into the controller/recorder by the user. The controller/recorder may keep track of all measurements for a certain patient, including pH and time of each pH measurement. The controller/recorder may also keep track of calibration information for a unique patient preventing the need to remove and recalibrate each pH sensor before another measurement if the controller/recorder had been used on a different patient previously. The above features enable use of a single controller/recorder in a clinical unit (e.g., ICU) thus obviating multiple controllers/recorders. The controller/recorder may have a printer function allowing it to print source documents for these readings, and/or may transmit (by wire or wirelessly) this data to a central station such as to archive these measurements.

In an alternative embodiment, additional inputs are provided to facilitate the above operations. For example, input 13 can solely be used to instruct the indicator/controller 8 to read and/or store the baseline pH. One or more other inputs can be provided to facilitate the reading and/or storing of other tests. For example, a second input 14 can be operated similarly to input 13 to enable the indicator/controller 8 to read and store a first stressed pH test. A third input 15 can be operated similarly to inputs 13 and 14 to enable the indicator/controller 8 to read and store a second stressed pH test. Any number of other or additional inputs can also be provided to handle additional stressed pH tests. In this exemplary embodiment, a differential input 16 can be provided to instruct the indicator/controller to calculate the differential between any of the above stressed pH tests and the baseline pH test. The differential can similarly be displayed at display 17.

As discussed in Section IV(C) above (Methods and Apparatus for Guiding Care Based on Determined pH), exemplary embodiments cover the guiding of many types of medical care in a variety of ways based on determined gastric function, which can be based on the gastric juice pH differential gastric content volume, etc. The exemplary embodiment of FIG. 2 can include a treatment display 18 that displays or otherwise indicates to an operator, such as a medical care provider, the recommended care or procedure. For example, in one exemplary embodiment, upon a change of at least 1 pH level, enteral feeding is to be immediately initiated and the feeding rate increased rapidly, e.g., start feeding at 25% of goal rate and increase feeding rate by 25% every 6 hours such that the goal is achieved in 18 hours. Thus, this recommended treatment could be displayed in treatment display 18.

In accordance with some exemplary embodiments, one or more components of the measuring apparatus 1 and/or indicator/controller 8 may need to be subjected to one or any combination of the following: service, cleaning, repair, replacement, calibration, or other operations. One or any combination of the above operations may need to be performed on a periodic basis, such as after a certain number of uses or after a certain period such as one week.

In this case, the indicator/controller 8 can include an output 11 to apprise an operator that the measuring apparatus 1 and/or indicator/controller 8 is ready for the operation to be performed or that the condition precedent for the operation has passed. The output can be in any form, such as a visual display (including but not limited to a written warning, blinking or lit light, etc.) or sound output (including a buzzer, siren, artificially generated voice, etc.), for example.

In another exemplary embodiment, a clock/timer is used to instruct the user that the apparatus needs to be calibrated, e.g., a two or three point calibration using USB buffers. For example, if it is desirable to calibrate the pH monitor (used for measuring pH from gastric juice aspirates) every 72 hours, then the timer would indicate after 72 hours has elapsed that the apparatus needs to be calibrated before a baseline pH test can be performed. Alternatively, if the pH recorder (used in conjunction with a catheter with a pH sensor) needs to be calibrated when a new sensor is used, then the controller/recorder may prompt for calibration if it does not recognize the sensor or unique identifier (e.g., MRN) associated with it, indicating that the particular sensor in use has already been calibrated.

In some exemplary embodiments, the indicator/controller 8 handles a single patient at a time. In these embodiments, the indicator/controller 8 can be located proximate the patient, such as at or adjacent to a patient's bed in an ICU, hospital room, etc.

However, the indicator/controller 8 of other exemplary embodiments can be adapted to handle multiple patients simultaneously or in succession, such that information of the multiple patients is stored and operated upon separately. This can be accomplished by entering patient identifying information, such as the patient's name, a code or medical record number representing the patient, etc., via identifying input 19. The identifying input 19 can use any currently known or later developed method or apparatus, such as a keypad, keyboard, voice actuation, etc. In fact, RFID technology can be used to perform the identifying input, wherein the information is transmitted from a patient's badge or wristband to the indicator/controller 8. In these exemplary embodiments, the identifying information is then displayed at identifying display 12.

In the above exemplary embodiment that is capable of handling multiple patients, the treatment display 18 can be used to display any variety of information relating to the patient identified in identifying input 12, such as any relevant updated information including results of the most recent pH test, most recent recommended treatment, etc., for example.

As another example, if the patient has already been subjected to baseline measurement and a medical care provider returns to the patient after 45 minutes, while the indicator/controller 8 could have been used on other patients in the meantime, the information corresponding to this patient may be accessed and displayed on the treatment display 18, e.g., "Baseline measurement performed 45 minutes ago. Patient ready for first post stimulant measurement." In this example, the number of minutes could change according to how much time has actually passed from the time the baseline measurement was performed. Also, the display 17 may display the most recent measurement value corresponding to the patient on whom the device is currently used.

b. Touchscreen Display

FIG. 3 is a schematic of an indicator/controller 20 in accordance with another exemplary embodiment. In this exemplary embodiment, software applications for performing operations, such as those discussed above with regard to the indicator/controller 8 of FIG. 2, are incorporated into another type of electronic device. i.e., a handheld electronic device, such as an IPAD®, that includes touchscreen displays enabling inputs to be performed via the display. The software can be used on other non-handheld devices or handheld devices, such as the mobile digital device IPHONE®, PDAs, etc. In this exemplary embodiment, all or some of the inputs discussed with regard to FIG. 2 may be the same except that touchscreen technology is used in this case rather than hard physical buttons. FIG. 3 shows the startup screen of an IPAD® (a handheld electronic device), where display 21 shows an icon corresponding to an application for the LCD, which can be identified as desired. For purposes of this exemplary description, the application can be identified as ipH.

Figure 4:
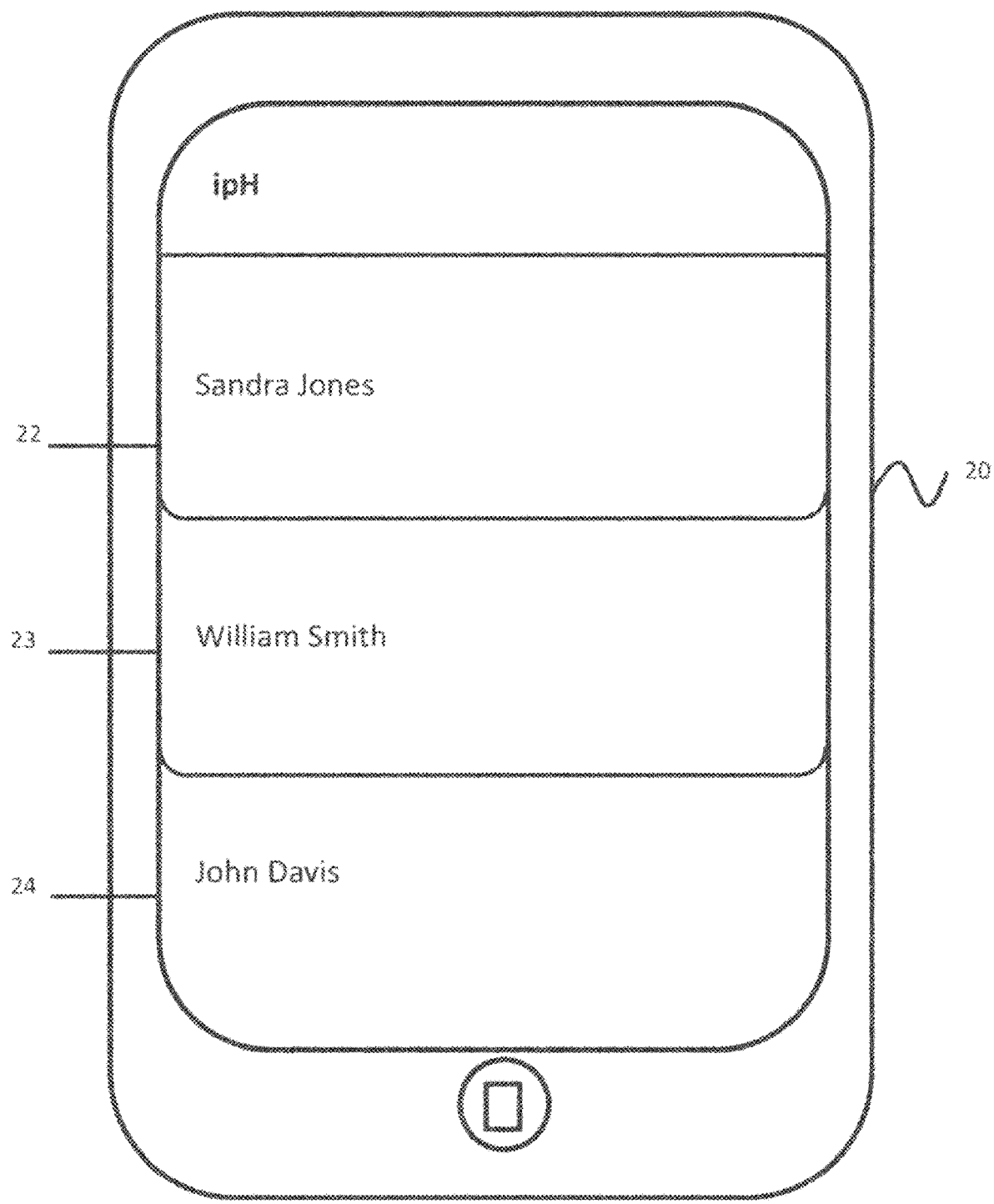
FIG. 4 is a schematic of a pop-up screen of the exemplary indicator/controller of FIG. 3.

FIG. 4 is a schematic of a pop-up screen that is displayed once the ipH is selected in the exemplary indicator/controller 20 of FIG. 3. The pop-up screen of FIG. 4 indicates the names or other identifying information of all patients 22, 23, 24 whose conditions are being monitored or who are otherwise under examination and/or treatment.

Figure 5:
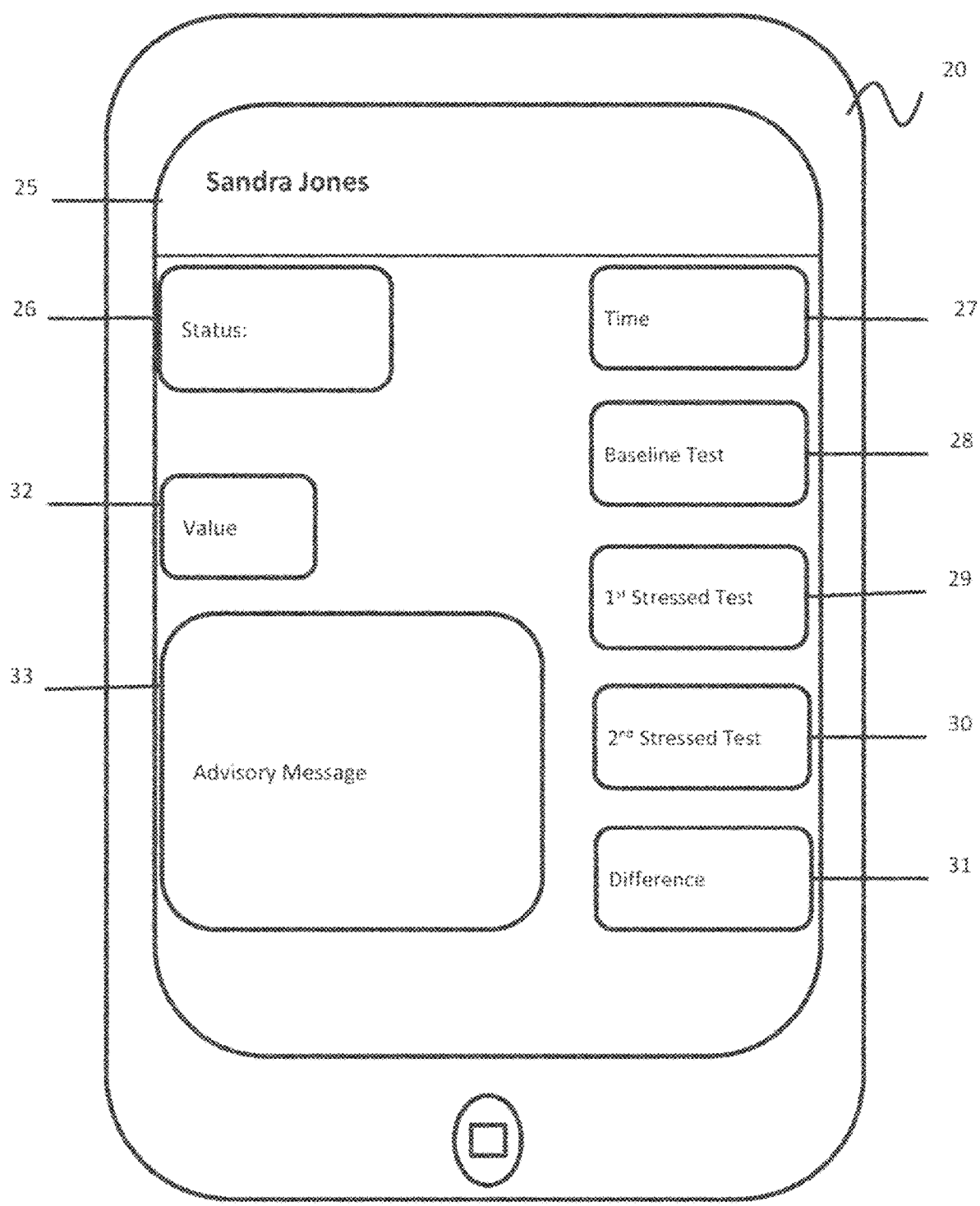
FIG. 5 is a schematic of another pop-up screen of the exemplary indicator/controller of FIG. 3.

Selecting the identifying information of any of the patients 22, 23, 24 instructs the indicator/controller 20 to read and display information relevant to the selected patient. FIG. 5 is a schematic of an exemplary pop-up screen displaying such information relevant to the selected patient, including updated test results, current treatment recommendations, etc. Although exemplary embodiments are intended to cover and include any relevant display configuration, the orientation of features of the exemplary embodiment of FIG. 5 is described below.

In the exemplary pop-up screen shown in FIG. 5, patient identifying information, such as the patient's name, can be displayed at patient identifying display 25, which can be disposed at a top section of the pop-up screen. This screen can also include a status display 26 that indicates any information relevant to the patient. For example, the status display 26 may indicate the most current medical or treatment status of the patient. In this example, for a new patient who has not been subjected to any testing, the status display 26 may indicate that the patient is "ready for testing." Alternatively, if the patient has undergone the baseline measurement and is waiting for post stimulant measurement, the message can be, for example, "baseline measurement performed, 20 minutes to go until first post stimulant measurement."

Alternatively, the same or other status information can be indicated on other more specifically tailored displays. For example, any time remaining until the stressed pH test is to be performed can be indicated in a timing display 27. In other words, the timing display 27 can indicate time remaining until the recommended administration of a subsequent test, such as one or more of the stressed pH tests. Still further, the timing display 27 may provide further indications beyond the time remaining as the time for testing approaches or passes, such as by flashing. This flashing or other indication, which can take any form, helps warn a medical care provider, such as a nurse, of the impending test or fact that the time for taking the test has passed, to enhance testing accuracy and reduce, minimize or prevent errors in administering the tests.

Additional displays can be provided on the pop-up screen to facilitate the testing. For example, baseline test display 28 and first stressed test display 29 can be provided to indicate pH values obtained by the baseline pH test and the first stressed pH test, respectively. Additional displays, such as a second stressed test display 30, can also be provided to indicate results of any subsequent pH tests.

Exemplary embodiments are intended to cover and include any relevant and applicable operation of the displays 28, 29, 30. For example, the pop-up screen can default to displaying generic identifying information, such as "baseline test," "first stressed test," and "second stressed test." In this exemplary embodiment, the above generic information identifying the display area may automatically be displayed. If an operator, such as a medical care provider, is interested in the baseline test measurement, the provider could touch the baseline test display 28 area, causing the display 28 to change and indicate the gastric juice pH measured during the baseline pH test. This pH measurement may be displayed continuously until a certain event, such as the display 28 area being touched again, or alternatively may be displayed for a certain period, such as a few seconds, allowing the display 28 to return to the generic display of "baseline test." The first stressed test display 29 and second stressed test display 30 may operate similarly to the baseline test display 28. Also, any number of stressed test displays may be included in the pop-up screen as applicable to accommodate different tests.

In another alternative embodiment, none of the displays 28, 29, 30 are automatically provided in all cases. In other words, the pop-up screen is not setup to default displays 28, 29, 30. Contrarily, displays 28, 29, 30 are only displayed after the relevant test is completed and pH measurements obtained. For example, the baseline test display 28 is only displayed after the baseline pH test is completed and the baseline pH determined. Otherwise, that portion of the pop-up screen is blank or alternatively is used to display other information. The baseline test display 28 otherwise operates similarly to the preceding exemplary embodiment.

The other displays 29, 30 are also operated as discussed above with regard to the baseline test display 28.

The pop-up screen may be configured to display any number of stressed tests that are conducted to accommodate additional tests. However, at some point, the number of tests causes the corresponding displays to become prohibitively small. In this case, or in other situations that are beneficial, the stressed test displays can be reconfigured so that each stressed test display displays results of multiple tests either at the same time, in succession, or in accordance with any other scheme that is practical or advantageous.

The pop-up screen can also include a difference display 31 that displays the differential between the baseline pH test and one of the stressed pH tests, or even between or among selected stressed pH tests. The difference display can be configured to operate in accordance with any of the operations of the displays 28, 29, 30 discussed above, or can operate differently. For example, pressing any two displays 28, 29, 30 in unison or succession could be used to instruct the indicator/controller 20 to display the pH differential between the pH values of the displays pressed. Alternatively, the difference display 31 may be configured to automatically display the pH differential between any two tests, such as the baseline pH test and the last stressed pH test conducted.

As yet another alternative, the difference display 31 may be used solely as an input to be pressed. In other words, the difference display 31 may be used to instruct the indicator/controller 20 to calculate the pH differential between any two tests, such as tests corresponding to the last two displays pressed or alternatively the last two tests conducted. In this embodiment, the pH differential is displayed at a separate pH value display 32.

The exemplary pop-up screen of FIG. 5 can also include a treatment display 33 that provides information similar to the exemplary treatment display 18 of the previously disclosed embodiments. For example, the treatment display 33 may display an advisory message recommending how to proceed with enteral feeding. As another example, if the value of gastric pH difference shown in either of displays 31 and 32 is negative or between 0-0.4 pH units, an additional message may be displayed in treatment display 33 if it is determined that the patient should not be fed for another 24 hours after which the above described process can be repeated. For example, this message can be: "Hold testing for 24 hours. Perform another baseline and post-stimulant measurement in 24 hours." If this is the case, then the time display 27 can be updated to blink or flash to indicate that no further action can be taken for the next 24 hours.

c. Other Exemplary Structures and Operations

Still other additional structures and operations can be used in conjunction with the methods and apparatus for guiding care discussed above. The exemplary structures and operations discussed below for determining gastric juice pH and for guiding care based on the determined gastric juice pH are not intended to be limiting, and instead are only provided for exemplary purposes.

For example, the gastric juice indicator/controller can be a recorder, such as a simple recorder, that communicates either by wire or wirelessly to a pH sensor or multiple pH sensors. The recorder can record pH (of the stomach, esophagus, etc.) in real time, and/or display the current pH on a display. The display can be appropriately located to be visible by a medical care provider or any other relevant viewer of the pH data.

This pH data can be presented in any format that is beneficial, such as in the form of a digital readout. e.g., pH 4.3. Multiple sensors and pH data can be monitored, and thus multiple pH measurements can be recorded or displayed in any format as discussed above. e.g., gastric pH 2.3, esophageal pH 6.8. Alternatively, this data can be recorded or displayed as a figure, such as in the form of a trendline, with the x-axis representing time, and the y-axis representing pH, for example.

In one exemplary embodiment, a fixed 1 hour window is used for this trendline, however exemplary embodiments are intended to cover any windows that are beneficial. In other exemplary embodiments, the scale of the x-axis can be changed. e.g., from 60 minutes, to 4 hours, to 12 hours, to 24 hours, if desirable. This feature may be beneficial by allowing an operator, such as a medical care provider, to view more acute changes, e.g., 60 minute view, or longer term changes. e.g., 24 hour view.

It may also be beneficial, especially when monitoring pH data from multiple sources, to depict the trendlines differently. For example, the gastric pH trendline can be shown differently than the esophageal pH trendline. As one example, one trendline can be shown as a solid line and the other as a dashed line, or one trendline can be one color (e.g., yellow) and the other trendline can be another color, e.g., blue.

In addition, it may be beneficial for the indicator/controller to have an alarm feature to signal various events. The alarm can be provided in any form that is usable or beneficial. For example, the alarm can be audible and can have other optional features, such as volume adjustments. In other words, the audible alarm can have different volume levels, and/or can be silenced or rendered mute under certain circumstances, such as if the patient is sleeping.

As disclosed above, the alarm can be used to signal various events, such as a sensed pH level traversing a threshold. For example, a patient may be administered an acid suppressant to maintain gastric pH greater than 4.0 units in order to reduce or prevent the formation of stress ulcers or alternatively to treat acute upper gastrointestinal bleeding. In such a patient, it may be beneficial to set the gastric pH alarm threshold level to a pH of 4.0 units, such that the alarm is triggered and outputs audible and/or visual signal(s) if the pH falls below 4.0 units. In another example, it may be desirable to set the alarm threshold to pH 5.0 units for monitoring esophageal pH to detect reflux/aspiration events in an ICU (and/or other areas of a hospital) that could place the patient at higher risk for the development of hospital acquired pneumonia.

In still other exemplary embodiments, the indicator/controller can receive signals of sensors providing data relating to multiple patients. In this example, the data can be transmitted either through wires or wirelessly to an indicator/controller operating as a central monitoring station, such as is done in related art ICUs for other vital signs, such as heart rhythm by EKG, heart rate, respiratory rate, and/or pulse oximetry. The central monitoring station may be located inside of the ICU, as is done in many related art ICUs, or in the case of patients on a hospital floor/ward (such as a non-ICU setting), the signal can be transmitted to and monitored in a facility located within or near the hospital but not necessarily in the immediate vicinity of the patient.

However, regardless of the location of the monitoring station, exemplary embodiments can include an alarm triggered based on thresholds that are set based on institutional guidelines, or alternatively based on thresholds that are more patient specific. This monitoring of gastric pH and/or esophageal pH can be performed on a wide variety of patients in a hospital, a skilled nursing facility, long term acute care facility, nursing home, or any other applicable environment. For example, infants or babies, such as those in a neonatal ICU or pediatric ICU, may benefit from this type of monitoring, although the form of the pH sensor in these situations may be adapted for such usages, such as by being smaller and consistent with the smaller size of the patient.

The embodiments disclosed above are intended to include any relevant, useful or beneficial currently known, related art or later developed technologies to perform the operations disclosed above. For example, some embodiments implement the above operations via hard-wired technologies, while others do so using wireless technologies, including wireless networks, Bluetooth, hospital's existing communication systems, including both hard-wired and wireless systems etc. For example, communication between catheters, sensors, monitors, central monitors, processors, etc., can be performed by any of the above technologies.

D. Exemplary Packaging of Equipment

1. Kit

Exemplary embodiments are intended to cover any beneficial grouping, packaging or presentation of any one or any combination of any of the apparatus and/or pharmaceuticals disclosed above. For example, a kit can be provided to facilitate detection of gastric function, and then guiding care based on the detected function.

In one exemplary embodiment, the kit includes at least one vial of pharmacological challenge agent, such as pentagastrin (750 mcg in 3 ml sterile buffer), a disposable pH probe (e.g., VersaFlex type, from Sierra Scientific Instruments, Los Angeles, Calif.), buffer solution for calibration of the pH probe/monitor (e.g., one test tube each of USP buffers 4.0 and 7.0. e.g., 30 ml in each test tube, i.e., a sufficient amount so that insertion of the probe covers enough of the probe to allow for calibration). The kit may also include 30 ml of a commercially available non-particulate antacid, which can be used if it is desirable to raise the baseline gastric juice pH prior to pentagastrin stimulation.

In another exemplary embodiment, the kit includes one vial of pharmacological challenge agent, such as pentagastrin (750 mcg in 3 ml sterile buffer), a disposable pH probe with 2 pH sensors (e.g., a distal sensor for measuring gastric pH and a sensor 20 proximal for monitoring of esophageal pH, from Sierra Scientific Instruments, Los Angeles, Calif.), buffer solution for calibration of the pH probe/monitor (e.g., 1 test tube each of USP buffers 4.0 and 7.0. e.g., 30 ml in each test tube, i.e., a sufficient amount so that insertion of the probe covers enough of the probe to allow for calibration). The kit can also include 30 ml of a commercially available non-particulate antacid, which can be used if it is desirable to raise the baseline gastric juice pH prior to pentagastrin stimulation as disclosed above in Section II.B. This single kit would allow for: 1) pentagastrin stimulated gastric pH measurements useful for determining the adequacy of gastric perfusion, e.g., useful at assessing the risk of stress ulcers and guiding nutrition management, 2) un-stimulated gastric pH measurements useful for assessing the adequacy of acid suppressant medication, and 3) esophageal pH measurements which could be used to guide patient management (e.g., patient position, enteral feeding route) to reduce the risk of aspiration of gastric contents.

The above exemplary embodiments are merely provided for illustrative purposes, and other exemplary embodiments are intended to cover any beneficial grouping, packaging or presentation of the disclosed apparatus and/or pharmaceuticals.

2. Processor

Some exemplary embodiments are intended to cover supply and packaging of only one of the elements disclosed above or various sub-combinations of the disclosed elements. For example, some exemplary embodiments are solely directed to a processor for guiding medical care of a patient based on detected gastric function. While the processor can be used with an administering device that administers a gastric acid stimulant, suppressant, or other pharmacological agent, as well as a measurement sensor that measures gastric juice pH, volume, motility, etc., some exemplary embodiments are directed solely to the processor that performs various determinations, calculations, etc., for the purpose of determining gastric function so that medical care can be guided based on the determined gastric function.

Exemplary embodiments are intended to cover all processors capable of performing all of the various heretofore-disclosed determinations, calculations, etc., for the purpose of determining gastric function. A few such processors are disclosed below for exemplary purposes only, and are not intended as an exhaustive list of processors covered by the invention. Also, the below disclosures are provided in the context of operations performed by the processors, because exemplary embodiments are intended to cover all currently known, related art, and later developed technologies for performing the relevant operations.

One exemplary processor is used with an administering device that administers a gastric acid stimulant or suppressant, and a pH sensor that measures the patient's gastric juice pH prior to the administration of the gastric acid stimulant or suppressant to obtain a baseline gastric juice pH, and that measures the patient's gastric juice pH after the administration of the gastric acid stimulant or suppressant to obtain a stressed gastric juice pH. The processor includes a determination unit that determines whether the baseline pH equals or exceeds a certain amount, and an instruction unit that provides instructions for the administering device to administer a gastric acid stimulant if the baseline gastric juice pH is equal to or exceeds the certain amount, or to administer a gastric acid suppressant if the baseline gastric juice pH is less than the certain amount. The processor also includes a calculation unit that calculates a pH differential between the baseline gastric juice pH and the stressed gastric juice pH to determine gastric function so that medical care can be guided based on the determined gastric function.

A second exemplary processor is used with an administering device that administers one of gastric acid stimulant and gastric acid suppressant, and a pH sensor that measures the patient's gastric juice pH prior to the administration of the one of gastric acid stimulant and gastric acid suppressant to obtain a baseline gastric juice pH, and that measures the patient's gastric juice pH after the administration of the one of gastric acid stimulant and gastric acid suppressant to obtain a stressed gastric juice pH. The processor includes a calculation unit that calculates a primary pH differential between the baseline gastric juice pH and the stressed gastric juice pH, and a primary guidance unit that provides advice for guiding medical care consistent with a relatively healthy gastric function if the calculated primary pH differential demonstrates an acute change in pH. The processor also includes an alternative guidance unit that provides instructions for conducting an alternative pH test if the calculated primary pH differential fails to demonstrate an acute change in pH. In the alternative pH test, the processor: a) instructs the pH sensor to measure the patient's gastric juice pH after the administration of the other of gastric acid stimulant and gastric acid suppressant to obtain an alternative stressed gastric juice pH, b) calculates an alternative pH differential between the baseline gastric juice pH and the alternative stressed gastric juice pH, c) provides advice for guiding medical care consistent with a relatively healthy gastric function if the calculated alternative pH differential demonstrates an acute change in pH, and d) provides advice for guiding medical care consistent with a relatively unhealthy gastric function if the calculated alternative pH differential fails to demonstrate an acute change in pH.

A third exemplary processor is used with stimulant and pharmacological agent administering devices, and a pH sensor that measures the patient's gastric juice pH to obtain a primary baseline gastric juice pH. The processor includes a determination unit that determines whether the primary baseline gastric juice pH equals or exceeds a certain amount, and a primary instruction unit that instructs the stimulant administering device to administer a gastric acid stimulant if the primary baseline gastric juice pH is determined to equal or exceed the certain amount. The processor also includes an alternative instruction unit that instructs that an alternative operation be performed if the primary baseline gastric juice pH is determined to be less than the certain amount. In the alternative operation, the processor: a) instructs the pharmacological agent administering device to administer a pharmacological agent to raise gastric juice pH, b) instructs the pH sensor to measure the patient's gastric juice pH after the pharmacological agent administration to obtain a secondary baseline gastric juice pH, and c) instructs the stimulant administering device to administers a gastric acid stimulant after the gastric juice pH has been raised. The processor also includes a measurement instruction unit that instructs the pH sensor to measure the patient's gastric juice pH after the gastric acid stimulant administration to obtain a stressed gastric juice pH, and a calculation unit that calculates a pH differential between: a) one of the primary and the secondary baseline gastric juice pH, and b) the stressed gastric juice pH, to determine gastric function, so that medical care can be guided based on the determined gastric function.

A fourth exemplary processor is used with an administering device that administers a minimum dosage of a gastric acid stimulant or suppressant, and a pH sensor that measures the patient's gastric juice pH prior to the administration of the minimum dosage of gastric acid stimulant or suppressant to obtain a baseline gastric juice pH, and that measures the patient's gastric juice pH after the administration of the minimum dosage of gastric acid stimulant or suppressant to obtain a primary stressed gastric juice pH. The processor includes a calculation unit that calculates a primary pH differential between the baseline gastric juice pH and the primary stressed gastric juice pH to determine gastric function, and a primary instruction unit that instructs medical care to be guided consistent with a relatively healthy gastric function if the calculated primary pH differential demonstrates an acute change in pH. The processor also includes an alternative instruction unit that instructs that an alternative test be conducted if the calculated primary pH differential fails to demonstrate an acute change in pH. In the alternative operation, the processor: a) instructs the administering device to administer a standard dosage of gastric acid stimulant or suppressant that exceeds the minimum dosage, b) instructs the pH sensor to measure the patient's gastric juice pH after the administration of the standard dosage of the gastric acid stimulant or suppressant to obtain an alternative stressed gastric juice pH, and c) calculates an alternative pH differential between the baseline gastric juice pH and the alternative stressed gastric juice pH, such that instructions are provided to guide medical care consistent with a relatively healthy gastric function if the calculated alternative pH differential demonstrates an acute change in pH, and instructions are provided to guide medical care consistent with a relatively unhealthy gastric function if the calculated alternative pH differential fails to demonstrate an acute change in pH.

A fifth exemplary processor is used with a pH sensor that measures the patient's gastric juice pH to obtain a baseline gastric juice pH, and an administering device that administers one of gastric acid stimulant and gastric acid suppressant. The processor includes an estimating unit that estimates a minimum period for a gastric response to the administration of the stimulant or suppressant, a pH measurement instruction unit that instructs the pH sensor to measure the patient's gastric juice pH approximately at the minimum period to obtain an initial stressed gastric juice pH, and a calculation unit that calculates an initial pH differential between the baseline gastric juice pH and the initial stressed gastric juice pH to determine gastric function. The processor also includes a primary instruction unit that instructs that medical care be guided consistent with a relatively healthy gastric function if the calculated initial pH differential demonstrates an acute change in pH, and an alternative instruction unit that instructs that a subsequent test be conducted if the calculated initial pH differential fails to demonstrate an acute change in pH. In the subsequent test, the processor: a) estimates a subsequent period for gastric response to administration of the stimulant or suppressant, the subsequent period exceeding the minimum period and being no greater than a duration of the patient's gastric response to the stimulant or suppressant, b) instructs the pH sensor to measure the patient's gastric juice pH approximately at the subsequent period to obtain a subsequent stressed gastric juice pH, and c) calculates a subsequent pH differential between the baseline gastric juice pH and the subsequent stressed gastric juice pH to determine gastric function, such that instructions are provided to guide medical care consistent with a relatively healthy gastric function if the calculated subsequent pH differential demonstrates an acute change in pH, and instructions are provided to guide medical care consistent with a relatively unhealthy gastric function if the calculated subsequent pH differential fails to demonstrate an acute change in pH.

A sixth exemplary processor is used with an administering device that administers a gastric acid stimulant or suppressant, and a pH sensor that measures the patient's gastric juice pH prior to the administration of the gastric acid stimulant or suppressant to obtain a baseline gastric juice pH, and that performs multiple measurements of the patient's gastric juice pH after the administration of the gastric acid stimulant or suppressant to obtain multiple stressed gastric juice pH values. The processor includes a calculation unit that calculates a rate of change of gastric juice pH based on the baseline gastric juice pH and the stressed gastric juice pH values, and a primary instruction unit that provides instructions to guide medical care consistent with a relatively healthy gastric function if the calculated rate of change of gastric juice pH demonstrates an acute rate of change. The processor also includes a secondary instruction unit that provides instructions to guide medical care consistent with a relatively unhealthy gastric function if the calculated rate of change of gastric juice pH fails to demonstrate an acute rate of change.

A seventh exemplary processor is used with an administering device that administers a gastric acid stimulant or suppressant, and a pH sensor that measures the patient's gastric juice pH prior to the administration of the gastric acid stimulant or suppressant to obtain a baseline gastric juice pH, and that measures the patient's gastric juice pH after the administration of the gastric acid stimulant or suppressant to obtain a stressed gastric juice pH. The processor includes a determination unit that determines a guidance pH differential suitable to guide care based on the baseline gastric juice pH, a calculation unit that calculates a measured pH differential between the baseline gastric juice pH and the stressed gastric juice pH, and a comparison unit that compares the guidance pH differential to the measured pH differential. The processor also includes a primary instruction unit that provides instructions to guide medical care based on a relatively healthy gastric function if the measured pH differential is equal to or exceeds the guidance pH differential, and an alternative instruction unit that provides instructions to guide medical care based on a relatively unhealthy gastric function if the measured pH differential is less than the guidance pH differential.

An eighth exemplary processor is used with an administering device that administers one of gastric acid stimulant and gastric acid suppressant, and a pH sensor that measures the patient's gastric juice pH prior to the administration of the one of gastric acid stimulant and gastric acid suppressant to obtain a baseline gastric juice pH, and that measures the patient's gastric juice pH after the administration of the one of gastric acid stimulant and gastric acid suppressant to obtain a stressed gastric juice pH. The processor includes a calculation unit that calculates a pH differential between the baseline gastric juice pH and the stressed gastric juice pH, and a primary instruction unit that provides advice to guide medical care consistent with a very healthy gastric function if the calculated pH differential demonstrates an acute change in pH. The processor also includes a secondary instruction unit that provides advice to guide medical care consistent with a moderately healthy gastric function if the calculated pH differential demonstrates a moderate change in pH, and a tertiary instruction unit that provides advice to guide medical care consistent with an unhealthy gastric function if the calculated pH differential fails to demonstrate at least a moderate change in pH.

A ninth exemplary processor is used with an administering device that administers a pharmacological challenge agent, and a volume sensor that measures gastric juice volume. The processor includes a determination unit that communicates with the volume sensor to determine gastric juice volume secreted a period after the administration of the pharmacological challenge agent, and a primary instruction unit that provides instructions to guide medical care consistent with a relatively healthy gastric function if the determined gastric juice volume secreted demonstrates an acute change in volume. The processor also includes a secondary instruction unit that provides advice to guide medical care consistent with a relatively unhealthy gastric function if the determined gastric juice volume secreted fails to demonstrate an acute change in volume.

A tenth exemplary processor is used with an administering device that administers a pharmacological challenge agent, and a motility sensor that measures the patient's gastrointestinal motility prior to the administration of the pharmacological challenge agent to determine a baseline motility, and that measures the patient's gastrointestinal motility after the pharmacological challenge agent administration to determine a stressed motility. The processor includes a calculation unit that communicates with the motility sensor to calculate a motility differential between the baseline motility and stressed motility, and a primary instruction unit that guides medical care consistent with a relatively healthy gastric function if the motility differential demonstrates an acute change in gastrointestinal motility. The processor also includes a secondary instruction unit that guides medical care consistent with a relatively unhealthy gastric function if the motility differential fails to demonstrate an acute change in gastrointestinal motility.

As discussed above, the above are disclosed for exemplary purposes only, and are not intended as an exhaustive list of processors covered by the invention.

3. Computer Program

As disclosed above in Section IV.D.2., some exemplary embodiments are intended to cover supply and packaging of only one of the elements disclosed above or various subcombinations of the disclosed elements. In addition to the exemplary processors disclosed above, some exemplary embodiments are solely directed to software or computer programs for guiding medical care of a patient based on detected gastric function. While the software or computer programs can be used with a processor, an administering device that administers a gastric acid stimulant, suppressant, or other pharmacological agent, as well as a measurement sensor that measures gastric juice pH, volume, motility, etc., some exemplary embodiments are directed solely to the software or computer programs that perform various determinations, calculations, etc., for the purpose of determining gastric function so that medical care can be guided based on the determined gastric function.

Exemplary embodiments are intended to cover all software or computer programs capable of performing the various heretofore-disclosed determinations, calculations, etc., for the purpose of determining gastric function. For example, exemplary embodiments are intended to cover all software or computer programs capable of enabling the processors disclosed above in Section IV.D.2, to implement the disclosed processes. In other words, exemplary embodiments are intended to cover all systems and processes that configure a document operating system to implement the disclosed processes. Exemplary embodiments are also intended to cover any and all currently known, related art or later developed non-transitory recording or storage mediums (such as a CD-ROM, DVD-ROM, hard drive, RAM, ROM, floppy disc, magnetic tape cassette, etc.) that record or store such software or computer programs. Exemplary embodiments are further intended to cover such software, computer programs, systems and/or processes provided through any other currently known, related art, or later developed medium (such as transitory mediums, carrier waves, etc.), usable for implementing the exemplary operations disclosed above.

In accordance with the exemplary embodiments, the disclosed computer programs can be executed in many exemplary ways, such as an application that is resident in the memory of a device or as a hosted application that is being executed on a server and communicating with the device application or browser via a number of standard protocols, such as TCP/IP, HTTP, XML, SOAP. REST, JSON and other sufficient protocols. The disclosed computer programs can be written in exemplary programming languages that execute from memory on the device or from a hosted server, such as BASIC, Cobol, C. C++, Java, Pascal, or scripting languages such as JavaScript, Python, Ruby, PHP, Perl or other sufficient programming languages.

V. Other Exemplary Types of Enhanced Care

In addition to the applications discussed above (which include and are not limited to guiding enteral feeding, mechanical ventilation, and use of vasoactive agents), the detected gastric function can be used to enhance care of patients in other ways. Exemplary embodiments are intended to cover and include any and all enhancements in care that can be provided based at least in part on detected gastric function. A few such enhancements are disclosed below, which are not intended to be limiting and are only provided as examples.

For example, pH levels can be correlated with other ICU monitoring to infer patient status and guidance of care. One embodiment confirms exocrine failure with a combination of low blood pressure, low cardiac output, and increased pH.

In fact, some of the exemplary embodiments disclosed below detect gastric function using techniques that do not include any of the disclosed gastric challenge test(s), and instead rely completely or partially on monitoring pH values over extended periods. This extended pH monitoring can be enhanced using techniques disclosed above in Section IV.B.3. Enhanced pH Measurements.

A. Disposition of Patients Within a Hospital

The detected gastric function can be used to guide the disposition of patients within a medical care facility, such as a hospital, nursing home, etc. For example, the gastric function of hospital patients entering an emergency room could be tested. Based on the detected gastric function, the patients could either be admitted to a standard (non-ICU) hospital room or admitted to an ICU. In fact, the detected gastric function could even be used in conjunction with other factors to determine whether the patient could be released or discharged from the hospital. For example, a patient could be discharged if the tested gastric pH differential exceeds 2 units, assuming that other aspects of the patient's health warrant discharge. A patient could be admitted to a standard (non-ICU) hospital room if the tested pH differential is 0.5 units-2 units. A patient could be admitted to an ICU if the tested pH differential is below 0.5 units. The detected gastric function could also be used in conjunction with other factors to determine admittance to an ICU or non-ICU room.

This test could similarly be performed on ICU patients. For example, ICU patients evidencing sufficient gastric function could be discharged from the ICU, while patients evidencing insufficient gastric function would remain in the ICU. In other words, negative gastric function test results (such as less than 1 pH unit decrease) suggests a suboptimal perfusion of the stomach/GI tract indicating that a patient is not ready to be discharged from the ICU. Contrarily, positive gastric function test results (such as at least 1 pH unit increase) suggests sufficient or optimal perfusion of the stomach/GI tract indicating that the patient is ready to be discharged from the ICU, assuming other aspects of the patient's health warrant discharge.

Esophageal pH monitoring could be performed in hospitalized patients who are being enterally feed into the stomach or proximal duodenum and who are at higher risk for aspiration (e.g. impaired mental status such as coma, or stroke or head injured patients with impaired airway reflexes). Measurements could be displayed at the bedside, at the nursing station, or even in a core analysis center (e.g. analogous to routine continuous ECG telemetry in patients at higher risk for cardiovascular events). Detection of reflux events could trigger an alarm, alerting clinicians to the possible risk of aspiration of gastric contents. The patient could be transferred to an ICU or other interventions could be done to minimize risk of aspiration (see section V(E)).

The above disclosures are only provided as examples and are not intended to be limiting. In fact, the exemplary embodiments are intended to cover usage of the above gastric function test to guide any dispositions of hospital or non-hospital patients that would be applicable or beneficial.

B. Adequacy of Resuscitation

Patients who have lost a significant amount of fluid (such as via evaporative losses, or diarrhea or vomit) or blood (either during surgery or from trauma) require the administration of intravenous fluid to "resuscitate" them, i.e., restore their intravascular volume. The related art does not provide sufficient indications as to whether the resuscitation has been adequate, i.e., whether the intravascular volume has been sufficiently restored.

However, the detected gastric function can be used as an indicator as to whether sufficient resuscitation has been achieved. The GI tract's perfusion is sensitive to inadequate intravascular circulatory volume, and thus the above gastric juice pH test may provide sufficient indication as to the adequacy of resuscitation.

For example, in exemplary embodiments employing pH differential, the resuscitation may be terminated after a sufficient pH differential is detected. Alternatively, in these exemplary embodiments, the pH differential may be tested after other indicators recommend termination of resuscitation. In this case, the determined gastric function, such as indicated by gastric juice pH differential, can be used as a confirmatory test for the other indicators. For example, in exemplary embodiments determining gastric function based on pH differential a tested gastric juice pH differential of at least 1 unit may confirm the adequacy of the resuscitation.

C. Detection of Risk for Stress Ulcers

The detection of gastric function as disclosed above can be used to identify patients at risk of stress ulcers. Some critically ill patients are at risk for the development of stress ulcers and possible bleeding from these ulcers. e.g., GI bleed. The most likely underlying cause for stress ulcers is gastric/gut hypoperfusion because the resulting ischemia makes the gastric lining susceptible to the acidic environment in the stomach. (See figure summarizing how poor perfusion is the underlying cause of stress ulcers in critical ill patients, as disclosed in Neligan, Patrick. "Stress Ulceration in Critical Care—What Causes It?" *Welcome to Critical Care Medicine Tutorials*. Critical Care Medical Tutorials. Web. 2 Jun. 2011. <http://www.ccmtutorials.com/support/ulcers/page_03.htm>., hereafter "Neligan," which is hereby incorporated in its entirety herein by reference.). It is therefore beneficial to identify patients at increased risk of stress ulcers and GI bleeding. Such patients can be administered more potent agents (e.g., proton pump inhibitors or PPIs) to neutralize the gastric acid, or in some cases administered by intravenous infusion (more potent) rather than standard intermittent dosing. In addition, additional interventions, e.g., increasing the cardiac output by increasing the circulating blood volume, can be performed to enhance gastric perfusion.

The gastric function tests disclosed above can be used to identify patients at risk for developing stress ulcers because, in order to respond to pentagastrin, the parietal cells of the stomach require a large amount of energy to decrease the pH. These cells have many mitochondria because they need to produce approximately a one million-fold increase in H+ concentration (intracellular pH of 7 units vs. gastric acid pH of 1 unit). Thus, a positive response to pentagastrin demonstrates that the patient is not at high risk for stress ulcers and may not need prophylaxis, or can be prophylaxed with a less potent acid suppressant such as the H2 receptor antagonist ranitidine also called Zantac. The patient failing to respond to a potent gastric acid stimulant, such as pentagastrin, with at least a 1 unit decrease in pH, suggests the need for more potent therapy, e.g. switch to proton pump inhibitor or intravenous infusion of a PPI, or strategies to increase gastric perfusion.

Another exemplary embodiment includes use of continuous gastric pH testing in patients at risk for stress ulcers. Gastric acid suppressants do not sufficiently raise pH above 4.0 pH units in many ICU patients, which is considered to be a therapeutic target, because pepsinogen is not converted to pepsin in an environment above 4 pH units. Continuous measurements of pH using an indwelling pH sensor, or intermittent, e.g., hourly, measurements of pH from this sensor or from aspirated gastric juice can be used to help guide the need for potent acid suppressants, e.g., PPIs, or guide dosing in patients at high risk for stress ulcers and GI bleeding. In this exemplary embodiment, the gastric stimulation test is performed, and patients exhibiting a robust response to pentagastrin are considered low risk so as to not require an acid suppressant or continuous pH monitoring. Patients with a negative response to pentagastrin are prescribed an acid suppressant and undergo continuous or intermittent pH monitoring. e.g., for 48 to 72 hours, in order to ascertain that acid suppressant dosing is adequate to achieve a less acidic pH (e.g., 4). Subsequently (e.g., 48-72 hours after the last stimulation test), the pentagastrin test can be repeated to see if the patient is still at risk. In the presence of acid suppressants, it is desirable to perform the pentagastrin challenge immediately prior to administration of the next dose of acid suppressant medication to avoid false negative results, because high levels of pharmacologically induced acid suppression can cause false negative results.

Acid suppression has been shown to reduce mortality and re-bleeding in ICU patients who have recently undergone endoscopic control of upper GI bleeding according to Lau et al. "Effect of Intravenous Omeprazole on Recurrent Bleeding After Endoscopic Treatment of Bleeding Peptic Ulcers." The New England Journal of Medicine 343:6 (2000): 310-316. Print., hereafter "Lau et al 2000," which is hereby incorporated in its entirety herein by reference. Acid suppression, and specifically maintaining gastric pH>6, is significant or otherwise important because, below pH 6, platelet aggregation is abolished and clot lysis occurs, which can predispose to re-bleeding according to van Rensburg et al. "Intragastric pH During Continuous Infusion With Pantoprazole in Patients With Bleeding Peptic Ulcer." The American Journal of Gastroenterology 98:12 (2003): 2635-2641. Print., hereafter "van Rensburg et al 2003" which is hereby incorporated in its entirety herein by reference. Despite the routine use of intravenous proton pump inhibitors (PPI) in this setting, mortality and re-bleeding continue to be significant problems in some patients after endoscopic control of UGI bleeding according to Lanas et al. "Clinical predictors of poor outcomes among patients with nonvariceal upper gastrointestinal bleeding in Europe." Alimentary Pharmacology and Therapeutics 33 (2011): 1225-1233. Print., hereafter "Lanas et al. 2011" which is hereby incorporated in its entirety herein by reference. This occurrence may be due to the fact that intravenous PPIs do not reliably maintain pH>6 in all patients. For example, it has been observed that a continuous infusion of pantoprazole (80 mg bolus then 8 mg/hr) has resulted in pH>6 only 64% of the time (van Rensburg et at 2003). In another example, intravenous administration of a PPI did not achieve a pH>6 in many patients according to Laine et al. "Intragastric pH With Oral vs Intravenous Bolus Plus Infusion Proton-Pump Inhibitor Therapy in Patients With Bleeding Ulcers." Gastroenterology 134:7 (2008): 1836-1841. Print., hereafter "Laine et al 2008" which is hereby incorporated in its entirety herein by reference.

In order to address this unmet need, continuous monitoring of gastric pH can be used to titrate the infusion of an acid suppressant (e.g., a PPI such as pantoprazole) in order to enhance adequate drug delivery or insure that adequate drug is being delivered. For example, in some patients, a higher infusion rate (e.g., 10 mg/hr of pantoprazole) may be needed to achieve this target pH, compared with typical dosing (8 mg/h). In contrast, continuous monitoring of gastric pH may reveal that some patients require a lower dose (e.g., 2 mg/hr) than a dosage that is typically used (8 mg/hr).

Clinical Algorithm to Achieve Target Gastric pH 6 to 6.5
Initial Gastric pH and Initial Intravenous Bolus and Infusion Rate

| Initial Gastric pH Reading | Initial IV PPI Dosing (Pantoprazole) |
|---|---|
| 1 to 3 | 80 mg bolus then 8 mh/hr infusion |
| 3 to 4 | 80 mg bolus then 8 mg/hr infusion |
| 4 to 5 | 80 mg bolus then 8 mg/hr infusion |
| 5 to 6 | 40 mg bolus then 4 mg/hr infusion |
| >6 | No bolus then 2 mg/hr infusion |

Subsequent Gastric pH and Subsequent Intravenous Bolus and Infusion Rate This repeat testing and dose titration should be done on an hourly basis for the first 6 hours, then every 3 hours thereafter

| Gastric pH Reading | IV PPI Dosing (Pantoprazole) |
|---|---|
| 1 to 3 | Additional 80 mg bolus & increase by 2 mg/hr |
| 3 to 4 | Additional 40 mg bolus & increase by 2 mg/hr |
| 4 to 5 | Additional 20 mg bolus & increase by 2 mg/hr |
| 5 to 6 | No bolus & increase by 2 mg/hr |
| >6 | Continue current rate |

D. Detection of Effect of Acid Suppressant Medication

Patients with chronic acid reflux are treated in the related art with oral acid suppressant medication, e.g., histamine 2 receptor antagonists (e.g. ranitidine or Zantac) or proton pump inhibitors, e.g., omeprazole. Some patients continue to have symptoms of acid reflux despite treatment with these agents. In these patients on acid suppressant medication, gastric pH can be measured before and after administration of a potent acid stimulant, e.g., 6 mcg/kg of pentagastrin. For this test, a lower dose of pentagastrin (1 mcg/kg) may be as (or substantially as) effective, given the flat dose response curve for pentagastrin in this dosing range and the desire to avoid side effects from the drug. This test is beneficially or even optimally performed within a few hours after the most recent dose of acid suppressant medication, e.g., 3 hours after oral omeprazole administration.

The gastric juice pH falling to an acidic or a very acidic level (e.g., pH 2 or 3) indicates that acid suppressant treatment is not effective or optimal. In this case, the dose of the same acid suppressant may be increased (within allowable limits), or the patient may be switched to a different acid suppressant medication. This procedure may be helpful to some patients because genetic differences may result in some patients having a better response to some medications than others. The gastric stimulation test can be repeated after enhancing or even optimizing dosing or changing to another drug in order to ascertain whether gastric acid secretion has become more inhibited by the new acid suppressant regimen.

There are several benefits to this use of the gastric stimulation testing. For example, this testing can result in fewer and/or less severe symptoms of acid reflux. In some cases, enhanced or more optimal medical management can result in surgery avoidance, e.g., Nissan fundoplication, which is performed in the related art for patients with intractable acid reflux despite acid suppressant medication. In contrast to related art monitoring of acid reflux, which requires monitoring of esophageal pH for a prolonged period of time, e.g., 24 hours, use of the gastric stimulation test takes less time (actual test 60 minutes duration), thereby impacting less of the patient's time and resulting in a more rapid diagnosis.

In another exemplary embodiment, the gastric stimulation testing can be performed in conjunction with the longer more standard esophageal pH monitoring, because these two tests may provide different but complimentary data. The gastric stimulation testing measures how well the acid suppressant medication reduces or prevents significant acidity of the stomach secretions under a provocative challenge. The more standard esophageal pH monitoring assesses for reflux of acid, which provides information on the competency of the lower esophageal sphincter (muscular band between the esophagus and stomach), which if functioning well reduces or minimizes reflux of stomach acid into the esophagus. In addition, although gastric pH is often monitored during ambulatory pH testing it may result in false negatives if the patient is not exposed to provocative stimulus for gastric acid secretion. For example, a particular patient on a potent acid suppressant may only have breakthrough acid secretion and resulting heartburn after ingesting a specific food, e.g. chocolate. If they do not ingest this type of food during their 24 hour ambulatory test they will not exhibit the break though acid secretion, hence their testing will falsely conclude that they have adequate acid suppression. In contrast, the provocative test with pentagastrin (or other potent acid stimulant) allows the clinician to quickly know if acid suppression is adequate even under conditions of maximal or near maximal stimulation.

E. Detection of Risk of Aspiration of Gastric Contents

Hospitalized patients, in particular those in an ICU, are at increased risk of aspiration of gastric contents. Examples of patients at risk for aspiration include, but are not limited to: 1) mechanically ventilated patients, 2) those with reduced mental status such as coma, somnolence, or delirimn, 3) those after severe stroke, head injury, or spinal cord injury, and 4) those with impaired airway reflexes and impaired swallowing function. Gastric contents (e.g., food, secretions, and in rare instances blood) can move backward into the esophagus if the lower esophageal sphincter is not competent. Contents that move sufficiently superior toward the head can enter the pharynx and/or the area of opening to the trachea. At least one relevant definition of aspiration in this context covers movement of these contents into the trachea and in particular the smaller airways and lung tissue, and can be a very serious medical complication, resulting in lung damage and possibly death.

While aspiration of any gastric contents can be harmful, aspiration of acidic gastric secretions can cause damage even in low volumes. In many patients, gastric contents leave the stomach and move or retrograde (backward) along the esophagus if the patient is supine and flat. Therefore, current ICU (and in some cases hospital) guidelines recommend that the head of the bed should be elevated by at least 30 degrees in hospitalized and other critically ill patients, especially those on a ventilator and those receiving enteral nutrition. If the head of the bed is elevated, gravity helps to prevent gastric contents from moving backward out of the stomach and into the esophagus.

The use of a sensor on the patient's body to enhance, improve, or even optimize patient positioning is disclosed in section IV(C)(3)(c). Insuring that the patient, rather than just the bed, is in a head-up position can reduce the risk of reflux of gastric contents and consequently the risk of aspiration of gastric contents.

In another exemplary embodiment used to reduce the risk of aspiration, a catheter with one or two pH sensors can be used to help determine whether the head of a patient's bed is sufficiently elevated to reduce the risk of, or prevent, aspiration. One exemplary embodiment includes two sensors, wherein one of the sensors can be at the tip (distal end) of the catheter or probe, and the other sensor can be a distance spaced away from the one sensor, such as approximately 15 cm spaced proximally from the one pH sensor.

Upon insertion of this probe with two sensors, a low pH (e.g., 2 or 3 units) measurement from the distal sensor indicates that this sensor is in the acid environment of the stomach, while a significantly higher pH (e.g., 6 or 7 units) indicates that the proximal sensor is in the esophagus. This structure enables continuous monitoring of the pH values from the two sensors. If there is adequate elevation of the head of the patient's bed, then the pH values measured by the proximal sensor should remain close to neutral pH, i.e., a pH of 7 units. Observing acidic values (e.g., 2 units to 4 or 5 units) from the proximal sensor indicates that gastric contents have been able to move into the esophagus, indicating that the head of the patient's bed should be elevated more. Continuous monitoring in this way enables medical care providers to detect associations between patient position and likelihood of movement of gastric contents into the esophagus. Measurements may be displayed at the patient's bedside, at the nursing station, or even in a core analysis center (e.g., analogous to routine continuous ECG telemetry in patients at higher risk for cardiovascular events). Detection of reflux events may trigger an alarm, alerting clinicians to the possible risk of aspiration of gastric contents.

Exemplary embodiments are intended to cover any useful application of the methodology disclosed above. For example, one exemplary embodiment determines whether gastric contents have moved into the esophagus based solely on esophageal pH. In other words, gastric contents are determined to have moved into the esophagus if the esophageal pH falls below a certain threshold. This threshold can be the same (static) for all patients in all circumstances. In one such example, gastric contents are determined to have moved into the esophagus if the esophageal pH falls below 6 pH units, for example. However, exemplary embodiments are intended to cover any and all relevant thresholds, such as pH units of 5.5, 5.0, 4.5, 4.0, 3.5, etc.

However, alternative embodiments set different esophageal pH thresholds for determining whether gastric contents have moved into the esophagus depending upon different circumstances. In one such embodiment, patient profile data including at least one of age, gender, fitness, weight, body composition, percentage of body fat, ethnicity, family history, personal medical history, and genetics, is used to set the threshold. In other embodiments, personal patient history and/or data can be used to set the threshold in addition, or as an alternative, to the above patient profile data. For example, a certain esophageal pH may be normal for some patients but evidence movement of gastric contents into the esophagus for other patients. In still other embodiments, other patient circumstances can be used to set the threshold in addition, or as an alternative, to the above patient profile data and/or personal patient history data. For example, patients suffering from or subject to certain medial conditions may warrant use of different thresholds.

The embodiments disclosed above use different thresholds that are either: 1) set or static for all patients in all circumstances; or 2) set depending on patient profiles, personal patient histories, and/or other patient circumstances. However, other exemplary embodiments cover still other different applications, including not using, or at least not solely relying on, set thresholds, and instead varying the threshold used to determine whether gastric contents have moved into the esophagus. For example, the esophageal pH threshold can be varied based on other measured data.

One such embodiment varies the esophageal pH threshold used to determine whether gastric contents have moved into the esophagus as a function of other data, such as gastric pH, for example. As an example, the esophageal pH threshold can be reduced for lower gastric pH measurements. The following chart provides one such embodiment for exemplary purposes only.

| Gastric Juice pH | Esophageal pH Threshold |
|---|---|
| <5.0 | 3.5 |
| 5.0-6.0 | 4.5 |
| >6.0 | 5.5 |

In the above embodiment, a lower gastric juice pH sets a lower esophageal pH threshold that is used to determine whether gastric contents have entered the esophagus. For example, the esophageal pH threshold used to determine whether gastric contents have entered the esophagus would be 3.5 units if the measured gastric juice pH is less than 5.0 units. In other words, in that case, an esophageal pH of 3.5 units or less would indicate movement of gastric contents into the esophagus.

Changing the esophageal pH threshold as disclosed above can be performed in any relevant manner. For example, gastric pH can be measured periodically and the esophageal pH threshold changed accordingly pursuant to the periodic gastric pH measurements. Alternatively, gastric juice pH can be measured semi-continuously or continuously to thereby enable the esophageal pH threshold to be updated on a semi-continuous or continuous basis.

Changing the esophageal pH threshold used to determine whether gastric contents have moved into the esophagus based on gastric pH can be beneficial in various respects. For example, this methodology provides a more accurate indication of whether gastric contents have moved into the esophagus by focusing on the differential between gastric pH and esophageal pH. In other words, a very acidic gastric juice measurement (such as 1-3 pH units) may indicate that reflux is not the cause of a mildly acidic esophageal pH (such as 4-5 pH units), whereas reflux may be occurring if a relatively mildly acidic gastric pH is measured (such as 5-6 pH units) for the same esophageal pH (i.e., 4-5 pH units).

The above differential between gastric pH and esophageal pH is provided for exemplary purposes only, and embodiments are intended to cover other differentials or types of differentials. For example, the esophageal pH threshold can be varied based on a set or static differential between gastric pH and esophageal pH, such as 2 pH units. In that case, the esophageal pH threshold would always be set at 2 pH units above the measured gastric pH. Alternatively, different differentials can be used for different gastric pH measurements. For example, larger pH differentials can be used to set the esophageal pH threshold for relatively low gastric juice pH measurements (e.g., 1-3 pH units), while smaller pH differentials can be used for relatively high gastric juice pH measurements (e.g., 4-5 pH units), or vice versa. In still other alternative embodiments, the differential between esophageal pH and gastric pH used to set the esophageal pH threshold can be varied based on data other than gastric pH, such as some or all of the data disclosed above relating to patient profiles, personal patient histories, and/or other patient circumstances.

Exemplary embodiments are intended to cover any other currently known or later developed technology to implement the above procedures. For example, one exemplary embodiment uses a single esophageal pH sensor, such as at a distal tip positioned in the esophagus. Proper position in the esophagus can be confirmed by standard methods, e.g., chest x-ray/KUB, or fluoroscopy. Alternatively, the sensor can be inserted into the stomach as evidenced by a low pH (e.g., 2 to 4 units), and then pulled back into the esophagus as manifested by an acute increase in the pH (e.g., to 6 or 7 units). Identification of the proper location of the esophageal sensor may be easier if a catheter with two sensors is used because the distal tip can measure gastric pH, while the proximal sensor can measure esophageal pH.

Figure 9:
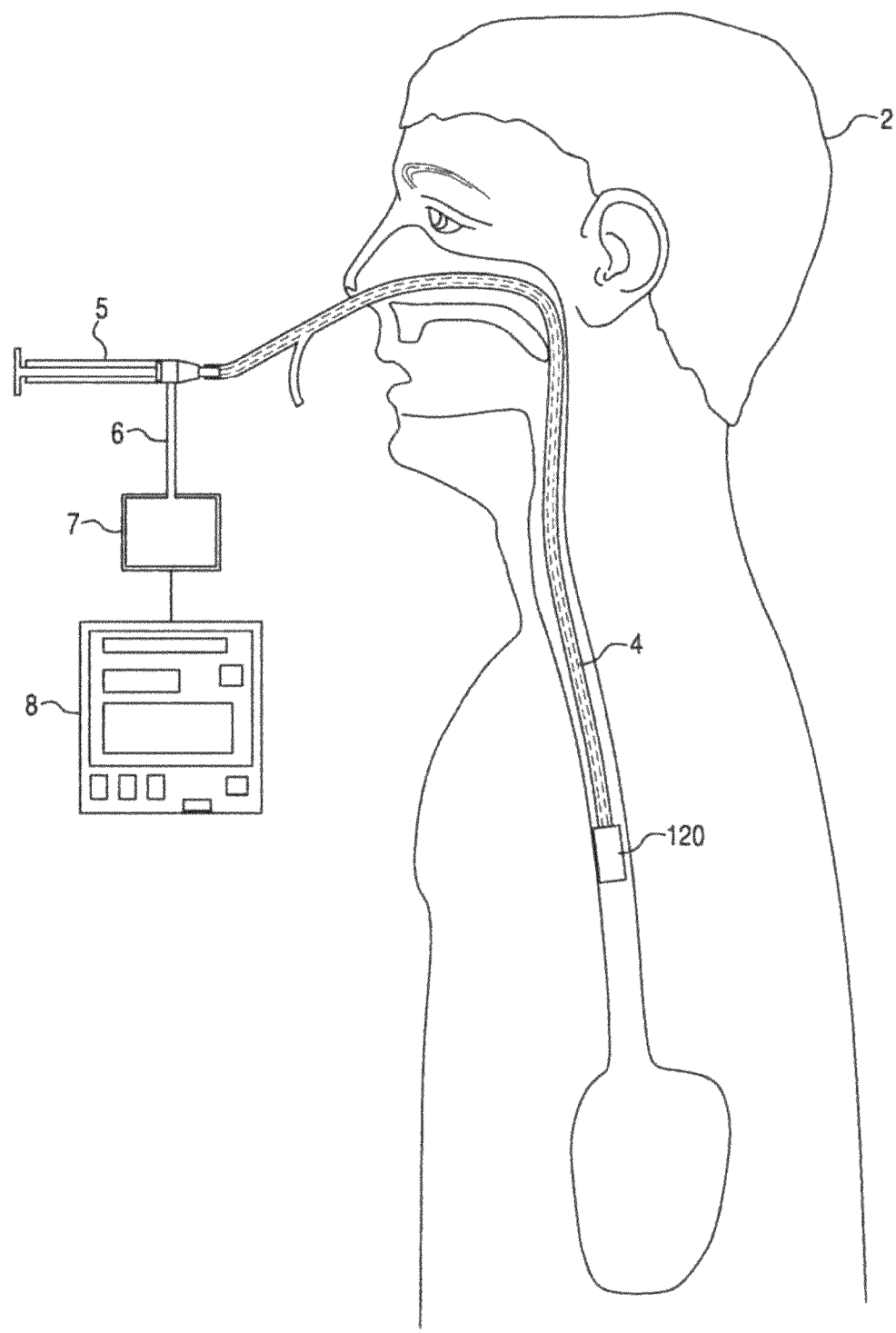
FIG. 9 is a schematic of an apparatus in accordance with another exemplary embodiment, and particularly shows an esophageal sensor to monitor a patient's esophageal pH.

FIG. 9 is a schematic of an apparatus in accordance with an exemplary embodiment that includes an esophageal sensor to monitor a patient's esophageal pH. As shown in FIG. 9, the esophageal sensor 120 is positioned in the esophagus, for example 10 to 20 CM proximal (superior) to the junction of the esophagus and the stomach, although any position in the esophagus may be appropriate. As with the exemplary embodiment shown in FIG. 1, an orogastric or nasogastric tube 4, exemplary syringe 5 for aspiration, and exemplary connector 6 for connection to a pH measuring device 7, 8, can be used to measure or otherwise determine the patient's esophageal pH. For example, the syringe or aspirator 5 provides a suction or other force so that esophageal contents are sucked or otherwise moved from the esophagus of the patient 2, through orogastric or nasogastric tube 4, and into a collector or other structure so that the pH of the contents can be measured. However, the methods and structures shown in FIG. 9 are merely provided for exemplary purposes, and exemplary embodiments are intended to cover any method and apparatus for determining esophageal pH.

The degree of elevation of the head of the patient's bed can be used to influence the likelihood of reflux of gastric contents and risk of gastric aspiration. Another common patient position in the ICU and hospital is sitting in a chair, which typically results in an even greater degree of head elevation relative to the stomach.

Monitoring of the pH values in the esophagus in the above exemplary embodiments is different from related art reflux testing that is performed in stable non-hospitalized patients for the purpose of diagnosing chronic reflux. Exemplary embodiments involve the use of these pH sensors in hospitalized, e.g. critically ill patients: 1) to determine the risk of aspiration of gastric contents, and 2) to guide proper patient positioning (e.g., adequate head of bed elevation) to reduce or minimize risk of aspiration of gastric contents. In addition, if reflux of gastric contents cannot be reduced or eliminated with enhanced or optimal patient position (i.e., elevation of the head of the patient's bed), then at least one of the following changes in patient management can be performed: 1) decreasing the rate or volumes of food introduced into the stomach, 2) switching to post-pyloric feeding thereby bypassing the stomach, and/or 3) enhancing or optimizing acid suppressant medication therapy.

Another exemplary embodiment uses esophageal impedance monitoring, such as disclosed in Bredenoord, Albert J., Radu Tutuian, Andre J. Smout, and Donald O. Castell. "Technology Review: Esophageal Impedance Monitoring." *American Journal of Gastroenterology* 102 (2007): 187-94. Print., hereafter "Bredenoord," which is hereby zin its entirety herein by reference, to determine risk of aspiration of gastric contents and to guide proper patient positioning and other patient management techniques, such as disclosed above. Intraluminal impedance monitoring can be used to detect the flow of liquids and gas through hollow viscera and it is useful in the evaluation of patients with PPI-resistant typical reflux symptoms, chronic unexplained cough, excessive belching, and rumination. In contrast to uses of this technology to diagnose chronic conditions, esophageal impendence monitoring can be used in hospitalized, e.g., critically ill, patients to determine whether there is reflux of gastric contents. If the pattern of change in impedance shows retrograde movement, then the patient is at higher risk of aspiration of gastric contents. More enhanced or optimal patient positioning can be attempted and the patient can continue to be monitored to determine whether this procedure reduces the reflux episodes as measured by the impendence monitoring. In addition, if reflux of gastric contents cannot be eliminated with enhanced or optimal patient positioning (i.e., head of bed elevated), then at least one of the following changes in patient management can be performed: 1) decreasing the rate or volumes of food introduced into the stomach, 2) switching to post-pyloric feeding thereby bypassing the stomach, and/or 3) enhancing or optimizing acid suppressant medication therapy.

Another exemplary embodiment combines esophageal pH monitoring and esophageal impendence monitoring to guide the proper positioning and care of hospitalized, e.g., critically ill, patients. Retrograde events by impendence monitoring can indicate retrograde movement of gastric contents and esophageal pH monitoring can be used to determine whether these gastric contents are acidic (e.g., pH 2 to 3 units), which significantly increases the likelihood of an acid aspiration event.

Such retrograde events can detrimentally affect patients' health. For example, one study reported that 89% of ventilated ICU patients had at least one episode of aspiration, with 48% acquiring pneumonia, and concluded that aspiration of gastric contents is common in critically ill tube-fed patients and is a major risk factor for pneumonia according to Methany et al. "Tracheobronchial aspiration of gastric contents in critically ill tube-fed patients: Frequency, outcomes, and risk factors." Critical Care Medicine 34:4 (2006): 1007-1015. Print., hereafter "Methany et al 2006," which is hereby incorporated in its entirety herein by reference. Aspiration also leads to greater use of hospital resources.

In addition, a high gastric pH may be a predictor of bad outcome. In one such example, exocrine failure (i.e., low gastric acid secretion) may be a predictor of aspiration and bad outcome. Thus, some embodiments perform the above monitoring to determine whether the pH is increasing over time, which may indicate that bicarbonate is entering the stomach from the small bowel. This retrograde movement of bicarbonate from the duodenum into stomach could be an indication that the patient has poor small bowel motility and may be at risk for aspiration.

In some patients, contents from the small bowel move retrograde (i.e., backwards) into the stomach. This retrograde movement of small bowel contents can be harmful, for example, if a patient is receiving post-pyloric enteral nutrition due to concerns of possible aspiration of gastric contents. In this setting, retrograde movement of tube feeds into the stomach may place the patient at higher risk for aspiration of tube feeds, which can cause pulmonary injury and/or pneumonia. Continuous or semi-continuous measurement of gastric pH can be used to allow the clinician to diagnose this reflux into the stomach.

The pH of the gastric contents is typically acidic and rarely as high as 7, whereas the pH of the duodenal (small bowel) contents is much less acidic (as compared to the gastric contents) due to the copious secretions of bicarbonate normally used to neutralize gastric acid that enters the small bowel. Therefore, observing intermittent "spikes" of increased pH in the stomach, e.g., from 3 to 6 may, strongly suggest that reflux is occurring from the small bowel into the stomach. In one example, if the patient is receiving tube feeds into the small bowel, a determination of this reflux can indicate that the post-pyloric tube should be repositioned to a more distal location. e.g., distal to the ligament of Treitz, which typically demarcates the duodenal-jejunal junction. There is a lower risk of reflux of tube feeds from this more distal location, however, difficulty in achieving this distal tube position makes it impractical to perform this procedure in all patients. Therefore, continuous measurement of gastric pH can be used to identify patients at higher risk for this reflux, and patients that would benefit from increased efforts to reposition the feeding tube more distally.

Exemplary embodiments are not limited to the specific sensor types, technologies and operations disclosed above. For example, numerous of the above embodiments include pH sensors. However, other types of sensors can be used to provide any data that may be beneficial or otherwise useful. In some such embodiments, sensors are used to measure relative volumes of liquid using currently known, related art or later developed technologies, such as measuring liquid volumes via resistance or conductivity. Some embodiments use the above relative volume measurements for various purposes, such as for reflux detection, motility determination, etc.

F. Gastric Residual Volume Monitoring

Other exemplary embodiments directly or indirectly monitor gastric residual volumes for the purpose of guiding care in numerous respects. Embodiments include various techniques for monitoring gastric residual volumes, such as using impedance sensors in the stomach to measure gastric emptying. In one embodiment, one or more impedance sensors are located near to, or on both sides of, the pylorus, which connects the stomach to the duodenum, i.e., the beginning of the small intestines.

The above impedance measurements may be beneficial in numerous respects. For example, an alternative technique is to remove gastric contents via an NG tube so that the contents can be measured outside of the patient's body. The contents can then be returned to the patient, discarded, etc. However, removal of gastric contents in this manner suffers from various disadvantages. For example, this technique can be messy, labor intensive, unpleasant from the patient's perspective, etc. However, impedance monitoring in accordance with various exemplary embodiments is not subject to this disadvantage, and is otherwise an easier and more accurate approach to measuring gastric residual volumes than aspirating gastric contents via an NG tube.

Care can be guided in numerous respects based on the measured gastric residual volumes. For example, high residuals can be an indicator to switch from gastric feeding to post-pyloric feeding to achieve various benefits, such as reflux avoidance.

G. Detection of Gut Ischemia in Intra-abdominal Hypertension

Intra-abdominal hypertension is relatively common in critically ill (ICU) patients. If left untreated, intra-abdominal hypertension can lead to abdominal compartment syndrome, which is often defined as elevated intra-abdominal pressure (e.g. >20 mm Hg) associated with new organ dysfunction or failure. This medical problem is disclosed in *World Society of the Abdominal Compartment Syndrome*. Web. 2 Jun. 2011. <http://www.wsacs.org/patients.php>., hereafter "World Society," which is hereby incorporated in its entirety herein by reference.

Related art methods to detect intra-abdominal hypertension (e.g., bladder pressure monitoring) do not indicate whether a patient with elevated intra-abdominal pressure has gut ischemia, which is one of the most feared complications of abdominal compartment syndrome. Therefore, in another exemplary embodiment, patients with elevated intra-abdominal pressure (e.g., greater than 15 mm Hg) can be subjected to the gastric stimulation testing. i.e., measurement of gastric pH, before and after administration of a pharmacological agent, e.g., the potent acid stimulant pentagastrin 6 mcg/kg subcutaneously.

A positive test. i.e., significant reduction in the pH, indicates that there is adequate gastric perfusion, and that therefore there is less likelihood of significant enough intra-abdominal pressure to compromise gut blood flow and cause ischemia or damage to these organs. In contrast, a negative test indicates that there is impaired gastric perfusion and that there is increased risk of ischemia to the gut, and thus it may be beneficial to consider further monitoring and perhaps intervention, e.g., surgery. A negative result will have greater predictive value if it is obtained after a positive gastric test result was observed earlier, and in particular before the development of intra-abdominal hypertension. This information more strongly suggests that the new onset of the intra-abdominal hypertension is the cause of the new negative gastric stimulation test.

In addition, in another exemplary embodiment, esophageal pH and/or esophageal manometry monitoring is also performed in critically ill patients to detect the risk of significant intra-abdominal hypertension. Increased pressure on the stomach (as occurring in intra-abdominal hypertension) increases the likelihood of gastric contents moving retrograde (backward) into the esophagus. Therefore, evidence of increasing reflux events (manifested by lower pH spikes in the esophagus, and/or a typical reflux pattern by manometry) indicates that there may be increased intra-abdominal pressure, which in combination with other clinical signs, e.g., new onset oliguria or increasing serum creatinine as signs of new renal failure, can trigger possible intervention, e.g., surgery such as opening the abdominal compartment to relieve the intra-abdominal hypertension.

H. Drug Absorption

In some patients, it is important to understand whether there is adequate oral absorption of important medications. These medications can include, but are not limited to, chemotherapy drugs to treat cancer, cardiac drugs to regulate the function of the heart, pain medications, etc. Less commonly, blood (plasma, serum) levels of an oral agent can be measured, and while used in pharmokinetic research studies, this measurement is impractical for most drugs in routine practice. Research methods for measuring gut absorption are also not practical in routine practice. Therefore, for most drugs, clinicians must guess if there is adequate absorption of orally administered drugs.

An important determinant of absorptive function is adequate gut perfusion. Any of the disclosed methods and apparatus for assessing the gut (e.g., gastric stimulation testing, small bowel pulse oximetry) can be used to guide care in this regard. For example, if a patient has poor pulsatilty of blood flow using small bowel intraluminal pulse oximetry and does not respond to a gastric stimulation test, then critical medications should be administered by some other route, e.g., intravenously, in order to avoid inadequate efficacy due to low oral drug absorption.

I. Enteral Tolerance

Results from different tests (e.g. pentagastrin stimulation, reflux monitoring) can be combined to provide additional information. In an exemplary embodiment, a patient who has a very robust response to a gastric acid stimulant AND has no observed reflux by esophageal impedance monitoring despite gastric feeding would be characterized as very low risk for enteral nutrition related complications, e.g. aspiration or bowel ischemia. In a contrasting exemplary embodiment, a patient who has a positive but less robust response to pentagastrin AND who also shows 10 reflux events per 24 hours would be characterized as being at higher risk of developing enteral nutrition related complications.

The above data and approach can even be combined with clinical information in many patients. In exemplary embodiments, any of the following events in conjunction with a lack of (or small) response to pentagastrin would indicate a higher risk of gut ischemia and/or feeding intolerance: new need for inotropic or vasoconstrictor agent, need for a higher dose of inotropic or vasoconstrictor agent, new evidence of lactatemia or metabolic acidosis, new or worsening hypotension, cardiac index if measured decreasing, e.g. to less than 2 liters/min/m$^2$.

In additional exemplary embodiments, even though these factors are of limited diagnostic value alone, additional factors such as abdominal pain, vomiting, abdominal distension (increased measured abdominal circumference), lack of bowel sounds, high gastric residuals, e.g. >250 ml, would indicate a higher risk for enteral feeding complications.

J. Combination of Methodologies in Guiding Care

The determination of a patient's status and guidance of care can be based on multiple factors and in exemplary embodiments these factors can be combined to enhance determining such status and subsequently guiding care. The exemplary factors that may prove beneficial include, but are not limited to, the following: the response to a gastric acid stimulant; the level, duration, and number of aspiration events; the dosage and type of acid suppressant medication; the dosage and type of enteral nutrition; the volume of gastric contents; the current medical condition being treated; and the personal medical history of the patient. Exemplary factors that could also prove beneficial include patient characteristics, including at least one of: age, gender, fitness, weight, body composition, percentage of body fat, ethnicity, family history, and genetics.

In an exemplary embodiment, an older patient being treated after cardiac surgery may combine a number of factors to help determine the status and guidance of care. In this embodiment their response to a gastric acid stimulant could be interpreted in light of the fact that older patients generally have fewer parietal cells and thus generally produce less gastric acid as a result. Given the response to the gastric acid stimulant and the severity of recovering from cardiac surgery, this patient may be started on enteral nutrition more cautiously and thus at a lower level. In an exemplary embodiment, the pH level is tracked over time to provide data on how their GI system reacts as they digest the enteral nutrition. In this exemplary embodiment, the pattern of the pH changes could indicate a healthier response to the nutrition and combined with the initial response to the gastric stimulant to help provide guidance that the nutrition level can be safely increased.

These previously mentioned factors may be beneficially combined in many different exemplary combinations. In one exemplary embodiment the factors may be monitored individually by the clinician, where the clinician assesses the data and derives a conclusion about the status of the patient. In another exemplary embodiment, the factors may be combined via algorithms that are coded into any number of exemplary systems, such as the monitor, hosted servers, etc. These algorithms would combine each factor in a number of exemplary ways. In one exemplary embodiment, each factor is normalized into a numerical scale that can be more easily combined with other factors. In this exemplary embodiment, each factor can then be combined through multiple exemplary methods. In one exemplary embodiment, the factors are added together resulting in a single numerical value or other exemplary symbol that can be interpreted as the status of the patient or an indication for the guidance of specific care.

In another exemplary embodiment, the factors are presented as trending data, with positively correlated data presented in one exemplary fashion and negatively correlated data presented in another fashion. In one exemplary embodiment, positively correlated data is presented as an upward arrow and negatively correlated data presented as a downward arrow. In another exemplary embodiment, positively correlated data is presented as a green colored symbol and negatively correlated data presented as a yellow or red colored symbol. In another exemplary embodiment, any data presented with a yellow color could be associated with the notion of caution in the status and subsequent guidance of specific care.

The factors and trends can be processed in many exemplary methods. In one exemplary embodiment, the factors are weighted based on the beneficial value of the information towards determining the status of the patient or an indication for the guidance of specific care. In one exemplary embodiment, the factors are given a numerical weight that is then multiplied by the factor to achieve a weighted factor. In one exemplary embodiment, these weighted factors could then be added together resulting in a single numerical value or other exemplary symbol that can be interpreted as the status of the patient or an indication for the guidance of specific care. In another exemplary embodiment, some weighted factors may be interpreted as a negative value and therefore subtracted from the total.

In one exemplary embodiment, the single numerical value that is a result of summing the weighted factors could be on a scale from 0 to 100 and be referred to as a "Nutrition Readiness" score. In this post gastric stimulation exemplary embodiment, the scale of the score could be interpreted as follows: 0-9 would signify there are severe issues and care should be adjusted; 10-29 would signify to wait for a follow-up test or start to feed at a low level; 30-69, would signify to start nutrition with "modest" goal and paying closer attention to monitoring the patient via impedance sensors for aspiration risk; 70-100 would signify to start nutrition and be more aggressive in accelerating toward goal.

In this post gastric stimulation exemplary embodiment, there are many factors and algorithms that may be used to potentially achieve a beneficial result. In one exemplary embodiment, a faster acid response, as indicated by a rapidly decreasing gastric pH measurement or rapidly increasing H+ concentration measurement, will generate a score more quickly and will be interpreted as a higher score. Such a faster acid response is an indication that the GI system is healthier and thus more likely to tolerate enteral nutrition and other specific care. In another exemplary embodiment, more acid being produced (ml) will be interpreted as a higher score, since this also is an indication that the GI system is healthier, allowing the clinician to feed more confidently at a higher goal. The amount of acid produced can be determined through a number of exemplary means, such as aspirating the gastric contents and measuring the resulting volume. In another exemplary embodiment, reflux events will be interpreted as lowering the score, with the score varying based on the severity and/or frequency of the reflux events. In another exemplary embodiment, the reflux data may potentially be interpreted as an alert if the severity and/or frequency exceeds a pre-defined threshold.

In another exemplary embodiment, a low score may trigger an alert to help the clinician or nurse understand there is an urgent need to attend the patient. This alert may be displayed in a number of exemplary ways. In one exemplary embodiment, the alert is displayed on the monitor near the patient as at least one of a numerical score, color coded data, symbol, flashing light, audible tone, and audible message. In another exemplary embodiment, the alert is displayed at a nurses station via standard data interfaces and user interfaces that are appropriate for existing and future systems.

Other embodiments involve monitoring factors over time and interpreting the factors via algorithms to potentially achieve a beneficial result. In one exemplary embodiment, if feeding at a low level, the score might remain yellow if the pH continues to stay high, indicating the patient may not be producing a sufficient level of gastric acid to tolerate the nutrition. In another exemplary embodiment, if pH measurements continue to lower during feeding, the score will increase since this is an indication the patient is tolerating the nutrition. In another exemplary embodiment, if pH is already at a low level and stays there over time with feeding, the score will increase since this is an indication gastric acid is being produced at potentially sufficient level to tolerate nutrition. In another exemplary embodiment, the level of nutrition will be factored in since a higher level of nutrition requires a higher output of gastric acid. In another exemplary embodiment, the type of feed will be factored in since feeds have different properties that relate to the ability to tolerate nutrition. In another exemplary embodiment, the score will factor in acid suppressant dosing and type, since the acid suppressant will affect the pH measurements and could indicate if sufficient gastric acid is being produced to tolerate nutrition.

K. Exemplary Processes and Devices in Guiding Care

There are many exemplary processes and devices for assessing the status of the patient and/or determining the guidance of specific care. These processes can be presented to the clinician in a number of advantageous ways.

In one exemplary process the following steps could be executed to achieve a beneficial result:

First, insert an exemplary pH sensing catheter either by the nasal or oral route into the stomach just like a standard feeding tube using routine procedures.

Second, confirm intragastric location by chest or abdominal radiograph.

Third, connect the catheter to an exemplary monitor.

Fourth, set up the Monitor. This step includes entering the weight in kilograms, or pounds, so that the monitor can calculate the required dose (mcg/kg). Optionally, administer a gastric acid buffer, such as 10 ml of Sodium Citrate, if suggested by the monitor (if low baseline pH).

Fifth, wait for screen statement "Inject x mg (y ml) of GastroStim drug", after which inject drug and then select monitor button "GastroStim drug injected"

Sixth, wait for up to 60 minutes for monitor to provide the results, which is based on exemplary algorithms. "Green" symbol indicates that gastric secretory function has been sufficient to significantly decrease gastric pH which is consistent with adequate gastric perfusion and energy capability to support enteral nutrition. "Yellow" symbol indicates that gastric secretory function has not been sufficient to significantly decrease gastric pH which may indicate there is not adequate gastric perfusion and energy capability to support enteral nutrition This exemplary process involves waiting at least 12 hours prior to repeating the above process.

In another exemplary process, the following steps could be executed to achieve a beneficial result:

First, insert an exemplary pH sensing catheter either by the nasal or oral route into the stomach just like a standard feeding tube using routine procedures.

Second, confirm intragastric location by chest or abdominal radiograph.

Third, connect the catheter to an exemplary monitor.

Fourth, set up the Monitor. This step includes entering the patients age and weight in kilograms, or pounds, so that the monitor can calculate the required dose (1 mcg/kg). The acid suppressant type and dosage as well as the nutrition type and dosage would be entered.

Fifth, wait for screen statement "Inject x mg (y ml) of GastroStim drug", after which inject drug and then select monitor button "GastroStim drug injected"

Sixth, wait for up to 60 minutes for monitor to provide the results, which is based on exemplary algorithms. The monitor will then display information such as the current pH, the pH differential, an exemplary summarized score such as the previously defined "Nutrition Readiness Score".

Seventh, push designated buttons when acid suppressant dosing and nutrition dosing events occur.

Eighth, continuously monitor the data to indicate the status of the patient and/or determining the guidance of specific care. The total number and severity of reflux events. The monitor could also display a graphical view of the pH and impedance data collected over time.

VI. Other Diagnostic Methodologies

While exemplary embodiments have been outlined above, it is evident that many alternatives, modifications and/or variations will be apparent to those skilled in the art. Accordingly, the above exemplary embodiments are intended to be illustrative and not limiting. Various changes can be made without departing from the spirit and scope of the invention as defined in the following claims.

A few other exemplary embodiments are outlined below. These embodiments are not intended to form a complete list of alternatives, and are merely provided for exemplary purposes.

A. Gastric Perfusion

In some exemplary embodiments, gastric perfusion can be directly monitored to predict gastric function. For example, as described below devices can be used to measure gastric tissue oxygenation, which is almost a direct reflection of the perfusion of the tissues. For example, if this monitoring indicates that there is very poor perfusion. e.g. gastric near infrared spectroscopy (NIRS) of 45%, this finding alone would indicate that the patient should not be fed enterally given the very high risk of non-occlusive bowel necrosis. On the other hand a more normal value of for example, 80% for NIRS of the stomach mucosa suggests that there is adequate perfusion at rest. However, it is possible that there may not sufficient reserve to increase perfusion in response to the increased metabolic demand of enteral feeding (digestion and absorption). Therefore, in this setting it may be particularly beneficial to administer a pharmacological challenge agent, such as pentagastrin, which should transiently increase the metabolic demand of the stomach. Thus, if gastric perfusion deteriorates (e.g. NIRS decreases from 80% to 60%) during the challenge this would suggest that there may not be sufficient reserve of perfusion for safe administration of enteral nutrition.

1. Near Infrared Spectroscopy

Exemplary embodiments include still other apparatus and methods for enhancing the monitoring and guidance of care for patients. In one example, a catheter provides near infrared spectroscopy (NIRS) data, which uses light transmission and absorption to measure tissue oxygen saturation (StO2) as described previously in other clinical settings.

This apparatus can be a stand-alone catheter, or the NIRS capability can be integrated into a tube with other uses. For example, this feature can be integrated into a currently known, related art or later developed 18F Salem Sump tube for naso- or -oro-gastric insertion, which allows for suctioning, administration of medications, and/or administration of tube feeds. This feature can be integrated into this type of tube that also contains pH and/or impedance sensors, allowing for even more uses. Alternatively, this feature can be integrated into a smaller tube for post-pyloric placement if it is desirable to tissue oxygen saturation in the small bowel. In yet another embodiment, the catheter can contain more than one NIRS sensor, thereby allowing simultaneous measurements of tissue oxygen saturation in multiple sites. e.g., in the stomach and small bowel.

Intraluminal tissue oxygenation monitoring with NIRS in the stomach and/or small bowel enables enhanced or optimal management of acutely ill patients in various respects. As disclosed above, used alone or in conjunction with other testing (e.g., gastric stimulation, intraluminal pulse oximetry), this operation can indicate the adequacy of gastric and small bowel tissue oxygenation, which can be used to guide decisions to initiate or terminate enteral nutrition as well as to initiate or terminate stress ulcer prophylaxis. This operation can also guide the care of patients with intra-abdominal hypertension to avoid gut ischemia and necrosis. The operation disclosed above differs from the related art, which suggests its potential use as a measure of global perfusion, in particular in the diagnosis of hemorrhagic shock.

2. Pulse Oximetry

Exemplary embodiments include other apparatus and methods for enhancing the monitoring and/or guidance of care for patients. In one example, a catheter provides pulse oximetry data, which uses reflected light to provide information about the arterial blood oxygen saturation (SpO2) and pulsatility of blood flow.

This apparatus can be a stand-alone catheter, or the pulse oximetry capability can be integrated into a tube with other uses. For example, this capability can be integrated into a currently known, related art, or later developed 18F Salem Sump tube for naso- or -oro-gastric insertion, which allows for suctioning, administration of medications, and/or administration of tube feeds. This capability can be integrated into this type of tube that also contains pH and/or impedance sensors, allowing for even more uses. Alternatively, this capability can be integrated into a smaller tube for post-pyloric placement when it is desirable to measure arterial blood oxygen saturation in the small bowel. In yet another embodiment, the catheter can contain more than one pulse oximetry sensor, thereby allowing simultaneous measurements of arterial blood oxygen saturation and pulsatility of blood flow in multiple sites, e.g., in the stomach and small bowel.

Intraluminal pulse oximetry in the stomach and/or small bowel allow for optimal management of acutely ill patients in various respects. For example, evidence of adequate arterial blood oxygen saturation and pulsatility of blood flow in the stomach indicates that there is adequate perfusion to support enteral nutrition. In another example, evidence of adequate arterial blood oxygen saturation and pulsatility of blood flow in the small bowel indicates that there is adequate perfusion to support enteral nutrition administered either into the stomach or small bowel. The above monitoring is particularly helpful in patients who may have compromised gastric or small bowel perfusion or oxygenation, either due to low cardiac output, low blood pressure, anemia, or even a fixed lesion, e.g. occlusive bowel ischemia. Feeding of patients at risk for bowel necrosis increases the risk of this devastating complication. Additional testing, e.g. gastric stimulation testing, can be added to provide confirmatory evidence for the presence or absence of adequate perfusion.

In another example, evidence of adequate arterial blood oxygen saturation and pulsatility of blood flow in the stomach indicates that there is adequate perfusion therefore the patient is at low risk for stress ulcers and stress ulcer prophylaxis is not indicated. It may be significant or important to identify these patients in order to not miss patients who may be at risk and go on to develop stress ulcers, upper GI bleeding, and even death. On the other hand, stress ulcer prophylaxis with acid suppressants has been shown to increase the risk of nosocomial pneumonia and C. difficile infection, so these drugs should be avoided if not needed. Additional testing, e.g., gastric stimulation testing, can be added to provide confirmatory evidence for the presence or absence of adequate perfusion.

Patients with intra-abdominal hypertension are at risk for abdominal compartment syndrome and gut ischemia. In another use of pulse oximetry, evidence of adequate arterial blood oxygen saturation and pulsatility of blood flow in the stomach and small intestine indicates that there is adequate perfusion therefore the patient is at low risk for gut ischemia. On the other hand, a loss or pulsatility in the small bowel of a patient with rising intraabdominal pressures strongly suggests that the gut may be at risk for ischemia and even necrosis. Additional testing, e.g., gastric stimulation testing, can be added to provide confirmatory evidence for the presence or absence of adequate perfusion.

In the above embodiments, the arterial oxygen saturation and pulsatility data can reinforce each other. For example, it is normal for the tracing to show good pulsatility consistent with adequate perfusion pressure and good blood flow to the area. At the same time, arterial oxygen saturation data indicates that the hemoglobin moving through this tissue are carrying oxygen. However, in some patients, the pulsatility component of the pulse oximetry monitoring is useful by itself since it can indicate the presence or absence of adequate pulsatile perfusion, the lack of which places the patient at increased risk for gut ischemia and its related complications, e.g., poor tolerance of enteral nutrition, stress ulcers, GI bleeding, non-occlusive bowel necrosis.

The above apparatus and methods differ from related art techniques that use pulse oximetry in the esophagus or on the surface of internal organs. Esophageal measurements do not necessarily reflect the adequacy of perfusion to the general splanchnic bed, most notably the stomach and small and large intestines. Use of pulse oximetry directly on the outside of organs, such as the stomach or intestine, is subject to certain limitations, including the fact that it can only be used in settings (e.g., intraoperatively) where there is direct access to the internal organ. In addition, the physiology of blood flow is typically preserved toward the outside of the structure, but is at highest risk on the inside of the structure, i.e., on the mucosal side. Intraluminal pulse oximetry in the stomach and small bowel avoid or otherwise address the above limitations, and enable enhanced or optimal management of acutely ill patients.

B. Gastric Volume

In some exemplary embodiments, gastric juice volume can be monitored to determine gastric function. This method may be particularly beneficial because the pH of acid secreted by the stomach's parietal cells is relatively constant (pH 0.9). A typical human stomach produces over 1 to 1.5 liters of gastric juice per day. Some of this gastric juice is acid, but there are other constituents, and in particular mucous secreted to protect the stomach lining (mucosa) from the corrosive effects of the acid. While basal (non-stimulated) gastric juice is low (e.g., 50-70 ml per hour), it can increase to several hundred ml per hour after stimulation with an acid stimulant (e.g., pentagastrin), assuming that gastric perfusion is adequate.

Thus, it may be beneficial to aspirate all gastric juice via an NGT, administer a gastric acid stimulant such as pentagastrin (6 mcg/kg subcutaneously), and then measure gastric juice volume secreted over a certain period, such as 30 minutes, for example between 15 and 45 minutes after pentagastrin administration. This may be accomplished by aspirating gastric juice at 15 minutes post injection, discarding the collected gastric juice, and then measuring the gastric volume after a relevant period or periods. For example, the gastric volume can be measured at both 30 minutes and 45 minutes after stimulant administration. In this case, the volumes collected are added together to provide the gastric volume used to determine gastric perfusion.

In one exemplary embodiment, a volume of greater than 100 ml (over 30 minute collection time) indicates a robust gastric secretory response, and indicates that the patient's gut is well perfused and is likely to tolerate enteral nutrition. In another exemplary embodiment, a volume of 25 ml (over the 30 minute collection time) indicates a poor gastric secretory response, and indicates that the patient's gut is not well perfused and appropriate management should follow (e.g., interventions to improve splanchnic perfusion such as fluid resuscitation, delay in enteral feeding, or more cautious initiation of enteral nutrition).

The gastric contents volume can be performed with the exemplary apparatus shown in FIG. 7. For example, as shown in FIG. 7, the aspirator 104 aspirates gastric contents by providing a suction or other force so that gastric contents are sucked or otherwise moved from the stomach of the patient 2, through the orogastric or nasogastric tube 106, and into the collector 108 or other structure. The volume sensor 110 measures the volume of gastric contents collected in the collector 108.

Other methods of collection of gastric juice volume can be performed. For example, it may be beneficial to connect the NGT to constant low wall suction, and continuously collect all NGT drainage from 1-60 minutes after pentagastrin administration. In this case, a volume of greater than 200 ml (over 60 minute collection time) indicates a robust gastric secretory response, thereby indicating that the patient's gut is well perfused and is likely to tolerate enteral nutrition. A volume of 50 ml (over the 60 minute collection time) indicates a poor gastric secretory response, thereby indicating that the patient's gut is not well perfused and appropriate management should follow (e.g., interventions to enhance splanchnic perfusion, such as fluid resuscitation, delay in enteral feeding, or more cautious initiation of enteral nutrition).

C. Motility

In another embodiment, intestinal contractions/motility may be monitored before and after administration of the pharmacological agent, such as pentagastrin. An increase of intestinal contractions/motility may alternatively be used to evidence a healthy or reasonably healthy gastric function and care may be provided accordingly.

Figure 12:
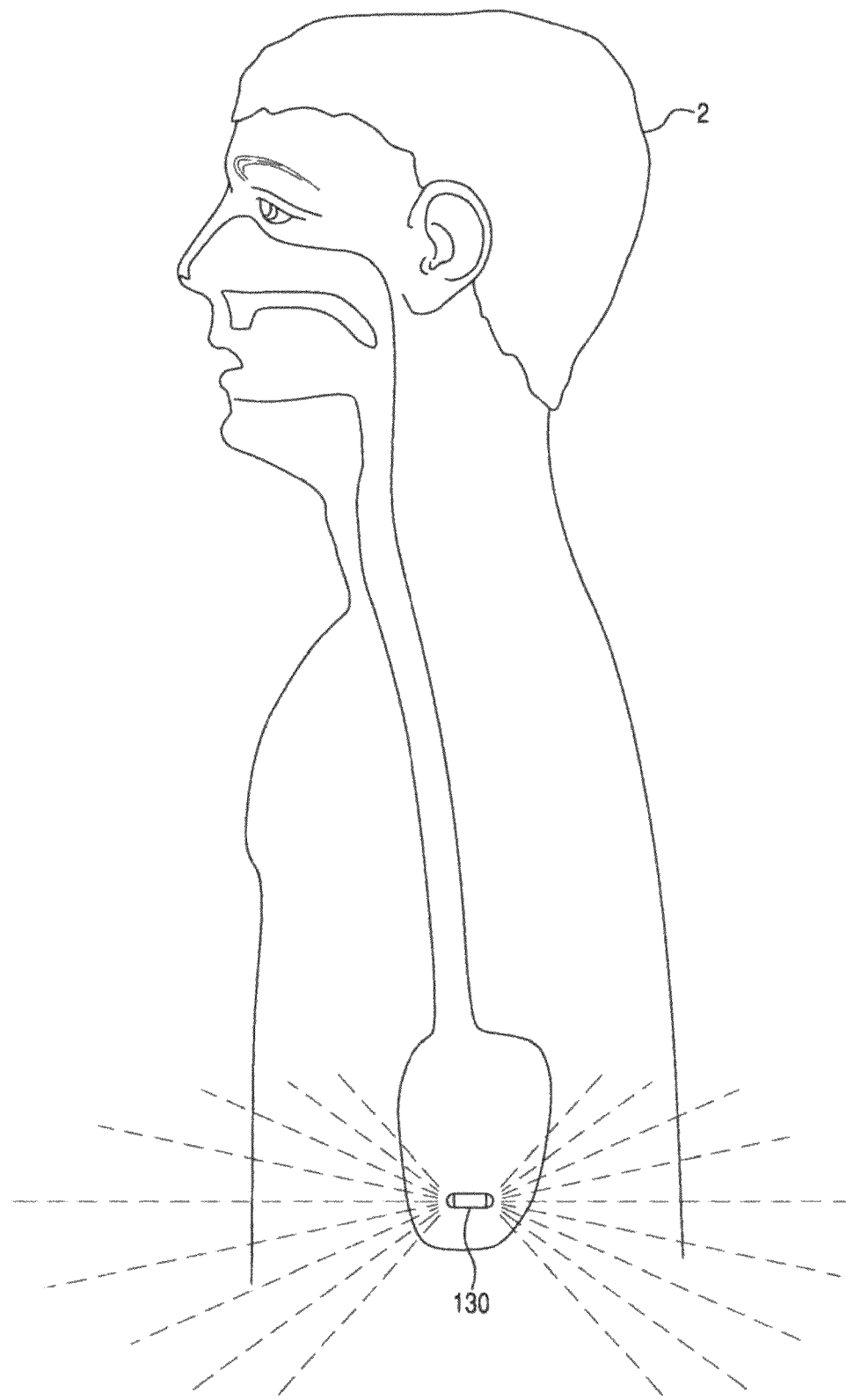
FIG. 12 is a schematic of an apparatus in accordance with another exemplary embodiment, and particularly shows a motility sensor that measures gastrointestinal motility.

FIG. 12 is a schematic of an apparatus in accordance with an exemplary embodiment that includes a motility sensor for measuring gastrointestinal motility. The exemplary embodiment of FIG. 12 includes a wireless motility sensor 130 that is disposed at an appropriate location to detect the patient's gastrointestinal motility, and wirelessly transmit the detected gastrointestinal motility values to any of the disclosed indicators/controllers 8, 20. However, the wireless sensor 130 shown in FIG. 12 is not intended to be limiting, and exemplary embodiments are intended to cover any method and apparatus for obtaining the gastrointestinal motility values. Pentagastrin may be used as the pharmacological challenge agent for the two alternative embodiments discussed above because, in healthy patients, it transiently increases blood flow in the gastric mucosa (lining of the stomach), causes contraction of smooth muscle of the LES, and increases motor activity of the colon and rectum. However, exemplary embodiments are not limited to the use of pentagastrin, and are intended to cover any currently known method, apparatus, pharmaceutical, etc., capable of providing the effects discussed above or other effects useful in guiding care based on determined gastric function.

In an exemplary embodiment, bowel sounds can be auscultated, and the presence of bowel sounds (in conjunction with results from changes in gastric pH changes after pharmacological challenge) can be used to guide decisions to initiate, modify, or terminate enteral feeding. Auscultation of bowel sounds can be performed directly, e.g., with a stethoscope, however, in one exemplary embodiment, bowel sounds are recorded with an electronic stethoscope or microphone, which is coupled with a recorder that can monitor, record, and enable display of continuous data. This exemplary embodiment enables detection of less intense sounds compared with direct auscultation. In other words, direct auscultation is more likely to only allow detection of bowel sounds that are louder, and the sampling period is shorter due to the need for the person listening to be tethered to the patient via the stethoscope. In contrast, use of an electronic stethoscope or microphone in conjunction with a recording device enables detection of less intense (less loud) and less frequent bowel sounds, which still indicate that there is adequate gastrointestinal motility to allow for enhanced, improved, and/or even successful enteral nutrition.

In another exemplary embodiment, the pattern of recorded bowel sounds can be interpreted in the context of the patient's care to determine if there is adequate motility. For example, the above embodiments can be performed alone or in conjunction with a pharmacological challenge. For example, administration of a prokinetic agent (e.g., metaclopromide, 10 mg every 6 hours intravenously, or erythromycin, 100 mg every 12 hours intravenously) can be performed, and an increase in bowel sounds can be used to help determine whether there is response to this medication and whether there is adequate motility for successful enteral nutrition. In another exemplary embodiment, bowel sounds and gastric juice pH can be analyzed after administration of pentagastrin, and the presence of both bowel sounds and a positive pH response (i.e. decrease) to pentagastrin provides a very high level of confidence that enteral nutrition can be initiated with enhanced, improved and/or successful tolerance by the patient.

D. Combination of Methodologies

Exemplary embodiments are also not limited to determining gastric function based on any one of gastric juice pH, gastric perfusion, and intestinal contractions/motility. For example, any or all of the methodologies can be used together to provide an accurate assessment of gastric function. In other words, any two or all three of these methodologies can be used together to more accurately determine gastric function.

In fact, one exemplary embodiment combines the collection of gastric juice pH information (e.g., decrease in pH in response to pentagastrin) and the collection of gastric juice volume information (e.g., increase in gastric juice volume in response to pentagastrin) in order to gain more sensitivity and specificity of the test. For example, patients having a positive response with regard to pH and volume will be most likely to tolerate enteral nutrition (or reducing other aspects of ICU care). Patients who have a negative response to both pH and volume will be very unlikely to tolerate enteral nutrition. Patients who have a positive response to one, but a negative response to the other, may be started on enteral nutrition but more cautiously i.e., a slower rate of feeding.

VII. Other Therapeutic Exemplary Embodiments

Many of the above embodiments are disclosed in the context of diagnostics. However, various embodiments are applicable solely and/or directly to therapeutics. Still other embodiments are applicable as combinations of diagnostics and therapeutics. Some of these embodiments, i.e., the embodiments applicable solely and/or directly to therapeutics as well as the other embodiments applicable as combinations of diagnostics and therapeutics, are disclosed below for exemplary purposes only, and the below disclosures are not intended as an exhaustive list of therapeutic applications encompassed by the various inventive concepts covered by the present disclosure.

A. Feeding Intolerance

Movement of food through the gastrointestinal tract, e.g., from the stomach into the small intestine and into the large intestine, can become impaired. This impairment has been observed, and is fairly common, in some hospitalized patients, including but not limited to ICU patients. This impairment and/or condition can be manifested in many contexts, such as intolerance to enteral feeding for example. This condition can lead to symptoms (e.g., nausea, anorexia, pain) and/or signs (e.g., high gastric residuals, vomiting, abdominal distension). Related art methods of treating the above signs and/or symptoms, such as erythromycin and metaclopramide, may not be sufficient in various respects and/or under certain circumstances.

In accordance with some exemplary embodiments, a gastric acid stimulant is administered to enhance perfusion (blood flow) to certain areas of the gastrointestinal tract. Enhancing perfusion in this manner enhances blood flow to various areas of the gastrointestinal tract, allowing certain cells to function more effectively.

Embodiments are intended to cover any gastric acid secretory stimulant that performs the function disclosed above, i.e., desirable effects on the gastrointestinal tract, such as by improving perfusion (blood flow) to the gastrointestinal tract to allow relevant cells to function more effectively. Some embodiments administer pentagastrin as a gastric acid stimulant to promote gastrointestinal health, including enhanced gastrointestinal perfusion and function, thereby preventing and/or treating many (or all of the) signs and symptoms of intolerance to enteral feeding. This procedure may provide beneficial effects with regard to perfusion and function of the stomach as well as more distally, e.g., small intestine.

Embodiments are intended to cover any route of administration that enables performance of the function disclosed above, i.e., desirable effects on the gastrointestinal tract, such as by improving perfusion (blood flow) to the gastrointestinal tract to allow relevant cells to function more effectively. Some embodiments use an intravenous route of administration due to the rapid onset and relatively predictable pharmacodynamics of intravenous administration. Intravenous administration also allows for a continuous infusion (e.g., 1 mcg/kg/hour), which may be beneficial in certain patients, such as patients receiving continuous enteral feeds (e.g., 80 ml/hour) into the stomach or small intestine.

However, as disclosed above, embodiments are intended to cover any practicable, useful or otherwise beneficial route of administration. In some patients, intramuscular, subcutaneous, and/or other routes of administration may be desirable. For example, for a patient receiving bolus (intermittent) tube feeds (e.g., 320 ml/4 hours), intramuscular and/or subcutaneous administration of a gastric secretory stimulant (e.g., pentagastrin 1 mcg/kg) prior to or after administration of food into the stomach can enhance or improve blood flow and motility within the gastrointestinal tract, thereby reducing, minimizing or preventing signs and symptoms of intolerance to enteral nutrition. It may be especially beneficial to perform this intramuscular and/or subcutaneous administration shortly prior to or soon after the food administration, such as within 30 minutes prior to or after the food administration. In some of these embodiments, the intramuscular and/or subcutaneous administration is performed immediately prior to or immediately after the food administration. In still other embodiments, the intramuscular and/or subcutaneous administration is performed during or concurrently with food administration.

Embodiments are intended to cover any stimulant dosage that enables performance of the function disclosed above, i.e., desirable effects on the gastrointestinal tract, such as by improving perfusion (blood flow) to the gastrointestinal tract to allow relevant cells to function more effectively. It may be beneficial to administer a stimulant dosage that has a favorable effect on the perfusion and function of the gastrointestinal tract, but that limits or prevents potential adverse effects. For example, an intravenous infusion of 0.5 to 1 mcg/kg/hour may provide the above beneficial effects but reduce, minimize or prevent certain adverse effects associated with much higher and rapidly administered doses of gastric stimulant. Intravenous administration of pentagastrin 0.5 mcg/kg (bolus administered) over 30 seconds has been associated with certain transient side effects, such as abdominal fullness and an urge to defecate. However, in some patients with an inadequate response to the drug (and in whom the drug is well tolerated), high doses can be administered, e.g., intravenous infusion of 4-10 mcg/kg/hour, or intravenous bolus over 30 seconds of 0.1 mcg/kg, or subcutaneous or intramuscular dose of 0.5 mcg/kg every 4 to 8 hours.

Embodiments are intended to be applied to any patient to achieve any beneficial effects, such as those disclosed above. For example, it is common for patients to receive enteral nutrition, often through a plastic tube or catheter inserted through the nose or mouth and into the stomach (naso- or oro-gastric), or into the small bowel (naso-duodenal or naso-jejunal), or through the skin of the abdomen and into the stomach or small bowel (e.g., PEG tube). Typically but not always, the above nutrition techniques are performed on critically ill patients in an intensive care unit. However, the above procedures can also be applied to other patients, such as those who are not-critically ill, and in other settings, such as hospital step-down units, hospital wards, nursing homes, long-term care or rehabilitation facilities, etc. It is even possible for the above procedures to be applied to people who are not located in any of the above facilities, such as those at home.

In one embodiment, a gastrointestinal stimulant (e.g., pentagastrin) is administered as a preventative (prophylactic) treatment in order to reduce, minimize or prevent signs and/or symptoms of gastrointestinal feeding intolerance. For example, the pentagastrin can be administered via bolus dosing (0.5 mcg/kg of pentagastrin subcutaneously, intramuscularly, or even intravenously) just prior to or just after bolus dosing of tube feeds, typically into the stomach.

However, the above embodiment is merely provided for exemplary purposes, and in accordance with another embodiment of prophylaxis, a continuous infusion of gastrointestinal stimulant (e.g., pentagastrin) is administered as a preventative (prophylactic) treatment in order to reduce, minimize or prevent signs and/or symptoms of gastrointestinal feeding intolerance. For example, pentagastrin 1 mcg/kg/hour infusion can be initiated 30 minutes prior to initiating an infusion of gastric and/or proximal small bowel tube feeds.

In yet another embodiment, gastrointestinal stimulant (e.g., pentagastrin) is administered to treat patients who have already exhibited signs and/or symptoms of intolerance to gastrointestinal tube feeds. For example, the pentagastrin can be administered via bolus dosing (0.5 mcg/kg of pentagastrin subcutaneously, intramuscularly, or even intravenously) for patients with signs and/or symptoms of intolerance, or a continuous infusion of pentagastrin (1 mcg/kg/hour) for a patient with signs and/or symptoms of intolerance.

The above procedures are disclosed in the context of therapeutics. However, embodiments are not intended to be limited to therapeutics, and can alternatively, or even additionally, be applied in the context of diagnostics. For example, in one embodiment, stimulant can be used for diagnostic purposes to assess a patient's readiness to begin enteral nutrition or for any other relevant diagnostic purpose (e.g., diagnostic for determining adequate resuscitation). Immediately or within several hours after the stimulant is administered for diagnostic purposes, the same type or a different stimulant can be administered (as described above) to either reduce, minimize, prevent or otherwise treat signs and/or symptoms of feeding intolerance. Alternatively, if the stimulant is being used to reduce, minimize, prevent or otherwise treat feeding intolerance, a diagnostic test (e.g., such as any of those provided in the present disclosure, including but not limited to determining adequacy of gastrointestinal tract to process nutrition) can be performed in the same patient, typically after a certain period, such as at least one hour, after discontinuation of the stimulant used previously.

What is claimed is:

1. A device for insertion into a stomach of a patient for use with enteral feeding, comprising:
   an indwelling tube having a length;
   one or more impedance sensors attached along the length of the indwelling tube, wherein the one or more impedance sensors are configured to detect a presence or passage of a bolus transitioning through the stomach;
   a controller in communication with the one or more impedance sensors, wherein the controller is configured to determine measurements of a volume of gastric contents by correlating the presence or passage of the bolus transitioning through the stomach to the volume of gastric contents such that the measurements of the volume of gastric contents provide guidance via the controller for patient care.

2. The device of claim 1 wherein the one or more impedance sensors are attached along the length at a position such that the sensors are placed within the stomach when the indwelling tube is inserted into the patient.

3. The device of claim 1 wherein the guidance for patient care comprises instructions provided via the controller to perform at least one of initiation, maintenance, increase, reduction, or termination of enteral feeding via the controller.

4. The device of claim 3 wherein the controller comprises a processor configured to provide the instructions.

5. The device of claim 1 wherein an intensity of treatment of the patient care is determined as a function of the measurements.

6. The device of claim 1 wherein the guidance for patient care comprises a nutritional readiness score determined from the measurements of the gastric volume.

7. The device of claim 1 wherein the guidance for patient care provided via the controller comprises a determination of initiating, terminating, or weaning enteral feeding via the controller.

8. The device of claim 1 wherein the guidance for patient care provided via the controller comprises a determination of modifying vasoactive agents, mechanical ventilation, acid suppressants, or motility agents via the controller.

9. The device of claim 1 wherein the controller is configured to provide the measurements on a continuous basis.

10. The device of claim 1 wherein the device is configured to measure the presence and passage of a stress agent configured to affect the measurement of the gastric volume.

11. The device of claim 10 wherein the stress agent comprises a bolus of food.

12. The device of claim 11 wherein the bolus of food comprises liquid food.

13. The device of claim 10 wherein the controller is configured to determine the gastric volume after the stress agent is provided to the patient.

14. The device of claim 1 wherein the controller is programmed to provide the guidance for patient care via the controller based on the measurements of the gastric volume.

15. The device of claim 14 wherein the controller is programmed to compare the measurements of gastric volume against aggregate measurements provided by the controller of gastric volume obtained from other patients having profile data correlated to the patient.

16. The device of claim 15 wherein the profile data comprises at least one of age, gender, fitness, weight, body composition, percentage of body fat, ethnicity, family history, personal medical history, and genetics.

17. The device of claim 14 wherein the controller is programmed to calculate a rate of change of the measurements of gastric volume.

18. The device of claim 1 wherein the one or more impedance sensors are configured to provide an indication of tube placement within the patient.

19. The device of claim 1 wherein the one or more impedance sensors are configured to provide an indication of gastric motility.

20. The device of claim 1 wherein the device is configured to measure the presence and passage of a gastric acid suppressant configured to affect the measurement of the gastric volume.

* * * * *

UNITED STATES PATENT AND TRADEMARK OFFICE
CERTIFICATE OF CORRECTION

PATENT NO. : 10,687,731 B2  
APPLICATION NO. : 15/360625  
DATED : June 23, 2020  
INVENTOR(S) : Elliott Bennett-Guerrero Page 1 of 1

It is certified that error appears in the above-identified patent and that said Letters Patent is hereby corrected as shown below:

On the Title Page

In item (72) Inventor, please replace "Elliott Bennet-Guerrero" with --Elliott Bennett-Guerrero--.

Signed and Sealed this  
Twenty-first Day of July, 2020

Andrei Iancu  
*Director of the United States Patent and Trademark Office*